US012589139B2

(12) United States Patent
Kupinski et al.

(10) Patent No.: US 12,589,139 B2
(45) Date of Patent: Mar. 31, 2026

(54) CLOSTRIDIAL NEUROTOXINS COMPRISING AN EXOGENOUS ACTIVATION LOOP

(71) Applicant: IPSEN BIOPHARM LIMITED, Wrexham (GB)

(72) Inventors: Adam Kupinski, Wrexham (GB); Laura Lovelock, Wrexham (GB)

(73) Assignee: Ipsen Biopharm Limited, Wrexham (GB)

( * ) Notice: Subject to any disclaimer, the term of this patent is extended or adjusted under 35 U.S.C. 154(b) by 1020 days.

(21) Appl. No.: 17/278,724

(22) PCT Filed: Sep. 27, 2019

(86) PCT No.: PCT/GB2019/052732
§ 371 (c)(1),
(2) Date: Mar. 23, 2021

(87) PCT Pub. No.: WO2020/065336
PCT Pub. Date: Apr. 2, 2020

(65) Prior Publication Data
US 2022/0211823 A1      Jul. 7, 2022

(30) Foreign Application Priority Data

Sep. 28, 2018     (GB) ...................................... 1815817

(51) Int. Cl.
| | |
|---|---|
| *C12P 21/06* | (2006.01) |
| *A61K 38/48* | (2006.01) |
| *C07K 14/33* | (2006.01) |
| *C12N 9/52* | (2006.01) |

(52) U.S. Cl.
CPC ............ *A61K 38/4893* (2013.01); *C12N 9/52* (2013.01); *C12P 21/06* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 2009/0048431 A1 | 2/2009 | Steward et al. | |
| 2009/0269358 A1* | 10/2009 | Shone .................... | A61K 39/08 536/23.7 |
| 2011/0111479 A1 | 5/2011 | Steward et al. | |
| 2014/0219983 A1* | 8/2014 | Madec ................... | C07K 14/48 514/44 R |
| 2018/0141982 A1 | 5/2018 | Anderson et al. | |
| 2022/0211823 A1 | 7/2022 | Kupinski et al. | |

FOREIGN PATENT DOCUMENTS

| | | | | |
|---|---|---|---|---|
| CZ | 302526 B6 * | 6/2011 | | |
| EP | 1 999 142 B1 | 7/2013 | | |
| WO | WO-0039310 A1 * | 7/2000 | .......... | C07K 14/195 |
| WO | 2010/020811 A1 | 2/2010 | | |
| WO | 2010090677 A1 | 8/2010 | | |
| WO | 2012/156743 A1 | 11/2012 | | |
| WO | 2013/091895 A1 | 6/2013 | | |
| WO | 2014/033441 A1 | 3/2014 | | |
| WO | 2014079495 A1 | 5/2014 | | |
| WO | 2014080206 A1 | 5/2014 | | |
| WO | 2015166242 A1 | 11/2015 | | |
| WO | 2016/110662 A1 | 7/2016 | | |
| WO | 2017/055274 A1 | 4/2017 | | |
| WO | 2017/201105 A1 | 11/2017 | | |
| WO | WO-2018009903 A2 * | 1/2018 | ............ | A61K 38/00 |
| WO | 2019152380 A1 | 8/2019 | | |
| WO | 2020065336 A1 | 4/2020 | | |

OTHER PUBLICATIONS

Machine translation of CZ 302526 B6 obtained from Google Patents on Oct. 11, 2024, 20 pages (Year: 2024).*
UniProt Database Accession No. Q00496, Jul. 2017, 13 pages (Year: 2017).*
International Search Report, issued Nov. 25, 2019, in PCT/GB2019/052732.
Chen et al., Peptides, 39:145-151 (2013).

* cited by examiner

*Primary Examiner* — David Steadman
(74) *Attorney, Agent, or Firm* — Proskauer Rose LLP

(57) ABSTRACT

An engineered clostridial neurotoxin comprising an activation loop that comprises an amino acid sequence of the formula Cys-(Xaa)$_a$-Ile-Asp/Glu-Gly-Arg-(Yaa)$_b$-Cys(SEQ ID NO: 1), wherein a is an integer from 1 to 10, b is an integer from 4 to 15, each iteration of Xaa and Yaa individually represents an amino acid, and the engineered clostridial neurotoxin is not BoNT/C1, a method for producing the same, a method of treating a disease or condition comprising administering the engineered clostridial neurotoxin or the corresponding di-chain clostridial neurotoxin, a composition comprising the engineered clostridial neurotoxin or the corresponding di-chain clostridial neurotoxin, and a polynucleotide encoding the engineered clostridial neurotoxin. A method for proteolytically processing a single-chain clostridial neurotoxin into a corresponding di-chain clostridial neurotoxin, the method comprising contacting the single-chain clostridial neurotoxin with enterokinase or factor Xa and a di-chain clostridial neurotoxin produced using such a method. A method for hydrolyzing a peptide bond of a polypeptide comprising contacting the polypeptide with an enterokinase.

8 Claims, 14 Drawing Sheets
Specification includes a Sequence Listing.

*FIG. 1*

| Protein id | aa start | Sequence | aa end | SEQ ID NO: |
|---|---|---|---|---|
| D_AB012112 | 437 | CLRLTKNSRDDSTC | 450 | 23 |
| DC_AB745660 | 437 | CLRLTRNSRDDSTC | 450 | 61 |
| C1_X62389 | 437 | CHKAIDGRSLYNKTLDC | 453 | 2 |
| CD_AB200360 | 437 | CHKAIDGRSLYNKTLDC | 453 | |
| A4_EU341307 | 430 | CVRGIITSKTKSLDEGYNKALNELC | 454 | 62 |
| A7_JQ954969 | 430 | CVRGIITSKTKSLDEGYNKALNDLC | 454 | 63 |
| A6_FJ981696 | 430 | CVRGIITSKTKSLDKGYNKALNDLC | 454 | 21 |
| A1_AF488749 | 430 | CVRGIITSKTKSLDKGYNKALNDLC | 454 | |
| A5_EU679004 | 430 | CVRGIITSKTKSLDEGYNKALNDLC | 454 | 63 |
| A3_DQ185900 | 426 | CVRGIIPFKTKSLDEGYNKALNYLC | 450 | 64 |
| A2_X73423 | 430 | CVRGIIPFKTKSLDEGYNKALNDLC | 454 | 65 |
| A8_KM233166 | 430 | CVRGIIPFKTKSLDEGYNKALNDLC | 454 | |
| H_KGO15617 | 428 | CSNSNTKNSLC | 438 | 66 |
| E9_JX424534 | 414 | CKNIVSVKGIRKSIC | 429 | 24 |
| E12_KM370319 | 414 | CKNIVSVKGIRKSIC | 429 | |
| E11_KF861875 | 411 | CTNIFSPKGIRKSIC | 426 | 67 |
| E10_KF861917 | 411 | CKNIVFSKGITKSIC | 426 | 68 |
| E7_JN695729 | 411 | CKNIVFSKGITKSIC | 426 | |
| E8_JN695730 | 411 | CKNIVFSKGITKSIC | 426 | |
| E5_AB037711 | 411 | CKNIVSVKGIRKSIC | 426 | 24 |
| E6_AM695759 | 411 | CKNIVFSKGIRKSIC | 426 | 69 |
| E4_AB088207 | 411 | CKNIVSVKGIRKSIC | 426 | 24 |
| E3_EF028403 | 411 | CKNIVSVKGIRKSIC | 426 | |
| E1_GQ244314 | 411 | CKNIVSVKGIRKSIC | 426 | |
| E2_EF028404 | 411 | CKNIVSVKGIRKSIC | 426 | |
| F7_GU213233 | 420 | CKSIVSKKGTKNSLC | 434 | 29 |
| F5_GU213211 | 428 | CLNSSFKKNTKKPLC | 442 | 28 |
| F1_GU213203 | 429 | CKSVIPRKGTKAPPRLC | 445 | 25 |
| F4_GU213214 | 429 | CKSIIPRKGTKAPPRLC | 445 | 27 |
| F2_GU213209 | 429 | CKSIIPRKGTKQSPSLC | 445 | 26 |
| F3_GU213227 | 429 | CKSIIPRKGTKQSPSLC | 445 | |
| F6_M92906 | 429 | CKSVIPRKGTKAPPRLC | 445 | 25 |
| T_P04958 | 439 | CKKIIPPTNIRENLYNRTASLTDLGGELC | 467 | 30 |
| G_X74162 | 436 | CKPVMYKNTGKSEQC | 450 | 31 |
| B4_EF051570 | 437 | CKSVKVPGIC | 446 | 70 |
| B8_JQ964806 | 437 | CKSVRAPGIC | 446 | 22 |
| B7_JQ354985 | 437 | CKSVKAPGIC | 446 | 71 |
| B6_AB302852 | 437 | CKSVRAPGIC | 446 | 22 |
| B2_AB084152 | 437 | CKSVRAPGIC | 446 | |
| B3_EF028400 | 437 | CKSVRAPGIC | 446 | |
| B1_AB232927 | 437 | CKSVKAPGIC | 446 | 71 |
| B5_EF033130 | 437 | CKSVKAPGIC | 446 | |
| X_BAQ12790 | 423 | CPRNGLLYNAIYRNSKNYLNNIDLEDKK TTSKTNVSYPCSLLNGC | 467 | 20 |

*FIG. 2C*
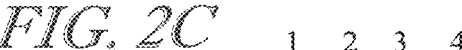
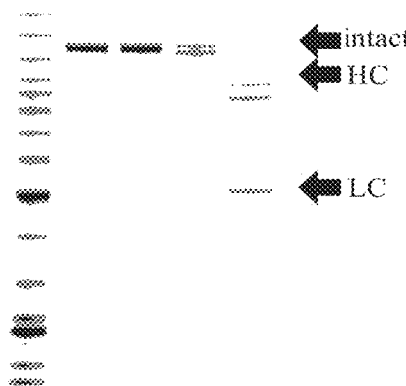
*FIG. 3A*
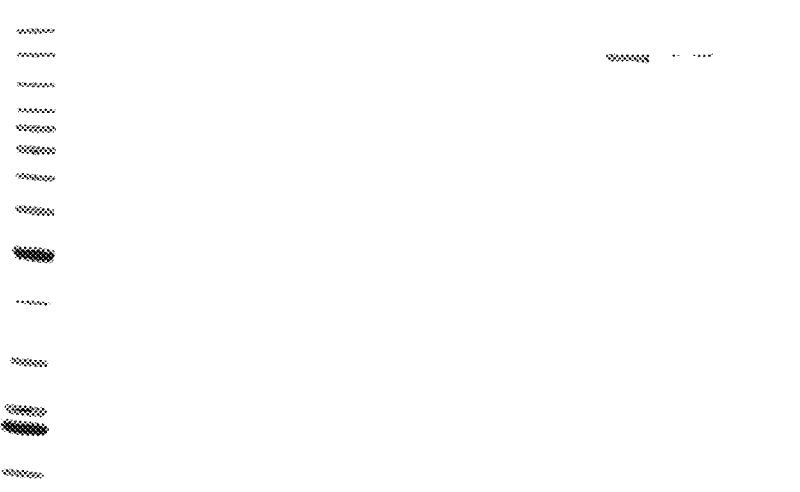

*FIG. 6*
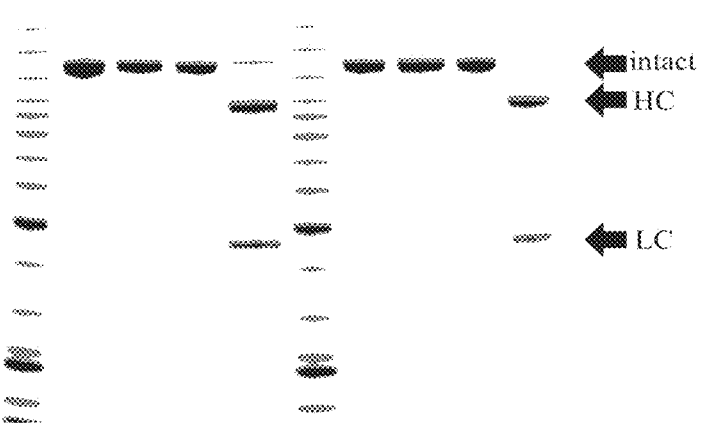
*FIG. 7A*    *FIG. 7B*
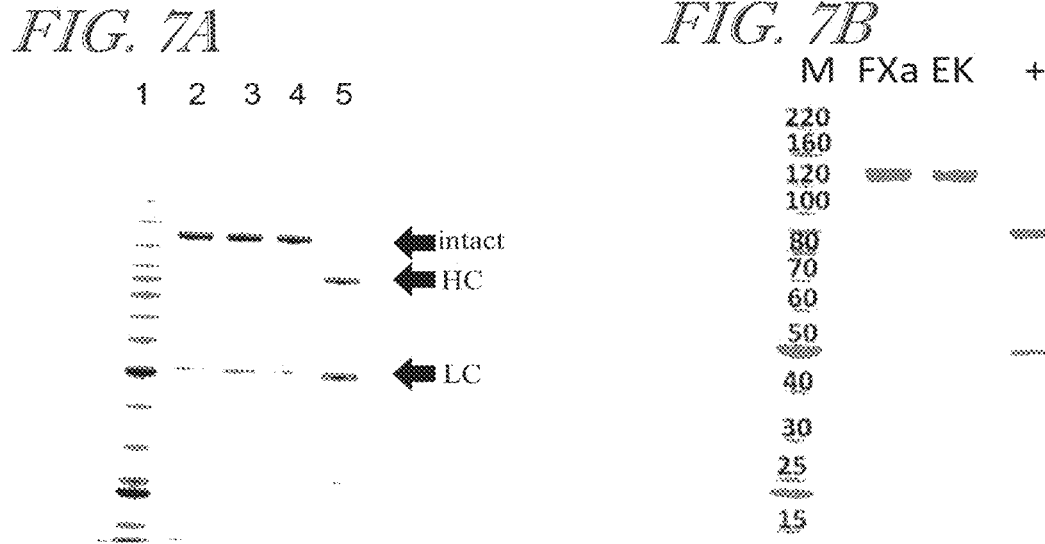

*FIG. 10*
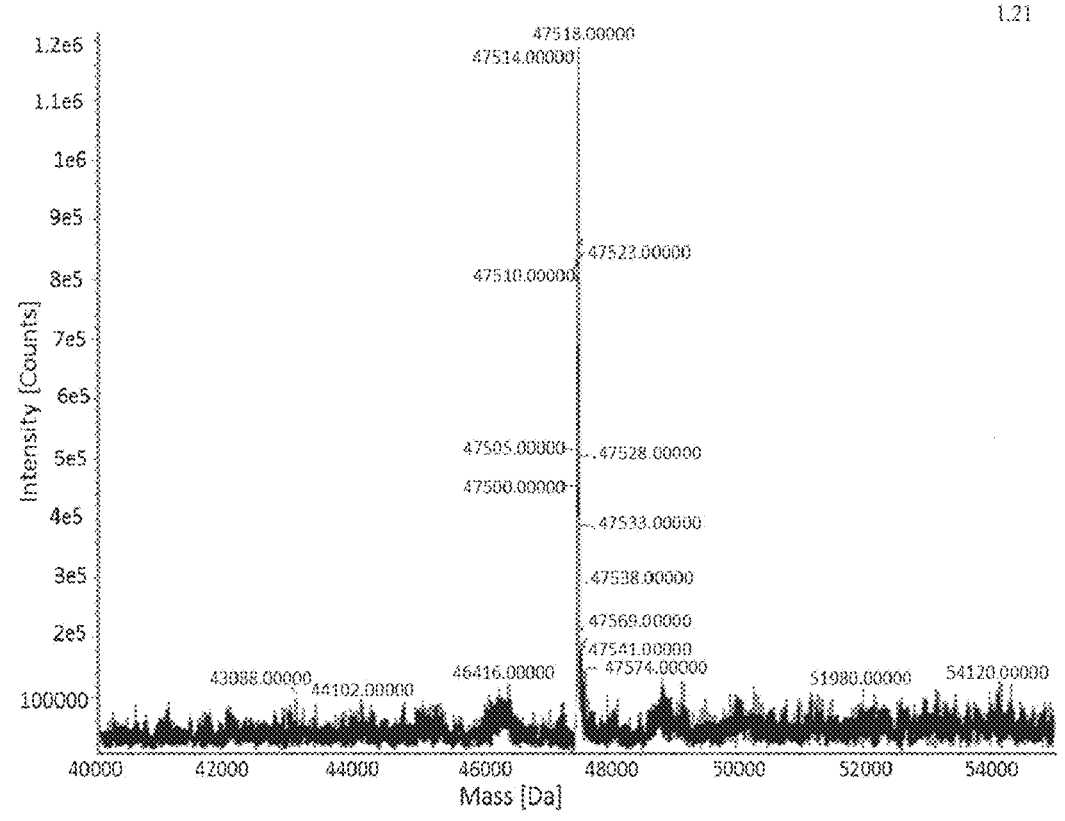
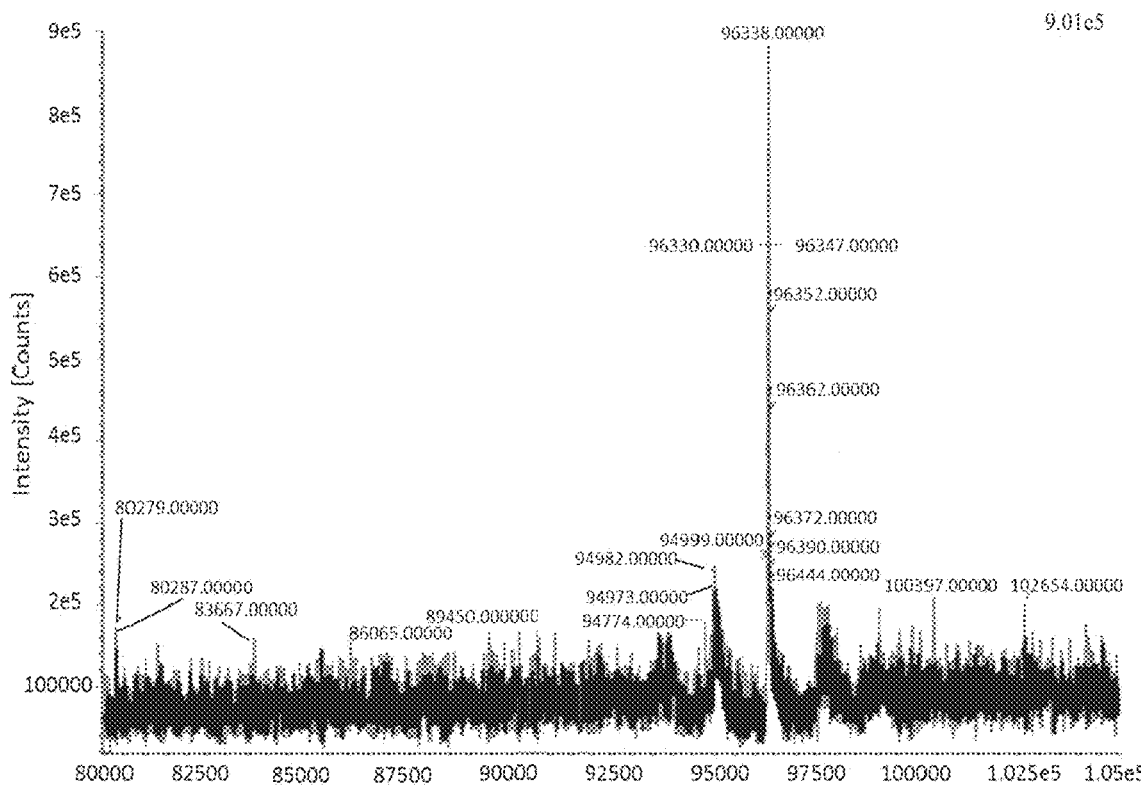

*FIG. 12*
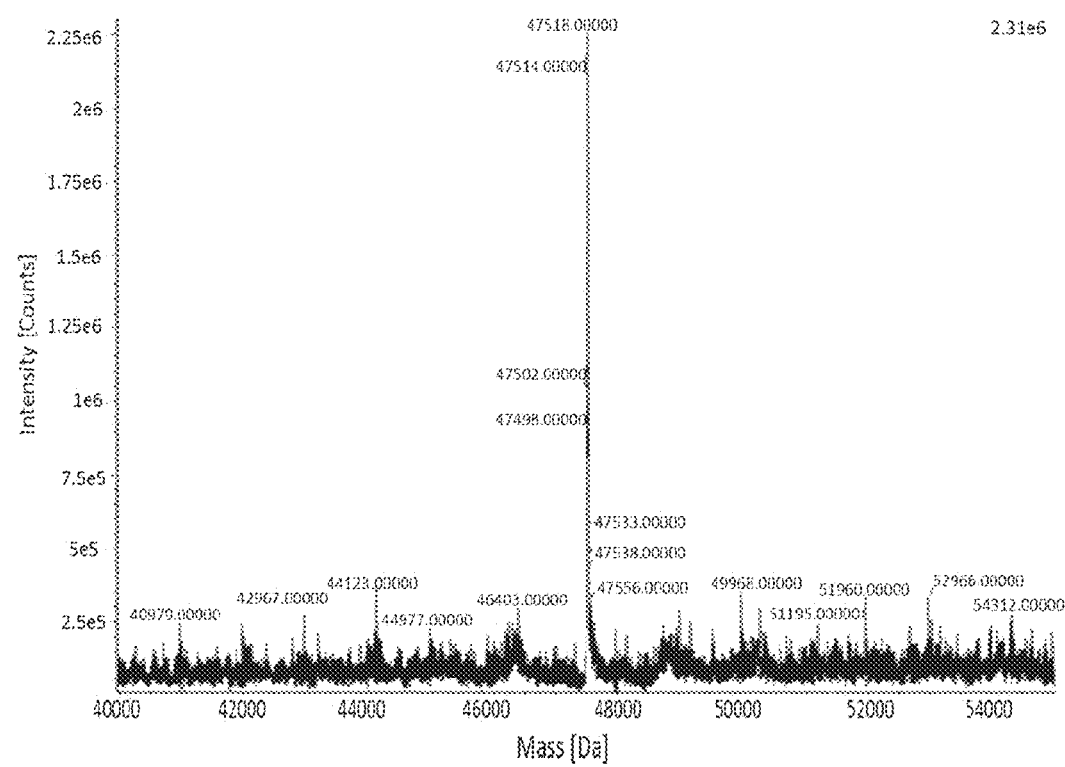
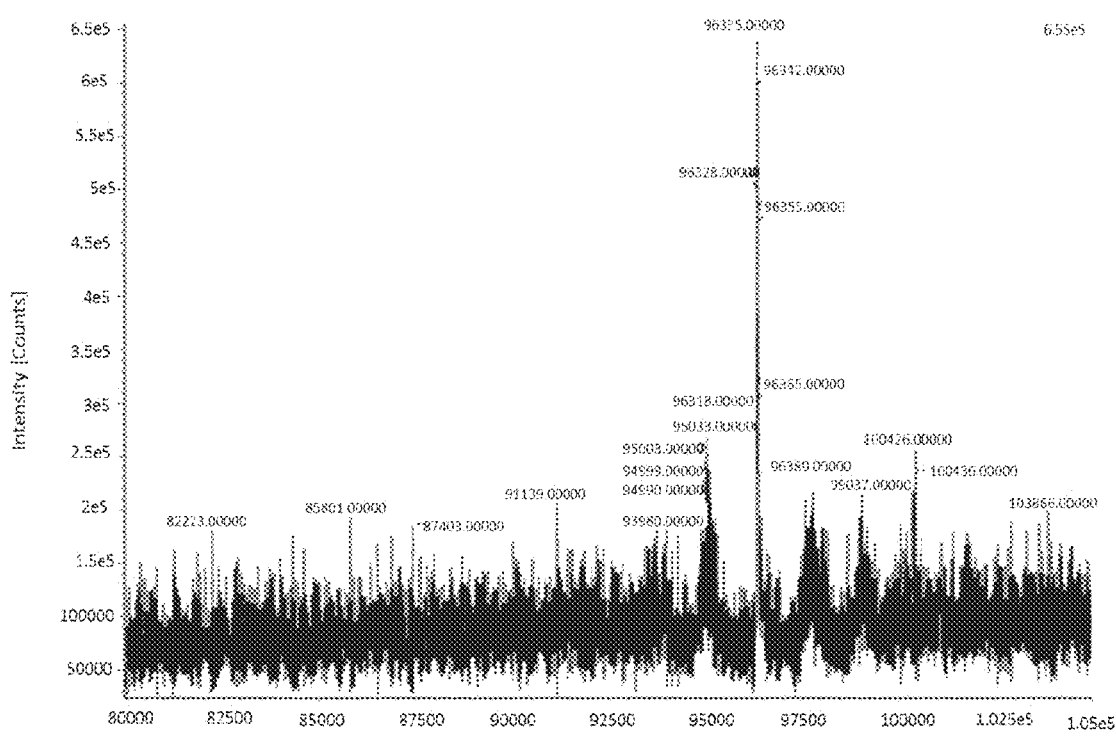

*FIG. 15*
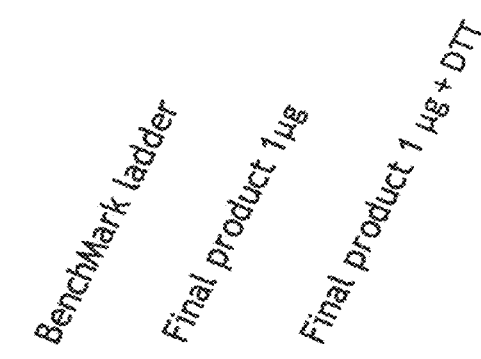
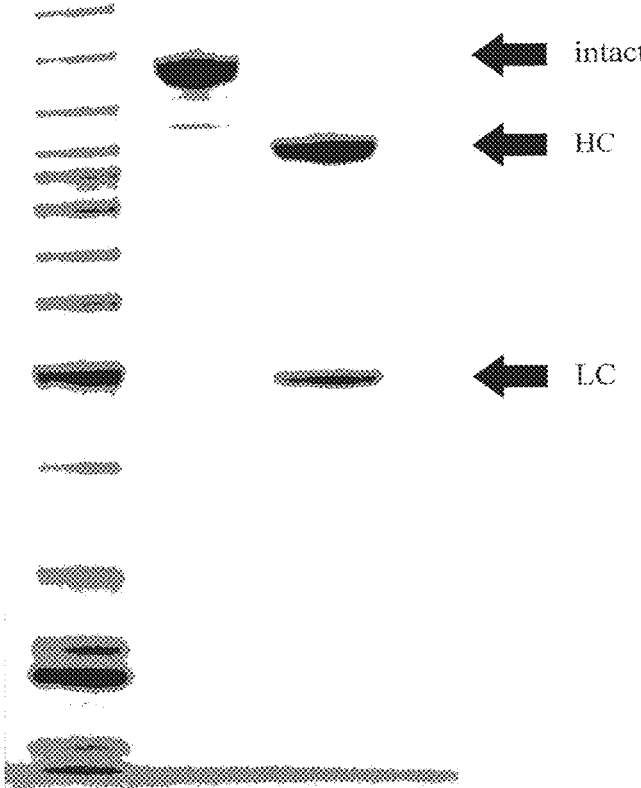

CLOSTRIDIAL NEUROTOXINS COMPRISING AN EXOGENOUS ACTIVATION LOOP

This application is a U.S. national stage filing of International Patent Application No. PCT/GB2019/052732, filed Sep. 27, 2019, which claims the priority of British Application No. 1815817.0, filed Sep. 28, 2018.

The instant application contains a Sequence Listing which has been submitted electronically in ASCII format and is hereby incorporated by reference in its entirety. Said ASCII copy, created on May 31, 2024, is named 79904-335825 SL.txt and is 349,679 bytes in size.

The present invention relates to clostridial neurotoxins and methods for activating and using the same.

Bacteria in the genus Clostridia produce highly potent and specific protein toxins, which can poison neurons and other cells to which they are delivered. Examples of such clostridial neurotoxins include the neurotoxins produced by *C. tetani* (TeNT) and by *C. botulinum* (BoNT) serotypes A-G, and X (see WO 2018/009903 A2), as well as those produced by *C. baratii* and *C. butyricum*.

Among the clostridial neurotoxins are some of the most potent toxins known. By way of example, botulinum neurotoxins have median lethal dose ($LD_{50}$) values for mice ranging from 0.5 to 5 ng/kg, depending on the serotype. Both tetanus and botulinum toxins act by inhibiting the function of affected neurons, specifically the release of neurotransmitters. While botulinum toxin acts at the neuromuscular junction and inhibits cholinergic transmission in the peripheral nervous system, tetanus toxin acts in the central nervous system.

Clostridial neurotoxins are expressed as single-chain polypeptides in *Clostridium*. Each clostridial neurotoxin has a catalytic light chain separated from the heavy chain (encompassing the N-terminal translocation domain and the C-terminal receptor binding domain) by an exposed region called the activation loop. During protein maturation proteolytic cleavage of the activation loop separates the light and heavy chain of the clostridial neurotoxin, which are held together by a disulphide bridge, to create fully active di-chain toxin. This process must be reproduced during recombinant toxin production.

Exogenous proteases such as trypsin or Lys-C are used for proteolytically activating single-chain clostridial neurotoxins. However, for some clostridial neurotoxins, incubation with Lys-C or trypsin results in partial or improper cleavage of the single-chain polypeptide resulting in the production of contaminating single-chain and/or inactive cleavage/degradation products (e.g. in the case of BoNT/E), necessitating purification of the full-length di-chain polypeptide. Thus, at present there is no universal exogenous protease for activation of clostridial neurotoxins. This is particularly problematic upon identification of a new clostridial neurotoxin or production of a modified (e.g. chimeric or hybrid) neurotoxin, which requires screening of multiple proteases to determine correct activation.

Botulinum neurotoxin serotype X (BoNT/X) was recently identified (WO 2018/009903 A2). It has been found that BoNT/X is particularly problematic to activate, and cleavage with trypsin or Lys-C completely degrades the polypeptide.

The present invention overcomes one or more of the above-mentioned problems.

The protease enterokinase exhibits a much higher substrate specificity compared to conventionally used trypsin and Lys-C. This protease recognises and cleaves immediately C-terminal to a DDDDK peptide sequence (SEQ ID NO: 72). Notably, this sequence is absent from all of the clostridial neurotoxin activation loops (see FIG. 1), thus enterokinase has previously been ruled out as a protease for use in activating clostridial neurotoxins.

The present inventors have surprisingly found that enterokinase recognises and cleaves immediately C-terminal to an IDGR sequence present in the BoNT/C1 activation loop (see FIG. 1). Advantageously, this sequence can also be recognised and cleaved by factor Xa, another protease exhibiting high substrate specificity (e.g. compared to trypsin and Lys-C). Moreover, the BoNT/C1 activation loop also has lysine and arginine residues, allowing cleavage by either lysine or trypsin. Thus, the present inventors have surprisingly found that the BoNT/C1 loop constitutes a universal activation loop for clostridial neurotoxins, thus providing the flexibility to use four different proteases.

In one aspect the invention provides a method for proteolytically processing a single-chain clostridial neurotoxin (e.g. of an engineered clostridial neurotoxin described herein) into a corresponding di-chain clostridial neurotoxin, the method comprising:
- a. providing a single-chain clostridial neurotoxin; and
- b. contacting the single-chain clostridial neurotoxin with enterokinase;
- wherein the single-chain clostridial neurotoxin has an activation loop comprising the polypeptide sequence Cys-(Xaa)$_a$-Ile-Asp/Glu-Gly-Arg-(Yaa)$_b$-Cys (SEQ ID NO: 1); and
- wherein enterokinase hydrolyses a peptide bond of the activation loop thereby producing a di-chain clostridial neurotoxin (e.g. an engineered di-chain clostridial neurotoxin described herein).

In a related aspect the invention provides a method for proteolytically processing a single-chain clostridial neurotoxin (e.g. of an engineered clostridial neurotoxin described herein) into a corresponding di-chain clostridial neurotoxin, the method comprising:
- a. providing a single-chain clostridial neurotoxin; and
- b. contacting the single-chain clostridial neurotoxin with factor Xa;
- wherein the single-chain clostridial neurotoxin has an activation loop comprising the polypeptide sequence Cys-(Xaa)$_a$-Ile-Asp/Glu-Gly-Arg-(Yaa)$_b$-Cys (SEQ ID NO: 1); and
- wherein factor Xa hydrolyses a peptide bond of the activation loop thereby producing a di-chain clostridial neurotoxin (e.g. an engineered di-chain clostridial neurotoxin described herein).

The single-chain clostridial neurotoxin is preferably an engineered single-chain clostridial neurotoxin of the present invention, wherein the activation loop is an exogenous activation loop. Advantageously, the present inventors have found that replacing an endogenous clostridial neurotoxin activation loop with an exogenous activation loop shown as SEQ ID NO: 1 (which contains a protease cleavage site in its natural context) overcomes problems associated with modifying an endogenous activation loop to insert a protease cleavage site (e.g. a factor Xa cleavage site, such as Ile-Asp-Gly-Arg [SEQ ID NO: 18] or Ile-Glu-Gly-Arg [SEQ ID NO: 19]). In particular, modifying an endogenous activation loop to insert a protease cleavage site can lead to conformational changes, which, in turn, can have a negative effect on cleavage efficiency (see Example 7 herein).

In a particularly preferred embodiment the methods of the present invention comprise the use of enterokinase.

In one aspect the present invention is directed to use of enterokinase for hydrolysing a peptide bond of a polypeptide (e.g. a clostridial neurotoxin) comprising a sequence shown as SEQ ID NO: 18 or SEQ ID NO: 19 (preferably SEQ ID NO: 18). Preferably enterokinase hydrolyses a peptide bond immediately C-terminal to SEQ ID NO: 18 or SEQ ID NO: 19 (more preferably SEQ ID NO: 18) comprised within the polypeptide sequence. In one embodiment a polypeptide comprises a polypeptide sequence shown as SEQ ID NO: 1 or a polypeptide sequence having at least 70% sequence identity to SEQ ID NO: 2 or SEQ ID NO: 3.

The present invention also provides a method for manufacturing an engineered clostridial neurotoxin, the method comprising:

a. identifying an endogenous activation loop of a clostridial neurotoxin, wherein the clostridial neurotoxin is characterised in that a peptide bond outside of the endogenous activation loop of the clostridial neurotoxin is hydrolysed by trypsin or Lys-C; and b. replacing the endogenous activation loop with an exogenous activation loop thereby providing an engineered clostridial neurotoxin, wherein the exogenous activation loop comprises the polypeptide sequence Cys-(Xaa)$_a$-Ile-Asp/Glu-Gly-Arg-(Yaa)$_b$-Cys (SEQ ID NO: 1).

The present invention also provides a method for manufacturing an engineered clostridial neurotoxin, the method comprising:

a. identifying an endogenous activation loop of a clostridial neurotoxin, wherein the clostridial neurotoxin is characterised in that the endogenous activation loop is inefficiently proteolytically processed by trypsin or Lys-C; and b. replacing the endogenous activation loop with an exogenous activation loop thereby providing an engineered clostridial neurotoxin, wherein the exogenous activation loop comprises the polypeptide sequence Cys-(Xaa)$_a$-Ile-Asp/Glu-Gly-Arg-(Yaa)$_b$-Cys (SEQ ID NO: 1).

In one embodiment the clostridial neurotoxin is characterised in that a peptide bond outside of the endogenous activation loop of the clostridial neurotoxin is hydrolysed by trypsin or Lys-C and the endogenous activation loop is inefficiently proteolytically processed by trypsin or Lys-C.

In embodiments where the endogenous activation loop is inefficiently proteolytically processed by trypsin (and preferably a peptide bond outside of the endogenous activation loop of the clostridial neurotoxin is not hydrolysed by trypsin), the method may further comprise contacting an engineered clostridial neurotoxin with trypsin, which is capable of hydrolysing a peptide bond in the exogenous activation loop of the engineered clostridial neurotoxin. Similarly, in embodiments where the endogenous activation loop is inefficiently proteolytically processed by Lys-C (and preferably a peptide bond outside of the endogenous activation loop of the clostridial neurotoxin is not hydrolysed by Lys-C), the method may further comprise contacting an engineered clostridial neurotoxin with Lys-C, which is capable of hydrolysing a peptide bond in the exogenous activation loop of the engineered clostridial neurotoxin.

In one embodiment a method comprises a step of screening a clostridial neurotoxin for its suitability for use in a method of the invention. The screening step may comprise determining whether a peptide bond outside of the endogenous activation loop of the clostridial neurotoxin is hydrolysed by trypsin or Lys-C. Alternatively or additionally, the screening step may comprise determining whether the endogenous activation loop of a clostridial neurotoxin is inefficiently proteolytically processed by trypsin or Lys-C.

In contrast to the clostridial neurotoxin (pre-engineering) in one embodiment an engineered clostridial neurotoxin of the invention is not inefficiently proteolytically processed by enterokinase or factor Xa and/or a peptide bond outside of the exogenous activation loop of the engineered clostridial neurotoxin is not hydrolysed by enterokinase or factor Xa. Thus, the clostridial neurotoxin (pre-engineering) is preferably resistant to proteolytic processing by enterokinase and/or factor Xa.

A clostridial neurotoxin may be identified as being suitable for engineering in a method of the invention by an assay comprising contacting 1 mg of clostridial neurotoxin with at least 0.25 μg of trypsin at ≥3350 units/mg or Lys-C at ≥200 units/mg in a 50 mM Tris-HCl pH 8.0, 50 mM NaCl reaction buffer for at least 5 hours at at least 4° C.

In one embodiment the assay comprises contacting 1 mg of clostridial neurotoxin with 0.25 μg of trypsin at ≥3350 units/mg (~1:611 molar ratio of clostridial neurotoxin to trypsin) or Lys-C at ≥200 units/mg (~1:734 molar ratio of clostridial neurotoxin to Lys-C) in a 50 mM Tris-HCl pH 8.0, 50 mM NaCl reaction buffer for 18 hours at 4° C.

In another embodiment the assay comprises contacting 1 mg of clostridial neurotoxin with 0.40 μg of trypsin at ≥3350 units/mg (~1:978 molar ratio of clostridial neurotoxin to trypsin) or Lys-C at ≥200 units/mg (~1:1174 molar ratio of clostridial neurotoxin to Lys-C) in a 50 mM Tris-HCl pH 8.0, 50 mM NaCl reaction buffer for 5 hours at 20° C.

The trypsin used is preferably commercially available TrypZean (Sigma #T3568). Trypsin may have a polypeptide sequence having at least 70% sequence identity to SEQ ID NO: 47. In one embodiment trypsin may have a polypeptide sequence having at least 80% or 90% sequence identity to SEQ ID NO: 47. Preferably trypsin may have a polypeptide sequence shown as SEQ ID NO: 47. One unit of said trypsin (Trypzean) is defined as the amount of enzyme that will produce a change of absorbance at 253 nm of 0.003 per min at pH 7.6 at 25° C. using 0.23 mM Na-Benzoyl-L-Arginine Ethyl Ester Solution (BAEE) as substrate in a reaction volume of 3.2 mL.

The Lys-C used is preferably commercially available Lys-C(Sigma #000000011047825001). Lys-C may have a polypeptide sequence having at least 70% sequence identity to SEQ ID NO: 48. In one embodiment Lys-C may have a polypeptide sequence having at least 80% or 90% sequence identity to SEQ ID NO: 48. Preferably Lys-C may have a polypeptide sequence shown as SEQ ID NO: 48. One unit of said Lys-C is defined as the amount of enzyme that will hydrolyze 1.0 μmol Tos-Gly-Pro-Lys-pNA per min at 25° C., pH 7.

If one or more cleavage products additional to those of the H-chain and L-chain of the clostridial neurotoxin are observed by SDS-PAGE (preferably when stained with Coomassie or a dye of equivalent sensitivity), then it is confirmed that a peptide bond outside of the endogenous activation loop of the clostridial neurotoxin is hydrolysed by trypsin or Lys-C. Preferably if at least 3, 4, 5, 6, 7, 8, 9 or 10 cleavage products additional to those of the chain and L-chain of the clostridial neurotoxin are observed by SDS-PAGE after carrying out an assay described above, then it is confirmed that a peptide bond outside of the endogenous activation loop of the clostridial neurotoxin is hydrolysed by trypsin or Lys-C.

Additionally or alternatively, if less than 70% of endogenous activation loop is proteolytically processed by trypsin or Lys-C to yield a di-chain clostridial neurotoxin (assessed by way of SDS-PAGE, preferably when stained with Coomassie or a dye of equivalent sensitivity, after carrying out an assay described above), then it is confirmed that the endogenous activation loop is inefficiently proteolytically cleaved by trypsin or Lys-C. Preferably if less than 60%, 50%, 40%, 30%, 10% or 5% of endogenous activation loop is proteolytically processed by trypsin or Lys-C (assessed by way of SDS-PAGE after carrying out an assay described above) then the clostridial neurotoxin can be characterised in that the endogenous activation loop is inefficiently proteolytically cleaved by trypsin or Lys-C. More preferably if less than 30% of endogenous activation loop is proteolytically processed by trypsin or Lys-C (assessed by way of SDS-PAGE after carrying out an assay described above) then the clostridial neurotoxin can be characterised in that the endogenous activation loop is inefficiently proteolytically cleaved by trypsin or Lys-C.

A clostridial neurotoxin (pre-engineering) is preferably one in which a peptide bond (either within or outside of the activation loop) is not, or is not substantially, hydrolysed by enterokinase or factor Xa. The term "not substantially hydrolysed" means that less than 10%, 5%, 4%, 3%, 2% or 1% of the clostridial neurotoxin present in a reaction contains a peptide bond that has been hydrolysed by enterokinase or factor Xa in a method of the invention.

In one embodiment a method of the invention further comprises contacting an engineered clostridial neurotoxin with enterokinase or factor Xa (more preferably enterokinase) thereby producing a corresponding di-chain engineered clostridial neurotoxin.

In one aspect the invention provides an engineered clostridial neurotoxin (e.g. obtainable by a method of the invention), wherein an endogenous activation loop of a clostridial neurotoxin has been replaced by an exogenous activation loop thereby providing an engineered clostridial neurotoxin, wherein the exogenous activation loop comprises the polypeptide sequence Cys-(Xaa)$_a$-Ile-Asp/Glu-Gly-Arg-(Yaa)$_b$-Cys (SEQ ID NO: 1).

In one embodiment the clostridial neurotoxin (pre-engineering) is characterised in that: a peptide bond outside of the endogenous activation loop of the clostridial neurotoxin is hydrolysed by trypsin or Lys-C. In one embodiment the clostridial neurotoxin (pre-engineering) is characterised in that: the endogenous activation loop is inefficiently proteolytically processed by trypsin or Lys-C. In another embodiment the clostridial neurotoxin (pre-engineering) is characterised in that: a peptide bond outside of the endogenous activation loop of the clostridial neurotoxin is hydrolysed by trypsin or Lys-C; and the endogenous activation loop is inefficiently proteolytically processed by trypsin or Lys-C. Confirmation of these features of the clostridial neurotoxin (pre-engineering) is preferably by way of an aforementioned assay.

The invention may comprise replacing an endogenous activation loop of any clostridial neurotoxin with an exogenous activation loop described herein. Preferably the clostridial neurotoxin is not BoNT/C1. The clostridial neurotoxin may be a botulinum neurotoxin or a tetanus neurotoxin. Preferably the clostridial neurotoxin is a botulinum neurotoxin (BoNT), such as BoNT/A, BoNT/B, BoNT/D, BoNT/E, BoNT/F, BoNT/G or BoNT/X.

In one embodiment a clostridial neurotoxin for use in the present invention is BoNT/X, BoNT/E or a BoNT/A1C1 hybrid. Preferably the clostridial neurotoxin is BoNT/X or BoNT/E, both of which have been characterised in that trypsin and/or Lys-C hydrolyses a peptide bond outside of the endogenous activation loop thereof, and/or in that both clostridial neurotoxins contain an endogenous activation loop that is inefficiently proteolytically processed by trypsin and/or Lys-C. Most preferably a clostridial neurotoxin for use in the present invention is BoNT/X.

The term "endogenous activation loop" as used herein means an activation loop present in a subject clostridial neurotoxin, e.g. a subject clostridial neurotoxin of the indicated serotype. For example, BoNT/A1 includes a BoNT/A1 heavy chain and light chain, thus the endogenous activation loop of BoNT/A1 is an A1 activation loop. For clostridial neurotoxin chimeras or hybrids, the person skilled in the art can identify the "endogenous activation loop", for example by determining the serotype(s) from which the L-chain and H$_N$ domain are derived. In some embodiments, a chimera or hybrid clostridial neurotoxin may have an endogenous activation loop that is a fusion of an activation loop from two different serotypes. By way of example, a chimeric clostridial neurotoxin such as BoNT/A1C1 has a BoNT/A1 light chain and translocation domain, thus the endogenous BoNT/A1C1 activation loop is an A1 activation loop. Examples of activation loops are provided in FIG. 1.

Preferably an "endogenous activation loop" is any activation loop that is not SEQ ID NO: 1. In one embodiment an "endogenous activation loop" is any activation loop that is not SEQ ID NO: 2 and/or SEQ ID NO: 3.

By contrast, an "exogenous activation loop" as used herein means an activation loop that is different to the endogenous activation loop present in a subject clostridial neurotoxin, e.g. a subject clostridial neurotoxin of the indicated serotype. For example, a BoNT/C1 activation loop has a different polypeptide sequence to a wild-type BoNT/A1 activation loop, therefore the BoNT/C1 activation loop is exogenous to BoNT/A1. For clostridial neurotoxin chimeras or hybrids, the person skilled in the art can determine whether an activation loop is an "exogenous activation loop", for example by determining the serotype(s) from which the L-chain and H$_N$ domain are derived. Where the L-chain is a BoNT/B L-chain and the H$_N$ domain is from BoNT/D, the endogenous activation loop may have a portion of a BoNT/B sequence and a portion of a BoNT/D sequence, and if an activation loop (e.g. a C1 activation loop) is different thereto, it is considered an "exogenous activation loop".

Determination of whether an activation loop is an "exogenous activation loop" may be made by aligning the sequence of a subject clostridial neurotoxin with the activation loop, and seeing if the activation loop is present in the subject clostridial neurotoxin sequence. If it is absent, then the activation loop can be identified as an exogenous activation loop.

Preferably, the entire endogenous activation loop is replaced by an exogenous activation loop described herein. However, in some embodiments a portion of the endogenous activation loop is replaced, such as at least 5, 10, 15, 20, 25, 30, 35 or 40 amino acid residues of the endogenous activation are replaced.

Replacement of an endogenous activation loop may be achieved by any method known in the art. For example, replacement might be achieved by way of an amino acid modification. In one embodiment an endogenous activation loop may be replaced by deleting one or more amino acid residues of the endogenous activation loop. An endogenous activation loop may be replaced by substituting one or more amino acid residues of the endogenous activation loop with amino acid residues of an exogenous activation loop. In some embodiments an endogenous activation loop (or a portion thereof) may be deleted, and an exogenous activation loop inserted, preferably at the position formally occupied by the endogenous activation loop. Alternatively, the endogenous activation loop may be retained in an engineered clostridial neurotoxin of the invention, and preferably inactivated (e.g. by way of mutation). It is preferred that the endogenous activation loop (or a portion thereof, more preferably the entire endogenous activation loop) is not present in the engineered clostridial neurotoxin of the invention. It is preferred that the exogenous activation loop occupies the position in the clostridial neurotoxin formally occupied by the endogenous activation loop.

Methods for modifying proteins by substitution, insertion or deletion of amino acid residues are known in the art and may be employed in the practice of the present invention. By way of example, amino acid modifications may be introduced by modification of a DNA sequence encoding a clostridial neurotoxin. This can be achieved using standard molecular cloning techniques, for example by site-directed mutagenesis where short strands of DNA (oligonucleotides) coding for the desired amino acid(s) are used to replace the original coding sequence using a polymerase enzyme, or by inserting/deleting parts of the gene with various enzymes (e.g., ligases and restriction endonucleases). Alternatively a modified gene sequence can be chemically synthesised.

In one embodiment an endogenous activation loop comprises a polypeptide sequence having at least 70% (e.g. at least 80% or 90%) sequence identity to SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71. In one embodiment an endogenous activation loop comprises a polypeptide sequence having at least 95% sequence identity to SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71. Preferably, an endogenous activation loop comprises a polypeptide sequence shown as SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71.

In one embodiment an endogenous activation loop comprises a polypeptide sequence having at least 70% (e.g. at least 80% or 90%) sequence identity to SEQ ID NO: 20, SEQ ID NO: 21, SEQ ID NO: 24, SEQ ID NO: 62, SEQ ID NO: 63, SEQ ID NO: 64, SEQ ID NO: 65, SEQ ID NO: 67, SEQ ID NO: 68 or SEQ ID NO: 69. In one embodiment an endogenous activation loop comprises a polypeptide sequence having at least 95% sequence identity to SEQ ID NO: 20, SEQ ID NO: 21, SEQ ID NO: 24, SEQ ID NO: 62, SEQ ID NO: 63, SEQ ID NO: 64, SEQ ID NO: 65, SEQ ID NO: 67, SEQ ID NO: 68 or SEQ ID NO: 69. Preferably, an endogenous activation loop comprises a polypeptide sequence shown as SEQ ID NO: 20, SEQ ID NO: 21, SEQ ID NO: 24, SEQ ID NO: 62, SEQ ID NO: 63, SEQ ID NO: 64, SEQ ID NO: 65, SEQ ID NO: 67, SEQ ID NO: 68 or SEQ ID NO: 69.

In one embodiment an endogenous activation loop comprises a polypeptide sequence having at least 70% (e.g. at least 80% or 90%) sequence identity to SEQ ID NO: 20, SEQ ID NO: 21 or SEQ ID NO: 24. In one embodiment an endogenous activation loop comprises a polypeptide sequence having at least 95% sequence identity to SEQ ID NO: 20, SEQ ID NO: 21 or SEQ ID NO: 24. Preferably, an endogenous activation loop comprises a polypeptide sequence shown as SEQ ID NO: 20, SEQ ID NO: 21 or SEQ ID NO: 24.

Preferably an endogenous activation loop comprises a polypeptide sequence having at least 70% (e.g. at least 80% or 90%) sequence identity to SEQ ID NO: 20. In one embodiment an endogenous activation loop comprises a polypeptide sequence having at least 95% sequence identity to SEQ ID NO: 20. More preferably, an endogenous activation loop comprises a polypeptide sequence shown as SEQ ID NO: 20.

Preferably an endogenous activation loop comprises a polypeptide sequence having at least 70% (e.g. at least 80% or 90%) sequence identity to SEQ ID NO: 21. In one embodiment an endogenous activation loop comprises a polypeptide sequence having at least 95% sequence identity to SEQ ID NO: 21. More preferably, an endogenous activation loop comprises a polypeptide sequence shown as SEQ ID NO: 21.

Preferably an endogenous activation loop comprises a polypeptide sequence having at least 70% (e.g. at least 80% or 90%) sequence identity to SEQ ID NO: 24. In one embodiment an endogenous activation loop comprises a polypeptide sequence having at least 95% sequence identity to SEQ ID NO: 24. More preferably, an endogenous activation loop comprises a polypeptide sequence shown as SEQ ID NO: 24.

The present invention encompasses methods and clostridial neurotoxins in which an endogenous activation loop has been replaced by an exogenous activation loop, such as an exogenous activation loop comprising a polypeptide shown as Cys-(Xaa)$_a$-Ile-Asp/Glu-Gly-Arg-(Yaa)$_b$-Cys (SEQ ID NO: 1). Xaa or Yaa can be any amino acid. The number of amino acids at position Xaa and Yaa are indicated by the letters 'a' and 'b', respectively. In one embodiment 'a' and 'b' can be any integer that allows for proteolytic cleavage of the activation loop and yields an active di-chain clostridial neurotoxin. In one embodiment 'a' is at least 1, 2, 3, 4, 5, 6, 7, 8, 9 or 10. In one embodiment 'b' is at least 1, 2, 3, 4, 5, 6, 7, 8, 9, 10, 11, 12, 13, 14 or 15. In one embodiment 'a' is ≤12, ≤11, ≤10, ≤9, ≤8, ≤7, ≤6, ≤5 or ≤4. In one embodiment 'b' is ≤20, ≤19, ≤18, ≤17, ≤16, ≤15, ≤14, ≤13, ≤12, ≤11, ≤10 or ≤9.

In one embodiment 'a' is 1-12, for example 1-10. Preferably 'a' is 1-7, such as 2-4. More preferably 'a' is 3. In one embodiment 'b' is 1-20, for example 4-15. Preferably 'b' is 6-10. More preferably 'b' is 8.

It is not intended that Xaa or Yaa be limited to only one type of amino acid. Thus, one or more residues present at position Xaa may be independently selected from the standard amino acids: aspartic acid, glutamic acid, arginine, lysine, histidine, asparagine, glutamine, serine, threonine, tyrosine, methionine, tryptophan, cysteine, alanine, glycine, valine, leucine, isoleucine, proline, and phenylalanine. One or more residues present at position Yaa may be independently selected from the standard amino acids: aspartic acid, glutamic acid, arginine, lysine, histidine, asparagine, glutamine, serine, threonine, tyrosine, methionine, tryptophan, cysteine, alanine, glycine, valine, leucine, isoleucine, proline, and phenylalanine. Preferably an amino acid at position Yaa (more preferably immediately C-terminal to the Arg residue of SEQ ID NO: 1) is not proline.

Alternatively/additionally, one or more residues present at position Xaa or Yaa may be independently selected from a non-standard amino acid (an amino acid that is not part of the standard set of 20 described above). By way of example, non-standard amino acids may include 4-hydroxyproline, 6-N-methyl lysine, 2-aminoisobutyric acid, isovaline, α-methyl serine, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitroglutamine, homoglutamine, pipecolic acid, tert-leucine, norvaline, 2-azaphenylalanine, 3-azaphenyl-alanine, 4-azaphenyl-alanine, L-Ornithine, L-2-amino-3-guanidinopropionic acid, or D-isomers of Lysine, Arginine and/or Ornithine, and 4-fluorophenylalanine. Methods for introducing non-standard amino acids into proteins are known in the art, and include recombinant protein synthesis using *E. coli* auxotrophic expression hosts.

Properties of the standard amino acids are indicated in the table below:

| AMINO ACID | | | SIDE CHAIN |
|---|---|---|---|
| Aspartic acid | Asp | D | Charged (acidic) |
| Glutamic acid | Glu | E | Charged (acidic) |
| Arginine | Arg | R | Charged (basic) |
| Lysine | Lys | K | Charged (basic) |
| Histidine | His | H | Uncharged (polar) |
| Asparagine | Asn | N | Uncharged (polar) |
| Glutamine | Gln | Q | Uncharged (polar) |
| Serine | Ser | S | Uncharged (polar) |
| Threonine | Thr | T | Uncharged (polar) |
| Tyrosine | Tyr | Y | Uncharged (polar) |
| Methionine | Met | M | Uncharged (polar) |
| Tryptophan | Trp | W | Uncharged (polar) |
| Cysteine | Cys | C | Uncharged (polar) |
| Alanine | Ala | A | Uncharged (hydrophobic) |
| Glycine | Gly | G | Uncharged (hydrophobic) |
| Valine | Val | V | Uncharged (hydrophobic) |
| Leucine | Leu | L | Uncharged (hydrophobic) |
| Isoleucine | Ile | I | Uncharged (hydrophobic) |
| Proline | Pro | P | Uncharged (hydrophobic) |
| Phenylalanine | Phe | F | Uncharged (hydrophobic) |

The following amino acids are considered charged amino acids: aspartic acid (negative), glutamic acid (negative), arginine (positive), and lysine (positive).

The sequence Ile-Asp/Glu-Gly-Arg (SEQ ID NO: 82) comprised in SEQ ID NO: 1 refers to the site surprisingly found by the present inventors to be recognised by enterokinase (as well as factor Xa). Preferably the sequence is Ile-Asp-Gly-Arg (SEQ ID NO: 18), e.g. Cys-(Xaa)$_a$-Ile-Asp-Gly-Arg-(Yaa)$_b$-Cys (SEQ ID NO: 83). It is believed that enterokinase and factor Xa hydrolyse a peptide bond immediately C-terminal to Arg of SEQ ID NO: 1 (i.e. the peptide bond between Arg and Yaa).

In one embodiment an amino acid residue at Xaa immediately N-terminal to Ile of SEQ ID NO: 1 is an uncharged hydrophobic amino acid, preferably alanine. In some embodiments 'a' is at least 2, and Xaa comprises at least a C-terminal uncharged polar amino acid and a charged basic amino acid immediately N-terminal thereto. The charged basic amino acid is preferably lysine. Thus in embodiments where 'a' is at least 2, Xaa may comprise at least Lys-Ala, wherein Ala is immediately N-terminal to Ile of SEQ ID NO: 1.

In one embodiment Xaa comprises or consists of the sequence HKA.

In one embodiment an amino acid residue at Yaa immediately C-terminal to Arg of SEQ ID NO: 1 is an uncharged polar amino acid, preferably serine. In some embodiments 'b' is at least 2, and Yaa comprises at least an N-terminal uncharged polar amino acid and an uncharged hydrophobic amino acid immediately C-terminal thereto. The uncharged hydrophobic amino acid is preferably leucine. Thus in embodiments where 'b' is at least 2, Yaa may comprise at least Ser-Leu, wherein Ser is immediately C-terminal to Arg of SEQ ID NO: 1.

In one embodiment Yaa comprises or consists of the sequence SLYNKTLDC (SEQ ID NO: 84).

In some embodiments an exogenous activation loop has at least 70% sequence identity to SEQ ID NO: 2. In one embodiment an exogenous activation loop has at least 80%, 85% or 90% sequence identity to SEQ ID NO: 2. Preferably an exogenous activation loop has at least 95% sequence identity to SEQ ID NO: 2. More preferably, an exogenous activation loop has at least 99% sequence identity to SEQ ID NO: 2.

In a particularly preferred embodiment an exogenous loop comprises SEQ ID NO: 2. More preferably an exogenous loop consists of SEQ ID NO: 2.

The exogenous loop may also be a variant of SEQ ID NO: 2, such as SEQ ID NO:3 or a sequence having at least 70% sequence identity thereto. SEQ ID NO: 3 is a variant of SEQ ID NO: 2 in which the enterokinase recognition site IDGR (SEQ ID NO: 18) has been mutated to IEGR. In one embodiment an exogenous activation loop has at least 80%, 85% or 90% sequence identity to SEQ ID NO: 3. Preferably an exogenous activation loop has at least 95% sequence identity to SEQ ID NO: 3. More preferably, an exogenous activation loop has at least 99% sequence identity to SEQ ID NO: 3

In a particularly preferred embodiment an exogenous loop comprises SEQ ID NO: 3. More preferably an exogenous loop consists of SEQ ID NO: 3.

A clostridial neurotoxin of the present invention (e.g. engineered clostridial neurotoxin) may be encoded by a nucleotide sequence having at least 70% sequence identity to SEQ ID NO: 4, SEQ ID NO: 6, SEQ ID NO: 8, SEQ ID NO: 10 or SEQ ID NO: 12. In one embodiment a clostridial neurotoxin of the present invention may be encoded by a nucleotide sequence having at least 80% or 90% sequence identity to SEQ ID NO: 4, SEQ ID NO: 6, SEQ ID NO: 8, SEQ ID NO: 10 or SEQ ID NO: 12. Preferably, a clostridial neurotoxin of the present invention may be encoded by a nucleotide sequence comprising (more preferably consisting of) SEQ ID NO: 4, SEQ ID NO: 6, SEQ ID NO: 8, SEQ ID NO: 10 or SEQ ID NO: 12.

A clostridial neurotoxin of the present invention (e.g. engineered clostridial neurotoxin) may comprise a polypeptide sequence having at least 70% sequence identity to SEQ ID NO: 5, SEQ ID NO: 7, SEQ ID NO: 9, SEQ ID NO: 11 or SEQ ID NO: 13. In one embodiment a clostridial neurotoxin of the present invention may comprise a polypeptide sequence having at least 80% or 90% sequence identity to SEQ ID NO: 5, SEQ ID NO: 7, SEQ ID NO: 9, SEQ ID NO: 11 or SEQ ID NO: 13. Preferably, a clostridial neurotoxin of the present invention may comprise (more preferably consist of) a polypeptide sequence shown as SEQ ID NO: 5, SEQ ID NO: 7, SEQ ID NO: 9, SEQ ID NO: 11 or SEQ ID NO: 13.

The clostridial neurotoxin of the present invention (e.g. engineered clostridial neurotoxin) is preferably BoNT/X, wherein the clostridial neurotoxin is encoded by a nucleotide sequence having at least 70% sequence identity to SEQ ID NO: 4. In one embodiment the clostridial neurotoxin is encoded by a nucleotide sequence having at least 80% or 90% sequence identity to SEQ ID NO: 4. Preferably the clostridial neurotoxin is encoded by a nucleotide sequence comprising (or consisting of) SEQ ID NO: 4. The clostridial neurotoxin of the present invention is preferably BoNT/X, wherein the clostridial neurotoxin comprises a polypeptide sequence having at least 70% sequence identity to SEQ ID NO: 5. In one embodiment the clostridial neurotoxin comprises a polypeptide sequence having at least 80% or 90% sequence identity to SEQ ID NO: 5. Preferably the clostridial neurotoxin comprises (or consists of) a polypeptide sequence shown as SEQ ID NO: 5.

The clostridial neurotoxin of the present invention (e.g. engineered clostridial neurotoxin) is preferably BoNT/E, wherein the clostridial neurotoxin is encoded by a nucleotide sequence having at least 70% sequence identity to SEQ ID NO: 10. In one embodiment the clostridial neurotoxin is encoded by a nucleotide sequence having at least 80% or 90% sequence identity to SEQ ID NO: 10. Preferably the clostridial neurotoxin is encoded by a nucleotide sequence comprising (or consisting of) SEQ ID NO: 10. The clostridial neurotoxin of the present invention is preferably BoNT/E, wherein the clostridial neurotoxin comprises a polypeptide sequence having at least 70% sequence identity to SEQ ID NO: 11. In one embodiment the clostridial neurotoxin comprises a polypeptide sequence having at least 80% or 90% sequence identity to SEQ ID NO: 11. Preferably the clostridial neurotoxin comprises (or consists of) a polypeptide sequence shown as SEQ ID NO: 11.

In some embodiments, the polypeptide sequences of the invention (or the nucleotide sequences encoding the same) may include a purification tag, such as a His-tag. It is intended that the present invention also encompasses polypeptide sequences (and nucleotide sequences encoding the same) where the purification tag is removed.

The present invention encompasses contacting a single-chain clostridial neurotoxin (e.g. an engineered clostridial neurotoxin of the invention) with a protease capable of hydrolysing a peptide bond in an activation loop of the single-chain clostridial neurotoxin thereby producing a di-chain clostridial neurotoxin. The protease may be an endo-peptidase. The protease may be enterokinase, factor Xa, Lys-C or trypsin. Preferably the protease is enterokinase or factor Xa, more preferably enterokinase.

The term "enterokinase" or "EK" encompasses enteroki-nases described herein, as well as any protease having structural and/or functional similarity (preferably structural and functional similarity) that is capable of hydrolysing a peptide bond of SEQ ID NO: 1. A suitable enterokinase is enterokinase light chain, which is commercially available from NEB (#P8070). One unit may be defined as the amount of enzyme required to cleave 25 μg of a MBP-EK-paramyo-sin-ΔSal substrate to 95% completion in 16 hours at 25° C. in a total reaction volume of 25 μl (20 mM Tris-HCl, 50 mM NaCl, 2 mM CaCl₂ (pH 8.0 @ 25° C.)).

In one embodiment an enterokinase comprises a polypeptide sequence having at least 70% sequence identity to SEQ ID NO: 49. In some embodiments an enterokinase com-prises a polypeptide sequence having at least 80% or 90% sequence identity to SEQ ID NO: 49. Preferably an enter-okinase comprises (more preferably consists of) SEQ ID NO: 49.

In some embodiments, enterokinase may further comprise a heavy chain, wherein the heavy and light-chains are connected by a disulphide bridge. Such enterokinases are commercially available (e.g. from R&D Systems).

The term "factor Xa" encompasses factor Xa described herein, as well as any protease having structural and/or functional similarity (preferably structural and functional similarity) that is capable of hydrolysing a peptide bond of SEQ ID NO: 1. A suitable factor Xa is commercially available from NEB (#P8010). One unit may be defined as the amount of factor Xa required to cleave 50 μg of an MBP fusion protein test substrate, MBP-ΔSal (substrate MBP-ΔSal is maltose-binding protein fused to a truncated form of paramyosin, with the amino acids 11e-Glu-Gly-Arg at the fusion joint) to 95% completion in 6 hours or less at 23° C. in a reaction volume of 50 μl (20 mM Tris-HCl, 100 mM NaCl, 2 mM CaCl₂ (pH 8.0)).

In one embodiment a factor Xa comprises a polypeptide sequence having a heavy chain with at least 70% sequence identity to SEQ ID NO: 50 and a light chain with at least 70% sequence identity to SEQ ID NO: 51, wherein the heavy and light-chain are connected by a disulphide bridge. In some embodiments a factor Xa comprises a polypeptide sequence having a heavy chain with at least 80% or 90% sequence identity to SEQ ID NO: 50 and a light chain with at least 80% or 90% sequence identity to SEQ ID NO: 51, wherein the heavy and light-chain are connected by a disulphide bridge. Preferably a factor Xa comprises (more preferably consists of) SEQ ID NO: 50 and SEQ ID NO: 51, wherein the heavy and light-chain are connected by a disulphide bridge.

The contacting can occur under any suitable conditions that result in the production of greater than 30%, 40%, 50% or 60% (preferably greater than 70%) of single-chain clostridial neurotoxin being proteolytically processed into the corresponding di-chain clostridial neurotoxin without, or without substantial, hydrolysis of a peptide bond outside of the activation loop of said clostridial neurotoxin. "Without substantial hydrolysis" may mean less than 5%, 4%, 3%, 2% or 1% of the clostridial neurotoxins contacted contain a peptide bond outside of the activation loop that has been hydrolysed by a protease in a method of the invention.

The skilled person can select appropriate reaction times, temperatures, buffers, and molar ratios of protease to single-chain clostridial neurotoxin to achieve the above. Optimi-sation of such conditions can be determined empirically using routine techniques, such as SDS-PAGE (e.g. stained with Coomassie or a dye of similar sensitivity) visual analysis of the reaction products following said contacting or spectrometric techniques (e.g. mass spectrometry).

When assessed by SDS-PAGE (e.g. stained with Coomassie or a dye of similar sensitivity), a method of the invention preferably results in the production of a clostridial neurotoxin L-chain and H-chain only.

In one embodiment the proteolytic processing by a pro-tease in a method of the invention results in the production of less than 5 degradation products of a clostridial neuro-toxin L-chain or H-chain, more preferably less than 4, 3, 2 or 1 degradation products. Preferably, the L-chain and H-chain produced by a method of the invention are full-length L-chain and H-chain.

Therefore, in a particularly preferred embodiment a pro-tease used in a method of the invention (e.g. enterokinase or factor Xa) hydrolyses only a peptide bond of SEQ ID NO: 1, more preferably only the peptide bond between Arg and Yaa of SEQ ID NO: 1.

In one embodiment the contacting occurs for at least 1 hour, e.g. at least 2, 4, 6, 8, 10, 12, 14, 16, 18 or 20 hours.

In one embodiment the contacting occurs at a temperature of at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C.

In one embodiment contacting occurs at a temperature of 1 to 10° C. (preferably about 4° C.).

Preferably contacting occurs at a temperature of 1 to 10° C. (more preferably about 4° C.) for 10-25 hours (preferably 15-20 hours).

In one embodiment contacting occurs at a temperature of 15-25° C. (preferably about 20° C.). Preferably contacting occurs at a temperature of 15-25° C. (more preferably about 20° C.) for 10-25 hours (preferably 15-20 hours).

In one embodiment contacting occurs at a temperature of 20-30° C. (preferably about 25° C.). Preferably contacting occurs at a temperature of 20-30° C. (more preferably about 25° C.) for 10-25 hours (preferably 15-20 hours).

A contacting step of a method of the invention may comprise the use of at least 1 μg of protease per mg of clostridial neurotoxin. In one embodiment a contacting step of a method of the invention comprises the use of at least 0.1, 0.2, 0.4, 0.5, 1, 2, 3, 4, 5, 6, 7, 8, 9, 10, 15 or 20 μg of protease per mg of clostridial neurotoxin. Preferably a contacting step of a method of the invention comprises the use of at least 2 μg (more preferably at least 4 μg) of protease per mg of clostridial neurotoxin.

In one embodiment a contacting step of a method of the invention comprises the use of ≤20 μg of protease per mg of clostridial neurotoxin. In one embodiment a contacting step of a method of the invention comprises the use of ≤15 μg of protease per mg of clostridial neurotoxin. Preferably a contacting step of a method of the invention comprises the use of ≤10 μg of protease per mg of clostridial neurotoxin. More preferably, a contacting step of a method of the invention comprises the use of ≤7 μg of protease per mg of clostridial neurotoxin A contacting step of a method of the invention may comprise the use of 0.1-20 μg of protease per mg of clostridial neurotoxin. In one embodiment a method of the invention may comprise the use of 1-10 μg of protease per mg of clostridial neurotoxin, preferably 4-7 μg of protease per mg of clostridial neurotoxin.

A contacting step of a method of the invention may comprise the use of at least 10, 20, 30, 40, 50, 60 or 70 units of enterokinase per mg of clostridial neurotoxin. Preferably, a contacting step of a method of the invention may comprise the use of at least 60 units of enterokinase (more preferably at least 70 units) per mg of clostridial neurotoxin. In some embodiments, a contacting step of a method of the invention may comprise the use of ≤150, ≤140, ≤130, ≤120, ≤110, ≤100, ≤90 units of enterokinase per mg of clostridial neurotoxin. Preferably, a contacting step of a method of the invention may comprise the use of ≤100 units of enterokinase (more preferably ≤90 units) per mg of clostridial neurotoxin. A contacting step of a method of the invention may comprise the use of 50-110 units of enterokinase per mg of clostridial neurotoxin. In one embodiment a method of the invention may comprise the use of 70-90 units of enterokinase per mg of clostridial neurotoxin, e.g. about 80 units of enterokinase per mg of clostridial neurotoxin.

A contacting step of a method of the invention may comprise the use of at least 0.5, 1, 2, 3, 4, or 5 units of factor Xa per mg of clostridial neurotoxin. Preferably, a contacting step of a method of the invention may comprise the use of at least 3 units of factor Xa (more preferably at least 4 units) per mg of clostridial neurotoxin. In some embodiments, a contacting step of a method of the invention may comprise the use of ≤15, ≤14, ≤13, ≤12, ≤11, ≤10, ≤9, ≤8 or ≤7 units of factor Xa per mg of clostridial neurotoxin. Preferably, a contacting step of a method of the invention may comprise the use of ≤8 units of factor Xa (more preferably ≤7 units) per mg of clostridial neurotoxin. A contacting step of a method of the invention may comprise the use of 0.5-15 units of factor Xa per mg of clostridial neurotoxin. In one embodiment a method of the invention may comprise the use of 1-10 units (preferably 4-7 units) of factor Xa per mg of clostridial neurotoxin, e.g. about 5 or 6 units of factor Xa per mg of clostridial neurotoxin.

A contacting step of a method of the invention may comprise the use of at least 0.02, 0.04, 0.06 or 0.08 units of Lys-C per mg of clostridial neurotoxin. Preferably, a contacting step of a method of the invention may comprise the use of at least 0.04 units of Lys-C per mg of clostridial neurotoxin. In some embodiments, a contacting step of a method of the invention may comprise the use of ≤0.5, ≤0.4 or ≤0.2 units of Lys-C per mg of clostridial neurotoxin. Preferably, a contacting step of a method of the invention may comprise the use of ≤0.2 units of Lys-C per mg of clostridial neurotoxin. A contacting step of a method of the invention may comprise the use of 0.02-0.5 units of Lys-C per mg of clostridial neurotoxin. Preferably, a method of the invention may comprise the use of 0.04-0.2 units of Lys-C per mg of clostridial neurotoxin.

A contacting step of a method of the invention may comprise the use of at least 0.1, 0.2, 0.3 or 0.4 units of trypsin per mg of clostridial neurotoxin. Preferably, a contacting step of a method of the invention may comprise the use of at least 0.4 units of trypsin per mg of clostridial neurotoxin. In some embodiments, a contacting step of a method of the invention may comprise the use of ≤2.5, ≤2.3, ≤2.1, ≤1.9 units of trypsin per mg of clostridial neurotoxin. Preferably, a contacting step of a method of the invention may comprise the use of ≤1.8 units of trypsin per mg of clostridial neurotoxin. A contacting step of a method of the invention may comprise the use of 0.1-2.5 units of trypsin per mg of clostridial neurotoxin. Preferably, a method of the invention may comprise the use of 0.3-2 units (more preferably 0.4-1.8 units) of trypsin per mg of clostridial neurotoxin.

In one embodiment the clostridial neurotoxin (e.g. pre-engineering) may be BoNT/X. A reference BoNT/X sequence is shown as SEQ ID NO: 33. A histidine-tagged version of BoNT/X is presented as SEQ ID NO: 34. A reference nucleotide sequence encoding BoNT/X is shown as SEQ ID NO: 32.

In one embodiment the clostridial neurotoxin (e.g. pre-engineering) may be BoNT/A. A reference BoNT/A sequence is shown as SEQ ID NO: 35.

In another embodiment the clostridial neurotoxin (e.g. pre-engineering) may be BoNT/B. A reference BoNT/B sequence is shown as SEQ ID NO: 36.

In another embodiment the clostridial neurotoxin (e.g. pre-engineering) may be BoNT/C. A reference BoNT/C$_1$ sequence is shown as SEQ ID NO: 37.

In another embodiment the clostridial neurotoxin (e.g. pre-engineering) may be BoNT/D. A reference BoNT/D sequence is shown as SEQ ID NO: 38.

In another embodiment the clostridial neurotoxin (e.g. pre-engineering) may be BoNT/E. A reference BoNT/E sequence is shown as SEQ ID NO: 39.

In another embodiment the clostridial neurotoxin (e.g. pre-engineering) may be BoNT/F. A reference BoNT/F sequence is shown as SEQ ID NO: 40.

In another embodiment the clostridial neurotoxin (e.g. pre-engineering) may be BoNT/G. A reference BoNT/G sequence is shown as SEQ ID NO: 41.

In another embodiment the clostridial neurotoxin (e.g. pre-engineering) may be TeNT. A reference TeNT sequence is shown as SEQ ID NO: 42.

As discussed above, clostridial neurotoxins are formed from two polypeptide chains, the heavy chain (H-chain), which has a molecular mass of approximately 100 kDa, and the light chain (L-chain), which has a molecular mass of approximately 50 kDa. The H-chain comprises a C-terminal targeting component (receptor binding domain or $H_C$ domain) and an N-terminal translocation component ($H_N$ domain).

Examples of light chain reference sequences include:
Botulinum type A neurotoxin: amino acid residues 1-448
Botulinum type B neurotoxin: amino acid residues 1-440
Botulinum type C1 neurotoxin: amino acid residues 1-441
Botulinum type D neurotoxin: amino acid residues 1-445
Botulinum type E neurotoxin: amino acid residues 1-422
Botulinum type F neurotoxin: amino acid residues 1-439
Botulinum type G neurotoxin: amino acid residues 1-441
Tetanus neurotoxin: amino acid residues 1-457

For recently-identified BoNT/X, the L-chain has been reported as corresponding to amino acids 1-439 thereof, with the L-chain boundary potentially varying by approximately 25 amino acids (e.g. 1-414 or 1-464).

The above-identified reference sequences should be considered a guide, as slight variations may occur according to sub-serotypes. By way of example, US 2007/0166332 (hereby incorporated by reference in its entirety) cites slightly different clostridial sequences:
Botulinum type A neurotoxin: amino acid residues M1-K448
Botulinum type B neurotoxin: amino acid residues M1-K441
Botulinum type C1 neurotoxin: amino acid residues M1-K449
Botulinum type D neurotoxin: amino acid residues M1-R445
Botulinum type E neurotoxin: amino acid residues M1-R422
Botulinum type F neurotoxin: amino acid residues M1-K439
Botulinum type G neurotoxin: amino acid residues M1-K446
Tetanus neurotoxin: amino acid residues M1-A457

A Translocation Domain is a molecule that enables translocation of a protease into a target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored [see Shone C. (1987) Eur. J. Biochem; vol. 167(1): pp. 175-180].

A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120].

Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The present invention also embraces variant translocation domains, so long as the variant domains still demonstrate the requisite translocation activity. By way of example, a variant may have at least 70%, preferably at least 80%, more preferably at least 90%, and most preferably at least 95% or at least 98% amino acid sequence homology with a reference translocation domain. The term fragment, when used in relation to a translocation domain, means a peptide having at least 20, preferably at least 40, more preferably at least 80, and most preferably at least 100 amino acid residues of the reference translocation domain. In the case of a clostridial translocation domain, the fragment preferably has at least 100, preferably at least 150, more preferably at least 200, and most preferably at least 250 amino acid residues of the reference translocation domain (eg. $H_N$ domain). Translocation 'fragments' of the present invention embrace fragments of variant translocation domains based on the reference sequences.

The Translocation Domain is preferably capable of formation of ion-permeable pores in lipid membranes under conditions of low pH. Preferably it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, such as the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. In one embodiment the $H_C$ function of the H-chain may be removed by deletion of the $H_C$ amino acid sequence (either at the DNA synthesis level, or at the post-synthesis level by nuclease or protease treatment). Alternatively, the $H_C$ function may be inactivated by chemical or biological treatment. Thus, in some embodiments the H-chain may be incapable of binding to the Binding Site on a target cell to which native clostridial neurotoxin (i.e. holotoxin) binds.

Examples of suitable (reference) Translocation Domains include:
Botulinum type A neurotoxin—amino acid residues (449-871)
Botulinum type B neurotoxin—amino acid residues (441-858)
Botulinum type C neurotoxin—amino acid residues (442-866)
Botulinum type D neurotoxin—amino acid residues (446-862)

Botulinum type E neurotoxin—amino acid residues (423-845)

Botulinum type F neurotoxin—amino acid residues (440-864)

Botulinum type G neurotoxin—amino acid residues (442-863)

Tetanus neurotoxin—amino acid residues (458-879)

The above-identified reference sequence should be considered a guide as slight variations may occur according to sub-serotypes. By way of example, US 2007/0166332 (hereby incorporated by reference thereto) cites slightly different clostridial sequences:

Botulinum type A neurotoxin—amino acid residues (A449-K871)

Botulinum type B neurotoxin—amino acid residues (A442-S858)

Botulinum type C neurotoxin—amino acid residues (T450-N866)

Botulinum type D neurotoxin—amino acid residues (D446-N862)

Botulinum type E neurotoxin—amino acid residues (K423-K845)

Botulinum type F neurotoxin—amino acid residues (A440-K864)

Botulinum type G neurotoxin—amino acid residues (S447-S863)

Tetanus neurotoxin—amino acid residues (S458-V879)

In the context of the present invention, a variety of clostridial neurotoxin $H_N$ regions comprising a translocation domain can be useful in aspects of the present invention with the proviso that these active fragments can facilitate the release of a non-cytotoxic protease (e.g. a clostridial L-chain) from intracellular vesicles into the cytoplasm of the target cell and thus participate in executing the overall cellular mechanism whereby a clostridial neurotoxin proteolytically cleaves a substrate. The $H_N$ regions from the heavy chains of clostridial neurotoxins are approximately 410-430 amino acids in length and comprise a translocation domain. Research has shown that the entire length of a $H_N$ region from a clostridial neurotoxin heavy chain is not necessary for the translocating activity of the translocation domain. Thus, aspects of this embodiment can include clostridial neurotoxin $H_N$ regions comprising a translocation domain having a length of, for example, at least 350 amino acids, at least 375 amino acids, at least 400 amino acids and at least 425 amino acids. Other aspects of this embodiment can include clostridial neurotoxin $H_N$ regions comprising translocation domain having a length of, for example, at most 350 amino acids, at most 375 amino acids, at most 400 amino acids and at most 425 amino acids.

For further details on the genetic basis of toxin production in *Clostridium botulinum* and *C. tetani*, we refer to Hender-son et al (1997) in *The Clostridia: Molecular Biology and Pathogenesis,* Academic press.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin. Examples of non-clostridial (reference) Translocation Domain origins include, but not be restricted to, the translocation domain of diphtheria toxin [O'Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.,* 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS,* 89, pp. 7934-7938], and amphiphilic peptides [Murata et al (1992) *Biochem.,* 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral (reference) Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E1 protein of SFV and the G protein of the G protein of VSV.

Use of the (reference) Translocation Domains listed in Table (below) includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

| Translocation Domain source | Amino acid residues | References |
|---|---|---|
| Diphtheria toxin | 194-380 | Silverman et al., 1994, J. Biol. Chem. 269, 22524-22532 London E., 1992, Biochem. Biophys. Acta., 1113, 25-51 |
| Domain II of pseudomonas exotoxin | 405-613 | Prior et al., 1992, Biochemistry 31, 3555-3559 Kihara & Pastan, 1994, Bioconj Chem. 5, 532-538 |
| Influenza virus haemagglutinin | GLFGAIAGFIENGWE GMIDGWYG (SEQ ID NO: 73), and Variants thereof | Plank et al., 1994, J. Biol. Chem. 269, 12918-12924 Wagner et al., 1992, PNAS, 89, 7934-7938 Murata et al., 1992, Biochemistry 31, 1986-1992 |

-continued

| Translocation Domain source | Amino acid residues | References |
|---|---|---|
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

Examples of clostridial neurotoxin $H_C$ domain reference sequences include:

BoNT/A—N872-1L1296

BoNT/B—E859-E1291

BoNT/C1—N867-E1291

BoNT/D—S863-E1276

BoNT/E—R846-K1252

BoNT/F—K865-E1274

BoNT/G—N864-E1297

TeNT—I880-D1315

For recently-identified BoNT/X, the $H_C$ domain has been reported as corresponding to amino acids 893-1306 thereof, with the domain boundary potentially varying by approximately 25 amino acids (e.g. 868-1306 or 918-1306).

The clostridial neurotoxins described herein may further comprise a translocation facilitating domain. Said domain facilitates delivery of the non-cytotoxic protease into the cytosol of the target cell and are described, for example, in WO 08/008803 and WO 08/008805, each of which is herein incorporated by reference thereto.

By way of example, suitable translocation facilitating domains include an enveloped virus fusogenic peptide domain, for example, suitable fusogenic peptide domains include influenzavirus fusogenic peptide domain (eg. influenza A virus fusogenic peptide domain of 23 amino acids), alphavirus fusogenic peptide domain (eg. Semliki Forest virus fusogenic peptide domain of 26 amino acids), vesiculovirus fusogenic peptide domain (eg. vesicular stomatitis virus fusogenic peptide domain of 21 amino acids), respirovirus fusogenic peptide domain (eg. Sendai virus fusogenic peptide domain of 25 amino acids), morbiliivirus fusogenic peptide domain (eg. Canine distemper virus fusogenic peptide domain of 25 amino acids), avulavirus fusogenic peptide domain (eg. Newcastle disease virus fusogenic peptide domain of 25 amino acids), henipavirus fusogenic peptide domain (eg. Hendra virus fusogenic peptide domain of 25 amino acids), metapneumovirus fusogenic peptide domain (eg. Human metapneumovirus fusogenic peptide domain of 25 amino acids) or spumavirus fusogenic peptide domain such as simian foamy virus fusogenic peptide domain; or fragments or variants thereof.

By way of further example, a translocation facilitating domain may comprise a clostridial neurotoxin $H_{CN}$ domain or a fragment or variant thereof. In more detail, a clostridial neurotoxin $H_{CN}$ translocation facilitating domain may have a length of at least 200 amino acids, at least 225 amino acids, at least 250 amino acids, at least 275 amino acids. In this regard, a clostridial neurotoxin $H_{CN}$ translocation facilitating domain preferably has a length of at most 200 amino acids, at most 225 amino acids, at most 250 amino acids, or at most 275 amino acids. Specific (reference) examples include:

Botulinum type A neurotoxin—amino acid residues (872-1110)

Botulinum type B neurotoxin—amino acid residues (859-1097)

Botulinum type C neurotoxin—amino acid residues (867-1111)

Botulinum type D neurotoxin—amino acid residues (863-1098)

Botulinum type E neurotoxin—amino acid residues (846-1085)

Botulinum type F neurotoxin—amino acid residues (865-1105)

Botulinum type G neurotoxin—amino acid residues (864-1105)

Tetanus neurotoxin—amino acid residues (880-1127)

The above sequence positions may vary a little according to serotype/sub-type, and further examples of suitable (reference) clostridial neurotoxin $H_{CN}$ domains include:

Botulinum type A neurotoxin—amino acid residues (874-1110)

Botulinum type B neurotoxin—amino acid residues (861-1097)

Botulinum type C neurotoxin—amino acid residues (869-1111)

Botulinum type D neurotoxin—amino acid residues (865-1098)

Botulinum type E neurotoxin—amino acid residues (848-1085)

Botulinum type F neurotoxin—amino acid residues (867-1105)

Botulinum type G neurotoxin—amino acid residues (866-1105)

Tetanus neurotoxin—amino acid residues (882-1127)

Any of the above-described facilitating domains may be combined with any of the previously described translocation domain peptides that are suitable for use in the present invention. Thus, by way of example, a non-clostridial facilitating domain may be combined with non-clostridial translocation domain peptide or with clostridial translocation domain peptide. Alternatively, a clostridial neurotoxin $H_{CN}$ translocation facilitating domain may be combined with a non-clostridial translocation domain peptide. Alternatively, a clostridial neurotoxin $H_{CN}$ facilitating domain may be combined or with a clostridial translocation domain peptide, examples of which include:

Botulinum type A neurotoxin—amino acid residues (449-1110)

Botulinum type B neurotoxin—amino acid residues (442-1097)

Botulinum type C neurotoxin—amino acid residues (450-1111)

Botulinum type D neurotoxin—amino acid residues (446-1098)

Botulinum type E neurotoxin—amino acid residues (423-1085)

Botulinum type F neurotoxin—amino acid residues (440-1105)

Botulinum type G neurotoxin—amino acid residues (447-1105)

Tetanus neurotoxin—amino acid residues (458-1127)

In some embodiments the clostridial neurotoxins of the present invention may lack a functional $H_C$ domain of a clostridial neurotoxin. Accordingly, said clostridial neurotoxins are not able to bind rat synaptosomal membranes (via a clostridial $H_C$ component) in binding assays as described in Shone et al. (1985) Eur. J. Biochem. 151, 75-82. In one embodiment, the clostridial neurotoxins preferably lack the last 50 C-terminal amino acids of a clostridial neurotoxin holotoxin. In another embodiment, the clostridial neurotoxins preferably lack the last 100, preferably the last 150, more preferably the last 200, particularly preferably the last 250, and most preferably the last 300 C-terminal amino acid residues of a clostridial neurotoxin holotoxin. Alternatively, the $H_C$ binding activity may be negated/reduced by mutagenesis—by way of example, referring to BoNT/A for convenience, modification of one or two amino acid residue mutations (W1266 to L and Y1267 to F) in the ganglioside binding pocket causes the $H_C$ region to lose its receptor binding function. Analogous mutations may be made to non-serotype A clostridial peptide components, e.g. a construct based on botulinum B with mutations (W1262 to L and Y1263 to F) or botulinum E (W1224 to L and Y1225 to F). Other mutations to the active site achieve the same ablation of $H_C$ receptor binding activity, e.g. Y1267S in botulinum type A toxin and the corresponding highly conserved residue in the other clostridial neurotoxins. Details of this and other mutations are described in Rummel et al (2004) (Molecular Microbiol. 51:631-634), which is hereby incorporated by reference thereto.

The $H_C$ peptide of a native clostridial neurotoxin comprises approximately 400-440 amino acid residues, and consists of two functionally distinct domains of approximately 25 kDa each, namely the N-terminal region (commonly referred to as the $H_{CN}$ peptide or domain) and the C-terminal region (commonly referred to as the Hoc peptide or domain). This fact is confirmed by the following publications, each of which is herein incorporated in its entirety by reference thereto: Umland TC (1997) Nat. Struct. Biol. 4: 788-792; Herreros J (2000) Biochem. J. 347: 199-204; Halpern J (1993) J. Biol. Chem. 268: 15, pp. 11188-11192; Rummel A (2007) PNAS 104: 359-364; Lacey DB (1998) Nat. Struct. Biol. 5: 898-902; Knapp (1998) Am. Cryst. Assoc. Abstract Papers 25: 90; Swaminathan and Eswaramoorthy (2000) Nat. Struct. Biol. 7: 1751-1759; and Rummel A (2004) Mol. Microbiol. 51(3), 631-643. Moreover, it has been well documented that the C-terminal region ($H_{CC}$), which constitutes the C-terminal 160-200 amino acid residues, is responsible for binding of a clostridial neurotoxin to its natural cell receptors, namely to nerve terminals at the neuromuscular junction—this fact is also confirmed by the above publications. Thus, reference throughout this specification to a clostridial heavy-chain lacking a functional heavy chain $H_C$ peptide (or domain) such that the heavy-chain is incapable of binding to cell surface receptors to which a native clostridial neurotoxin binds means that the clostridial heavy-chain simply lacks a functional Hoc peptide. In other words, the Hoc peptide region may be either partially or wholly deleted, or otherwise modified (e.g. through conventional chemical or proteolytic treatment) to inactivate its native binding ability for nerve terminals at the neuromuscular junction.

Thus, in one embodiment, a clostridial neurotoxin $H_N$ peptide of the present invention lacks part of a C-terminal peptide portion ($H_{CC}$) of a clostridial neurotoxin and thus lacks the $H_C$ binding function of native clostridial neurotoxin. By way of example, in one embodiment, the C-terminally extended clostridial $H_N$ peptide lacks the C-terminal 40 amino acid residues, or the C-terminal 60 amino acid residues, or the C-terminal 80 amino acid residues, or the C-terminal 100 amino acid residues, or the C-terminal 120 amino acid residues, or the C-terminal 140 amino acid residues, or the C-terminal 150 amino acid residues, or the C-terminal 160 amino acid residues of a clostridial neurotoxin heavy-chain. In another embodiment, the clostridial $H_N$ peptide of the present invention lacks the entire C-terminal peptide portion ($H_{CC}$) of a clostridial neurotoxin and thus lacks the $H_C$ binding function of native clostridial neurotoxin. By way of example, in one embodiment, the clostridial $H_N$ peptide lacks the C-terminal 165 amino acid residues, or the C-terminal 170 amino acid residues, or the C-terminal 175 amino acid residues, or the C-terminal 180 amino acid residues, or the C-terminal 185 amino acid residues, or the C-terminal 190 amino acid residues, or the C-terminal 195 amino acid residues of a clostridial neurotoxin heavy-chain. By way of further example, the clostridial $H_N$ peptide of the present invention lacks a clostridial $H_{CC}$ reference sequence selected from the group consisting of:

Botulinum type A neurotoxin—amino acid residues (Y1111-L1296)

Botulinum type B neurotoxin—amino acid residues (Y1098-E1291)

Botulinum type C neurotoxin—amino acid residues (Y1112-E1291)

Botulinum type D neurotoxin—amino acid residues (Y1099-E1276)

Botulinum type E neurotoxin—amino acid residues (Y1086-K1252)

Botulinum type F neurotoxin—amino acid residues (Y1106-E1274)

Botulinum type G neurotoxin—amino acid residues (Y1106-E1297)

Tetanus neurotoxin—amino acid residues (Y1128-D1315).

The above-identified reference sequences should be considered a guide as slight variations may occur according to sub-serotypes.

The present invention is suitable for application to many different varieties of clostridial neurotoxin. Thus, in the context of the present invention, the term "clostridial neurotoxin" embraces toxins produced by *C. botulinum* (botulinum neurotoxin serotypes A, B, C1, D, E, F, G, H, and X), *C. tetani* (tetanus neurotoxin), *C. butyricum* (botulinum neurotoxin serotype E), and *C. baratii* (botulinum neurotoxin serotype F), as well as modified clostridial neurotoxins or derivatives derived from any of the foregoing. The term "clostridial neurotoxin" also embraces botulinum neurotoxin serotype H. Preferably the clostridial neurotoxin is not BoNT/C1.

Botulinum neurotoxin (BoNT) is produced by *C. botulinum* in the form of a large protein complex, consisting of BoNT itself complexed to a number of accessory proteins. There are at present nine different classes of botulinum neurotoxin, namely: botulinum neurotoxin serotypes A, B, C1, D, E, F, G, H, and X all of which share similar structures and modes of action. Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

BoNTs are absorbed in the gastrointestinal tract, and, after entering the general circulation, bind to the presynaptic membrane of cholinergic nerve terminals and prevent the release of their neurotransmitter acetylcholine. BoNT/B, BoNT/D, BoNT/F and BoNT/G cleave synaptobrevin/vesicle-associated membrane protein (VAMP); BoNT/C1, BoNT/A and BoNT/E cleave the synaptosomal-associated protein of 25 kDa (SNAP-25); and BoNT/C1 cleaves syntaxin. BoNT/X has been found to cleave SNAP-25, VAMP1, VAMP2, VAMP3, VAMP4, VAMP5, Ykt6, and syntaxin 1.

Tetanus toxin is produced in a single serotype by *C. tetani*. *C. butyricum* produces BoNT/E, while *C. baratii* produces BoNT/F.

The term "clostridial neurotoxin" is also intended to embrace modified clostridial neurotoxins and derivatives thereof, including but not limited to those described below. A modified clostridial neurotoxin or derivative may contain one or more amino acids that has been modified as compared to the native (unmodified) form of the clostridial neurotoxin, or may contain one or more inserted amino acids that are not present in the native (unmodified) form of the clostridial neurotoxin. By way of example, a modified clostridial neurotoxin may have modified amino acid sequences in one or more domains relative to the native (unmodified) clostridial neurotoxin sequence. Such modifications may modify functional aspects of the toxin, for example biological activity or persistence. Thus, in one embodiment, the engineered clostridial neurotoxin of the invention is an engineered modified clostridial neurotoxin, or an engineered modified clostridial neurotoxin derivative, or an engineered clostridial neurotoxin derivative.

A modified clostridial neurotoxin may have one or more modifications in the amino acid sequence of the heavy chain (such as a modified $H_C$ domain), wherein said modified heavy chain binds to target nerve cells with a higher or lower affinity than the native (unmodified) clostridial neurotoxin. Such modifications in the $H_C$ domain can include modifying residues in the ganglioside binding site of the $H_C$ domain or in the protein (SV2 or synaptotagmin) binding site that alter binding to the ganglioside receptor and/or the protein receptor of the target nerve cell. Examples of such modified clostridial neurotoxins are described in WO 2006/027207 and WO 2006/114308, both of which are hereby incorporated by reference in their entirety.

A modified clostridial neurotoxin may have one or more modifications in the amino acid sequence of the light chain, for example modifications in the substrate binding or catalytic domain which may alter or modify the SNARE protein specificity of the modified L-chain. Examples of such modified clostridial neurotoxins are described in WO 2010/120766 and US 2011/0318385, both of which are hereby incorporated by reference in their entirety.

A modified clostridial neurotoxin may comprise one or more modifications that increases or decreases the biological activity and/or the biological persistence of the modified clostridial neurotoxin. For example, a modified clostridial neurotoxin may comprise a leucine- or tyrosine-based motif, wherein said motif increases or decreases the biological activity and/or the biological persistence of the modified clostridial neurotoxin. Suitable leucine-based motifs include xDxxxLL (SEQ ID NO: 74), xExxxLL (SEQ ID NO: 75), xExxxIL (SEQ ID NO: 76), and xExxxLM (SEQ ID NO: 77) (wherein x is any amino acid). Suitable tyrosine-based motifs include Y-x-x-Hy (SEQ ID NO: 78) (wherein Hy is a hydrophobic amino acid). Examples of modified clostridial neurotoxins comprising leucine- and tyrosine-based motifs are described in WO 2002/08268, which is hereby incorporated by reference in its entirety.

The term "clostridial neurotoxin" is intended to embrace hybrid and chimeric clostridial neurotoxins. A hybrid clostridial neurotoxin comprises at least a portion of a light chain from one clostridial neurotoxin or subtype thereof, and at least a portion of a heavy chain from another clostridial neurotoxin or clostridial neurotoxin subtype. In one embodiment the hybrid clostridial neurotoxin may contain the entire light chain from one clostridial neurotoxin subtype and the heavy chain from another clostridial neurotoxin subtype. In another embodiment, a chimeric clostridial neurotoxin may contain a portion (e.g. the binding domain) of the heavy chain of one clostridial neurotoxin subtype, with another portion of the heavy chain being from another clostridial neurotoxin subtype. Similarly or alternatively, the therapeutic element may comprise light chain portions from different clostridial neurotoxins. Such hybrid or chimeric clostridial neurotoxins are useful, for example, as a means of delivering the therapeutic benefits of such clostridial neurotoxins to patients who are immunologically resistant to a given clostridial neurotoxin subtype, to patients who may have a lower than average concentration of receptors to a given clostridial neurotoxin heavy chain binding domain, or to patients who may have a protease-resistant variant of the membrane or vesicle toxin substrate (e.g., SNAP-25, VAMP and syntaxin). Hybrid and chimeric clostridial neurotoxins are described in U.S. Pat. No. 8,071,110, which publication is hereby incorporated by reference in its entirety. Thus, in one embodiment, the engineered clostridial neurotoxin of the invention is an engineered hybrid clostridial neurotoxin, or an engineered chimeric clostridial neurotoxin.

In a particularly preferred embodiment, a clostridial neurotoxin is BoNT/X comprising at least one domain from a non-BoNT/X clostridial neurotoxin (e.g. a BoNT/X hybrid or chimera).

For example, in one embodiment a clostridial neurotoxin of the invention (comprising an exogenous activation loop) may comprise:

i. A BoNT/X L-chain and a non-BoNT/X $H_N$ and $H_C$ domain;

ii. A BoNT/X $H_N$ domain and a non-BoNT/X L-chain and $H_C$ domain iii. A BoNT/X $H_C$ domain and a non-BoNT/X L-chain and $H_N$ domain;

iv. A BoNT/X L-chain and $H_N$ domain and a non-BoNT/X $H_C$ domain v. A BoNT/X L-chain and $H_C$ domain and a non-BoNT/X $H_N$ domain; or vi. A BoNT/X $H_N$ domain and $H_C$ domain and a non-BoNT/X L-chain.

In one embodiment an engineered clostridial neurotoxin of the invention comprises a BoNT/X L-chain and $H_N$ domain and a BoNT/A $H_C$ domain. In one embodiment an engineered clostridial neurotoxin of the invention comprising a BoNT/X L-chain and $H_N$ domain and a BoNT/A $H_C$ domain is encoded by a nucleotide sequence comprising at least 70% sequence identity to SEQ ID NO: 6. In one embodiment an engineered clostridial neurotoxin of the invention comprising a BoNT/X L-chain and $H_N$ domain and a BoNT/A $H_C$ domain is encoded by a nucleotide sequence comprising at least 80% or 90% sequence identity to SEQ ID NO: 6. Preferably an engineered clostridial neurotoxin of the invention comprising a BoNT/X L-chain and $H_N$ domain and a BoNT/A $H_C$ domain is encoded by a nucleotide sequence comprising (more preferably consisting of) SEQ ID NO: 6. In one embodiment an engineered clostridial neurotoxin of the invention comprising a BoNT/X L-chain and $H_N$ domain and a BoNT/A $H_C$ domain comprises a polypeptide sequence having at least 70% sequence identity to SEQ ID NO: 7. In one embodiment an engineered clostridial neurotoxin of the invention comprising a BoNT/X L-chain and $H_N$ domain and a BoNT/A $H_C$ domain comprises a polypeptide sequence having at least 80% or 90% sequence identity to SEQ ID NO: 7. Preferably an engineered clostridial neurotoxin of the invention comprising a BoNT/X L-chain and $H_N$ domain and a BoNT/A $H_C$ domain comprises (more preferably consists of) a polypeptide sequence shown as SEQ ID NO: 7.

In one embodiment an engineered clostridial neurotoxin of the invention comprises a BoNT/X L-chain and $H_N$ domain and a BoNT/B $H_C$ domain. In one embodiment an engineered clostridial neurotoxin of the invention comprising a BoNT/X L-chain and $H_N$ domain and a BoNT/A $H_C$ domain is encoded by a nucleotide sequence comprising at least 70% sequence identity to SEQ ID NO: 8. In one embodiment an engineered clostridial neurotoxin of the invention comprising a BoNT/X L-chain and $H_N$ domain and a BoNT/A $H_C$ domain is encoded by a nucleotide sequence comprising at least 80% or 90% sequence identity to SEQ ID NO: 8. Preferably an engineered clostridial neurotoxin of the invention comprising a BoNT/X L-chain and $H_N$ domain and a BoNT/A $H_C$ domain is encoded by a nucleotide sequence comprising (more preferably consisting of) SEQ ID NO: 8. In one embodiment an engineered clostridial neurotoxin of the invention comprising a BoNT/X L-chain and $H_N$ domain and a BoNT/A $H_C$ domain comprises a polypeptide sequence having at least 70% sequence identity to SEQ ID NO: 9. In one embodiment an engineered clostridial neurotoxin of the invention comprising a BoNT/X L-chain and $H_N$ domain and a BoNT/A $H_C$ domain comprises a polypeptide sequence having at least 80% or 90% sequence identity to SEQ ID NO: 9. Preferably an engineered clostridial neurotoxin of the invention comprising a BoNT/X L-chain and $H_N$ domain and a BoNT/A $H_C$ domain comprises (more preferably consists of) a polypeptide sequence shown as SEQ ID NO: 9.

In one embodiment an engineered clostridial neurotoxin of the invention comprises a BoNT/X L-chain and $H_N$ domain and a BoNT/C $H_C$ domain. In one embodiment an engineered clostridial neurotoxin of the invention comprises a BoNT/X L-chain and $H_N$ domain and a BoNT/D $H_C$ domain. In one embodiment an engineered clostridial neurotoxin of the invention comprises a BoNT/X L-chain and $H_N$ domain and a BoNT/E $H_C$ domain. In one embodiment an engineered clostridial neurotoxin of the invention comprises a BoNT/X L-chain and $H_N$ domain and a BoNT/F $H_C$ domain. In one embodiment an engineered clostridial neurotoxin of the invention comprises a BoNT/X L-chain and $H_N$ domain and a BoNT/G $H_C$ domain. In one embodiment an engineered clostridial neurotoxin of the invention comprises a BoNT/X L-chain and $H_N$ domain and a TeNT $H_C$ domain.

In one embodiment, a clostridial neurotoxin is BoNT/A comprising at least one domain from a non-BoNT/A clostridial neurotoxin.

For example, in one embodiment a clostridial neurotoxin of the invention (comprising an exogenous activation loop) may comprise:

i. A BoNT/A L-chain and a non-BoNT/A $H_N$ and $H_C$ domain;

ii. A BoNT/A $H_N$ domain and a non-BoNT/A L-chain and $H_C$ domain iii. A BoNT/A $H_C$ domain and a non-BoNT/A L-chain and $H_N$ domain;

iv. A BoNT/A L-chain and $H_N$ domain and a non-BoNT/A $H_C$ domain v. A BoNT/A L-chain and $H_C$ domain and a non-BoNT/A $H_N$ domain; or vi. A BoNT/A $H_N$ domain and $H_C$ domain and a non-BoNT/A L-chain.

In one embodiment an engineered clostridial neurotoxin of the invention comprises a BoNT/A L-chain and $H_N$ domain and a BoNT/C1 $H_C$ domain. In one embodiment an engineered clostridial neurotoxin of the invention comprising a BoNT/A L-chain and $H_N$ domain and a BoNT/C1 $H_C$ domain is encoded by a nucleotide sequence comprising at least 70% sequence identity to SEQ ID NO: 12. In one embodiment an engineered clostridial neurotoxin of the invention comprising a BoNT/A L-chain and $H_N$ domain and a BoNT/C1 He domain is encoded by a nucleotide sequence comprising at least 80% or 90% sequence identity to SEQ ID NO: 12. Preferably an engineered clostridial neurotoxin of the invention comprising a BoNT/A L-chain and $H_N$ domain and a BoNT/C1 $H_C$ domain is encoded by a nucleotide sequence comprising (more preferably consisting of) SEQ ID NO: 12. In one embodiment an engineered clostridial neurotoxin of the invention comprising a BoNT/A L-chain and $H_N$ domain and a BoNT/C1 $H_C$ domain comprises a polypeptide sequence having at least 70% sequence identity to SEQ ID NO: 13. In one embodiment an engineered clostridial neurotoxin of the invention comprising a BoNT/A L-chain and $H_N$ domain and a BoNT/C1 $H_C$ domain comprises a polypeptide sequence having at least 80% or 90% sequence identity to SEQ ID NO: 13. Preferably an engineered clostridial neurotoxin of the invention comprising a BoNT/A L-chain and $H_N$ domain and a BoNT/C1 $H_C$ domain comprises (more preferably consists of) a polypeptide sequence shown as SEQ ID NO: 13.

In one embodiment an engineered clostridial neurotoxin of the invention comprises a BoNT/A L-chain and $H_N$ domain and a BoNT/B $H_C$ domain. In one embodiment an engineered clostridial neurotoxin of the invention comprises a BoNT/A L-chain and $H_N$ domain and a BoNT/D $H_C$ domain. In one embodiment an engineered clostridial neurotoxin of the invention comprises a BoNT/A L-chain and $H_N$ domain and a BoNT/E $H_C$ domain. In one embodiment an engineered clostridial neurotoxin of the invention comprises a BoNT/A L-chain and $H_N$ domain and a BoNT/F $H_C$ domain. In one embodiment an engineered clostridial neurotoxin of the invention comprises a BoNT/A L-chain and $H_N$ domain and a BoNT/G $H_C$ domain. In one embodiment an engineered clostridial neurotoxin of the invention comprises a BoNT/A L-chain and $H_N$ domain and a BoNT/X $H_C$ domain. In one embodiment an engineered clostridial neurotoxin of the invention comprises a BoNT/A L-chain and $H_N$ domain and a TeNT $H_C$ domain.

For example, in one embodiment a clostridial neurotoxin of the invention (comprising an exogenous activation loop) may comprise:

i. A BoNT/B L-chain and a non-BoNT/B $H_N$ and $H_C$ domain;

ii. A BoNT/B $H_N$ domain and a non-BoNT/B L-chain and $H_C$ domain iii. A BoNT/B $H_C$ domain and a non-BoNT/B L-chain and $H_N$ domain;

iv. A BoNT/B L-chain and $H_N$ domain and a non-BoNT/B $H_C$ domain v. A BoNT/B L-chain and $H_C$ domain and a non-BoNT/B $H_N$ domain; or vi. A BoNT/B $H_N$ domain and $H_C$ domain and a non-BoNT/B L-chain.

For example, in one embodiment a clostridial neurotoxin of the invention (comprising an exogenous activation loop) may comprise:

i. A BoNT/D L-chain and a non-BoNT/XD $H_N$ and $H_C$ domain;

ii. A BoNT/D $H_N$ domain and a non-BoNT/D L-chain and $H_C$ domain iii. A BoNT/D $H_C$ domain and a non-BoNT/D L-chain and $H_N$ domain;

iv. A BoNT/D L-chain and $H_N$ domain and a non-BoNT/D $H_C$ domain v. A BoNT/D L-chain and $H_C$ domain and a non-BoNT/D $H_N$ domain; or vi. A BoNT/D $H_N$ domain and $H_C$ domain and a non-BoNT/D L-chain.

For example, in one embodiment a clostridial neurotoxin of the invention (comprising an exogenous activation loop) may comprise:

i. A BoNT/E L-chain and a non-BoNT/E $H_N$ and $H_C$ domain;

ii. A BoNT/E $H_N$ domain and a non-BoNT/E L-chain and $H_C$ domain iii. A BoNT/E $H_C$ domain and a non-BoNT/E L-chain and $H_N$ domain;

iv. A BoNT/E L-chain and $H_N$ domain and a non-BoNT/E $H_C$ domain v. A BoNT/E L-chain and $H_C$ domain and a non-BoNT/E $H_N$ domain; or vi. A BoNT/E $H_N$ domain and $H_C$ domain and a non-BoNT/E L-chain.

For example, in one embodiment a clostridial neurotoxin of the invention (comprising an exogenous activation loop) may comprise:

i. A BoNT/F L-chain and a non-BoNT/F $H_N$ and $H_C$ domain;

ii. A BoNT/F $H_N$ domain and a non-BoNT/F L-chain and $H_C$ domain iii. A BoNT/F $H_C$ domain and a non-BoNT/F L-chain and $H_N$ domain;

iv. A BoNT/F L-chain and $H_N$ domain and a non-BoNT/F $H_C$ domain v. A BoNT/F L-chain and $H_C$ domain and a non-BoNT/F $H_N$ domain; or vi. A BoNT/F $H_N$ domain and $H_C$ domain and a non-BoNT/F L-chain.

For example, in one embodiment a clostridial neurotoxin of the invention (comprising an exogenous activation loop) may comprise:

i. A BoNT/G L-chain and a non-BoNT/G $H_N$ and $H_C$ domain;

ii. A BoNT/G $H_N$ domain and a non-BoNT/G L-chain and $H_C$ domain iii. A BoNT/G $H_C$ domain and a non-BoNT/G L-chain and $H_N$ domain;

iv. A BoNT/G L-chain and $H_N$ domain and a non-BoNT/G $H_C$ domain v. A BoNT/G L-chain and $H_C$ domain and a non-BoNT/G $H_N$ domain; or vi. A BoNT/G $H_N$ domain and $H_C$ domain and a non-BoNT/G L-chain.

For example, in one embodiment a clostridial neurotoxin of the invention (comprising an exogenous activation loop) may comprise:

i. A TeNT L-chain and a non-TeNT $H_N$ and $H_C$ domain;

ii. A TeNT $H_N$ domain and a non-TeNT L-chain and $H_C$ domain iii. A TeNT $H_C$ domain and a non-TeNT L-chain and $H_N$ domain;

iv. A TeNT L-chain and $H_N$ domain and a non-TeNT $H_C$ domain v. A TeNT L-chain and $H_C$ domain and a non-TeNT $H_N$ domain; or vi. A TeNT $H_N$ domain and $H_C$ domain and a non-TeNT L-chain.

The term "clostridial neurotoxin" may also embrace newly discovered botulinum neurotoxin protein family members expressed by non-clostridial microorganisms, such as the *Enterococcus* encoded toxin which has closest sequence identity to BoNT/X, the *Weissella oryzae* encoded toxin called BoNT/Wo (NCBI Ref Seq: WP_027699549.1), which cleaves VAMP2 at W89-W90, the *Enterococcus faecium* encoded toxin (GenBank: OT022244.1), which cleaves VAMP2 and SNAP25, and the *Chryseobacterium pipero* encoded toxin (NCBI Ref.Seq: WP_034687872.1).

The term "clostridial neurotoxin" is intended to embrace re-targeted clostridial neurotoxins. In a re-targeted clostridial neurotoxin, the clostridial neurotoxin is modified to include an exogenous ligand known as a Targeting Moiety (TM). The TM is selected to provide binding specificity for a desired target cell, and as part of the re-targeting process the native binding portion of the clostridial neurotoxin (e.g. the $H_C$ domain, or the Hoc domain) may be removed. Re-targeting technology is described, for example, in: EP-B-0689459; WO 1994/021300; EP-B-0939818; U.S. Pat. Nos. 6,461,617; 7,192,596; WO 1998/007864; EP-B-0826051; U.S. Pat. Nos. 5,989,545; 6,395,513; 6,962,703; WO 1996/033273; EP-B-0996468; U.S. Pat. No. 7,052,702; WO 1999/017806; EP-B-1107794; U.S. Pat. No. 6,632,440; WO 2000/010598; WO 2001/21213; WO 2006/059093; WO 2000/62814; WO 2000/04926; WO 1993/15766; WO 2000/61192; and WO 1999/58571; all of which are hereby incorporated by reference in their entirety. Thus, in one embodiment, the engineered clostridial neurotoxin of the invention is an engineered re-targeted clostridial neurotoxin. The engineered clostridial neurotoxin of the present invention may lack a functional $H_C$ domain of a clostridial neurotoxin and also lack any functionally equivalent TM. Accordingly, said polypeptides lack the natural binding function of a clostridial neurotoxin and are not able to bind rat synaptosomal membranes (via a clostridial He component, or via any functionally equivalent TM) in binding assays as described in Shone et al. (1985) Eur. J. Biochem. 151, 75-82. In one embodiment, the TM is preferably not a Wheat Germ Agglutinin (WGA) peptide.

In one embodiment an engineered clostridial neurotoxin of the invention may comprise an engineered $LH_N$ polypeptide described herein.

In one embodiment an engineered clostridial neurotoxin may comprise an engineered $LH_N$ polypeptide described herein and a targeting moiety (TM).

Reference engineered $LH_N$ polypeptide sequences are presented herein as SEQ ID NOs: 53-60, however the engineered $LH_N$ polypeptide sequence may have at least 70% sequence identity to any of SEQ ID NOs: 53-60. In one embodiment the engineered $LH_N$ polypeptide sequence may have at least 80% or 90% sequence identity to any of SEQ ID NOs: 53-60. Preferably the engineered $LH_N$ polypeptide sequence comprises (more preferably consists of) any of SEQ ID NOs: 53-60.

In one embodiment a TM may comprise anthrax toxin protective antigen (PA) or a fragment thereof. A reference sequence for PA is shown as SEQ ID NO: 52. In some embodiments PA comprises a polypeptide sequence having at least 70% sequence identity to SEQ ID NO: 52 or a fragment thereof. In some embodiments PA comprises a polypeptide sequence having at least 80% or 90% sequence identity to SEQ ID NO: 52 or a fragment thereof. In other embodiments PA comprises (or consists of) a polypeptide sequence shown as SEQ ID NO: 52 or a fragment thereof.

Thus, in one embodiment an engineered clostridial neurotoxin of the present invention may comprise: a clostridial neurotoxin non-cytotoxic protease domain, a clostridial neurotoxin translocation domain (e.g. $LH_N$ of a clostridial neurotoxin), and a TM comprising PA or a fragment thereof. Said engineered clostridial neurotoxin comprises an exogenous activation loop comprising polypeptide sequence Cys-$(Xaa)_a$-Ile-Asp/Glu-Gly-Arg-$(Yaa)_b$-Cys (SEQ ID NO: 1).

Thus, in one embodiment, an engineered clostridial neurotoxin comprises PA or a fragment thereof and $LH_N$/A, $LH_N$/B, $LH_N$/D, $LH_N$/E, $LH_N$/F, $LH_N$/G, $LH_N$/X or $LH_N$/TeNT, wherein the endogenous clostridial neurotoxin activation loop has been replaced with an exogenous activation loop comprising polypeptide sequence Cys-$(Xaa)_a$-Ile-Asp/Glu-Gly-Arg-$(Yaa)_b$-Cys (SEQ ID NO: 1).

Lys-C is not suitable for use with conventional clostridial neurotoxins comprising $LH_N$ and a PA TM, as Lys-C hydrolyses one or more peptide bonds outside of the endogenous activation loop of said clostridial neurotoxin, for example it has been found that Lys-C hydrolyses one or more peptide bonds in the PA TM.

Thus, in some embodiments, an engineered clostridial neurotoxin comprises PA (or a fragment thereof) and:

i. Amino acid residues 1-871 of SEQ ID NO: 35
    ii. Amino acid residues 1-858 of SEQ ID NO: 36
    iii. Amino acid residues 1-862 of SEQ ID NO: 38
    iv. Amino acid residues 1-845 of SEQ ID NO: 39
    v. Amino acid residues 1-864 of SEQ ID NO: 40
    vi. Amino acid residues 1-863 of SEQ ID NO: 41
    vii. Amino acid residues 1-879 of SEQ ID NO: 42 or
    viii. Amino acid residues 1-924 of SEQ ID NO: 33;

wherein the endogenous clostridial neurotoxin activation loop has been replaced with an exogenous activation loop comprising polypeptide sequence Cys-$(Xaa)_a$-Ile-Asp/Glu-Gly-Arg-$(Yaa)_b$-Cys (SEQ ID NO: 1).

In one embodiment an engineered clostridial neurotoxin has a polypeptide sequence with at least 70% sequence identity to a polypeptide comprising:

a. SEQ ID NO: 52; and
    b. SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60.

In one embodiment an engineered clostridial neurotoxin has a polypeptide sequence with at least 80% or 90% sequence identity to a polypeptide comprising:

a. SEQ ID NO: 52; and
    b. SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60.

Preferably an engineered clostridial neurotoxin has a polypeptide sequence comprising:

a. SEQ ID NO: 52; and
    b. SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60.

In one embodiment an engineered clostridial neurotoxin has a polypeptide sequence with at least 70% sequence identity to a polypeptide comprising:

a. a fragment of SEQ ID NO: 52; and
    b. SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60.

In one embodiment an engineered clostridial neurotoxin has a polypeptide sequence with at least 80% or 90% sequence identity to a polypeptide comprising:

a. a fragment of SEQ ID NO: 52; and
    b. SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60.

Preferably an engineered clostridial neurotoxin has a polypeptide sequence comprising:

a. a fragment of SEQ ID NO: 52; and
    b. SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60.

In one embodiment a PA fragment may be PAd1, which is located at residues 1-258 of SEQ ID NO: 52. In one embodiment a PA fragment may be PAd2, which is located at residues 259-487 of SEQ ID NO: 52. In one embodiment a PA fragment may be PAd3, which is located at residues 488-594 of SEQ ID NO: 52. In one embodiment a PA fragment may be PAd4, which is located at residues 595-735 of SEQ ID NO: 52. In other embodiments a PA fragment may contain any combination of PAd1, PAd2, PAd3 or PAd4.

Full-length 83 kDa PA (PA83) may be proteolytically processed by a furin or other furin-like protease thus removing an N-terminal fragment (PA20). The 63 kDa processed form, known as PA63 is an oligomerisable form of PA.

In one embodiment the PA fragment may comprise (or consist of) one or more of PA63, PAd3-d4, PAd2-d4, and PAd4.

In one embodiment the PA fragment may be a C-terminal receptor-binding domain of PA or a PA fragment (or variant) thereof that retains binding activity to ANTXR2 or a nociceptor neuron binding protein.

The present invention also embraces clostridial neurotoxins that have a non-native protease cleavage site. In such clostridial neurotoxins, the native protease cleavage site (also known as the activation site, as described above) is modified or replaced with a protease cleavage site that is not native to that clostridial neurotoxin (i.e. an exogenous cleavage site). Such a site will require an exogenous protease for cleavage, which allows for improved control over the timing and location of cleavage events. Non-native protease cleavage sites that may be employed in clostridial neurotoxins include:

```
TEV (Tobacco Etch virus)
                              (SEQ ID NO: 79)
(ENLYFQ↓G)

Thrombin
                              (SEQ ID NO: 80)
(LVPR↓GS)

PreScission
                              (SEQ ID NO: 81)
(LEVLFQ↓GP).
```

Additional protease cleavage sites include recognition sequences that are cleaved by a non-cytotoxic protease, for example by the light chain of a clostridial neurotoxin. These include the SNARE (e.g. SNAP-25, syntaxin, VAMP) protein recognition sequences that are cleaved by non-cytotoxic proteases such as the light chain of a clostridial neurotoxin. Clostridial neurotoxins comprising non-native protease cleavage sites are described in U.S. Pat. No. 7,132,259, EP 1206554-B2 and US 2007/0166332, all of which are hereby incorporated by reference in their entirety. Also embraced by the term protease cleavage site is an intein, which is a self-cleaving sequence. The self-splicing reaction is controllable, for example by varying the concentration of reducing agent present.

The present invention also embraces clostridial neurotoxins comprising a "destructive cleavage site". In said clostridial neurotoxins, a non-native protease cleavage site is incorporated into the clostridial neurotoxin, at a location chosen such that cleavage at said site will decrease the activity of, or inactivate, the clostridial neurotoxin. The destructive protease cleavage site can be susceptible to cleavage by a local protease, in the event that the clostridial neurotoxin, following administration, migrates to a non-target location. Suitable non-native protease cleavage sites include those described above. Clostridial neurotoxins comprising a destructive cleavage site are described in WO 2010/094905 and WO 2002/044199, both of which are hereby incorporated by reference in their entirety.

The engineered clostridial neurotoxins of the present invention, especially the light chain component thereof, may be PEGylated—this may help to increase stability, for example duration of action of the light chain component. PEGylation is particularly preferred when the light chain comprises a BoNT/A, B or C1 protease. PEGylation preferably includes the addition of PEG to the N-terminus of the light chain component. By way of example, the N-terminus of a light chain may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is hereby incorporated by reference in its entirety.

The engineered clostridial neurotoxins of the present invention may be free from the complexing proteins that are present in a naturally occurring clostridial neurotoxin complex.

The engineered clostridial neurotoxins of the present invention can be produced using recombinant nucleic acid technologies. Thus, in one embodiment, an engineered clostridial neurotoxin (as described above) is a recombinant engineered clostridial neurotoxin.

In another aspect, the present invention provides a nucleic acid (for example, a DNA) comprising a nucleic acid sequence encoding an engineered clostridial neurotoxin as described above. In one embodiment, the nucleic acid sequence is prepared as part of a DNA vector comprising a promoter and a terminator.

In a preferred embodiment, the vector has a promoter selected from:

| Promoter | Induction Agent | Typical Induction Condition |
| --- | --- | --- |
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |

In another preferred embodiment, the vector has a promoter selected from:

| Promoter | Induction Agent | Typical Induction Condition |
| --- | --- | --- |
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |
| T5-lac operator | IPTG | 0.2 mM (0.05-2.0 mM) |

The nucleic acid molecules of the invention may be made using any suitable process known in the art. Thus, the nucleic acid molecules may be made using chemical synthesis techniques. Alternatively, the nucleic acid molecules of the invention may be made using molecular biology techniques.

The DNA construct of the present invention is preferably designed in silico, and then synthesised by conventional DNA synthesis techniques.

The above-mentioned nucleic acid sequence information is optionally modified for codon-biasing according to the ultimate host cell (e.g. *E. coli*) expression system that is to be employed.

In one aspect the present invention provides a nucleotide sequence encoding an engineered clostridial neurotoxin of the present invention. The nucleotide sequence comprises a sequence having at least 70% sequence identity to SEQ ID NO: 4, SEQ ID NO: 6, SEQ ID NO: 8, SEQ ID NO: 10 or SEQ ID NO: 12. In one embodiment the nucleotide sequence comprises a sequence having at least 80% or 90% sequence identity to SEQ ID NO: 4, SEQ ID NO: 6, SEQ ID NO: 8, SEQ ID NO: 10 or SEQ ID NO: 12. Preferably the nucleotide sequence comprises (more preferably consists of) SEQ ID NO: 4, SEQ ID NO: 6, SEQ ID NO: 8, SEQ ID NO: 10 or SEQ ID NO: 12.

The nucleotide sequence of the invention encodes a polypeptide comprising SEQ ID NO: 1.

The terms "nucleotide sequence" and "nucleic acid" are used synonymously herein. Preferably the nucleotide sequence is a DNA sequence.

The invention provides a method of producing a single-chain (engineered) clostridial neurotoxin protein having a light chain and a heavy chain, the method comprising expressing a nucleic acid described herein in a suitable host cell, lysing the host cell to provide a host cell homogenate containing the single-chain (engineered) clostridial neurotoxin protein, and isolating the single-chain (engineered) clostridial neurotoxin protein. In one aspect, the present invention provides a method for proteolytically processing an (engineered) clostridial neurotoxin of the present invention into a corresponding di-chain clostridial neurotoxin, the method comprising contacting the (engineered) clostridial neurotoxin with a protease (preferably an endopeptidase, such as enterokinase or factor Xa) thereby producing a di-chain clostridial neurotoxin (e.g. wherein the light chain and heavy chain are joined together by a disulphide bond).

The present invention therefore provides a di-chain clostridial neurotoxin obtainable by a method of the invention.

The term "obtainable" as used herein also encompasses the term "obtained". In one embodiment the term "obtainable" means obtained.

A clostridial neurotoxin of the present invention suitably finds utility in medicine or in cosmetics. In use, the clostridial neurotoxin is preferably in a di-chain form.

The (engineered) clostridial neurotoxins of the invention may be used to prevent or treat certain medical or cosmetic diseases and conditions. Thus, in a further aspect, the present invention provides an (engineered) clostridial neurotoxin as described above, for use in medicine.

In a related aspect, the present invention provides an (engineered) clostridial neurotoxin as described above, for use in the prevention or treatment of a disease or condition selected from: a condition associated with unwanted immune secretion, strabismus, blepharospasm, squint, dystonia (e.g. spasmodic dystonia, oromandibular dystonia, focal dystonia, tardive dystonia, laryngeal dystonia, limb dystonia, cervical dystonia), torticollis (e.g. spasmodic tor-ticollis), beauty therapy (cosmetic) applications benefiting from cell/muscle incapacitation (via SNARE down-regula-tion or inactivation), neuromuscular disorder or condition of ocular motility (e.g. concomitant strabismus, vertical stra-bismus, lateral rectus palsy, nystagmus, dysthyroid myopa-thy), writer's cramp, blepharospasm, bruxism, Wilson's disease, tremor, tics, segmental myoclonus, spasms, spas-ticity due to chronic multiple sclerosis, spasticity resulting in abnormal bladder control, animus, back spasm, charley horse, tension headaches, levator pelvic syndrome, spina bifida, tardive dyskinesia, Parkinson's disease, stuttering, hemifacial spasm, eyelid disorder, cerebral palsy, focal spasticity, spasmodic colitis, neurogenic bladder, anismus, limb spasticity, tics, tremors, bruxism, anal fissure, achala-sia, dysphagia, lacrimation, hyperhydrosis, excessive sali-vation, excessive gastrointestinal secretions, muscle pain (e.g. pain from muscle spasms), headache pain (e.g. tension headache), brow furrows, skin wrinkles, cancer, uterine disorders, uro-genital disorders, urogenital-neurological dis-orders, chronic neurogenic inflammation, and a smooth muscle disorder.

Where an (engineered) clostridial neurotoxin of the inven-tion comprises a BoNT/X sequence (or portion thereof) said clostridial neurotoxin may be able to target other types of secretory cells other than neurons, due to its ability to cleave VAMP4, VAMP5 and/or Ykt6. In some embodiments, the secretory cell targeted is a secretory immune cell. A "secre-tory immune cell" as used herein, refers to immune cells that secrets cytokines, chemokines, or antibodies. Such secretory immune cells may be innate immune cells including, with-out limitation, natural killer cells, mast cells, eosinophils, basophils, macrophages, neutrophils, and dendritic cells. Secretory immune cells that secret antibodies (e.g. white blood cells) may also be targeted by the clostridial neuro-toxins of the present disclosure. Non-limiting examples of antibody secreting cells include, without limitation, plasma B cells, plasmocytes, plasmacytes, and effector B cells. In some embodiments, the clostridial neurotoxin may modulate an immune response. Thus, further contemplated herein are therapeutic use of a clostridial neurotoxin of the invention to treat a condition associated with unwanted secretion, pref-erably unwanted immune secretion. Conditions associated with unwanted immune secretion include, without limita-tion: inflammation, psoriasis, allergy, haemophagocytic lymphohistiocytosis, and alcoholic pancreatic disease.

In one aspect, the invention provides a pharmaceutical composition comprising an (engineered) clostridial neuro-toxin or a di-chain clostridial neurotoxin of the invention and a pharmaceutically acceptable carrier, excipient, adju-vant, propellant and/or salt.

The (engineered) clostridial neurotoxins of the present invention may be formulated for oral, parenteral, continuous infusion, inhalation or topical application. Compositions suitable for injection may be in the form of solutions, suspensions or emulsions, or dry powders which are dis-solved or suspended in a suitable vehicle prior to use.

In the case of an (engineered) clostridial neurotoxin that is to be delivered locally, the (engineered) clostridial neu-rotoxin may be formulated as a cream (e.g. for topical application), or for sub-dermal injection.

Local delivery means may include an aerosol, or other spray (e.g. a nebuliser). In this regard, an aerosol formula-tion of an (engineered) clostridial neurotoxin enables deliv-ery to the lungs and/or other nasal and/or bronchial or airway passages. (Engineered) clostridial neurotoxins of the inven-tion may be administered to a patient by intrathecal or epidural injection in the spinal column at the level of the spinal segment involved in the innervation of an affected organ.

A preferred route of administration is via laproscopic and/or localised, particularly intramuscular, injection.

The dosage ranges for administration of the (engineered) clostridial neurotoxins of the present invention are those to produce the desired therapeutic effect. It will be appreciated that the dosage range required depends on the precise nature of the (engineered) clostridial neurotoxin or composition, the route of administration, the nature of the formulation, the age of the patient, the nature, extent or severity of the patient's condition, contraindications, if any, and the judge-ment of the attending physician. Variations in these dosage levels can be adjusted using standard empirical routines for optimisation.

Suitable daily dosages (per kg weight of patient) are in the range 0.0001-1 ng/kg, preferably 0.0001-0.5 ng/kg, more preferably 0.002-0.5 ng/kg, and particularly preferably 0.004-0.5 ng/kg. The unit dosage can vary from less than 1 picogram to 30 ng, but typically will be in the region of 0.01 to 1 ng per dose, which may be administered daily or preferably less frequently, such as weekly or six monthly.

A particularly preferred dosing regimen is based on 0.05 ng of (engineered) clostridial neurotoxin as the 1× dose. In this regard, preferred dosages are in the range 1×-100× (i.e. 0.05-5 ng).

Fluid dosage forms are typically prepared utilising the (engineered) clostridial neurotoxin and a pyrogen-free ster-ile vehicle. The (engineered) clostridial neurotoxin, depend-ing on the vehicle and concentration used, can be either dissolved or suspended in the vehicle. In preparing solutions the (engineered) clostridial neurotoxin can be dissolved in the vehicle, the solution being made isotonic if necessary by addition of sodium chloride and sterilised by filtration through a sterile filter using aseptic techniques before filling into suitable sterile vials or ampoules and sealing. Alterna-tively, if solution stability is adequate, the solution in its sealed containers may be sterilised by autoclaving. Advan-tageously additives such as buffering, solubilising, stabilis-ing, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using asep-tic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcu-taneous or intradermal injection, are prepared in substan-tially the same manner, except that the sterile components are suspended in the sterile vehicle, instead of being dis-solved and sterilisation cannot be accomplished by filtration.

The components may be isolated in a sterile state or alternatively it may be sterilised after isolation, e.g. by gamma irradiation.

Advantageously, a suspending agent for example polyvinylpyrrolidone is included in the composition(s) to facilitate uniform distribution of the components.

Administration in accordance with the present invention may take advantage of a variety of delivery technologies including microparticle encapsulation, viral delivery systems or high-pressure aerosol impingement.

Embodiments related to the various methods of the invention are intended to be applied equally to other methods, the clostridial neurotoxins, e.g. engineered clostridial neurotoxins (whether in single-chain or di-chain forms), uses or pharmaceutical compositions, and vice versa.

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Nonence 208-214 (1993); Align-M, see, e.g., Ivo Van Walle et al., Align-M—A New Algorithm for Multiple Alignment of Highly Divergent Sequences, 20(9) Bioinformatics: 1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

ALIGNMENT SCORES FOR DETERMINING SEQUENCE IDENTITY

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 | limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Sci- The percent identity is then calculated as:

$$\frac{\text{Total number of identical matches}}{[\text{length of the longer sequence plus the number of gaps introduced into the longer sequence in order to align the two sequences}]} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions

| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and amino-acylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in Xenopus oocytes by microinjection of mutated mRNA and chemically amino-acylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-aza-phenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be con-verted to non-naturally occurring species by in vitro chemi-cal modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as deter-mined by such techniques as nuclear magnetic resonance, crystallography, electron diffraction or photoaffinity label-ing, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and mate-rials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a clostridial neurotoxin" includes a plurality of such candidate agents and reference to "the clostridial neurotoxin" includes reference to one or more clostridial neurotoxins and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

FIG. 1 shows a comparison of the protein sequence of the activation loop for all BoNT serotypes and a tetanus toxin with two flanking cysteines forming a disulphide bridge connecting the light and heavy chain of a toxin molecule. Factor Xa cleavage site (IDGR) in BoNT/C1 and BoNT/CD underlined.

FIGS. 2A-C show that all four proteases tested: trypsin (TrypZean), Lys-C, factor Xa (FXa) and enterokinase (EK) have the ability to cleave BoNT/C1 activation loop and create a di-chain molecule as compared to C-protease untreated control. (FIG. 2A,B) BoNT/C1(0) (SEQ ID NO: 15) treated with Factor Xa (FXa), enterokinase (EK) and trypsin (1-16 hour time course) as indicated tested by SDS-PAGE in non-reducing (FIG. 2A) and reducing conditions (FIG. 2B). Similarly, proteolytic digest by Lys-C creates di-chain molecules of BoNT/C1 (FIG. 2C). Both trypsin and Lys-C show off-target cleavage within the heavy chain of BoNT/C1. 1-Benchmark (5ul); 2-Control sample (-LysC)-DTT; 3-Control sample (-LysC)+DTT; 4-Activated-DTT; 5-Activated +DTT.

FIG. 3A shows BoNT/X cleavage by Lys-C. Samples were tested in non-reduced and reduced (+DTT) conditions. 1-Benchmark (5ul); 2-No protease control; 3-LysC 0.125 µg/ml; 4-LysC 0.25 µg/ml; 5-LysC 0.5 µg/ml; 6-LysC 1 µg/ml; 7-LysC 2 µg/ml; 8-LysC 4 µg/ml; 9-No protease control +DTT; 10-LysC 0.125 µg/ml +DTT; 11-LysC 0.25 µg/ml +DTT; 12-LysC 0.5 µg/ml +DTT; 13-LysC 1 µg/ml +DTT; 14-LysC 2 µg/ml +DTT; 15-LysC 4 µg/ml +DTT; and 16-Benchmark (5ul).

FIG. 6 shows engineered BoNT/E (SEQ ID NO: 11) treated with indicated proteases and successful BONT di-chain formation evident by comparison between non-reduced (-DTT) and reduced (+DTT) conditions. 1-Benchmark (5ul); 2-Control sample (−EK)−DTT; 3-Control sample (−EK) +DTT; 4-Activated (+EK)−DTT; 5-Activated (+EK) +DTT; 11-Benchmark (5ul); 6-Control sample (−FXa)−DTT; 7-Control sample (−FXa) +DTT; 8-Activated (+FXa)−DTT; 9-Activated (+FXa) +DTT.

FIG. 7A shows engineered BoNT/A1C1 (SEQ ID NO: 13) treated with Factor Xa protease and successful BONT di-chain formation evident by comparison between non-reduced (-DTT) and reduced (+DTT) conditions. 1-Bench-Mark ladder; 2-Control (−FXa −DTT); 3-Control (−FXa +DTT); 4-Activated (+FXa −DTT); 5-Activated (+FXa +DTT). FIG. 7B shows cleavage of BoNT/A1 with FXa or EK after 2 hours compared to a positive control (di-chain BoNT/A1).

FIG. 10 shows intact mass analysis of reduced engineered BoNT/E (SEQ ID NO: 11) activated by enterokinase with an indicated mass of 47518Da and 96338Da.

FIG. 12 shows intact mass analysis of reduced engineered BoNT/E (SEQ ID NO: 11) activated by factor Xa with an indicated mass of 47518Da and 96335Da.

46) treated with Lys-C. 1-Benchmark (5ul); 2-empty; 3-SEQ ID NO: 44 +EK −DTT; 4-SEQ ID NO: 44 +EK +DTT; 5-SEQ ID NO: 44−EK −DTT; 6-SEQ ID NO: 44−EK +DTT; 7-Benchmark; 8-SEQ ID NO: 46−LysC −DTT; 9-SEQ ID NO: 46−LysC −DTT; 10-SEQ ID NO: 46 +LysC −DTT; 11-SEQ ID NO: 46 −LysC +DTT; 12-SEQ ID NO: 46 −LysC +DTT; and 13-SEQ ID NO: 46 +LysC +DTT.

Figure 14:
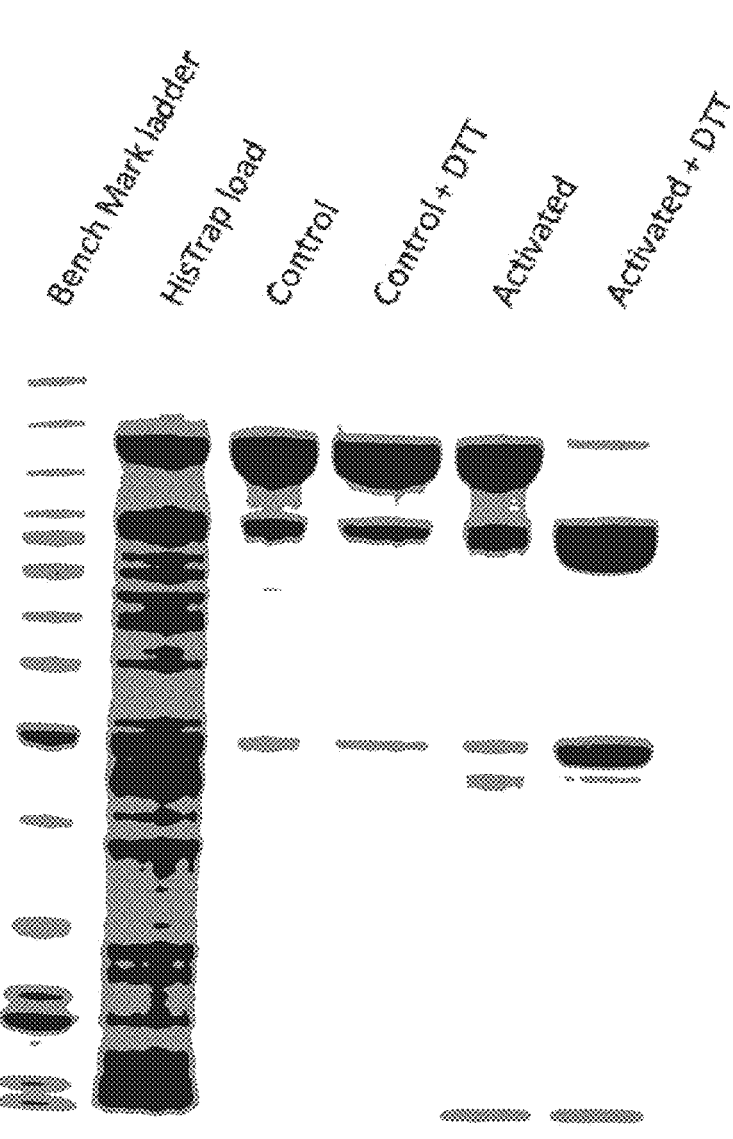

FIG. 14 shows activation of engineered BoNT/XA (SEQ ID NO: 7) with FXa.

FIG. 15 shows activation of engineered BoNT/XB (SEQ ID NO: 9) with FXa.

```
SEQUENCE LISTING
Where an initial Met amino acid residue or a corresponding initial codon is
indicated in any of the following SEQ ID NOs, said residue/codon is
optional.
(C1 Activation Loop Consensus Sequence)
                                                              SEQ ID NO: 1
Cys-(Xaa)ₐ-Ile-Asp/Glu-Gly-Arg-(Yaa)ᵦ-Cys (C1 Activation Loop)
                                                              SEQ ID NO: 2
CHKAIDGRSLYNKTLDC (C1 Activation Loop Variant)
                                                              SEQ ID NO: 3
CHKAIEGRSLYNKTLDC (Nucleotide Sequence of BoNT/X with a C1 Activation Loop)
                                                              SEQ ID NO: 4
ATGAAACTGGAAATCAACAAATTCAACTACAACGATCCGATCGATGGCATTAATGTTATTACCATGCG

TCCGCCTCGTCATAGCGATAAAATCAATAAAGGTAAAGGTCCGTTCAAAGCCTTTCAGGTGATTAAAA

ACATTTGGATTGTGCCGGAACGCTACAACTTTACCAATAATACCAACGATCTGAACATTCCGAGCGAA

CCGATTATGGAAGCAGATGCCATTTATAACCCGAACTATCTGAATACCCCGAGCGAAAAAGATGAATT

TCTGCAGGGTGTTATCAAAGTGCTGGAACGCATTAAAAGCAAACCGGAAGGTGAAAAACTGCTGGAAC

TGATTAGCAGCAGCATTCCGCTGCCGCTGGTTAGCAATGGTGCACTGACCCTGAGCGATAATGAAACC

ATTGCATATCAAGAGAACAACAACATTGTGAGCAATCTGCAGGCAAACCTGGTTATTTATGGTCCGGG

TCCTGATATTGCAAATAATGCAACCTATGGTCTGTATAGCACCCCGATTAGTAATGGTGAAGGTACAC

TGAGCGAAGTTAGCTTTAGCCCGTTTTATCTGAAACCGTTTGATGAAAGCTATGGCAATTATCGTAGC

CTGGTGAATATCGTGAACAAATTCGTGAAACGTGAATTTGCACCTGATCCGGCAAGCACCCTGATGCA

TGAACTGGTTCATGTTACCCATAATCTGTATGGTATTAGCAACCGCAACTTCTACTATAACTTTGACA

CCGGCAAAATTGAAACCAGCCGTCAGCAGAATAGCCTGATTTTTGAAGAACTGCTGACCTTTGGTGGC

ATTGATAGCAAAGCAATTAGCAGCCTGATCATCAAGAAAATTATCGAAACCGCCAAGAACAACTATAC

CACGCTGATTAGCGAACGCCTGAATACCGTTACCGTTGAAAATGATCTGCTGAAATATATCAAAAACA

AAATCCCGGTTCAGGGTCGTCTGGGTAACTTTAAACTGGATACCGCAGAATTCGAGAAAAAGCTGAAT

ACCATTCTGTTTGTGCTGAACGAAAGCAATCTGGCACAGCGTTTTAGCATTCTGGTTCGTAAACATTA

CCTGAAAGAACGTCCGATTGATCCGATTTATGTGAACATTCTCGGATGACAATAGCTACAGCACCCTGG

AAGGTTTTAACATTAGCAGTCAGGGTAGCAATGATTTCCAAGGTCAGCTGCTGGAAAGCAGCTATTTT

GAAAAAATTGAAAGCAATGCCCTGCGTGCCTTTATCAAAATTTGTCATAAAGCCATTGATGGTCGCAG

CCTGTATAACAAAACCCTGGATTGTATTGAGGTGGAAAACAAAGACCTGTTTCTGATTAGCAACAAAG

ATAGCCTGAACGATATTAACCTGAGCGAAGAAAAAATCAAACCGGAAACCACCGTGTTCTTCAAAGAT

AAACTGCCTCCGCAGGATATTACGCTGAGCAATTATGATTTTACCGAAGCCAATAGCATTCCGAGCAT

TAGCCAGCAGAACATTCTGGAACGTAATGAAGAACTGTATGAACCGATTCGCAATAGCCTGTTTGAAA

TCAAAACCATCTATGTGGATAAGCTGACCACCTTTCATTTTCTGGAAGCCCAGAATATTGATGAGAGC
```

-continued

```
ATTGATAGCAGCAAAATTCGTGTTGAACTGACCGATAGCGTTGATGAAGCACTGAGCAATCCGAATAA

AGTTTATAGCCCGTTCAAGAACATGAGCAACACCATTAATAGCATTGAAACCGGTATTACCAGCACCT

ACATCTTTTATCAGTGGCTGCGTAGCATCGTGAAAGATTTTAGTGATGAAACCGGCAAAATCGACGTG

ATTGATAAAAGCAGCGATACCCTGGCAATTGTTCCGTATATTGGTCCGCTGCTGAATATTGGTAATGA

TATTCGTCATGGCGATTTTGTGGGTGCAATTGAACTGGCAGGCATTACCGCACTGCTGGAATATGTTC

CGGAATTTACCATTCCGATTCTGGTTGGTCTGGAAGTTATTGGTGGCGAACTGGCACGTGAACAGGTT

GAAGCAATTGTTAATAATGCCCTGGATAAACGCGATCAGAAATGGGCAGAAGTTTACAATATTACCAA

AGCACAGTGGTGGGGCACCATTCATTTACAGATTAATACCCGTCTGGCCCATACCTATAAAGCCCTGA

GCCGTCAGGCAAATGCCATTAAAATGAATATGGAATTTCAGCTGGCCAACTACAAAGGCAACATTGAT

GATAAAGCCAAGATCAAAAACGCCATCAGCGAAACCGAAATTCTGCTGAACAAAAGCGTTGAACAGGC

CATGAAAAACACCGAGAAATTCATGATTAAACTGAGCAACAGCTACCTGACCAAAGAAATGATTCCGA

AAGTTCAGGACAACCTGAAAAACTTTGATCTGGAAACCAAAAAGACCCTGGACAAGTTCATCAAAGAG

AAAGAAGATATCCTGGGCACCAATCTGAGCAGCAGCCTGCGTCGTAAAGTTAGCATTCGTCTGAATAA

AAACATTGCCTTCGACATCAACGATATCCCGTTTAGCGAATTTGATGATCTGATCAACCAGTACAAAA

ACGAGATCGAAGATTATGAAGTGCTGAATCTGGGTGCAGAAGATGGCAAAATCAAAGATCTGAGCGGT

ACAACCAGCGATATCAATATTGGTTCAGATATCGAACTGGCCGATGGTCGTGAAAATAAAGCGATTAA

GATTAAAGGCAGCGAGAACAGCACCATCAAAATTGCAATGAACAAATATCTGCGTTTTAGCGCGACCG

ATAACTTTAGCATTAGCTTTTGGATCAAACATCCGAAACCGACCAATCTGCTTAATAACGGTATTGAA

TATACCCTGGTCGAGAACTTTAATCAGCGTGGTTGGAAAATTAGCATCCAGGATAGCAAACTGATTTG

GTATCTGCGCGATCACAATAACAGCATCAAAATCGTTACACCGGATTATATTGCGTTTAATGGCTGGA

ACCTGATTACCATTACAAACAATCGTAGCAAAGGCAGCATCGTGTATGTTAACGGTAGCAAAATTGAA

GAGAAGGACATTAGCAGCATTTGGAATACCGAAGTGGATGATCCGATTATCTTCCGCCTGAAAAATAA

CCGTGATACCCAGGCATTTACCCTGCTGGATCAGTTTAGCATTTATCGCAAAGAACTGAACCAGAACG

AAGTGGTGAAACTGTATAACTACTACTTCAACAGCAACTACATTCGCGATATTTGGGGTAATCCGCTG

CAGTACAACAAAAAATACTATCTGCAGACCCAGGACAAACCTGGTAAAGGTCTGATCCGCGAATATTG

GAGCAGCTTTGGTTATGATTATGTGATTCTGAGCGATAGCAAGACCATTACCTTTCCGAATAATATCC

GTTATGGTGCCCTGTATAATGGTAGCAAAGTGCTGATCAAGAACAGCAAAAAACTGGATGGTCTGGTG

CGCAATAAAGATTTCATTCAGCTGGAAATCGATGGCTATAATATGGGTATTAGCGCAGATCGCTTTAA

CGAGGATACCAACTATATTGGCACCACCTATGGTACAACCCATGATCTGACCACCGATTTTGAAATTA

TTCAGCGCCAAGAGAAATACCGCAATTATTGTCAGCTGAAAACCCCGTATAACATCTTTCATAAAAGC

GGTCTGATGAGCACCGAAACCAGCAAACCGACCTTCCATGATTATCGCGATTGGGTTTATAGCAGCGC

ATGGTATTTTCAGAACTATGAAAATCTGAACCTGCGCAAACATACCAAAACCAACTGGTATTTTATCC

CGAAAGATGAAGGTTGGGATGAAGATCTGGAAGTGCTGTTTCAGGGTCCGCATCATCACCACCATCAC

CATCATCATCACTGA
```

(Polypeptide Sequence of BoNT/X with a C1 Activation Loop)

SEQ ID NO: 5

```
MKLEINKFNYNDPIDGINVITMRPPRHSDKINKGKGPFKAFQVIKNIWIVPERYNFTNNTNDLNIPSE

PIMEADAIYNPNYLNTPSEKDEFLQGVIKVLERIKSKPEGEKLLELISSSIPLPLVSNGALTLSDNET

IAYQENNNIVSNLQANLVIYGPGPDIANNATYGLYSTPISNGEGTLSEVSFSPFYLKPFDESYGNYRS

LVNIVNKFVKREFAPDPASTLMHELVHVTHNLYGISNRNFYYNFDTGKIETSRQQNSLIFEELLTFGG

IDSKAISSLIIKKIIETAKNNYTTLISERLNTVTVENDLLKYIKNKIPVQGRLGNFKLDTAEFEKKLN
```

-continued

TILFVLNESNLAQRFSILVRKHYLKERPIDPIYVNILDDNSYSTLEGFNISSQGSNDFQGQLLESSYF

EKIESNALRAFIKICHKAIDGRSLYNKTLDCIEVENKDLFLISNKDSLNDINLSEEKIKPETTVFFKD

KLPPQDITLSNYDFTEANSIPSISQQNILERNEELYEPIRNSLFEIKTIYVDKLTTFHFLEAQNIDES

IDSSKIRVELTDSVDEALSNPNKVYSPFKNMSNTINSIETGITSTYIFYQWLRSIVKDFSDETGKIDV

IDKSSDTLAIVPYIGPLLNIGNDIRHGDFVGAIELAGITALLEYVPEFTIPILVGLEVIGGELAREQV

EAIVNNALDKRDQKWAEVYNITKAQWWGTIHLQINTRLAHTYKALSRQANAIKMNMEFQLANYKGNID

DKAKIKNAISETEILLNKSVEQAMKNTEKFMIKLSNSYLTKEMIPKVQDNLKNFDLETKKTLDKFIKE

KEDILGTNLSSSLRRKVSIRLNKNIAFDINDIPFSEFDDLINQYKNEIEDYEVLNLGAEDGKIKDLSG

TTSDINIGSDIELADGRENKAIKIKGSENSTIKIAMNKYLRFSATDNFSISFWIKHPKPTNLLNNGIE

YTLVENFNQRGWKISIQDSKLIWYLRDHNNSIKIVTPDYIAFNGWNLITITNNRSKGSIVYVNGSKIE

EKDISSIWNTEVDDPIIFRLKNNRDTQAFTLLDQFSIYRKELNQNEVVKLYNYYFNSNYIRDIWGNPL

QYNKKYYLQTQDKPGKGLIREYWSSFGYDYVILSDSKTITFPNNIRYGALYNGSKVLIKNSKKLDGLV

RNKDFIQLEIDGYNMGISADRFNEDTNYIGTTYGTTHDLTTDFEIIQRQEKYRNYCQLKTPYNIFHKS

GLMSTETSKPTFHDYRDWVYSSAWYFQNYENLNLRKHTKTNWYFIPKDEGWDEDLEVLFQGPHHHHHH

HHHH (Nucleotide Sequence of BoNT/XA [LH$_N$X-H$_C$A] with a C1 Activation Loop)

SEQ ID NO: 6

ATGAAACTGGAAATCAACAAATTCAACTACAACGATCCGATCGATGGCATTAATGTTATTACCATGCG

TCCGCCTCGTCATAGCGATAAAATCAATAAAGGTAAAGGTCCGTTCAAAGCCTTTCAGGTGATTAAAA

ACATTTGGATTGTGCCGGAACGCTACAACTTTACCAATAATACCAACGATCTGAACATTCCGAGCGAA

CCGATTATGGAAGCAGATGCCATTTATAACCCGAACTATCTGAATACCCCGAGCGAAAAAGATGAATT

TCTGCAGGGTGTTATCAAAGTGCTGGAACGCATTAAAAGCAAACCGGAAGGTGAAAAACTGCTGGAAC

TGATTAGCAGCAGCATTCCGCTGCCGCTGGTTAGCAATGGTGCACTGACCCTGAGCGATAATGAAACC

ATTGCATATCAAGAGAACAACAACATTGTGAGCAATCTGCAGGCAAACCTGGTTATTTATGGTCCGGG

TCCTGATATTGCAAATAATGCAACCTATGGTCTGTATAGCACCCCGATTAGTAATGGTGAAGGTACAC

TGAGCGAAGTTAGCTTTAGCCCGTTTTATCTGAAACCGTTTGATGAAAGCTATGGCAATTATCGTAGC

CTGGTGAATATCGTGAACAAATTCGTGAAACGTGAATTTGCACCTGATCCGGCAAGCACCCTGATGCA

TGAACTGGTTCATGTTACCCATAATCTGTATGGTATTAGCAACCGCAACTTCTACTATAACTTTGACA

CCGGCAAAATTGAAACCAGCCGTCAGCAGAATAGCCTGATTTTTGAAGAACTGCTGACCTTTGGTGGC

ATTGATAGCAAAGCAATTAGCAGCCTGATCATCAAGAAAATTATCGAAACCGCCAAGAACAACTATAC

CACGCTGATTAGCGAACGCCTGAATACCGTTACCGTTGAAAATGATCTGCTGAAATATATCAAAAACA

AAATCCCGGTTCAGGGTCGTCTGGGTAACTTTAAACTGGATACCGCAGAATTCGAGAAAAAGCTGAAT

ACCATTCTGTTTGTGCTGAACGAAAGCAATCTGGCACAGCGTTTTAGCATTCTGGTTCGTAAACATTA

CCTGAAAGAACGTCCGATTGATCCGATTTATGTGAACATTCTGGATGACAATAGCTACAGCACCCTGG

AAGGTTTTAACATTAGCAGTCAGGGTAGCAATGATTTTCAGGGCCAGCTGCTGGAAAGCAGCTATTTT

GAAAAAATTGAATCCAATGCGCTGCGTGCCTTTATCAAAATTTGTCATAAAGCCATTGATGGTCGCAG

CCTGTATAACAAAACCCTGGATTGTATTGAAGTGGAAAACAAAGACCTGTTCCTGATTAGCAATAAAG

ATAGCCTGAACGATATCAACCTGAGCGAAGAAAAAATCAAACCGGAAACCACCGTGTTCTTCAAAGAT

AAACTGCCTCCGCAGGATATTACCCTGAGCAATTATGATTTTACCGAAGCCAATAGCATTCCGAGCAT

TAGCCAGCAGAACATTCTGGAACGTAATGAAGAACTGTATGAACCGATTCGCAATAGCCTGTTTGAAA

TCAAAACCATCTATGTGGATAAGCTGACCACCTTTCATTTTCTGGAAGCCCAGAATATTGATGAGAGC

ATTGATAGCAGCAAAATTCGTGTTGAACTGACCGATAGCGTTGATGAAGCACTGAGCAATCCGAATAA

-continued

```
AGTTTATAGCCCGTTCAAGAACATGAGCAACACCATTAATAGCATTGAAACCGGTATTACCAGCACCT

ACATCTTTTATCAGTGGCTGCGTAGCATCGTGAAAGATTTTAGTGATGAAACCGGCAAAATCGACGTG

ATTGATAAAAGCAGCGATACCCTGGCCATTGTTCCGTATATTGGTCCGCTGCTGAATATTGGTAATGA

TATTCGTCATGGCGATTTTGTGGGTGCAATTGAACTGGCAGGCATTACCGCACTGCTGGAATATGTTC

CGGAATTTACCATTCCGATTCTGGTTGGTCTGGAAGTTATTGGTGGCGAACTGGCACGTGAACAGGTT

GAAGCAATTGTTAATAATGCCCTGGATAAACGCGATCAGAAATGGGCAGAAGTTTACAATATTACCAA

AGCACAGTGGTGGGGCACCATTCATTTACAGATTAATACCCGTCTGGCCCATACCTATAAAGCCCTGA

GCCGTCAGGCAAATGCCATTAAAATGAATATGGAATTTCAGCTGGCCAACTACAAAGGCAACATTGAT

GATAAAGCCAAGATCAAAAACGCCATCAGCGAAACCGAAATTCTGCTGAACAAAAGCGTTGAACAGGC

CATGAAAAACACCGAGAAATTCATGATTAAACTGAGCAACAGCTACCTGACCAAAGAAATGATTCCGA

AAGTTCAGGACAACCTGAAAAACTTTGATCTGGAAACCAAAAAGACCCTGGACAAGTTCATCAAAGAG

AAAGAAGATATCCTGGGCACCAATCTGAGCAGCAGCCTGCGTCGTAAAGTTAGCATTCGTCTGAATAA

AAACATTGCCTTCGACATCAACGATATCCCGTTTAGCGAATTTGATGATCTGATCAACCAGTACAAAA

ACGAGATCGAAGATTATGAAGTGCTGAATCTGGGTGCAGAAGATGGCAAAATCAAAGATCTGAGCGGT

ACAACCAGCGATATTAACATTGGTAGCGATATCGAAATCATCAACACCAGCATTCTGAATCTGCGCTA

TGAAAGCAATCATCTGATTGATCTGAGCCGTTATGCGTCCAAAATCAATATTGGCAGCAAAGTGAATT

TCGACCCGATCGATAAAAATCAGATCCAGCTGTTTAATCTGGAAAGCTCCAAAATTGAGGTGATTCTG

AAAAACGCGATTGTGTACAATAGCATGTATGAGAATTTCTCAACCAGCTTCTGGATTCGCATTCCGAA

ATACTTTAACAGCATCAGCCTGAACAACGAGTATACCATTATCAACTGCATGGAAAACAATAGCGGTT

GGAAAGTGAGCCTGAATTATGGTGAAATTATCTGGACCCTGCAGGATACCCAAGAAATCAAACAGCGT

GTTGTGTTCAAATACAGCCAGATGATTAACATCAGCGATTACATTAACCGCTGGATCTTTGTTACCAT

TACCAACAATCGCCTGAATAACAGCAAGATCTATATTAACGGTCGTCTGATTGACCAGAAACCGATTA

GTAATCTGGGTAATATTCATGCCAGCAACAACATCATGTTCAAACTGGATGGTTGTCGTGATACCCAT

CGTTATATTTGGATCAAGTATTTTAACCTGTTTGATAAAGAACTGAACGAAAAAGAAATTAAGGATCT

GTATGATAACCAGTCCAATAGCGGCATCCTGAAGGATTTTTGGGGTGATTATCTGCAGTATGACAAAC

CGTATTATATGCTGAACCTGTACGATCCGAACAAATATGTGGATGTGAATAATGTGGGTATCCGTGGC

TATATGTATCTGAAAGGTCCGCGTGGTAGCGTTATGACCACCAACATTTATCTGAATAGCAGCCTGTA

TCGTGGCACCAAATTCATCATCAAAAAATACGCCAGCGGCAACAAAGATAATATTGTGCGTAATAATG

ACCGCGTGTATATCAATGTGGTGGTGAAGAATAAAGAATATCGTCTGGCAACCAATGCAAGCCAGGCA

GGCGTTGAAAAAATTCTGAGCGCACTGGAAATCCCGGATGTGGGTAATCTGAGCCAGGTTGTTGTTAT

GAAAAGCAAAAATGATCAGGGCATCACCAACAAGTGCAAAATGAATCTGCAGGACAATAACGGCAACG

ACATTGGTTTTATTGGCTTTCACCAGTTTAACAACATTGCCAAACTGGTTGCGAGCAATTGGTATAAT

CGTCAGATTGAACGTAGCAGTCGTACCCTGGGTTGTAGCTGGGAATTTATTCCGGTTGATGATGGTTG

GGGTGAACGTCCGCTGCATCATCACCACCATCACCATCACCACCATTAA
```

(Polypeptide Sequence of BoNT/XA [LH$_N$X-H$_C$A] with a C1 Activation Loop)

SEQ ID NO: 7

```
MKLEINKFNYNDPIDGINVITMRPPRHSDKINKGKGPFKAFQVIKNIWIVPERYNFTNNTNDLNIPSE

PIMEADAIYNPNYLNTPSEKDEFLQGVIKVLERIKSKPEGEKLLELISSSIPLPLVSNGALTLSDNET

IAYQENNNIVSNLQANLVIYGPGPDIANNATYGLYSTPISNGEGTLSEVSFSPFYLKPFDESYGNYRS

LVNIVNKFVKREFAPDPASTLMHELVHVTHNLYGISNRNFYYNFDTGKIETSRQQNSLIFEELLTFGG

IDSKAISSLIIKKIIETAKNNYTTLISERLNTVTVENDLLKYIKNKIPVQGRLGNFKLDTAEFEKKLN
```

-continued
TILFVLNESNLAQRFSILVRKHYLKERPIDPIYVNILDDNSYSTLEGFNISSQGSNDFQGQLLESSYF

EKIESNALRAFIKICHKAIDGRSLYNKTLDCIEVENKDLFLISNKDSLNDINLSEEKIKPETTVFFKD

KLPPQDITLSNYDFTEANSIPSISQQNILERNEELYEPIRNSLFEIKTIYVDKLTTFHFLEAQNIDES

IDSSKIRVELTDSVDEALSNPNKVYSPFKNMSNTINSIETGITSTYIFYQWLRSIVKDFSDETGKIDV

IDKSSDTLAIVPYIGPLLNIGNDIRHGDFVGAIELAGITALLEYVPEFTIPILVGLEVIGGELAREQV

EAIVNNALDKRDQKWAEVYNITKAQWWGTIHLQINTRLAHTYKALSRQANAIKMNMEFQLANYKGNID

DKAKIKNAISETEILLNKSVEQAMKNTEKFMIKLSNSYLTKEMIPKVQDNLKNFDLETKKTLDKFIKE

KEDILGTNLSSSLRRKVSIRLNKNIAFDINDIPFSEFDDLINQYKNEIEDYEVLNLGAEDGKIKDLSG

TTSDINIGSDIEIINTSILNLRYESNHLIDLSRYASKINIGSKVNFDPIDKNQIQLFNLESSKIEVIL

KNAIVYNSMYENFSTSFWIRIPKYFNSISLNNEYTIINCMENNSGWKVSLNYGEIIWTLQDTQEIKQR

VVFKYSQMINISDYINRWIFVTITNNRLNNSKIYINGRLIDQKPISNLGNIHASNNIMFKLDGCRDTH

RYIWIKYFNLFDKELNEKEIKDLYDNQSNSGILKDFWGDYLQYDKPYYMLNLYDPNKYVDVNNVGIRG

YMYLKGPRGSVMTTNIYLNSSLYRGTKFIIKKYASGNKDNIVRNNDRVYINVVVKNKEYRLATNASQA

GVEKILSALEIPDVGNLSQVVVMKSKNDQGITNKCKMNLQDNNGNDIGFIGFHQFNNIAKLVASNWYN

RQIERSSRTLGCSWEFIPVDDGWGERPLHHHHHHHHHH (Nucleotide Sequence of BoNT/XB [LH$_N$X-H$_C$B] with a C1 Activation Loop)

SEQ ID NO: 8
ATGAAACTGGAAATCAACAAATTCAACTACAACGATCCGATCGATGGCATTAATGTTATTACCATGCG

TCCGCCTCGTCATAGCGATAAAATCAATAAAGGTAAAGGTCCGTTCAAAGCCTTTCAGGTGATTAAAA

ACATTTGGATTGTGCCGGAACGCTACAACTTTACCAATAATACCAACGATCTGAACATTCCGAGCGAA

CCGATTATGGAAGCAGATGCCATTTATAACCCGAACTATCTGAATACCCCGAGCGAAAAAGATGAATT

TCTGCAGGGTGTTATCAAAGTGCTGGAACGCATTAAAAGCAAACCGGAAGGTGAAAAACTGCTGGAAC

TGATTAGCAGCAGCATTCCGCTGCCGCTGGTTAGCAATGGTGCACTGACCCTGAGCGATAATGAAACC

ATTGCATATCAAGAGAACAACAACATTGTGAGCAATCTGCAGGCAAACCTGGTTATTTATGGTCCGGG

TCCTGATATTGCAAATAATGCAACCTATGGTCTGTATAGCACCCCGATTAGTAATGGTGAAGGTACAC

TGAGCGAAGTTAGCTTTAGCCCGTTTTATCTGAAACCGTTTGATGAAAGCTATGGCAATTATCGTAGC

CTGGTGAATATCGTGAACAAATTCGTGAAACGTGAATTTGCACCTGATCCGGCAAGCACCCTGATGCA

TGAACTGGTTCATGTTACCCATAATCTGTATGGTATTAGCAACCGCAACTTCTACTATAACTTTGACA

CCGGCAAAATTGAAACCAGCCGTCAGCAGAATAGCCTGATTTTTGAAGAACTGCTGACCTTTGGTGGC

ATTGATAGCAAAGCAATTAGCAGCCTGATCATCAAGAAAATTATCGAAACCGCCAAGAACAACTATAC

CACGCTGATTAGCGAACGCCTGAATACCGTTACCGTTGAAAATGATCTGCTGAAATATATCAAAAACA

AAATCCCGGTTCAGGGTCGTCTGGGTAACTTTAAACTGGATACCGCAGAATTCGAGAAAAAGCTGAAT

ACCATTCTGTTTGTGCTGAACGAAAGCAATCTGGCACAGCGTTTTAGCATTCTGGTTCGTAAACATTA

CCTGAAAGAACGTCCGATTGATCCGATTTATGTGAACATTCTGGATGACAATAGCTACAGCACCCTGG

AAGGTTTTAACATTAGCAGTCAGGGTAGCAATGATTTTCAGGGCCAGCTGCTGGAAAGCAGCTATTTT

GAAAAAATTGAATCCAATGCGCTGCGTGCCTTTATCAAAATTTGTCATAAAGCCATTGATGGTCGCAG

CCTGTATAACAAAACCCTGGATTGTATTGAAGTGGAAAACAAAGACCTGTTCCTGATTAGCAATAAAG

ATAGCCTGAACGATATCAACCTGAGCGAAGAAAAAATCAAACCGGAAACCACCGTGTTCTTCAAAGAT

AAACTGCCTCCGCAGGATATTACCCTGAGCAATTATGATTTTACCGAAGCCAATAGCATTCCGAGCAT

TAGCCAGCAGAACATTCTGGAACGTAATGAAGAACTGTATGAACCGATTCGCAATAGCCTGTTTGAAA

TCAAAACCATCTATGTGGATAAGCTGACCACCTTTCATTTTCTGGAAGCCCAGAATATTGATGAGAGC

ATTGATAGCAGCAAAATTCGTGTTGAACTGACCGATAGCGTTGATGAAGCACTGAGCAATCCGAATAA

-continued

```
AGTTTATAGCCCGTTCAAGAACATGAGCAACACCATTAATAGCATTGAAACCGGTATTACCAGCACCT

ACATCTTTTATCAGTGGCTGCGTAGCATCGTGAAAGATTTTAGTGATGAAACCGGCAAAATCGACGTG

ATTGATAAAAGCAGCGATACCCTGGCCATTGTTCCGTATATTGGTCCGCTGCTGAATATTGGTAATGA

TATTCGTCATGGCGATTTTGTGGGTGCAATTGAACTGGCAGGCATTACCGCACTGCTGGAATATGTTC

CGGAATTTACCATTCCGATTCTGGTTGGTCTGGAAGTTATTGGTGGCGAACTGGCACGTGAACAGGTT

GAAGCAATTGTTAATAATGCCCTGGATAAACGCGATCAGAAATGGGCAGAAGTTTACAATATTACCAA

AGCACAGTGGTGGGGCACCATTCATTTACAGATTAATACCCGTCTGGCCCATACCTATAAAGCCCTGA

GCCGTCAGGCAAATGCCATTAAAATGAATATGGAATTTCAGCTGGCCAACTACAAAGGCAACATTGAT

GATAAAGCCAAGATCAAAAACGCCATCAGCGAAACCGAATTCTGCTGAACAAAGCGTTGAACAGGC

CATGAAAAACACCGAGAAATTCATGATTAAACTGAGCAACAGCTACCTGACCAAAGAAATGATTCCGA

AAGTTCAGGACAACCTGAAAAACTTTGATCTGGAAACCAAAAAGACCCTGGACAAGTTCATCAAAGAG

AAAGAAGATATCCTGGGCACCAATCTGAGCAGCAGCCTGCGTCGTAAAGTTAGCATTCGTCTGAATAA

AAACATTGCCTTCGACATCAACGATATCCCGTTTAGCGAATTTGATGATCTGATCAACCAGTACAAAA

ACGAGATCGAAGATTATGAAGTGCTGAATCTGGGTGCAGAAGATGGCAAAATCAAAGATCTGAGCGGT

ACAACCAGCGATATTAACATTGGTAGCGATATCGAAATCCTGAACAACATTATTCTGAACCTGCGCTA

TAAAGATAACAACCTGATTGATCTGAGTGGCTATGGTGCAAAAGTTGAAGTTTATGATGGTGTGGAAC

TGAACGACAAAAACCAGTTCAAACTGACCAGCAGCGCAAATTCAAAAATTCGCGTTACCCAGAACCAG

AACATCATTTTTAACAGCGTGTTTCTGGATTTCAGCGTGAGCTTTTGGATTCGTATTCCGAAATATAA

GAACGACGGCATCCAGAACTATATCCACAATGAATATACCATCATCAACTGCATGAAGAATAACAGCG

GTTGGAAAATTAGCATCCGTGGCAATCGTATTATTTGGACCCTGATCGATATTAATGGCAAAACCAAG

AGCGTGTTTTTCGAGTATAACATCCGTGAAGATATCAGCGAATACATCAACCGTTGGTTTTTTGTGAC

CATTACCAACAATCTGAACAACGCCAAAATCTACATTAACGGCAAACTGGAAAGCAACACCGATATCA

AAGATATTCGTGAAGTGATTGCCAACGGCGAGATTATCTTTAAACTGGATGGTGATATTGATCGCACC

CAGTTTATTTGGATGAAATACTTCAGCATCTTCAACACCGAACTGAGCCAGAGCAATATTGAAGAACG

CTATAAAATCCAGAGCTACAGCGAGTATCTGAAAGACTTTTGGGGTAATCCGCTGATGTACAACAAAG

AATACTACATGTTTAATGCCGGTAACAAAAACAGCTATATCAAACTGAAAAAGGATAGTCCGGTGGGT

GAAATTCTGACCCGTAGCAAATATAACCAGAATAGCAAGTATATCAACTATCGCGATCTGTACATCGG

CGAGAAATTTATCATTCGTCGTAAAAGCAACTCCCAGAGCATTAACGATGATATTGTGCGCAAAGAGG

ATTACATCTACCTGGATTTTTTCAACCTGAATCAAGAGTGGCGTGTGTACACCTATAAGTACTTCAAA

AAAGAAGAAATGAAACTGTTTCTGGCACCGATCTATGATAGCGACGAATTTTACAATACCATTCAGAT

TAAAGAATATGATGAACAGCCGACCTATAGCTGTCAGCTGCTGTTTAAAAAGGATGAAGAAAGCACGG

ATGAAATTGGCCTGATTGGTATCCATCGTTTTTATGAAAGCGGCATCGTGTTCGAAGAGTACAAAGAT

TATTTCTGCATCAGCAAATGGTATCTTAAAGAGGTGAAACGCAAACCGTATAATCTGAAACTGGGTTG

CAATTGGCAGTTCATCCCGAAAGATGAAGGTTGGACCGAACATCATCACCACCATCACCATCATCATC

ACTGA
```

(Polypeptide Sequence of BoNT/XB [LH$_N$X-H$_C$B] with a C1 Activation Loop)

SEQ ID NO: 9

```
MKLEINKFNYNDPIDGINVITMRPPRHSDKINKGKGPFKAFQVIKNIWIVPERYNFTNNTNDLNIPSE

PIMEADAIYNPNYLNTPSEKDEFLQGVIKVLERIKSKPEGEKLLELISSSIPLPLVSNGALTLSDNET

IAYQENNNIVSNLQANLVIYGPGPDIANNATYGLYSTPISNGEGTLSEVSFSPFYLKPFDESYGNYRS

LVNIVNKFVKREFAPDPASTLMHELVHVTHNLYGISNRNFYYNFDTGKIETSRQQNSLIFEELLTFGG
```

-continued

IDSKAISSLIIKKIIETAKNNYTTLISERLNTVTVENDLLKYIKNKIPVQGRLGNFKLDTAEFEKKLN

TILFVLNESNLAQRFSILVRKHYLKERPIDPIYVNILDDNSYSTLEGFNISSQGSNDFQGQLLESSYF

EKIESNALRAFIKICHKAIDGRSLYNKTLDCIEVENKDLFLISNKDSLNDINLSEEKIKPETTVFFKD

KLPPQDITLSNYDFTEANSIPSISQQNILERNEELYEPIRNSLFEIKTIYVDKLTTFHFLEAQNIDES

IDSSKIRVELTDSVDEALSNPNKVYSPFKNMSNTINSIETGITSTYIFYQWLRSIVKDFSDETGKIDV

IDKSSDTLAIVPYIGPLLNIGNDIRHGDFVGAIELAGITALLEYVPEFTIPILVGLEVIGGELAREQV

EAIVNNALDKRDQKWAEVYNITKAQWWGTIHLQINTRLAHTYKALSRQANAIKMNMEFQLANYKGNID

DKAKIKNAISETEILLNKSVEQAMKNTEKFMIKLSNSYLTKEMIPKVQDNLKNFDLETKKTLDKFIKE

KEDILGTNLSSSLRRKVSIRLNKNIAFDINDIPFSEFDDLINQYKNEIEDYEVLNLGAEDGKIKDLSG

TTSDINIGSDIEILNNIILNLRYKDNNLIDLSGYGAKVEVYDGVELNDKNQFKLTSSANSKIRVTQNQ

NIIFNSVFLDFSVSFWIRIPKYKNDGIQNYIHNEYTIINCMKNNSGWKISIRGNRIIWTLIDINGKTK

SVFFEYNIREDISEYINRWFFVTITNNLNNAKIYINGKLESNTDIKDIREVIANGEIIFKLDGDIDRT

QFIWMKYFSIFNTELSQSNIEERYKIQSYSEYLKDFWGNPLMYNKEYYMFNAGNKNSYIKLKKDSPVG

EILTRSKYNQNSKYINYRDLYIGEKFIIRRKSNSQSINDDIVRKEDYIYLDFFNLNQEWRVYTYKYFK

KEEMKLFLAPIYDSDEFYNTIQIKEYDEQPTYSCQLLFKKDEESTDEIGLIGIHRFYESGIVFEEYKD

YFCISKWYLKEVKRKPYNLKLGCNWQFIPKDEGWTEHHHHHHHHHH (Nucleotide Sequence of BoNT/E with a C1 Activation Loop)

SEQ ID NO: 10 atgccgaaaatcaactctttcaactacaacgacccggttaacgaccgtaccatcctgtatatcaaacc gggtggttgccaggagttctacaaatctttcaacatcatgaaaaacatctggatcatcccggaacgta acgttatcggtaccaccccgcaggacttccacccgccgacctctctgaaaaacggtgactcttcttac tacgacccgaactacctccagtctgacgaagaaaaagaccgtttcctgaaaatcgttaccaaaatctt caaccgtatcaacaacaacctgtctggtggtatcctgctggaagaactgtctaaagctaacccgtacc tgggtaacgacaacaccccggacaaccagttccacatcggtgacgcttctgctgttgaaatcaaattc tctaacggttctcaggacatcctgctgccgaacgttatcatcatgggtgctgaaccggacctgttcga aaccaactcttctaacatctctctgcgtaacaactacatgccgtctaaccacggtttcggttctatcg ctatcgttaccttctctccggaatactcttttccgtttcaacgacaacagcatgaacgagttcatccag gacccggctctgaccctgatgcaccaactgatctattctctgcacggtctgtacggtgctaaaggtat caccaccaaatacaccatcacccagaaacagaacccgctgatcaccaacatccgtggtaccaacatcg aagagttcctgaccttcggtggtaccgacctgaacatcatcacctctgctcagtctaacgacatctac accaacctgctggctgactacaaaaaaatcgcttctaaactgtctaaagttcaggtttctaacccgct gctgaacccgtacaaagacgttttcgaagctaaatacggtctggacaaagacgcttctggtatctact ctgttaacatcaacaaattcaacgacatcttcaaaaaactgtactctttcaccgagttcgacctggcg accaaattccaggttaaatgccgtcagacctacatcggtcagtacaaatacttcaaactgtctaacct gctgaacgactctatctacaacatctctgaaggttacaacatcaacaacctgaaagttaacttccgtg gtcagaacgctaacctgaacccgcgtatcatcaccccgatcaccggtcgtggtctggttaaaaaaatc atccgtttcTGCCACAAAGCGATTGATGGCCGCTCTCTCTATAACAAAACGCTGGATTGCatcgaaat caacaacggtgaactgttcttcgttgcttctgaaaactcttacaacgacgacaacatcaacacccga aagaaatcgacgacaccgttacctctaacaacaactacgaaaacgacctggaccaggttatcctgaac ttcaactctgaatctgctccgggtctgtctgacgaaaaactgaacctgaccatccagaacgacgctta catcccgaaatacgactctaacggtacctctgacatcgaacagcacgacgttaacgaactgaacgttt tcttctacctggacgctcagaaagttccggaaggtgaaaacaacgttaacctgacctcttctatcgac -continued accgctctgctggaacagccgaaaatctacaccttcttctcttctgagttcatcaacaacgttaacaa accggttcaggctgctctgttcgtttcttggattcagcaggttctggttgacttcaccaccgaagcta accagaaatctaccgttgacaaaatcgctgacatctctatcgttgttccgtacatcggtctggctctg aacatcggtaacgaagctcagaaaggtaacttcaaagacgctctggaactgctgggtgctggtatcct gctggagttcgaaccggaactgctgatcccgaccatcctggttttcaccatcaaatctttcctgggtt cttctgacaacaaaaacaaagttatcaaagctatcaacaacgctctgaaagaacgtgacgaaaaatgg aaagaagtttactctttcatcgtttctaactggatgaccaaaatcaacacccagttcaacaaacgtaa agaacagatgtaccaggctctccagaaccaggttaacgctatcaaaaccatcatcgaatctaaataca actcttacaccctggaagaaaaaaacgaactgaccaacaaatacgacatcaaacagatcgaaaacgaa ctgaaccagaaagtttctatcgctatgaacaacatcgaccgtttcctgaccgaatcttctatctctta cctgatgaaactcatcaacgaagttaaaatcaacaaactgcgtgaatacgacgaaaacgttaaaacct acctgctgaactacatcatccagcacggttctatcctgggtgaatctcagcaggaactgaactctatg gttaccgacaccctgaacaactctatcccgttcaaactgtcttcttacaccgacgacaaaatcctGAT CTCTTACTTCAACAAATTCTTTAAAcgcATTAAGAGTTCATCGGTTctgaatATGCGGTACAAAAATG ATAAAtatGTCGATACTTCTGGATATgatAGCAATATCAACATTAACGGCGACGTGTATAAATATccg ACAAATAAAAACCAGTTTGGGATATATAACGACAAGctgTCGGAGGTCAATattTCTCAAAACGACta tATCattTACGATAATaaaTATAAAAACTTTAGCATTAGTtttTGGGTTcgtATACCTAATtatGACA ATAaaattGTAAATGTGAATAACGAGTATACCATTATAAACTGTATGcgcGACAATAACAGTGGTTGG AAGGTATCGctgAACCATAATGAGATTATCTGGACCctgcagGATAATgcaGGTATAAACCAGAAACT GGCTTTTAACTATGGAAACGCAAATGGGATCTCAGATTACATTaataaaTGGatttttGTTaccATTA CGAACGATcgcTTAGGCGACTCAAAACTTTATATTAATggcAATctgATAGATCAGAAATCAATCTTA AATTTGGGCAATATTCATGTCTCTgatAACATCTTGTTCAAGATCGTTAATTGCAGTTACACTcgtTA TATTGGCATTCGTTACTTTAATATCTTCgataaaGAActgGACGAGACGGAAATCcagACTCTGTATT

CAAACGAGCCCAATACTAATATATTGAAAGATTTTTGGGGTAACTATCTTTTATATGATAAAGAATAC

TATCTCCTGaatGTATTGAAGCCAAACAATTTCATAGATAGACGCAAGGATAGCACATTAAGTATCAA

CAATATCAGATCTACTATActgttaGCAAATCGCCTcTACTCCggtATTAAAGTGAAGATTcagCGGG

TTAATAACTCCAGTACCAATGATAATCTGGTCCGTAAGAACGATCAGGTATACATcaatTTCGTCGCG

AGCAAAACTcatCTCTTCCCGCTTTACGCCgatACAGCTACGACAAACAAGGAAAAAACCATAAAAAT

TTCCAGCTCCGGAAACAGATTCAATCAAGTAGTTGTAATGAACTCTGTGGGTaatAATTGTACGATGA

ACTTTaagAATAACAATGGGAACAATattGGACTTTTGGGCTTcAAAGCCGACACAGTGGTGGCGTCC

ACCTGGTATTACACGcacATGcggGACCATACGAATTCGAACGGTTGCTTCTGGAACTTTATCTCGGA

AgaaCACGGGTGGCAAGAAAAA (Polypeptide Sequence of BoNT/E with a C1 Activation Loop)

SEQ ID NO: 11
MPKINSFNYNDPVNDRTILYIKPGGCQEFYKSFNIMKNIWIIPERNVIGTTPQDFHPPTSLKNGDSSY

YDPNYLQSDEEKDRFLKIVTKIFNRINNNLSGGILLEELSKANPYLGNDNTPDNQFHIGDASAVEIKF

SNGSQDILLPNVIIMGAEPDLFETNSSNISLRNNYMPSNHGFGSIAIVTFSPEYSFRFNDNSMNEFIQ

DPALTLMHQLIYSLHGLYAKGITTKYTITQKQNPLITNIRGTNIEEFLTFGGTDLNIITSAQSNDIY

TNLLADYKKIASKLSKVQVSNPLLNPYKDVFEAKYGLDKDASGIYSVNINKFNDIFKKLYSFTEFDLA

TKFQVKCRQTYIGQYKYFKLSNLLNDSIYNISEGYNINNLKVNFRGQNANLNPRIITPITGRGLVKKI

IRFCHKAIDGRSLYNKTLDCIEINNGELFFVASENSYNDDNINTPKEIDDTVTSNNNYENDLDQVILN

-continued

FNSESAPGLSDEKLNLTIQNDAYIPKYDSNGTSDIEQHDVNELNVFFYLDAQKVPEGENNVNLTSSID

TALLEQPKIYTFFSSEFINNVNKPVQAALFVSWIQQVLVDFTTEANQKSTVDKIADISIVVPYIGLAL

NIGNEAQKGNFKDALELLGAGILLEFEPELLIPTILVFTIKSFLGSSDNKNKVIKAINNALKERDEKW

KEVYSFIVSNWMTKINTQFNKRKEQMYQALQNQVNAIKTIIESKYNSYTLEEKNELTNKYDIKQIENE

LNQKVSIAMNNIDRFLTESSISYLMKLINEVKINKLREYDENVKTYLLNYIIQHGSILGESQQELNSM

VTDTLNNSIPFKLSSYTDDKILISYFNKFFKRIKSSSVLNMRYKNDKYVDTSGYDSNININGDVYKYP

TNKNQFGIYNDKLSEVNISQNDYIIYDNKYKNFSISFWVRIPNYDNKIVNVNNEYTIINCMRDNNSGW

KVSLNHNEIIWTLQDNAGINQKLAFNYGNANGISDYINKWIFVTITNDRLGDSKLYINGNLIDQKSIL

NLGNIHVSDNILFKIVNCSYTRYIGIRYFNIFDKELDETEIQTLYSNEPNTNILKDFWGNYLLYDKEY

YLLNVLKPNNFIDRRKDSTLSINNIRSTILLANRLYSGIKVKIQRVNNSSTNDNLVRKNDQVYINFVA

SKTHLFPLYADTATTNKEKTIKISSSGNRFNQVVVMNSVGNNCTMNFKNNNGNNIGLLGFKADTVVAS

TWYYTHMRDHTNSNGCFWNFISEEHGWQEK.

(Nucleotide Sequence of BoNT/A1C1 with a C1 Activation Loop)

SEQ ID NO: 12

ATGCCATTCGTCAACAAGCAATTCAACTACAAAGACCCAGTCAACGGCGTCGACATCGCATACATCAA

GATTCCGAACGCCGGTCAAATGCAGCCGGTTAAGGCTTTTAAGATCCACAACAAGATTTGGGTTATCC

CGGAGCGTGACACCTTCACGAACCCGGAAGAAGGCGATCTGAACCCGCCACCGGAAGCGAAGCAAGTC

CCTGTCAGCTACTACGATTCGACGTACCTGAGCACGGATAACGAAAAGATAACTACCTGAAAGGTGT

GACCAAGCTGTTCGAACGTATCTACAGCACGGATCTGGGTCGCATGCTGCTGACTAGCATTGTTCGCG

GTATCCCGTTCTGGGGTGGTAGCACGATTGACACCGAACTGAAGGTTATCGACACTAACTGCATTAAC

GTTATTCAACCGGATGGTAGCTATCGTAGCGAAGAGCTGAATCTGGTCATCATTGGCCCGAGCGCAGA

CATTATCCAATTCGAGTGCAAGAGCTTTGGTCACGAGGTTCTGAATCTGACCCGCAATGGCTATGGTA

GCACCCAGTACATTCGTTTTTCGCCGGATTTTACCTTCGGCTTTGAAGAGAGCCTGGAGGTTGATACC

AATCCGTTGCTGGGTGCGGGCAAATTCGCTACCGATCCGGCTGTCACGCTGGCCCATgAACTGATCcA

CGCAGGCCACCGCCTGTACGGCATTGCCATCAACCCAAACCGTGTGTTCAAGGTTAATACGAATGCAT

ACTACGAGATGAGCGGCCTGGAAGTCAGCTTCGAAGAACTGCGCACCTTCGGTGGCCATGACGCTAAA

TTCATTGACAGCTTGCAAGAGAATGAGTTCCGTCTGTACTACTATAACAAATTCAAAGACATTGCAAG

CACGTTGAACAAGGCCAAAAGCATCGTTGGTACTACCGCGTCGTTGCAGTATATGAAGAATGTGTTTA

AAGAGAAGTACCTGCTGTCCGAGGATACCTCCGGCAAGTTTAGCGTTGATAAGCTGAAGTTTGACAAA

CTGTACAAGATGCTGACCGAGATTTACACCGAGGACAACTTTGTGAAATTCTTCAAAGTGTTGAATCG

TAAAAACCTATCTGAATTTTGACAAAGCGGTTTTCAAGATTAACATCGTGCCGAAGGTGAACTACACCA

TCTATGACGGTTTTAACCTGCGTAACACCAACCTGGCGGCGAACTTTAACGGTCAGAATACGGAAATC

AACAACATGAATTTCACGAAGTTGAAGAACTTCACGGGTCTGTTCGAGTTCTATAAGCTGCTGTGCCA

CAAAGCGATTGATGGCCGCTCTCTCTATAACAAAACGCTGGATTGCATTAAGGTAAACAATTGGGATC

TGTTCTTTTCGCCATCCGAAGATAATTTTACCAACGACCTGAACAAGGGTGAAGAAATCACCAGCGAT

ACGAATATTGAAGCAGCGGAAGAGAATATCAGCCTGGATCTGATCCAGCAGTACTATCTGACCTTTAA

CTTCGACAATGAACCGGAGAACATTAGCATTGAGAATCTGAGCAGCGACATTATCGGTCAGCTGGAAC

TGATGCCGAATATCGAACGTTTCCCGAACGGCAAAAAGTACGAGCTGGACAAGTACACTATGTTCCAT

TACCTGCGTGCACAGGAGTTTGAACACGGTAAAAGCCGTATCGCGCTGACCAACAGCGTTAACGAGGC

CCTGCTGAACCCGAGCCGTGTCTATACCTTCTTCAGCAGCGACTATGTTAAGAAAGTGAACAAAGCCA

CTGAGGCCGCGATGTTCCTGGGCTGGGTGGAACAGCTGGTATATGACTTCACGGACGAGACGAGCGAA

GTGAGCACTACCGACAAAATTGCTGATATTACCATCATTATCCCGTATATTGGTCCGGCACTGAACAT

-continued

TGGCAACATGCTGTACAAAGACGATTTTGTGGGTGCCCTGATCTTCTCCGGTGCCGTGATTCTGCTGG

AGTTCATTCCGGAGATTGCGATCCCGGTGTTGGGTACCTTCGCGCTGGTGTCCTACATCGCGAATAAG

GTTCTGACGGTTCAGACCATCGATAACGCGCTGTCGAAACGTAATGAAAAATGGGACGAGGTTTACAA

ATACATTGTTACGAATTGGCTGGCGAAAGTCAATACCCAGATCGACCTGATCCGTAAGAAAATGAAAG

AGGCGCTGGAGAATCAGGCGGAGGCCACCAAAGCAATTATCAACTACCAATACAACCAGTACACGGAA

GAAGAGAAGAATAACATTAACTTCAATATCGATGATTTGAGCAGCAAGCTGAATGAATCTATCAACAA

AGCGATGATCAATATCAACAAGTTTTTGAATCAGTGTAGCGTTTCGTACCTGATGAATAGCATGATTC

CGTATGGCGTCAAACGTCTGGAGGACTTCGACGCCAGCCTGAAAGATGCGTTGCTGAAATACATTTAC

GACAATCGTGGTACGCTGATTGGCCAAGTTGACCGCTTGAAAGACAAAGTTAACAATACCCTGAGCAC

CGACATCCCATTTCAACTGAGCAAGTATGTTGATAATCAACGTCTGTTGAGCACTTTCACCGAGTATA

TCAAAAACATTAATGACAGCAAAATTCTGAGCCTGCAGAATCGTAAGAATACGCTGGTAGATACCAGT

GGATATAATGCGGAAGTCTCAGAAGAGGGTGATGTACAGCTGAACCCGATCTTTCCGTTCGACTTTAA

ACTGGGGTCTAGTGGTGAAGATCGCGGTAAAGTGATCGTTACCCAAAACGAGAACATTGTGTATAACA

GCATGTACGAGAGTTTCTCAATTTCTTTCTGGATTCGCATCAATAAATGGGTTTCTAATTTGCCTGGC

TATACCATCATTGATAGCGTCAAAAACAACTCGGGCTGGTCGATTGGCATTATTAGCAACTTTCTGGT

GTTTACCCTGAAACAGAATGAGGATTCGGAACAGAGCATTAACTTCTCCTACGACATCAGCAACAATG

CACCAGGGTATAACAAATGGTTCTTCGTAACGGTGACGAACAATATGATGGGCAATATGAAAATCTAC

ATTAACGGGAAACTTATCGACACCATTAAAGTGAAAGAGCTTACTGGGATCAATTTTAGTAAAACCAT

TACCTTTGAGATCAACAAAATTCCGGACACGGGTCTGATTACCTCCGATTCGGATAATATCAATATGT

GGATTCGCGACTTTTATATCTTCGCCAAAGAACTTGATGGCAAAGATATCAACATTTTGTTTAATTCC

CTGCAGTATACCAATGTCGTTAAGGACTATTGGGGCAATGATCTCCGCTACAATAAAGAATACTACAT

GGTTAACATCGACTATCTCAATCGCTACATGTATGCTAACTCGCGTCAAATTGTGTTTAACACACGTC

GTAACAACAACGATTTTAACGAAGGTTATAAAATCATTATCAAACGGATCCGCGGCAATACGAACGAT

ACTCGTGTTCGTGGCGGTGACATTCTGTATTTCGACATGACGATTAATAATAAAGCGTACAATCTGTT

CATGAAGAACGAAACCATGTACGCCGATAACCATTCCACTGAAGATATCTACGCAATCGGACTTCGCG

AACAGACCAAAGACATTAACGACAACATCATCTTTCAGATTCAACCGATGAATAATACCTACTACTAT

GCCTCCCAGATCTTCAAAAGTAATTTCAACGGCGAAAACATTTCAGGCATTTGCTCAATCGGCACTTA

TCGGTTCCGGTTAGGTGGTGATTGGTATCGTCACAACTACCTTGTTCCCACAGTGAAACAAGGCAACT

ATGCATCGCTCTTAGAAAGCACATCTACGCATTGGGGTTTTGTGCCAGTCAGTGAATAA (Polypeptide Sequence of BoNT/A1C1 with a C1 Activation Loop)

SEQ ID NO: 13

MPFVNKQFNYKDPVNGVDIAYIKIPNAGQMQPVKAFKIHNKIWVIPERDTFTNPEEGDLNPPPEAKQV

PVSYYDSTYLSTDNEKDNYLKGVTKLFERIYSTDLGRMLLTSIVRGIPFWGGSTIDTELKVIDTNCIN

VIQPDGSYRSEELNLVIIGPSADIIQFECKSFGHEVLNLTRNGYGSTQYIRFSPDFTFGFEESLEVDT

NPLLGAGKFATDPAVTLAHELIHAGHRLYGIAINPNRVFKVNTNAYYEMSGLEVSFEELRTFGGHDAK

FIDSLQENEFRLYYYNKFKDIASTLNKAKSIVGTTASLQYMKNVFKEKYLLSEDTSGKFSVDKLKFDK

LYKMLTEIYTEDNFVKFFKVLNRKTYLNFDKAVFKINIVPKVNYTIYDGFNLRNTNLAANFNGQNTEI

NNMNFTKLKNFTGLFEFYKLL<u>CHKAIDGRSLYNKTLDC</u>IKVNNWDLFFSPSEDNFTNDLNKGEEITSD

TNIEAAEENISLDLIQQYYLTFNFDNEPENISIENLSSDIIGQLELMPNIERFPNGKKYELDKYTMFH

YLRAQEFEHGKSRIALTNSVNEALLNPSRVYTFFSSDYVKKVNKATEAAMFLGWVEQLVYDFTDETSE

VSTTDKIADITIIIPYIGPALNIGNMLYKDDFVGALIFSGAVILLEFIPEIAIPVLGTFALVSYIANK

-continued

VLTVQTIDNALSKRNEKWDEVYKYIVTNWLAKVNTQIDLIRKKMKEALENQAEATKAIINYQYNQYTE

EEKNNINFNIDDLSSKLNESINKAMININKFLNQCSVSYLMNSMIPYGVKRLEDFDASLKDALLKYIY

DNRGTLIGQVDRLKDKVNNTLSTDIPFQLSKYVDNQRLLSTFTEYIKNINDSKILSLQNRKNTLVDTS

GYNAEVSEEGDVQLNPIFPFDFKLGSSGEDRGKVIVTQNENIVYNSMYESFSISFWIRINKWVSNLPG

YTIIDSVKNNSGWSIGIISNFLVFTLKQNEDSEQSINFSYDISNNAPGYNKWFFVTVTNNMMGNMKIY

INGKLIDTIKVKELTGINFSKTITFEINKIPDTGLITSDSDNINMWIRDFYIFAKELDGKDINILFNS

LQYTNVVKDYWGNDLRYNKEYYMVNIDYLNRYMYANSRQIVFNTRRNNNDFNEGYKIIIKRIRGNTND

TRVRGGDILYFDMTINNKAYNLFMKNETMYADNHSTEDIYAIGLREQTKDINDNIIFQIQPMNNTYYY

ASQIFKSNFNGENISGICSIGTYRFRLGGDWYRHNYLVPTVKQGNYASLLESTSTHWGFVPVSE (Nucleotide Sequence of BoNT/C1(O) (Endonedative))

SEQ ID NO: 14

ATGCCGATCACGATTAATAATTTCAACTATAGCGATCCGGTGGACAATAAGAATATTCTGTATCGGA

TACTCATCTGAATACGCTGGCTAACGAACCGGAGAAAGCGTTCCGCATCACAGGCAACATCTGGGTTA

TTCCCGATCGCTTTTCACGCAACAGCAACCCTAATCTGAACAAACCTCCTCGTGTCACCAGTCCTAAA

TCCGGTTATTACGACCCAAACTATCTGAGTACGGATAGCGATAAAGATCCCTTTCTGAAAGAGATCAT

TAAGCTGTTCAAACGCATTAACTCTCGCGAAATTGGGGAAGAGCTGATCTATCGGCTTTCGACAGATA

TCCCGTTCCCAGGTAACAATAATACCCCGATTAATACTTTCGACTTTGATGTTGATTTCAATTCTGTG

GATGTGAAAACGCGTCAAGGCAATAATTGGGTGAAAACTGGTAGCATTAACCCGAGTGTAATTATCAC

AGGTCCCCGTGAGAACATCATCGACCCGGAAACCTCTACCTTCAAGCTGACGAACAACACGTTTGCTG

CACAGGAAGGGTTTGGTGCCCTGTCAATCATTTCCATCTCACCGCGTTTCATGTTAACCTACTCCAAT

GCCACAAATGATGTTGGCGAAGGACGTTTTAGCAAATCAGAATTTTGCATGGACCCAATTCTCATTCT

GATGGgCacGCTGAACaATGCGATGCACAACTTGTATGGCATTGCTATTCCAAACGATCAAACCATTA

GCTCCGTTACCAGTAATATCTTCTATAGCCAGTATAATGTCAAATTGGAGTATGCCGAAATTTACGCC

TTTGGAGGCCCCGACCATTGACCTGATTCCGAAATCTGCACGCAAATACTTCGAAGAAAAGGCGTTAGA

TTACTATCGCAGCATCGCGAAACGCCTGAACTCGATTACCACGGCCAATCCGTCGTCGTTCAACAAAT

ACATTGGTGAATATAAACAGAAACTGATTCGCAAATATCGGTTTGTCGTAGAAAGCTCTGGTGAAGTG

ACTGTAAACCGCAACAAATTTGTCGAACTCTACAACGAGTTGACCCAAATCTTTACCGAGTTTAACTA

CGCAAAGATCTATAACGTACAGAACCGCAAGATTTATCTTAGCAATGTATACACACCGGTTACTGCGA

ACATCTTAGACGACAATGTGTATGATATTCAGAATGGCTTTAACATCCCGAAATCAAATCTGAACGTT

CTGTTTATGGGCCAGAACCTGAGTCGTAATCCAGCACTGCGTAAAGTGAACCCGGAAAATATGCTCTA

CTTGTTTACCAAATTTTGCCACAAAGCGATTGATGGCCGCTCTCTCTATAACAAAACGCTGGATTGTC

GTGAGTTACTTGTGAAGAACACTGATTTACCGTTCATTGGGGATATCTCCGACGTGAAAACCGATATC

TTCCTGCGCAAAGACATTAATGAAGAAACGGAAGTCATCTATTACCCCGACAATGTGAGCGTTGATCA

GGTCATTTTATCGAAGAACACCTCCGAACATGGTCAGTTGGATTTGCTGTACCCTAGCATTGACTCGG

AGAGTGAAATCCTTCCGGGCGAAAATCAAGTGTTTTACGACAACCGTACCCAAAATGTTGATTATTTG

AATTCTTATTACTACCTGGAATCTCAGAAATTGAGCGACAATGTGGAAGATTTCACGTTCACACGCTC

CATTGAGGAAGCGCTGGATAATAGCGCGAAAGTGTATACGTATTTCCCTACCTTGGCGAATAAAGTAA

ATGCTGGTGTCCAGGGAGGCTTATTTCTGATGTGGGCGAATGATGTGGTAGAAGATTTTACGACCAAT

ATTTTGCGTAAGGACACCTTAGATAAAATTAGCGATGTTAGCGCCATCATCCCCTATATTGGCCCAGC

ACTGAATATCTCGAACTCTGTGCGTCGCGGAAACTTCACCGAAGCATTTGCGGTGACCGGGGTTACTA

TTCTGTTGGAAGCCTTTCCGGAGTTTACTATTCCGGCGCTGGGTGCGTTTGTGATTTATTCGAAAGTA

CAAGAACGCAATGAAATTATCAAAACCATCGATAATTGCCTGGAACAACGCATTAAACGCTGGAAGGA

-continued

```
TTCTTATGAATGGATGATGGGCACCTGGTTATCCCGTATTATCACACAGTTTAACAACATCTCGTATC

AGATGTACGATTCACTGAACTACCAAGCAGGGGCGATCAAAGCCAAGATCGACTTAGAATACAAGAAA

TATTCAGGTAGCGATAAAGAGAATATTAAAAGCCAGGTTGAAAACCTGAAGAACTCTCTGGATGTCAA

AATTTCAGAGGCTATGAACAACATTAACAAATTTATCCGCGAATGTAGCGTCACGTATCTGTTTAAAA

ACATGCTCCCGAAAGTGATTGATGAGCTCAACGAGTTTGATCGCAACACAAAGGCCAAACTGATTAAC

CTGATTGATAGTCACAATATTATTTTAGTCGGTGAAGTTGACAAGCTGAAGGCTAAGGTCAATAACAG

CTTTCAGAACACTATTCCGTTTAATATTTTCTCCTATACGAACAATAGTCTGCTGAAAGACATTATCA

ACGAATACTTCAACAATATTAATGACAGCAAAATTCTGAGCCTGCAGAATCGTAAGAATACGCTGGTA

GATACCAGTGGATATAATGCGGAAGTCTCAGAAGAGGGTGATGTACAGCTGAACCCGATCTTTCCGTT

CGACTTTAAACTGGGGTCTAGTGGTGAAGATCGCGGTAAAGTGATCGTTACCCAAAACGAGAACATTG

TGTATAACAGCATGTACGAGAGTTTCTCAATTTCTTTCTGGATTCGCATCAATAAATGGGTTTCTAAT

TTGCCTGGCTATACCATCATTGATAGCGTCAAAAACAACTCGGGCTGGTCGATTGGCATTATTAGCAA

CTTTCTGGTGTTTACCCTGAAACAGAATGAGGATTCGGAACAGAGCATTAACTTCTCCTACGACATCA

GCAACAATGCACCAGGGTATAACAAATGGTTCTTCGTAACGGTGACGAACAATATGATGGGCAATATG

AAAATCTACATTAACGGGAAACTTATCGACACCATTAAAGTGAAAGAGCTTACTGGGATCAATTTTAG

TAAAACCATTACCTTTGAGATCAACAAAATTCCGGACACGGGTCTGATTACCTCCGATTCGGATAATA

TCAATATGTGGATTCGCGACTTTTATATCTTCGCCAAAGAACTTGATGGCAAAGATATCAACATTTTG

TTTAATTCCCTGCAGTATACCAATGTCGTTAAGGACTATTGGGGCAATGATCTCCGCTACAATAAAGA

ATACTACATGGTTAACATCGACTATCTCAATCGCTACATGTATGCTAACTCGCGTCAAATTGTGTTTA

ACACACGTCGTAACAACAACGATTTTAACGAAGGTTATAAAATCATTATCAAACGGATCCGCGGCAAT

ACGAACGATACTCGTGTTCGTGGCGGTGACATTCTGTATTTCGACATGACGATTAATAATAAAGCGTA

CAATCTGTTCATGAAGAACGAAACCATGTACGCCGATAACCATTCCACTGAAGATATCTACGCAATCG

GACTTCGCGAACAGACCAAAGACATTAACGACAACATCATCTTTCAGATTCAACCGATGAATAATACC

TACTACTATGCCTCCCAGATCTTCAAAAGTAATTTCAACGGCGAAAACATTTCAGGCATTTGCTCAAT

CGGCACTTATCGGTTCCGGTTAGGTGGTGATTGGTATCGTCACAACTACCTTGTTCCCACAGTGAAAC

AAGGCAACTATGCATCGCTCTTAGAAAGCACATCTACGCATTGGGGTTTTGTGCCAGTCAGTGAAtaa tg
```

(Polypeptide Sequence of BoNT/C1(0) (Endoneqative))

SEQ ID NO: 15

```
MPITNNFNYSDPVDNKNILYLDTHLNTLANEPEKAFRITGNIWVIPDRFSRNSNPNLNKPPRVTSPK

SGYYDPNYLSTDSDKDPFLKEIIKLFKRINSREIGEELIYRLSTDIPFPGNNNTPINTFDFDVDFNSV

DVKTRQGNNWVKTGSINPSVIITGPRENIIDPETSTFKLTNNTFAAQEGFGALSIISISPRFMLTYSN

ATNDVGEGRFSKSEFCMDPILILMGTLNNAMHNLYGIAIPNDQTISSVTSNIFYSQYNVKLEYAEIYA

FGGPTIDLIPKSARKYFEEKALDYYRSIAKRLNSITTANPSSFNKYIGEYKQKLIRKYRFVVESSGEV

TVNRNKFVELYNELTQIFTEFNYAKIYNVQNRKIYLSNVYTPVTANILDDNVYDIQNGFNIPKSNLNV

LFMGQNLSRNPALRKVNPENMLYLFTKFCHKAIDGRSLYNKTLDCRELLVKNTDLPFIGDISDVKTDI

FLRKDINEETEVIYYPDNVSVDQVILSKNTSEHGQLDLLYPSIDSESEILPGENQVFYDNRTQNVDYL

NSYYYLESQKLSDNVEDFTFTRSIEEALDNSAKVYTYFPTLANKVNAGVQGGLFLMWANDVVEDFTTN

ILRKDTLDKISDVSAIIPYIGPALNISNSVRRGNFTEAFAVTGVTILLEAFPEFTIPALGAFVIYSKV

QERNEIIKTIDNCLEQRIKRWKDSYEWMMGTWLSRIITQFNNISYQMYDSLNYQAGAIKAKIDLEYKK

YSGSDKENIKSQVENLKNSLDVKISEAMNNINKFIRECSVTYLFKNMLPKVIDELNEFDRNTKAKLIN
```

-continued
LIDSHNIILVGEVDKLKAKVNNSFQNTIPFNIFSYTNNSLLKDIINEYFNNINDSKILSLQNRKNTLV

DTSGYNAEVSEEGDVQLNPIFPFDFKLGSSGEDRGKVIVTQNENIVYNSMYESFSISFWIRINKWVSN

LPGYTIIDSVKNNSGWSIGIISNFLVFTLKQNEDSEQSINFSYDISNNAPGYNKWFFVTVTNNMMGNM

KIYINGKLIDTIKVKELTGINFSKTITFEINKIPDTGLITSDSDNINMWIRDFYIFAKELDGKDINIL

FNSLQYTNVVKDYWGNDLRYNKEYYMVNIDYLNRYMYANSRQIVFNTRRNNNDFNEGYKIIIKRIRGN

TNDTRVRGGDILYFDMTINNKAYNLFMKNETMYADNHSTEDIYAIGLREQTKDINDNIIFQIQPMNNT

YYYASQIFKSNFNGENISGICSIGTYRFRLGGDWYRHNYLVPTVKQGNYASLLESTSTHWGFVPVSE (Nucleotide Sequence of BoNT/C1)

SEQ ID NO: 16

ATGCCGATCACGATTAATAATTTCAACTATAGCGATCCGGTGGACAATAAGAATATTCTGTATCTGGA

TACTCATCTGAATACGCTGGCTAACGAACCGGAGAAAGCGTTCCGCATCACAGGCAACATCTGGGTTA

TTCCCGATCGCTTTTCACGCAACAGCAACCCTAATCTGAACAAACCTCCTCGTGTCACCAGTCCTAAA

TCCGGTTATTACGACCCAAACTATCTGAGTACGCGGATAGCGATAAAGATCCCTTTCTGAAAGAGATCAT

TAAGCTGTTCAAACGCATTAACTCTCGCGAAATTGGGGAAGAGCTGATCTATCGGCTTTCGACAGATA

TCCCGTTCCCAGGTAACAATAATACCCCGATTAATACTTTCGACTTTGATGTTGATTTCAATTCTGTG

GATGTGAAAACGCGTCAAGGCAATAATTGGGTGAAAACTGGTAGCATTAACCCGAGTGTAATTATCAC

AGGTCCCCGTGAGAACATCATCGACCCGGAAACCTCTACCTTCAAGCTGACGAACAACACGTTTGCTG

CACAGGAAGGGTTTGGTGCCCTGTCAATCATTTCCATCTCACCGCGTTTCATGTTAACCTACTCCAAT

GCCACAAATGATGTTGGCGAAGGACGTTTTAGCAAATCAGAATTTTGCATGGACCCAATTCTCATTCT

GATGCACGAGCTGAACCATGCGATGCACAACTTGTATGGCATTGCTATTCCAAACGATCAAACCATTA

GCTCCGTTACCAGTAATATCTTCTATAGCCAGTATAATGTCAAATTGGAGTATGCCGAAATTTACGCC

TTTGGAGGCCCCGACCATTGACCTGATTCCGAAATCTGCACGCAAATACTTCGAAGAAAAGGCGTTAGA

TTACTATCGCAGCATCGCGAAACGCCTGAACTCGATTACCACGGCCAATCCGTCGTCGTTCAACAAAT

ACATTGGTGAATATAAACAGAAACTGATTCGCAAATATCGGTTTGTCGTAGAAAGCTCTGGTGAAGTG

ACTGTAAACCGCAACAAATTTGTCGAACTCTACAACGAGTTGACCCAAATCTTTACCGAGTTTAACTA

CGCAAAGATCTATAACGTACAGAACCGCAAGATTTATCTTAGCAATGTATACACACCGGTTACTGCGA

ACATCTTAGACGACAATGTGTATGATATTCAGAATGGCTTTAACATCCCGAAATCAAATCTGAACGTT

CTGTTTATGGGCCAGAACCTGAGTCGTAATCCAGCACTGCGTAAAGTGAACCCGGAAAATATGCTCTA

CTTGTTTACCAAATTTTGCCACAAAGCGATTGATGGCCGCTCTCTCTATAACAAAACGCTGGATTGTC

GTGAGTTACTTGTGAAGAACACTGATTTACCGTTCATTGGGGATATCTCCGACGTGAAAACCGATATC

TTCCTGCGCAAAGACATTAATGAAGAAACGGAAGTCATCTATTACCCCGACAATGTGAGCGTTGATCA

GGTCATTTTATCGAAGAACACCTCCGAACATGGTCAGTTGGATTGCTGTACCCTAGCATTGACTCGG

AGAGTGAAATCCTTCCGGGCGAAATCAAGTGTTTTACGACAACCGTACCCAAATGTTGATTATTTG

AATTCTTATTACTACCTGGAATCTCAGAAATTGAGCGACAATGTGGAAGATTTCACGTTCACACGCTC

CATTGAGGAAGCGCTGGATAATAGCGCGAAAGTGTATACGTATTTCCCTACCTTGGCGAATAAAGTAA

ATGCTGGTGTCCAGGGAGGCTTATTTCTGATGTGGGCGAATGATGTGGTAGAAGATTTTACGACCAAT

ATTTTGCGTAAGGACACCTTAGATAAAATTAGCGATGTTAGCGCCATCATCCCCTATATTGGCCCAGC

ACTGAATATCTCGAACTCTGTGCGTCGCGGAAACTTCACCGAAGCATTTGCGGTGACCGGGGTTACTA

TTCTGTTGGAAGCCTTTCCGGAGTTTACTATTCCGGCGCTGGGTGCGTTTGTGATTTATTCGAAAGTA

CAAGAACGCAATGAAATTATCAAAACCATCGATAATTGCCTGGAACAACGCATTAAACGCTGGAAGGA

TTCTTATGAATGGATGATGGGCACCTGGTTATCCCGTATTATCACACAGTTTAACAACATCTCGTATC

AGATGTACGATTCACTGAACTACCAAGCAGGGGCGATCAAAGCCAAGATCGACTTAGAATACAAGAAA

-continued

```
TATTCAGGTAGCGATAAAGAGAATATTAAAAGCCAGGTTGAAAACCTGAAGAACTCTCTGGATGTCAA

AATTTCAGAGGCTATGAACAACATTAACAAATTTATCCGCGAATGTAGCGTCACGTATCTGTTTAAAA

ACATGCTCCCGAAAGTGATTGATGAGCTCAACGAGTTTGATCGCAACACAAAGGCCAAACTGATTAAC

CTGATTGATAGTCACAATATTATTTTAGTCGGTGAAGTTGACAAGCTGAAGGCTAAGGTCAATAACAG

CTTTCAGAACACTATTCCGTTTAATATTTTCTCCTATACGAACAATAGTCTGCTGAAAGACATTATCA

ACGAATACTTCAACAATATTAATGACAGCAAAATTCTGAGCCTGCAGAATCGTAAGAATACGCTGGTA

GATACCAGTGGATATAATGCGGAAGTCTCAGAAGAGGGTGATGTACAGCTGAACCCGATCTTTCCGTT

CGACTTTAAACTGGGGTCTAGTGGTGAAGATCGCGGTAAAGTGATCGTTACCCAAAACGAGAACATTG

TGTATAACAGCATGTACGAGAGTTTCTCAATTTCTTTCTGGATTCGCATCAATAAATGGGTTTCTAAT

TTGCCTGGCTATACCATCATTGATAGCGTCAAAAACAACTCGGGCTGGTCGATTGGCATTATTAGCAA

CTTTCTGGTGTTTACCCTGAAACAGAATGAGGATTCGGAACAGAGCATTAACTTCTCCTACGACATCA

GCAACAATGCACCAGGGTATAACAAATGGTTCTTCGTAACGGTGACGAACAATATGATGGGCAATATG

AAAATCTACATTAACGGGAAACTTATCGACACCATTAAAGTGAAAGAGCTTACTGGGATCAATTTTAG

TAAAACCATTACCTTTGAGATCAACAAAATTCCGGACACGGGTCTGATTACCTCCGATTCGGATAATA

TCAATATGTGGATTCGCGACTTTTATATCTTCGCCAAAGAACTTGATGGCAAAGATATCAACATTTTG

TTTAATTCCCTGCAGTATACCAATGTCGTTAAGGACTATTGGGGCAATGATCTCCGCTACAATAAAGA

ATACTACATGGTTAACATCGACTATCTCAATCGCTACATGTATGCTAACTCGCGTCAAATTGTGTTTA

ACACACGTCGTAACAACAACGATTTTAACGAAGGTTATAAAATCATTATCAAACGGATCCGCGGCAAT

ACGAACGATACTCGTGTTCGTGGCGGTGACATTCTGTATTTCGACATGACGATTAATAATAAAGCGTA

CAATCTGTTCATGAAGAACGAAACCATGTACGCCGATAACCATTCCACTGAAGATATCTACGCAATCG

GACTTCGCGAACAGACCAAAGACATTAACGACAACATCATCTTTCAGATTCAACCGATGAATAATACC

TACTACTATGCCTCCCAGATCTTCAAAAAGTAATTTCAACGGCGAAAACATTTCAGGCATTTGCTCAAT

CGGCACTTATCGGTTCCGGTTAGGTGGTGATTGGTATCGTCACAACTACCTTGTTCCCACAGTGAAAC

AAGGCAACTATGCATCGCTCTTAGAAAGCACATCTACGCATTGGGGTTTTGTGCCAGTCAGTGAAtaa
```

(Polypeptide Sequence of BoNT/C1)

SEQ ID NO: 17

```
MPITINNFNYSDPVDNKNILYLDTHLNTLANEPEKAFRITGNIWVIPDRFSRNSNPNLNKPPRVTSPK

SGYYDPNYLSTDSDKDPFLKEIIKLFKRINSREIGEELIYRLSTDIPFPGNNNTPINTFDFDVDFNSV

DVKTRQGNNWVKTGSINPSVIITGPRENIIDPETSTFKLTNNTFAAQEGFGALSIISISPRFMLTYSN

ATNDVGEGRFSKSEFCMDPILILMHELNHAMHNLYGIAIPNDQTISSVTSNIFYSQYNVKLEYAEIYA

FGGPTIDLIPKSARKYFEEKALDYYRSIAKRLNSITTANPSSFNKYIGEYKQKLIRKYRFVVESSGEV

TVNRNKFVELYNELTQIFTEFNYAKIYNVQNRKIYLSNVYTPVTANILDDNVYDIQNGFNIPKSNLNV

LFMGQNLSRNPALRKVNPENMLYLFTKFCHKAIDGRSLYNKTLDCRELLVKNTDLPFIGDISDVKTDI

FLRKDINEETEVIYYPDNVSVDQVILSKNTSEHGQLDLLYPSIDSESEILPGENQVFYDNRTQNVDYL

NSYYYLESQKLSDNVEDFTFTRSIEEALDNSAKVYTYFPTLANKVNAGVQGGLFLMWANDVVEDFTTN

ILRKDTLDKISDVSAIIPYIGPALNISNSVRRGNFTEAFAVTGVTILLEAFPEFTIPALGAFVIYSKV

QERNEIIKTIDNCLEQRIKRWKDSYEWMMGTWLSRIITQFNNISYQMYDSLNYQAGAIKAKIDLEYKK

YSGSDKENIKSQVENLKNSLDVKISEAMNNINKFIRECSVTYLFKNMLPKVIDELNEFDRNTKAKLIN

LIDSHNIILVGEVDKLKAKVNNSFQNTIPFNIFSYTNNSLLKDIINEYFNNINDSKILSLQNRKNTLV

DTSGYNAEVSEEGDVQLNPIFPFDFKLGSSGEDRGKVIVTQNENIVYNSMYESFSISFWIRINKWVSN

LPGYTIIDSVKNNSGWSIGIISNFLVFTLKQNEDSEQSINFSYDISNNAPGYNKWFFVTVTNNMMGNM
```

-continued

KIYINGKLIDTIKVKELTGINFSKTITFEINKIPDTGLITSDSDNINMWIRDFYIFAKELDGKDINIL

FNSLQYTNVVKDYWGNDLRYNKEYYMVNIDYLNRYMYANSRQIVFNTRRNNNDFNEGYKIIIKRIRGN

TNDTRVRGGDILYFDMTINNKAYNLFMKNETMYADNHSTEDIYAIGLREQTKDINDNIIFQIQPMNNT

YYYASQIFKSNFNGENISGICSIGTYRFRLGGDWYRHNYLVPTVKQGNYASLLESTSTHWGFVPVSE (Enterokinase and Factor Xa Cleavage Site)
                                                             SEQ ID NO: 18
IDGR (Enterokinase and Factor Xa Cleavage Site Variant)
                                                             SEQ ID NO: 19
IEGR (BoNT/X Activation Loop)
                                                             SEQ ID NO: 20
CPRNGLLYNAIYRNSKNYLNNIDLEDKKTTSKTNVSYPCSLLNGC (BoNT/A1 & A6 Activation Loop)
                                                             SEQ ID NO: 21
CVRGIITSKTKSLDKGYNKALNDLC (BoNT/B2, B3 & B6 Activation Loop)
                                                             SEQ ID NO: 22
CKSVRAPGIC (BoNT/D Activation Loop)
                                                             SEQ ID NO: 23
CLRLTKNSRDDSTC (BoNT/E1 to E5, E9 & E12 Activation Loop)
                                                             SEQ ID NO: 24
CKNIVSVKGIRKSIC (BoNT/F1 and F6 Activation Loop)
                                                             SEQ ID NO: 25
CKSVIPRKGTKAPPRLC (BoNT/F2 and F3 Activation Loop)
                                                             SEQ ID NO: 26
CKSIIPRKGTKQSPSLC (BoNT/F4 Activation Loop)
                                                             SEQ ID NO: 27
CKSIIPRKGTKAPPRLC (BoNT/F5 Activation Loop)
                                                             SEQ ID NO: 28
CLNSSFKKNTKKPLC (BoNT/F7 Activation Loop)
                                                             SEQ ID NO: 29
CKSIVSKKGTKNSLC (TeNT Activation Loop)
                                                             SEQ ID NO: 30
CKKIIPPTNIRENLYNRTASLTDLGGELC (BoNT/G Activation Loop)
                                                             SEQ ID NO: 31
CKPVMYKNTGKSEQC (Nucleotide Sequence of Wild-Type BoNT/X-10HT)
                                                             SEQ ID NO: 32
ATGAAACTGGAAATCAACAAATTCAACTACAACGATCCGATCGATGGCATTAATGTTATTACCATGCGTCCGCCT

CGTCATAGCGATAAAATCAATAAAGGTAAAGGTCCGTTCAAAGCCTTTCAGGTGATTAAAAACATTTGGATTGTG

CCGGAACGCTACAACTTTACCAATAATACCAACGATCTGAACATTCCGAGCGAACCGATTATGGAAGCAGATGCC

ATTTATAACCCGAACTATCTGAATACCCCGAGCGAAAAAGATGAATTTCTGCAGGGTGTTATCAAAGTGCTGGAA

CGCATTAAAAGCAAACCGGAAGGTGAAAAACTGCTGGAACTGATTAGCAGCAGCATTCCGCTGCCGCTGGTTAGC

AATGGTGCACTGACCCTGAGCGATAATGAAACCATTGCATATCAAGAGAACAACAACATTGTGAGCAATCTGCAG

GCAAACCTGGTTATTTATGGTCCGGGTCCTGATATTGCAAATAATGCAACCTATGGTCTGTATAGCACCCCGATT

AGTAATGGTGAAGGTACACTGAGCGAAGTTAGCTTTAGCCCGTTTTATCTGAAACCGTTTGATGAAAGCTATGGC

-continued

```
AATTATCGTAGCCTGGTGAATATCGTGAACAAATTCGTGAAACGTGAATTTGCACCTGATCCGGCAAGCACCCTG

ATGCATGAACTGGTTCATGTTACCCATAATCTGTATGGTATTAGCAACCGCAACTTCTACTATAACTTTGACACC

GGCAAAATTGAAACCAGCCGTCAGCGAATAGCCTGATTTTTGAAGAACTGCTGACCTTTGGTGGCATTGATAGC

AAAGCAATTAGCAGCCTGATCATCAAGAAAATTATCGAAACCGCCAAGAACAACTATACCACGCTGATTAGCGAA

CGCCTGAATACCGTTACCGTTGAAAATGATCTGCTGAAATATATCAAAAACAAAATCCCGGTTCAGGGTCGTCTG

GGTAACTTTAAACTGGATACCGCAGAATTCGAGAAAAAGCTGAATACCATTCTGTTTGTGCTGAACGAAAGCAAT

CTGGCACAGCGTTTTAGCATTCTGGTTCGTAAACATTACCTGAAAGAACGTCCGATTGATCCGATTTATGTGAAC

ATTCTGGATGACAATAGCTACAGCACCCTGGAAGGTTTTAACATTAGCAGTCAGGGTAGCAATGATTTCCAAGGT

CAGCTGCTGGAAAGCAGCTATTTTGAAAAAATTGAAAGCAATGCCCTGCGTGCCTTCATTAAAATCTGTCCGCGT

AATGGTCTGCTGTATAATGCCATTTATCGCAACAGCAAAAACTACCTGAACAACATTGATCTGGAAGATAAAAAG

ACCACGAGCAAAACCAATGTTAGCTATCCGTGTAGCCTGCTGAATGGTTGTATTGAAGTTGAAAACAAAGACCTG

TTCCTGATTAGCAACAAAGATAGCCTGAACGATATTAACCTGAGCGAAGAAAAAATCAAACCGGAAACCACCGTG

TTCTTCAAAGATAAACTGCCTCCGCAGGATATTACGCTGAGCAATTATGATTTTACCGAAGCCAATAGCATTCCG

AGCATTAGCCAGCAGAACATTCTGGAACGTAATGAAGAACTGTATGAACCGATTCGCAATAGCCTGTTTGAAATC

AAAACCATCTATGTGGATAAGCTGACCACCTTTCATTTTCTGGAAGCCCAGAATATTGATGAGAGCATTGATAGC

AGCAAAATTCGTGTTGAACTGACCGATAGCGTTGATGAAGCACTGAGCAATCCGAATAAAGTTTATAGCCCGTTC

AAGAACATGAGCAACACCATTAATAGCATTGAAACCGGTATTACCAGCACCTACATCTTTTATCAGTGGCTGCGT

AGCATCGTGAAAGATTTTAGTGATGAAACCGGCAAAATCGACGTGATTGATAAAAGCAGCGATACCCTGGCAATT

GTTCCGTATATTGGTCCGCTGCTGAATATTGGTAATGATATTCGTCATGGCGATTTTGTGGGTGCAATTGAACTG

GCAGGCATTACCGCACTGCTGGAATATGTTCCGGAATTTACCATTCCGATTCTGGTTGGTCTGGAAGTTATTGGT

GGCGAACTGGCACGTGAACAGGTTGAAGCAATTGTTAATAATGCCCTGGATAAACGCGATCAGAAATGGGCAGAA

GTTTACAATATTACCAAAGCACAGTGGTGGGGCACCATTCATTTACAGATTAATACCCGTCTGGCCCATACCTAT

AAAGCCCTGAGCCGTCAGGCAAATGCCATTAAAATGAATATGGAATTTCAGCTGGCCAACTACAAAGGCAACATC

GATGATAAAGCCAAAATCAAAAACGCCATCAGCGAAACCGAAATCCTGCTGAACAAAAGCGTTGAACAGGCAATG

AAAAACACCGAGAAATTCATGATCAAACTGAGCAACAGCTATCTGACCAAAGAAATGATTCCGAAAGTGCAGGAT

AACCTGAAAAATTTCGATCTGGAAACCAAGAAAACCCTGGACAAATTTATCAAAGAGAAAGAGGACATTCTGGGC

ACCAATCTGAGCAGCAGCCTGCGTCGTAAAGTTAGCATTCGTCTGAATAAAAACATTGCCTTCGACATCAACGAT

ATCCCGTTTAGCGAATTTGATGATCTGATCAACCAGTACAAAAACGAGATCGAAGATTATGAAGTGCTGAATCTG

GGTGCAGAAGATGGGAAAATCAAAGATCTGAGCGGTACAACCAGCGATATCAATATTGGTTCAGATATCGAACTG

GCCGATGGTCGTGAAAATAAAGCCATTAAGATTAAAGGCAGCGAGAACAGCACCATCAAAATTGCAATGAACAAA

TATCTGCGTTTTAGCGCGACCGATAACTTTAGCATTAGCTTTTGGATCAAACATCCGAAACCGACCAATCTGCTT

AATAACGGTATTGAATATACCCTGGTCGAGAACTTTAATCAGCGTGGTTGGAAAATTAGCATCCAGGATAGCAAA

CTGATTTGGTATCTGCGCGATCACAATAACAGCATCAAAATCGTTACACCGGATTATATTGCGTTTAATGGCTGG

AACCTGATTACCATTACAAACAATCGTAGCAAAGGCAGCATTGTGTATGTGAACGGTAGCAAAATTGAAGAGAAG

GATATTAGCAGCATCTGGAATACCGAAGTGGATGATCCGATTATCTTTCGCCTGAAAAACAATCGCGATACCCAG

GCGTTTACCCTGCTGGATCAGTTTAGCATTTATCGGAAAGAACTGAACCAGAACGAAGTGGTGAAACTGTATAAC

TACTACTTCAACAGCAACTACATTCGCGATATTTGGGGTAATCCGCTGCAGTACAACAAAAAATACTATCTGCAG

ACCCAGGACAAACCTGGTAAAGGTCTGATCCGCGAATATTGGAGCAGCTTTGGTTATGATTATGTGATTCTGAGC

GATAGCAAGACGATTACCTTTCCGAATAATATCCGTTATGGTGCCCTGTATAACGGCAGCAAAGTTCTGATCAAA

AATAGCAAAAAACTGGATGGTCTGGTGCGCAATAAAGATTTCATTCAGCTGGAAATCGATGGCTATAATATGGGT
```

-continued

ATTAGCGCAGATCGCTTTAACGAGGATACCAACTATATTGGCACCACCTATGGTACAACCCATGATCTGACCACC

GATTTTGAAATTATTCAGCGCCAAGAGAAATACCGCAATTATTGTCAGCTGAAAACCCCGTATAACATCTTTCAT

AAAAGCGGTCTGATGAGCACCGAAACCAGCAAACCGACCTTTCATGATTATCGTGACTGGGTTTATAGCAGCGCA

TGGTATTTTCAGAACTATGAAAATCTGAACCTGCGCAAACATACCAAAACCAACTGGTATTTTATCCCGAAAGAT

GAAGGTTGGGATGAAGATCTTGAAGTTCTGTTTCAGGGTCCGCATCATCACCACCATCACCATCATCATCAC (Polypeptide Sequence of BoNT/X)

SEQ ID NO: 33

MKLEINKFNYNDPIDGINVITMRPPRHSDKINKGKGPPKAFQVIKNIWIVPERYNFTNNT

NDLNIPSEPIMEADAIYNPNYLNTPSEKDEFLQGVIKVLERIKSKPEGEKLLELISSSIP

LPLVSNGALTLSDNETIAYQENNNIVSNLQANLVIYGPGPDIANNATYGLYSTPISNGEG

TLSEVSFSPFYLKPFDESYGNYRSLVNIVNKFVKREFAPDPASTLMHELVHVTHNLYGIS

NRNFYYNFDTGKIETSRQQNSLIFEELLTFGGIDSKAISSLIIKKIIETAKNNYTTLISE

RLNTVTVENDLLKYIKNKIPVQGRLGNFKLDTAEFEKKLNTILFVLNESNLAQRFSILVR

KHYLKERPIDPIYVNILDDNSYSTLEGFNISSQGSNDFQGQLLESSYFEKIESNALRAFI

KICPRNGLLYNAIYRNSKNYLNNIDLEDKKTTSKTNVSYPCSLLNGCIEVENKDLFLISN

KDSLNDINLSEEKIKPETTVFFKDKLPPQDITLSNYDFTEANSIPSISQQNILERNEELY

EPIRNSLFEIKTIYVDKLTTFHFLEAQNIDESIDSSKIRVELTDSVDEALSNPNKVYSPF

KNMSNTINSIETGITSTYIFYQWLRSIVKDFSDETGKIDVIDKSSDTLAIVPYIGPLLNI

GNDIRHGDFVGAIELAGITALLEYVPEFTIPILVGLEVIGGELAREQVEAIVNNALDKRD

QKWAEVYNITKAQWWGTIHLQINTRLAHTYKALSRQANAIKMNMEFQLANYKGNIDDKAK

IKNAISETEILLNKSVEQAMKNTEKFMIKLSNSYLTKEMIPKVQDNLKNFDLETKKTLDK

FIKEKEDILGTNLSSSLRRKVSIRLNKNIAFDINDIPFSEFDDLINQYKNEIEDYEVLNL

GAEDGKIKDLSGTTSDINIGSDIELADGRENKAIKIKGSENSTIKIAMNKYLRFSATDNF

SISFWIKHPKPTNLLNNGIEYTLVENFNQRGWKISIQDSKLIWYLRDHNNSIKIVTPDYI

AFNGWNLITITNNRSKGSIVYVNGSKIEEKDISSIWNTEVDDPIIFRLKNNRDTQAFTLL

DQFSIYRKELNQNEVVKLYNYYFNSNYIRDIWGNPLQYNKKYYLQTQDKPGKGLIREYWS

SFGYDYVILSDSKTITFPNNIRYGALYNGSKVLIKNSKKLDGLVRNKDFIQLEIDGYNMG

ISADRFNEDTNYIGTTYGTTHDLTTDFEIIQRQEKYRNYCQLKTPYNIFHKSGLMSTETS

KPTFHDYRDWVYSSAWYFQNYENLNLRKHTKTNWYFIPKDEGWDED (Polypeptide Sequence of Wild-Type BoNT/X-10HT)

SEQ ID NO: 34

MKLEINKFNYNDPIDGINVITMRPPRHSDKINKGKGPPKAFQVIKNIWIVPERYNFTNNTNDLNIPSEPIMEADA

IYNPNYLNTPSEKDEFLQGVIKVLERIKSKPEGEKLLELISSSIPLPLVSNGALTLSDNETIAYQENNNIVSNLQ

ANLVIYGPGPDIANNATYGLYSTPISNGEGTLSEVSFSPFYLKPFDESYGNYRSLVNIVNKFVKREFAPDPASTL

MHELVHVTHNLYGISNRNFYYNFDTGKIETSRQQNSLIFEELLTFGGIDSKAISSLIIKKIIETAKNNYTTLISE

RLNTVTVENDLLKYIKNKIPVQGRLGNFKLDTAEFEKKLNTILFVLNESNLAQRFSILVRKHYLKERPIDPIYVN

ILDDNSYSTLEGFNISSQGSNDFQGQLLESSYFEKIESNALRAFIKICPRNGLLYNAIYRNSKNYLNNIDLEDKK

TTSKTNVSYPCSLLNGCIEVENKDLFLISNKDSLNDINLSEEKIKPETTVFFKDKLPPQDITLSNYDFTEANSIP

SISQQNILERNEELYEPIRNSLFEIKTIYVDKLTTFHFLEAQNIDESIDSSKIRVELTDSVDEALSNPNKVYSPF

KNMSNTINSIETGITSTYIFYQWLRSIVKDFSDETGKIDVIDKSSDTLAIVPYIGPLLNIGNDIRHGDFVGAIEL

AGITALLEYVPEFTIPILVGLEVIGGELAREQVEAIVNNALDKRDQKWAEVYNITKAQWWGTIHLQINTRLAHTY

KALSRQANAIKMNMEFQLANYKGNIDDKAKIKNAISETEILLNKSVEQAMKNTEKFMIKLSNSYLTKEMIPKVQD

NLKNEDLETKKTLDKFIKEKEDILGTNLSSSLRRKVSIRLNKNIAFDINDIPFSEFDDLINQYKNEIEDYEVLNL

-continued

GAEDGKIKDLSGTTSDINIGSDIELADGRENKAIKIKGSENSTIKIAMNKYLRFSATDNESISFWIKHPKPTNLL

NNGIEYTLVENFNQRGWKISIQDSKLIWYLRDHNNSIKIVTPDYIAFNGWNLITITNNRSKGSIVYVNGSKIEEK

DISSIWNTEVDDPIIFRLKNNRDTQAFTLLDQFSIYRKELNQNEVVKLYNYYFNSNYIRDIWGNPLQYNKKYYLQ

TQDKPGKGLIREYWSSFGYDYVILSDSKTITFPNNIRYGALYNGSKVLIKNSKKLDGLVRNKDFIQLEIDGYNMG

ISADRFNEDTNYIGTTYGTTHDLTTDFEIIQRQEKYRNYCQLKTPYNIFHKSGLMSTETSKPTFHDYRDWVYSSA

WYFQNYENLNLRKHTKTNWYFIPKDEGWDEDLEVLFQGPHHHHHHHHHH (BoNT/A - UniProt P10845)

MPFVNKQFNYKDPVNGVDIAYIKIPNVGQMQPVKAFKIHNKIWVIPERDTFTNPEEGDLN                     SEQ ID NO: 35

PPPEAKQVPVSYYDSTYLSTDNEKDNYLKGVTKLFERIYSTDLGRMLLTSIVRGIPFWGG

STIDTELKVIDTNCINVIQPDGSYRSEELNLVIIGPSADIIQFECKSFGHEVLNLTRNGY

GSTQYIRFSPDFTFGFEESLEVDTNPLLGAGKFATDPAVTLAHELIHAGHRLYGIAINPN

RVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKV

LNRKTYLNFDKAVFKINIVPKVNYTIYDGFNLRNTNLAANFNGQNTEINNMNFTKLKNFT

GLFEFYKLLCVRGIITSKTKSLDKGYNKALNDLCIKVNNWDLFFSPSEDNFTNDLNKGEE

ITSDTNIEAAEENISLDLIQQYYLTFNFDNEPENISIENLSSDIIGQLELMPNIERFPNG

KKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSG

AVILLEFIPEIAIPVLGTFALVSYIANKVLTVQTIDNALSKRNEKWDEVYKYIVTNWLAK

VNTQIDLIRKKMKEALENQAEATKAIINYQYNQYTEEEKNNINFNIDDLSSKLNESINKA

MININKFLNQCSVSYLMNSMIPYGVKRLEDFDASLKDALLKYIYDNRGTLIGQVDRLKDK

VNNTLSTDIPFQLSKYVDNQRLLSTFTEYIKNIINTSILNLRYESNHLIDLSRYASKINI

GSKVNFDPIDKNQIQLFNLESSKIEVILKNAIVYNSMYENFSTSFWIRIPKYFNSISLNN

EYTIINCMENNSGWKVSLNYGEIIWTLQDTQEIKQRVVFKYSQMINISDYINRWIFVTIT

NNRLNNSKIYINGRLIDQKPISNLGNIHASNNIMFKLDGCRDTHRYIWIKYFNLFDKELN

EKEIKDLYDNQSNSGILKDFWGDYLQYDKPYYMLNLYDPNKYVDVNNVGIRGYMYLKGPR

GSVMTTNIYLNSSLYRGTKFIIKKYASGNKDNIVRNNDRVYINVVVKNKEYRLATNASQA

GVEKILSALEIPDVGNLSQVVVMKSKNDQGITNKCKMNLQDNNGNDIGFIGFHQFNNIAK

LVASNWYNRQIERSSRTLGCSWEFIPVDDGWGERPL (BoNT/B - UniProt P10844)

MPVTINNFNYNDPIDNNNIIMMEPPFARGTGRYYKAFKITDRIWIIPERYTFGYKPEDFN                     SEQ ID NO: 36

KSSGIFNRDVCEYYDPDYLNTNDKKNIFLQTMIKLFNRIKSKPLGEKLLEMIINGIPYLG

DRRVPLEEFNTNIASVTVNKLISNPGEVERKKGIFANLIIFGPGPVLNENETIDIGIQNH

FASREGFGGIMQMKFCPEYVSVFNNVQENKGASIFNRRGYFSDPALILMHELIHVLHGLY

GIKVDDLPIVPNEKKFFMQSTDAIQAEELYTFGGQDPSIITPSTDKSIYDKVLQNFRGIV

DRLNKVLVCISDPNININIYKNKFKDKYKFVEDSEGKYSIDVESFDKLYKSLMFGFTETN

IAENYKIKTRASYFSDSLPPVKIKNLLDNEIYTIEEGFNISDKDMEKEYRGQNKAINKQA

YEEISKEHLAVYKIQMCKSVKAPGICIDVDNEDLFFIADKNSFSDDLSKNERIEYNTQSN

YIENDFPINELILDTDLISKIELPSENTESLTDFNVDVPVYEKQPAIKKIFTDENTIFQY

LYSQTFPLDIRDISLTSSFDDALLFSNKVYSFFSMDYIKTANKVVEAGLFAGWVKQIVND

-continued

FVIEANKSNTMDKIADISLIVPYIGLALNVGNETAKGNFENAFEIAGASILLEFIPELLI

PVVGAFLLESYIDNKNKIIKTIDNALTKRNEKWSDMYGLIVAQWLSTVNTQFYTIKEGMY

KALNYQAQALEEIIKYRYNIYSEKEKSNINIDFNDINSKLNEGINQAIDNINNFINGCSV

SYLMKKMIPLAVEKLLDFDNTLKKNLLNYIDENKLYLIGSAEYEKSKVNKYLKTIMPFDL

SIYTNDTILIEMFNKYNSEILNNIILNLRYKDNNLIDLSGYGAKVEVYDGVELNDKNQFK

LTSSANSKIRVTQNQNIIFNSVFLDFSVSFWIRIPKYKNDGIQNYIHNEYTIINCMKNNS

GWKISIRGNRIIWTLIDINGKTKSVFFEYNIREDISEYINRWFFVTITNNLNNAKIYING

KLESNTDIKDIREVIANGEIIFKLDGDIDRTQFIWMKYFSIFNTELSQSNIEERYKIQSY

SEYLKDFWGNPLMYNKEYYMFNAGNKNSYIKLKKDSPVGEILTRSKYNQNSKYINYRDLY

IGEKFIIRRKSNSQSINDDIVRKEDYIYLDFFNLNQEWRVYTYKYFKKEEEKLFLAPISD

SDEFYNTIQIKEYDEQPTYSCQLLFKKDEESTDEIGLIGIHRFYESGIVFEEYKDYFCIS

KWYLKEVKRKPYNLKLGCNWQFIPKDEGWTE (BoNT/C - UniProt P18640)                              SEQ ID NO: 37

MPITINNFNYSDPVDNKNILYLDTHLNTLANEPEKAFRITGNIWVIPDRFSRNSNPNLNK

PPRVTSPKSGYYDPNYLSTDSDKDPFLKEIIKLFKRINSREIGEELIYRLSTDIPFPGNN

NTPINTFDFDVDFNSVDVKTRQGNNWVKTGSINPSVIITGPRENIIDPETSTFKLTNNTF

AAQEGFGALSIISISPRFMLTYSNATNDVGEGRFSKSEFCMDPILILMHELNHAMHNLYG

IAIPNDQTISSVTSNIFYSQYNVKLEYAEIYAFGGPTIDLIPKSARKYFEEKALDYYRSI

AKRLNSITTANPSSFNKYIGEYKQKLIRKYRFVVESSGEVTVNRNKFVELYNELTQIFTE

FNYAKIYNVQNRKIYLSNVYTPVTANILDDNVYDIQNGFNIPKSNLNVLFMGQNLSRNPA

LRKVNPENMLYLFTKFCHKAIDGRSLYNKTLDCRELLVKNTDLPFIGDISDVKTDIFLRK

DINEETEVIYYPDNVSVDQVILSKNTSEHGQLDLLYPSIDSESEILPGENQVFYDNRTQN

VDYLNSYYYLESQKLSDNVEDFTFTRSIEEALDNSAKVYTYFPTLANKVNAGVQGGLFLM

WANDVVEDFTTNILRKDTLDKISDVSAIIPYIGPALNISNSVRRGNFTEAFAVTGVTILL

EAFPEFTIPALGAFVIYSKVQERNEIIKTIDNCLEQRIKRWKDSYEWMMGTWLSRIITQF

NNISYQMYDSLNYQAGAIKAKIDLEYKKYSGSDKENIKSQVENLKNSLDVKISEAMNNIN

KFIRECSVTYLFKNMLPKVIDELNEFDRNTKAKLINLIDSHNIILVGEVDKLKAKVNNSF

QNTIPFNIFSYTNNSLLKDIINEYFNNINDSKILSLQNRKNTLVDTSGYNAEVSEEGDVQ

LNPIFPFDFKLGSSGEDRGKVIVTQNENIVYNSMYESFSISFWIRINKWVSNLPGYTIID

SVKNNSGWSIGIISNFLVFTLKQNEDSEQSINFSYDISNNAPGYNKWFFVTVTNNMMGNM

KIYINGKLIDTIKVKELTGINFSKTITFEINKIPDTGLITSDSDNINMWIRDFYIFAKEL

DGKDINILFNSLQYTNVVKDYWGNDLRYNKEYYMVNIDYLNRYMYANSRQIVFNTRRNNN

DFNEGYKIIIKRIRGNTNDTRVRGGDILYFDMTINNKAYNLFMKNETMYADNHSTEDIYA

IGLREQTKDINDNIIFQIQPMNNTYYYASQIFKSNFNGENISGICSIGTYRFRLGGDWYR

HNYLVPTVKQGNYASLLESTSTHWGFVPVSE (BoNT/D - UniProt P19321)                              SEQ ID NO: 38

MTWPVKDFNYSDPVNDNDILYLRIPQNKLITTPVKAFMITQNIWVIPERFSSDTNPSLSK

PPRPTSKYQSYYDPSYLSTDEQKDTFLKGIIKLFKRINERDIGKKLINYLVVGSPFMGDS

STPEDTFDFTRHTTNIAVEKFENGSWKVTNIITPSVLIFGPLPNILDYTASLTLQGGQSN

PSFEGFGTLSILKVAPEFLLTFSDVTSNQSSAVLGKSIFCMDPVIALMHELTHSLHQLYG

INIPSDKRIRPQVSEGFFSQDGPNVQFEELYTFGGLDVEIIPQIERSQLREKALGHYKDI

-continued

AKRLNNINKTIPSSWISNIDKYKKIFSEKYNFDKDNTGNFVVNIDKFNSLYSDLTNVMSE

VVYSSQYNVKNRTHYFSRHYLPVFANILDDNIYTIRDGFNLTNKGFNIENSGQNIERNPA

LQKLSSESVVDLFTKVCLRLTKNSRDDSTCIKVKNNRLPYVADKDSISQEIFENKIITDE

TNVQNYSDKFSLDESILDGQVPINPEIVDPLLPNVNMEPLNLPGEEIVFYDDITKYVDYL

NSYYYLESQKLSNNVENITLTTSVEEALGYSNKIYTFLPSLAEKVNKGVQAGLFLNWANE

VVEDFTTNIMKKDTLDKISDVSVIIPYIGPALNIGNSALRGNFNQAFATAGVAFLLEGFP

EFTIPALGVFTFYSSIQEREKIIKTIENCLEQRVKRWKDSYQWMVSNWLSRITTQFNHIN

YQMYDSLSYQADAIKAKIDLEYKKYSGSDKENIKSQVENLKNSLDVKISEAMNNINKFIR

ECSVTYLFKNMLPKVIDELNKFDLRTKTELINLIDSHNIILVGEVDRLKAKVNESFENTM

PFNIFSYTNNSLLKDIINEYFNSINDSKILSLQNKKNALVDTSGYNAEVRVGDNVQLNTI

YTNDFKLSSSGDKIIVNLNNNILYSAIYENSSVSFWIKISKDLTNSHNEYTIINSIEQNS

GWKLCIRNGNIEWILQDVNRKYKSLIFDYSESLSHTGYTNKWFFVTITNNIMGYMKLYIN

GELKQSQKIEDLDEVKLDKTIVFGIDENIDENQMLWIRDFNIFSKELSNEDINIVYEGQI

LRNVIKDYWGNPLKFDTEYYIINDNYIDRYIAPESNVLVLVQYPDRSKLYTGNPITIKSV

SDKNPYSRILNGDNIILHMLYNSRKYMIIRDTDTIYATQGGECSQNCVYALKLQSNLGNY

GIGIFSIKNIVSKNKYCSQIFSSFRENTMLLADIYKPWRFSFKNAYTPVAVTNYETKLLS

TSSFWKFISRDPGWVE (BoNT/E - UniProt Q00496)

SEQ ID NO: 39

MPKINSFNYNDPVNDRTILYIKPGGCQEFYKSFNIMKNIWIIPERNVIGTTPQDFHPPTS

LKNGDSSYYDPNYLQSDEEKDRFLKIVTKIFNRINNNLSGGILLEELSKANPYLGNDNTP

DNQFHIGDASAVEIKFSNGSQDILLPNVIIMGAEPDLFETNSSNISLRNNYMPSNHRFGS

IAIVTFSPEYSFRFNDNCMNEFIQDPALTLMHELIHSLHGLYGAKGITTKYTITQKQNPL

ITNIRGTNIEEFLTFGGTDLNIITSAQSNDIYTNLLADYKKIASKLSKVQVSNPLLNPYK

DVFEAKYGLDKDASGIYSVNINKFNDIFKKLYSFTEFDLRTKFQVKCRQTYIGQYKYFKL

SNLLNDSIYNISEGYNINNLKVNFRGQNANLNPRIITPITGRGLVKKIIRFCKNIVSVKG

IRKSICIEINNGELFFVASENSYNDDNINTPKEIDDTVTSNNNYENDLDQVILNFNSESA

PGLSDEKLNLTIQNDAYIPKYDSNGTSDIEQHDVNELNVFFYLDAQKVPEGENNVNLTSS

IDTALLEQPKIYTFFSSEFINNVNKPVQAALFVSWIQQVLVDFTTEANQKSTVDKIADIS

IVVPYIGLALNIGNEAQKGNFKDALELLGAGILLEFEPELLIPTILVFTIKSFLGSSDNK

NKVIKAINNALKERDEKWKEVYSFIVSNWMTKINTQFNKRKEQMYQALQNQVNAIKTIIE

SKYNSYTLEEKNELTNKYDIKQIENELNQKVSIAMNNIDRFLTESSISYLMKIINEVKIN

KLREYDENVKTYLLNYIIQHGSILGESQQELNSMVTDTLNNSIPFKLSSYTDDKILISYF

NKFFKRIKSSSVLNMRYKNDKYVDTSGYDSNININGDVYKYPTNKNQFGIYNDKLSEVNI

SQNDYIIYDNKYKNFSISFWVRIPNYDNKIVNVNNEYTIINCMRDNNSGWKVSLNHNEII

WTFEDNRGINQKLAFNYGNANGISDYINKWIFVTITNDRLGDSKLYINGNLIDQKSILNL

GNIHVSDNILFKIVNCSYTRYIGIRYFNIFDKELDETEIQTLYSNEPNTNILKDFWGNYL

LYDKEYYLLNVLKPNNFIDRRKDSTLSINNIRSTILLANRLYSGIKVKIQRVNNSSTNDN

LVRKNDQVYINFVASKTHLFPLYADTATTNKEKTIKISSSGNRFNQVVVMNSVGNCTMNF

KNNNGNNIGLLGFKADTVVASTWYYTHMRDHTNSNGCFWNFISEEHGWQEK

-continued (BoNT/F - UniProt A7GBG3)

SEQ ID NO: 40

MPVVINSFNYNDPVNDDTILYMQIPYEEKSKKYYKAFEIMRNVWIIPERNTIGTDPSDFD

PPASLENGSSAYYDPNYLTTDAEKDRYLKTTIKLFKRINSNPAGEVLLQEISYAKPYLGN

EHTPINEFHPVTRTTSVNIKSSTNVKSSIILNLLVLGAGPDIFENSSYPVRKLMDSGGVY

DPSNDGFGSINIVTESPEYEYTENDISGGYNSSTESFIADPAISLAHELIHALHGLYGAR

GVTYKETIKVKQAPLMIAEKPIRLEEFLTEGGQDLNIITSAMKEKIYNNLLANYEKIATR

LSRVNSAPPEYDINEYKDYFQWKYGLDKNADGSYTVNENKFNEIYKKLYSFTEIDLANKF

KVKCRNTYFIKYGFLKVPNLLDDDIYTVSEGFNIGNLAVNNRGQNIKLNPKIIDSIPDKG

LVEKIVKFCKSVIPRKGTKAPPRLCIRVNNRELFFVASESSYNENDINTPKEIDDTTNLN

NNYRNNLDEVILDYNSETIPQISNQTLNTLVQDDSYVPRYDSNGTSEIEEHNVVDLNVFF

YLHAQKVPEGETNISLTSSIDTALSEESQVYTFFSSEFINTINKPVHAALFISWINQVIR

DFTTEATQKSTFDKIADISLVVPYVGLALNIGNEVQKENFKEAFELLGAGILLEFVPELL

IPTILVFTIKSFIGSSENKNKIIKAINNSLMERETKWKEIYSWIVSNWLTRINTQFNKRK

EQMYQALQNQVDAIKTVIEYKYNNYTSDERNRLESEYNINNIREELNKKVSLAMENIERF

ITESSIFYLMKLINEAKVSKLREYDEGVKEYLLDYISEHRSILGNSVQELNDLVTSTLNN

SIPFELSSYTNDKILILYFNKLYKKIKDNSILDMRYENNKFIDISGYGSNISINGDVYIY

STNRRNQFGIYSSKPSEVNIAQNNDIIYNGRYQNFSISFWVRIPKYFNKVNLNNEYTIIDC

IRNNNSGWKISLNYNKIIWTLQDTAGNNQKLVFNYTQMISISDYINKWIFVTITNNRLGN

SRIYINGNLIDEKSISNLGDIHVSDNILFKIVGCNDTRYVGIRYFKVFDTELGKTEIETL

YSDEPDPSILKDFWGNYLLYNKRYYLLNLLRTDKSITQNSNFLNINQQRGVYQKPNIFSN

TRLYTGVEVIIRKNGSTDISNTDNFVRKNDLAYINVVDRDVEYRLYADISIAKPEKIIKL

IRTSNSNNSLGQIIVMDSIGNNCTMNFQNNNGGNIGLLGFHSNNLVASSWYYNNIRKNTS

SNGCFWSFISKEHGWQEN (BoNT/G - UniProt Q60393)

SEQ ID NO: 41

MPVNIKXFNYNDPINNDDIIMMEPFNDPGPGTYYKAFRIIDRIWIVPERFTYGFQPDQFN

ASTGVFSKDVYEYYDPTYLKTDAEKDKFLKTMIKLFNRINSKPSGQRLLDMIVDAIPYLG

NASTPPDKFAANVANVSINKKIIQPGAEDQIKGLMTNLIIFGPGPVLSDNFTDSMIMNGH

SPISEGFGARMMIRFCPSCLNVFNNVQENKDTSIFSRRAYFADPALTLMHELIHVLHGLY

GIKISNLPITPNTKEFFMQHSDPVQAEELYTFGGHDPSVISPSTDMNIYNKALQNFQDIA

NRLNIVSSAQGSGIDISLYKQIYKNKYDFVEDPNGKYSVDKDKFDKLYKALMFGFTETNL

AGEYGIKTRYSYFSEYLPPIKTEKLLDNTIYTQNEGFNIASKNLKTEFNGQNKAVNKEAY

EEISLEHLVIYRIAMCKPVMYKNTGKSEQCIIVNNEDLFFIANKDSFSKDLAKAETIAYN

TQNNTIENNFSIDQLILDNDLSSGIDLPNENTEPFTNFDDIDIPVYIKQSALKKIFVDGD

SLFEYLHAQTFPSNIENLQLTNSLNDALRNNNKVYTFFSTNLVEKANTVVGASLFVNWVK

GVIDDFTSESTQKSTIDKVSDVSIIIPYIGPALNVGNETAKENFKNAFEIGGAAILMEFI

PELIVPIVGFFTLESYVGNKGHIIMTISNALKKRDQKWTDMYGLIVSQWLSTVNTQFYTI

KERMYNALNNQSQAIEKIIEDQYNRYSEEDKMNINIDFNDIDFKLNQSINLAINNIDDFI

NQCSISYLMNRMIPLAVKKLKDFDDNLKRDLLEYIDTNELYLLDEVNILKSKVNRHLKDS

IPFDLSLYTKDTILIQVFNNYISNISSNAILSLSYRGGRLIDSSGYGATMNVGSDVIFND

IGNGQFKLNNSENSNITAHQSKFVVYDSMFDNFSINFWVRTPKYNNNDIQTYLQNEYTII

-continued

```
SCIKNDSGWKVSIKGNRIIWTLIDVNAKSKSIFFEYSIKDNISDYINKWFSITITNDRLG

NANIYINGSLKKSEKILNLDRINSSNDIDFKLINCTDTTKFVWIKDFNIFGRELNATEVS

SLYWIQSSTNTLKDFWGNPLRYDTQYYLFNQGMQNIYIKYFSKASMGETAPRTNFNNAAI

NYQNLYLGLRFIIKKASNSRNINNDNIVREGDYIYLNIDNISDESYRVYVLVNSKEIQTQ

LFLAPINDDPTFYDVLQIKKYYEKTTYNCQILCEKDTKTFGLFGIGKFVKDYGYVWDTYD

NYFCISQWYLRRISENINKLRLGCNWQFIPVDEGWTE
```

(TeNT - UniProt P04958)

SEQ ID NO: 42

```
MPITINNFRYSDPVNNDTIIMMEPPYCKGLDIYYKAFKITDRIWIVPERYEFGTKPEDFN

PPSSLIEGASEYYDPNYLRTDSDKDRFLQTMVKLFNRIKNNVAGEALLDKIINAIPYLGN

SYSLLDKFDTNSNSVSFNLLEQDPSGATTKSAMLTNLIIFGPGPVLNKNEVRGIVLRVDN

KNYFPCRDGFGSIMQMAFCPEYVPTFDNVIENITSLTIGKSKYFQDPALLLMHELIHVLH

GLYGMQVSSHEIIPSKQEIYMQHTYPISAEELFTFGGQDANLISIDIKNDLYEKTLNDYK

AIANKLSQVTSCNDPNIDIDSYKQIYQQKYQFDKDSNGQYIVNEDKFQILYNSIMYGFTE

IELGKKFNIKTRLSYFSMNHDPVKIPNLLDDTIYNDTEGFNIESKDLKSEYKGQNMRVNT

NAFRNVDGSGLVSKLIGLCKKIIPPTNIRENLYNRTASLTDLGGELCIKIKNEDLTFIAE

KNSFSEEPFQDEIVSYNTKNKPLNFNYSLDKIIVDYNLQSKITLPNDRTTPVTKGIPYAP

EYKSNAASTIEIHNIDDNTIYQYLYAQKSPTTLQRITMTNSVDDALINSTKIYSYFPSVI

SKVNQGAQGILFLQWVRDIIDDFTNESSQKTTIDKISDVSTIVPYIGPALNIVKQGYEGN

FIGALETTGVVLLLEYIPEITLPVIAALSIAESSTQKEKIIKTIDNFLEKRYEKWIEVYK

LVKAKWLGTVNTQFQKRSYQMYRSLEYQVDAIKKIIDYEYKIYSGPDKEQIADEINNLKN

KLEEKANKAMININIFMRESSRSFLVNQMINEAKKQLLEFDTQSKNILMQYIKANSKFIG

ITELKKLESKINKVFSTPIPFSYSKNLDCWVDNEEDIDVILKKSTILNLDINNDIISDIS

GFNSSVITYPDAQLVPGINGKAIHLVNNESSEVIVHKAMDIEYNDMFNNFTVSFWLRVPK

VSASHLEQYGTNEYSIISSMKKHSLSIGSGWSVSLKGNNLIWTLKDSAGEVRQITFRDLP

DKFNAYLANKWVFITITNDRLSSANLYINGVLMGSAEITGLGAIREDNNITLKLDRCNNN

NQYVSIDKFRIFCKALNPKEIEKLYTSYLSITFLRDFWGNPLRYDTEYYLIPVASSSKDV

QLKNITDYMYLTNAPSYTNGKLNIYYRRLYNGLKFIIKRYTPNNEIDSFVKSGDFIKLYV

SYNNNEHIVGYPKDGNAFNNLDRILRVGYNAPGIPLYKKMEAVKLRDLKTYSVQLKLYDD

KNASLGLVGTHNGQIGNDPNRDILIASNWYFNHLKDKILGCDWYFVPTDEGWTND
```

(Nucleotide Sequence of LH$_N$/A1 with an EK Cleavage Site)

SEQ ID NO: 43

```
ATGGAGTTCGTTAACAAACAGTTCAACTATAAAGACCCAGTTAACGGTGTTGACATTGCTTACATCAAAATCCCG

AACGCTGGCCAGATGCAGCCGGTAAAGGCATTCAAAATCCACAACAAAATCTGGGTTATCCCGGAACGTGATACC

TTTACTAACCCGGAAGAAGGTGACCTGAACCCGCCACCGGAAGCGAAACAGGTGCCGGTATCTTACTATGACTCC

ACCTACCTGTCTACCGATAACGAAAAGGACAACTACCTGAAAGGTGTTACTAAACTGTTCGAGCGTATTTACTCC

ACCGACCTGGGCCGTATGCTGCTGACTAGCATCGTTCGCGGTATCCCGTTCTGGGGCGGTTCTACCATCGATACC

GAACTGAAAGTAATCGACACTAACTGCATCAACGTTATTCAGCCGGACGGTTCCTATCGTTCCGAAGAACTGAAC

CTGGTGATCATCGGCCCGTCTGCTGATATCATCCAGTTCGAGTGTAAGAGCTTTGGTCACGAAGTTCTGAACCTC

ACCCGTAACGGCTACGGTTCCACTCAGTACATCCGTTTCTCTCCGGACTTCACCTTCGGTTTTGAAGAATCCCTG

GAAGTAGACACGAACCCACTGCTGGGCGCTGGTAAATTCGCAACTGATCCTGCGGTTACCCTGGCTCACGAACTG

ATTCATGCAGGCCACCGCCTGTACGGTATCGCCATCAATCCGAACCGTGTCTTCAAAGTTAACACCAACGCGTAT

TACGAGATGTCCGGTCTGGAAGTTAGCTTCGAAGAACTGCGTACTTTTGGCGGTCACGACGCTAAATTCATCGAC
```

-continued

TCTCTGCAAGAAAACGAGTTCCGTCTGTACTACTATAACAAGTTCAAAGATATCGCATCCACCCTGAACAAAGCG

AAATCCATCGTGGGTACCACTGCTTCTCTCCAGTACATGAAGAACGTTTTTAAAGAAAAATACCTGCTCAGCGAA

GACACCTCCGGCAAATTCTCTGTAGACAAGTTGAAATTCGATAAACTTTACAAAATGCTGACTGAAATTTACACC

GAAGACAACTTCGTTAAGTTCTTTAAAGTTCTGAACCGCAAAACCTATCTGAACTTCGACAAGGCAGTATTCAAA

ATCAACATCGTGCCGAAAGTTAACTACACTATCTACGATGGTTTCAACCTGCGTAACACCAACCTGGCTGCTAAT

TTTAACGGCCAGAACACGGAAATCAACAACATGAACTTCACAAAACTGAAAAACTTCACTGGTCTGTTCGAGTTT

TACAAGCTGCTGTGCGTCGACGGCATCATTACCTCCAAAACTAAATCTGACGATGACGATAAAAACAAAGCGCTG

AACCTGCAGTGTATCAAGGTTAACAACTGGGATTTATTCTTCAGCCCGAGTGAAGACAACTTCACCAACGACCTG

AACAAAGGTGAAGAAATCACCTCAGATACTAACATCGAAGCAGCCGAAGAAAACATCTCGCTGGACCTGATCCAG

CAGTACTACCTGACCTTTAATTTCGACAACGAGCCGGAAAACATTTCTATCGAAAACCTGAGCTCTGATATCATC

GGCCAGCTGGAACTGATGCCGAACATCGAACGTTTCCCAAACGGTAAAAAGTACGAGCTGGACAAATATACCATG

TTCCACTACCTGCGCGCGCAGGAATTTGAACACGGCAAATCCCGTATCGCACTGACTAACTCCGTTAACGAAGCT

CTGCTCAACCCGTCCCGTGTATACACCTTCTTCTCTAGCGACTACGTGAAAAAGGTCAACAAAGCGACTGAAGCT

GCAATGTTCTTGGGTTGGGTTGAACAGCTTGTTTATGATTTTACCGACGAGACGTCCGAAGTATCTACTACCGAC

AAAATTGCGGATATCACTATCATCATCCCGTACATCGGTCCGGCTCTGAACATTGGCAACATGCTGTACAAAGAC

GACTTCGTTGGCGCACTGATCTTCTCCGGTGCGGTGATCCTGCTGGAGTTCATCCCGGAAATCGCCATCCCGGTA

CTGGGCACCTTTGCTCTGGTTTCTTACATTGCAAACAAGGTTCTGACTGTACAAACCATCGACAACGCGCTGAGC

AAACGTAACGAAAAATGGGATGAAGTTTACAAATATATCGTGACCAACTGGCTGGCTAAGGTTAATACTCAGATC

GACCTCATCCGCAAAAAAATGAAAGAAGCACTGGAAAACCAGGCGGAAGCTACCAAGGCAATCATTAACTACCAG

TACAACCAGTACACCGAGGAAGAAAAAAACAACATCAACTTCAACATCGACGATCTGTCCTCTAAACTGAACGAA

TCCATCAACAAAGCTATGATCAACATCAACAAGTTCCTGAACCAGTGCTCTGTAAGCTATCTGATGAACTCCATG

ATCCCGTACGGTGTTAAACGTCTGGAGGACTTCGATGCGTCTCTGAAAGACGCCCTGCTGAAATACATTTACGAC

AACCGTGGCACTCTGATCGGTCAGGTTGATCGTCTGAAGGACAAAGTGAACAATACCTTATCGACCGACATCCCT

TTTCAGCTCAGTAAATATGTCGATAACCAACGCCTTTTGTCCACTCTAGAAGCACACCATCATCACCACCATCAC

CATCACCAT (Polypeptide Sequence of LH$_N$/A1 with an EK Cleavage Site)

SEQ ID NO: 44

MEFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHEL

IHAGHRLYGIAINPNRVFKVNTNAYYEMSGLEVSFEELRTEGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKVLNRKTYLNFDKAVFK

INIVPKVNYTIYDGFNLRNTNLAANFNGQNTEINNMNFTKLKNFTGLFEFYKLLCVDGIITSKTKSDDDDKNKAL

NLQCIKVNNWDLFFSPSEDNFTNDLNKGEEITSDTNIEAAEENISLDLIQQYYLTFNFDNEPENISIENLSSDII

GQLELMPNIERFPNGKKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSGAVILLEFIPEIAIPV

LGTFALVSYIANKVLTVQTIDNALSKRNEKWDEVYKYIVTNWLAKVNTQIDLIRKKMKEALENQAEATKAIINYQ

YNQYTEEEKNNINFNIDDLSSKLNESINKAMININKFLNQCSVSYLMNSMIPYGVKRLEDFDASLKDALLKYIYD

NRGTLIGQVDRLKDKVNNTLSTDIPFQLSKYVDNQRLLSTLEAHHHHHHHHHH

-continued (Nucleotide Sequence of BoNT with a Native A1 Loop)

SEQ ID NO: 45

ATGAAACTGGAAATCAACAAATTCAACTACAACGATCCGATCGATGGCATTAATGTTATTACCATGCGTCCGCCT

CGTCATAGCGATAAAATCAATAAAGGTAAAGGTCCGTTCAAAGCCTTTCAGGTGATTAAAAACATTTGGATTGTG

CCGGAACGCTACAACTTTACCAATAATACCAACGATCTGAACATTCCGAGCGAACCGATTATGGAAGCAGATGCC

ATTTATAACCCGAACTATCTGAATACCCCGAGCGAAAAAGATGAATTTCTGCAGGGTGTTATCAAAGTGCTGGAA

CGCATTAAAAGCAAACCGGAAGGTGAAAAACTGCTGGAACTGATTAGCAGCAGCATTCCGCTGCCGCTGGTTAGC

AATGGTGCACTGACCCTGAGCGATAATGAAACCATTGCATATCAAGAGAACAACAACATTGTGAGCAATCTGCAG

GCAAACCTGGTTATTTATGGTCCGGGTCCTGATATTGCAAATAATGCAACCTATGGTCTGTATAGCACCCCGATT

AGTAATGGTGAAGGTACACTGAGCGAAGTTAGCTTTAGCCCGTTTTATCTGAAACCGTTTGATGAAAGCTATGGC

AATTATCGTAGCCTGGTGAATATCGTGAACAAATTCGTGAAACGTGAATTTGCACCTGATCCGGCAAGCACCCTG

ATGCATGAACTGGTTCATGTTACCCATAATCTGTATGGTATTAGCAACCGCAACTTCTACTATAACTTTGACACC

GGCAAAATTGAAACCAGCCGTCAGCAGAATAGCCTGATTTTTGAAGAACTGCTGACCTTTGGTGGCATTGATAGC

AAAGCAATTAGCAGCCTGATCATCAAGAAAATTATCGAAACCGCCAAGAACAACTATACCACGCTGATTAGCGAA

CGCCTGAATACCGTTACCGTTGAAAATGATCTGCTGAAATATATCAAAAACAAAATCCCGGTTCAGGGTCGTCTG

GGTAACTTTAAACTGGATACCGCAGAATTCGAGAAAAAGCTGAATACCATTCTGTTTGTGCTGAACGAAAGCAAT

CTGGCACAGCGTTTTAGCATTCTGGTTCGTAAACATTACCTGAAAGAACGTCCGATTGATCCGATTTATGTGAAC

ATTCTGGATGACAATAGCTACAGCACCCTGGAAGGTTTTAACATTAGCAGTCAGGGTAGCAATGATTTCCAAGGT

CAGCTGCTGGAAAGCAGCTATTTTGAAAAAAATTGAAAGCAATGCCCTGCGTGCCTTCATTAAAATCTGTCCGCGT

AATGGTCTGCTGTATAATGCCATTTATCGCAACAGCAAAAATCTGGAAGTTCTGTTTCAGGGTCCGCATCATCAC

CACCATCACCATCATCATCACCTGGAAGTGTTATTTCAGGGACCGTATCTGAATAACATTGATCTGGAAGATAAA

AAGACCACGAGCAAAACCAATGTTAGCTATCCGTGTAGCCTGCTGAATGGTTGTATTGAAGTTGAAAACAAAGAC

CTGTTCCTGATTAGCAACAAAGATAGCCTGAACGATATTAACCTGAGCGAAGAAAAAATCAAACCGGAAACCACC

GTGTTCTTCAAAGATAAACTGCCTCCGCAGGATATTACGCTGAGCAATTATGATTTTACCGAAGCCAATAGCATT

CCGAGCATTAGCCAGCAGAACATTCTGGAACGTAATGAAGAACTGTATGAACCGATTCGCAATAGCCTGTTTGAA

ATCAAAACCATCTATGTGGATAAGCTGACCACCTTTCATTTTCTGGAAGCCCAGAATATTGATGAGAGCATTGAT

AGCAGCAAAATTCGTGTTGAACTGACCGATAGCGTTGATGAAGCACTGAGCAATCCGAATAAAGTTTATAGCCCG

TTCAAGAACATGAGCAACACCATTAATAGCATTGAAACCGGTATTACCAGCACCTACATCTTTTATCAGTGGCTG

CGTAGCATCGTGAAAGATTTTAGTGATGAAACCGGCAAAATCGACGTGATTGATAAAAGCAGCGATACCCTGGCA

ATTGTTCCGTATATTGGTCCGCTGCTGAATATTGGTAATGATATTCGTCATGGCGATTTTGTGGGTGCAATTGAA

CTGGCAGGCATTACCGCACTGCTGGAATATGTTCCGGAATTTACCATTCCGATTCTGGTTGGTCTGGAAGTGATT

GGTGGCGAACTGGCACGTGAACAGGTTGAAGCAATTGTTAATAATGCCCTGGATAAACGCGATCAGAAATGGGCA

GAAGTTTACAATATTACCAAAGCACAGTGGTGGGGCACCATTCATTTACAGATTAATACCCGTCTGGCCCATACC

TATAAAGCCCTGAGCCGTCAGGCAAATGCCATTAAAATGAATATGGAATTTCAGCTGGCCAACTACAAAGGCAAC

ATTGATGATAAAGCCAAGATCAAAAACGCCATCAGCGAAACCGAAATTCTGCTGAACAAAAGCGTTGAACAGGCC

ATGAAAAACACCGAGAAATTCATGATTAAACTGAGCAACAGCTACCTGACCAAAGAAATGATTCCGAAAGTTCAG

GACAACCTGAAAAACTTTGACCTGGAAACCAAAAAAACCCTGGACAAGTTCATCAAAGAGAAAGAAGATATCCTG

GGCACCAATCTGAGCAGCAGCCTGCGTCGTAAAGTTAGCATTCGTCTGAATAAAAACATTGCCTTCGACATCAAC

GATATCCCGTTTAGCGAATTTGATGATCTGATCAACCAGTACAAAAACGAGATCGAAGATTATGAAGTGCTGAAT

CTGGGTGCAGAAGATGGCAAAATCAAAGATCTGAGCGGTACCAACCAGCGATATCAATATTGGTTCAGATATCGAA

CTGGCCGATGGTCGTGAAAATAAAGCCATTAAGATTAAAGGCAGCGAGAACAGCACCATCAAAATTGCAATGAAC

-continued

```
AAATATCTGCGTTTTAGCGCCACCGATAACTTTAGCATTAGCTTTTGGATCAAACATCCGAAACCGACCAATCTG

CTTAATAACGGTATTGAATATACCCTGGTCGAGAACTTTAATCAGCGTGGTTGGAAAATTAGCATCCAGGATAGC

AAACTGATTTGGTATCTGCGCGATCACAATAACAGCATCAAAATCGTTACACCGGATTATATTGCGTTTAATGGC

TGGAACCTGATCACCATTACGAATAATCGTAGCAAAGGCAGCATCGTGTATGTGAATGGTAGCAAAATTGAAGAG

AAGGACATTAGCAGCATTTGGAATACCGAAGTGGATGATCCGATTATCTTCCGCCTGAAAAATAACCGTGATACC

CAGGCATTTACCCTGCTGGATCAGTTTAGCATTTATCGGAAAGAACTGAACCAGAACGAAGTGGTGAAACTGTAT

AACTACTACTTCAACAGCAACTACATTCGCGATATTTGGGGTAATCCGCTGCAGTACAACAAAAAATACTATCTG

CAGACCCAGGACAAACCTGGTAAAGGTCTGATCCGCGAATATTGGAGCAGCTTTGGTTATGATTATGTGATTCTG

AGCGATAGCAAGACGATTACCTTTCCGAACAATATCCGTTATGGTGCCCTGTATAACGGTAGCAAAGTTCTGATC

AAGAACAGCAAGAAATTAGATGGTCTGGTGCGCAATAAAGATTTCATTCAGCTGGAAATCGATGGCTATAATATG

GGTATTAGCGCAGATCGCTTTAACGAGGATACCAACTATATTGGCACCACCTATGGTACAACCCATGATCTGACC

ACCGATTTTGAAATTATTCAGCGCCAAGAGAAATACCGCAATTATTGTCAGCTGAAAACCCCGTATAACATCTTT

CATAAAAGCGGTCTGATGAGCACCGAAACCAGCAAACCGACCTTCCATGATTATCGCGATTGGGTTTATAGCAGC

GCATGGTATTTTCAGAACTATGAAAATCTGAACCTGCGCAAACATACCAAAACCAACTGGTATTTTATCCCGAAA

GATGAAGGTTGGGACGAAGAT
```

(Polypeptide Sequence of BoNT with a Native A1 Loop)

SEQ ID NO: 46

```
MKLEINKFNYNDPIDGINVITMRPPRHSDKINKGKGPPFKAFQVIKNIWIVPERYNFTNNTNDLNIPSEPIMEADA

IYNPNYLNTPSEKDEFLQGVIKVLERIKSKPEGEKLLELISSSIPLPLVSNGALTLSDNETIAYQENNNIVSNLQ

ANLVIYGPGPDIANNATYGLYSTPISNGEGTLSEVSFSPFYLKPFDESYGNYRSLVNIVNKFVKREFAPDPASTL

MHELVHVTHNLYGISNRNFYYNFDTGKIETSRQQNSLIFEELLTFGGIDSKAISSLIIKKIIETAKNNYTTLISE

RLNTVTVENDLLKYIKNKIPVQGRLGNFKLDTAEFEKKLNTILFVLNESNLAQRFSILVRKHYLKERPIDPIYVN

ILDDNSYSTLEGFNISSQGSNDFQGQLLESSYFEKIESNALRAFIKICPRNGLLYNAIYRNSKNLEVLFQGPHHH

HHHHHHHLEVLFQGPYLNNIDLEDKKTTSKTNVSYPCSLLNGCIEVENKDLFLISNKDSLNDINLSEEKIKPETT

VFFKDKLPPQDITLSNYDFTEANSIPSISQQNILERNEELYEPIRNSLFEIKTIYVDKLTTFHFLEAQNIDESID

SSKIRVELTDSVDEALSNPNKVYSPFKNMSNTINSIETGITSTYIFYQWLRSIVKDFSDETGKIDVIDKSSDTLA

IVPYIGPLLNIGNDIRHGDFVGAIELAGITALLEYVPEFTIPILVGLEVIGGELAREQVEAIVNNALDKRDQKWA

EVYNITKAQWWGTIHLQINTRLAHTYKALSRQANAIKMNMEFQLANYKGNIDDKAKIKNAISETEILLNKSVEQA

MKNTEKFMIKLSNSYLTKEMIPKVQDNLKNEDLETKKTLDKFIKEKEDILGTNLSSSLRRKVSIRLNKNIAFDIN

DIPFSEFDDLINQYKNEIEDYEVLNLGAEDGKIKDLSGTTSDINIGSDIELADGRENKAIKIKGSENSTIKIAMN

KYLRFSATDNFSISFWIKHPKPTNLLNNGIEYTLVENFNQRGWKISIQDSKLIWYLRDHNNSIKIVTPDYIAFNG

WNLITITNNRSKGSIVYVNGSKIEEKDISSIWNTEVDDPIIFRLKNNRDTQAFTLLDQFSIYRKELNQNEVVKLY

NYYFNSNYIRDIWGNPLQYNKKYYLQTQDKPGKGLIREYWSSFGYDYVILSDSKTITFPNNIRYGALYNGSKVLI

KNSKKLDGLVRNKDFIQLEIDGYNMGISADRFNEDTNYIGTTYGTTHDLTTDFEIIQRQEKYRNYCQLKTPYNIF

HKSGLMSTETSKPTFHDYRDWVYSSAWYFQNYENLNLRKHTKTNWYFIPKDEGWDED
```

(Polypeptide Sequence of Trypsin)

SEQ ID NO: 47

```
MHPLLILAFVGAAVAFPSDDDDKIVGGYTCAENSVPYQVSLNAGYHFCGGSLINDQWVVS

AAHCYQYHIQVRLGEYNIDVLEGGEQFIDASKIIRHPKYSSWTLDNDILLIKLSTPAVIN

ARVSTLALPSACASGSTECLISGWGNTLSSGVNYPDLLQCLEAPLLSHADCEASYPGEIT

NNMICAGFLEGGKDSCQGDSGGPVACNGQLQGIVSWGYGCAQKGKPGVYTKVCNYVDWIQ

ETIAANS
```

-continued (Polypeptide Sequence of Lys-C)

SEQ ID NO: 48

G V S G S C N I D V V C P E G N G H R D V I R S V A A Y S K Q G T M W C T G

S L V N N S A N D K K M Y F L T A N H C G M T T A A I A S S M V V Y W N Y Q

N S T C R A P G S S S S G A N G D G S L A Q S Q T G A V V R A T N A A S D F

T L L E L N T A A N P A Y N L F W A G W D R R D Q N F A G A T A I H H P N V

A E K R I S H S T V A T E I S G Y N G A T G T S H L H V F W Q A S G G V T E

P G S S G S P I Y S P E K R V L G Q L H 211 G G P S S C S A T G A D R S D Y

Y G R V F T S W T G G G T S A T R L S D W L D A A G T G A Q F I D G L D S T

G T P P V (Polypeptide Sequence of Enterokinase Light Chain)

SEQ ID NO: 49

IVGGSDSREGAWPWVVALYFDDQQVCGASLVSRDWLVSAAHCVYGRNMEPSKWKAVLGLH

MASNLTSPQIETRLIDQIVINRHYNKRRKNNDIAMMHLEMKVNYTDYIQPICLPEENQVF

PPGRICSIAGWGALIYQGSTADVLQEADVPLLSNEKCQQQMPEYNITENMVCAGYDAGGV

DSCQGDSGGPLMCQENNRWLLAGVTSFGYQCALPNRPGVYARVPRFTEWIQSFLH (Polypeptide Sequence of Factor Xa Heavy Chain)

SEQ ID NO: 50

IVGGRDCAEGECPWQALLVNEENEGFCGGTILNEFYVLTAAHCLHQAKRFTVRVGDRNTEQEEGNEMAHEVEMTV

KHSRFVKETYDFDIAVLRLKTPIRFRRNVAPACLPEKDWAEATLMTQKTGIVSGFGRTHEKGRLSSTLKMLEVPY

VDRSTCKLSSSFTITPNMFCAGYDTQPEDACQGDSGGPHVTRFKDTYFVTGIVSWGEGCARKGKFGVYTKVSNFL

KWIDKIMKARAGAAGSRGHSEAPATWTVPPPLPL (Polypeptide Sequence of Factor Xa Light Chain)

SEQ ID NO: 51

ANSFLEEVKQGNLERECLEEACSLEEAREVFEDAEQTDEFWSKYKDGDQCEGHPCLNQGHCKDGIGDYTCTCAEG

FEGKNCEFSTREICSLDNGGCDQFCREERSEVRCSCAHGYVLGDDSKSCVSTERFPCGKFTQGRS (Polypeptide Sequence of Anthrax Toxin Protective Antigen - NCBI Ref Seq:
NP_052806)

SEQ ID NO: 52

1  mkkrkvlipl malstilvss tgnlevigae vkqenrllne sesssqgllg yyfsdlnfqa 61  pmvvtssttg dlsipssele nipsenqyfq saiwsgfikv kksdeytfat sadnhvtmwv 121  ddqevinkas nsnkirlekg rlyqikiqyq renptekgld fklywtdsqn kkevissdnl 181  qlpelkqkss nsrkkrstsa gptvpdrdnd gipdsleveg ytvdvknkrt flspwisnih 241  ekkgltkyks spekwstasd pysdfekvtg ridknvspea rhplvaaypi vhvdmeniil 301  sknedqstqn tdsqtrtisk ntstsrthts evhgnaevha sffdiggsys agfsnsnsst 361  vaidhslsla gertwaetmg lntadtarin aniryvntgt apiynvlptt slvlgknqtl 421  atikakenql sqilapnnyy psknlapial naqddfsstp itmnynqfle lektkqlrld 481  tdqvygniat ynfengrvrv dtgsnwsevl pqiqettari ifngkdlnlv erriaavnps 541  dplettkpdm tlkealkiaf gfnepngnlq yqgkditefd fnfdqqtsqn iknqlaelna 601  tniytvldki klnakmnili rdkrfhydrn niavgadesv vkeahrevin ssteglllni 661  dkdirkilsg yiveiedteg lkevindryd mlnisslrqd gktfidfkky ndklplyisn 721  pnykvnvyav tkentiinps engdtstngi kkilifskkg yeig (LH$_N$/A with a C1 Activation Loop)

SEQ ID NO: 53

MPFVNKQFNYKDPVNGVDIAYIKIPNVGQMQPVKAFKIHNKIWVIPERDTFTNPEEGDLN

PPPEAKQVPVSYYDSTYLSTDNEKDNYLKGVTKLFERIYSTDLGRMLLTSIVRGIPFWGG

STIDTELKVIDTNCINVIQPDGSYRSEELNLVIIGPSADIIQFECKSFGHEVLNLTRNGY

-continued

```
GSTQYIRFSPDFTFGFEESLEVDTNPLLGAGKFATDPAVTLAHELIHAGHRLYGIAINPN

RVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKV

LNRKTYLNFDKAVFKINIVPKVNYTIYDGFNLRNTNLAANFNGQNTEINNMNFTKLKNFT

GLFEFYKLLCHKAIDGRSLYNKTLDCIKVNNWDLFFSPSEDNFTNDLNKGEE

ITSDTNIEAAEENISLDLIQQYYLTFNFDNEPENISIENLSSDIIGQLELMPNIERFPNG

KKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSG

AVILLEFIPEIAIPVLGTFALVSYIANKVLTVQTIDNALSKRNEKWDEVYKYIVTNWLAK

VNTQIDLIRKKMKEALENQAEATKAIINYQYNQYTEEEKNNINFNIDDLSSKLNESINKA

MININKFLNQCSVSYLMNSMIPYGVKRLEDFDASLKDALLKYIYDNRGTLIGQVDRLKDK

VNNTLSTDIPFQLSKYVDNQRLLSTFTEYIK
```

(LH<sub>N</sub>/B with a C1 Activation Loop) SEQ ID NO: 54

```
MPVTINNFNYNDPIDNNNIIMMEPPFARGTGRYYKAFKITDRIWIIPERYTEGYKPEDFN

KSSGIFNRDVCEYYDPDYLNTNDKKNIFLQTMIKLFNRIKSKPLGEKLLEMIINGIPYLG

DRRVPLEEFNTNIASVTVNKLISNPGEVERKKGIFANLIIFGPGPVLNENETIDIGIQNH

FASREGFGGIMQMKFCPEYVSVFNNVQENKGASIFNRRGYFSDPALILMHELIHVLHGLY

GIKVDDLPIVPNEKKFFMQSTDAIQAEELYTFGGQDPSIITPSTDKSIYDKVLQNFRGIV

DRLNKVLVCISDPNININIYKNKFKDKYKFVEDSEGKYSIDVESFDKLYKSLMFGFTETN

IAENYKIKTRASYFSDSLPPVKIKNLLDNEIYTIEEGFNISDKDMEKEYRGQNKAINKQA

YEEISKEHLAVYKIQMCHKAIDGRSLYNKTLDCIDVDNEDLFFIADKNSFSDDLSKNE

RIEYNTQSNYIENDFPINELILDTDLISKIELPSENTESLTDFNVDVPVYEKQPAIKKIF

TDENTIFQYLYSQTFPLDIRDISLTSSFDDALLFSNKVYSFFSMDYIKTANKVVEAGLFA

GWVKQIVNDFVIEANKSNTMDKIADISLIVPYIGLALNVGNETAKGNFENAFEIAGASIL

LEFIPELLIPVVGAFLLESYIDNKNKIIKTIDNALTKRNEKWSDMYGLIVAQWLSTVNTQ

FYTIKEGMYKALNYQAQALEEIIKYRYNIYSEKEKSNINIDFNDINSKLNEGINQAIDNI

NNFINGCSVSYLMKKMIPLAVEKLLDFDNTLKKNLLNYIDENKLYLIGSAEYEKSKVNKY

LKTIMPFDLSIYTNDTILIEMFNKYNS
```

(LH<sub>N</sub>/D with a C1 Activation Loop) SEQ ID NO: 55

```
MTWPVKDFNYSDPVNDNDILYLRIPQNKLITTPVKAFMITQNIWVIPERFSSDTNPSLSK

PPRPTSKYQSYYDPSYLSTDEQKDTFLKGIIKLFKRINERDIGKKLINYLVVGSPFMGDS

STPEDTFDFTRHTTNIAVEKFENGSWKVTNIITPSVLIFGPLPNILDYTASLTLQGGQQSN

PSFEGFGTLSILKVAPEFLLTFSDVTSNQSSAVLGKSIFCMDPVIALMHELTHSLHQLYG

INIPSDKRIRPQVSEGFFSQDGPNVQFEELYTFGGLDVEIIPQIERSQLREKALGHYKDI

AKRLNNINKTIPSSWISNIDKYKKIFSEKYNFDKDNTGNFVVNIDKFNSLYSDLTNVMSE

VVYSSQYNVKNRTHYFSRHYLPVFANILDDNIYTIRDGFNLTNKGFNIENSGQNIERNPA

LQKLSSESVVDLFTKVCHKAIDGRSLYNKTLDCIKVKNNRLPYVADKDSISQEIFENKIITDE

TNVQNYSDKFSLDESILDGQVPINPEIVDPLLPNVNMEPLNLPGEEIVFYDDITKYVDYL

NSYYYLESQKLSNNVENITLTTSVEEALGYSNKIYTFLPSLAEKVNKGVQAGLFLNWANE

VVEDFTTNIMKKDTLDKISDVSVIIPYIGPALNIGNSALRGNENQAFATAGVAFLLEGFP
```

-continued

EFTIPALGVFTFYSSIQEREKIIKTIENCLEQRVKRWKDSYQWMVSNWLSRITTQFNHIN

YQMYDSLSYQADAIKAKIDLEYKKYSGSDKENIKSQVENLKNSLDVKISEAMNNINKFIR

ECSVTYLFKNMLPKVIDELNKFDLRTKTELINLIDSHNIILVGEVDRLKAKVNESFENTM

PFNIFSYTNNSLLKDIINEYFN (LH<sub>N</sub>/E with a C1 Activation Loop)

SEQ ID NO: 56

MPKINSFNYNDPVNDRTILYIKPGGCQEFYKSFNIMKNIWIIPERNVIGTTPQDFHPPTS

LKNGDSSYYDPNYLQSDEEKDRFLKIVTKIFNRINNNLSGGILLEELSKANPYLGNDNTP

DNQFHIGDASAVEIKFSNGSQDILLPNVIIMGAEPDLFETNSSNISLRNNYMPSNHRFGS

IAIVTESPEYSFRFNDNCMNEFIQDPALTLMHELIHSLHGLYGAKGITTKYTITQKQNPL

ITNIRGTNIEEFLTFGGTDLNIITSAQSNDIYTNLLADYKKIASKLSKVQVSNPLLNPYK

DVFEAKYGLDKDASGIYSVNINKFNDIFKKLYSFTEFDLRTKFQVKCRQTYIGQYKYFKL

SNLLNDSIYNISEGYNINNLKVNFRGQNANLNPRIITPITGRGLVKKIIRFCHKAIDGR

SLYNKTLDCIEINNGELFFVASENSYNDDNINTPKEIDDTVTSNNNYENDLDQVILNFNS

ESAPGLSDEKLNLTIQNDAYIPKYDSNGTSDIEQHDVNELNVFFYLDAQKVPEGENNVNL

TSSIDTALLEQPKIYTFFSSEFINNVNKPVQAALFVSWIQQVLVDFTTEANQKSTVDKIA

DISIVVPYIGLALNIGNEAQKGNFKDALELLGAGILLEFEPELLIPTILVFTIKSFLGSS

DNKNKVIKAINNALKERDEKWKEVYSFIVSNWMTKINTQFNKRKEQMYQALQNQVNAIKT

IIESKYNSYTLEEKNELTNKYDIKQIENELNQKVSIAMNNIDRFLTESSISYLMKIINEV

KINKLREYDENVKTYLLNYIIQHGSILGESQQELNSMVTDTLNNSIPFKLSSYTDDKILI

SYFNKFFK (LH<sub>N</sub>/F with a C1 Activation Loop)

SEQ ID NO: 57

MPVVINSFNYNDPVNDDTILYMQIPYEEKSKKYYKAFEIMRNVWIIPERNTIGTDPSDFD

PPASLENGSSAYYDPNYLTTDAEKDRYLKTTIKLFKRINSNPAGEVLLQEISYAKPYLGN

EHTPINEFHPVTRTTSVNIKSSTNVKSSIILNLLVLGAGPDIFENSSYPVRKLMDSGGVY

DPSNDGFGSINIVTFSPEYEYTFNDISGGYNSSTESFIADPAISLAHELIHALHGLYGAR

GVTYKETIKVKQAPLMIAEKPIRLEEFLTFGGQDLNIITSAMKEKIYNNLLANYEKIATR

LSRVNSAPPEYDINEYKDYFQWKYGLDKNADGSYTVNENKFNEIYKKLYSFTEIDLANKF

KVKCRNTYFIKYGFLKVPNLLDDDIYTVSEGFNIGNLAVNNRGQNIKLNPKIIDSIPDKG

LVEKIVKFCHKAIDGRSLYNKTLDCIRVNNRELFFVASESSYNENDINTPKEIDDTTNLN

NNYRNNLDEVILDYNSETIPQISNQTLNTLVQDDSYVPRYDSNGTSEIEEHNVVDLNVFF

YLHAQKVPEGETNISLTSSIDTALSEESQVYTFFSSEFINTINKPVHAALFISWINQVIR

DFTTEATQKSTFDKIADISLVVPYVGLALNIGNEVQKENFKEAFELLGAGILLEFVPELL

IPTILVFTIKSFIGSSENKNKIIKAINNSLMERETKWKEIYSWIVSNWLTRINTQFNKRK

EQMYQALQNQVDAIKTVIEYKYNNYTSDERNRLESEYNINNIREELNKKVSLAMENIERF

ITESSIFYLMKLINEAKVSKLREYDEGVKEYLLDYISEHRSILGNSVQELNDLVTSTLNN

SIPFELSSYTNDKILILYFNKLYK (LH<sub>N</sub>/G with a C1 Activation Loop)

SEQ ID NO: 58

MPVNIKXFNYNDPINNDDIIMMEPFNDPGPGTYYKAFRIIDRIWIVPERFTYGFQPDQFN

ASTGVFSKDVYEYYDPTYLKTDAEKDKFLKTMIKLFNRINSKPSGQRLLDMIVDAIPYLG

NASTPPDKFAANVANVSINKKIIQPGAEDQIKGLMTNLIIFGPGPVLSDNFTDSMIMNGH

SPISEGFGARMMIRFCPSCLNVFNNVQENKDTSIFSRRAYFADPALTLMHELIHVLHGLY

-continued

GIKISNLPITPNTKEFFMQHSDPVQAEELYTFGGHDPSVISPSTDMNIYNKALQNFQDIA

NRLNIVSSAQGSGIDISLYKQIYKNKYDEVEDPNGKYSVDKDKFDKLYKALMFGFTETNL

AGEYGIKTRYSYFSEYLPPIKTEKLLDNTIYTQNEGFNIASKNLKTEFNGQNKAVNKEAY

EEISLEHLVIYRIAMCHKAIDGRSLYNKTLDCIIVNNEDLFFIANKDSFSKDLAKAETIAYN

TQNNTIENNFSIDQLILDNDLSSGIDLPNENTEPFTNFDDIDIPVYIKQSALKKIFVDGD

SLFEYLHAQTFPSNIENLQLTNSLNDALRNNNKVYTFFSTNLVEKANTVVGASLFVNWVK

GVIDDFTSESTQKSTIDKVSDVSIIIPYIGPALNVGNETAKENFKNAFEIGGAAILMEFI

PELIVPIVGFFTLESYVGNKGHIIMTISNALKKRDQKWTDMYGLIVSQWLSTVNTQFYTI

KERMYNALNNQSQAIEKIIEDQYNRYSEEDKMNINIDFNDIDFKLNQSINLAINNIDDFI

NQCSISYLMNRMIPLAVKKLKDFDDNLKRDLLEYIDTNELYLLDEVNILKSKVNRHLKDS

IPFDLSLYTKDTILIQVFNNYIS (LH<sub>N</sub>/TeNT with a C1 Activation Loop)

MPITINNFRYSDPVNNDTIIMMEPPYCKGLDIYYKAFKITDRIWIVPERYEFGTKPEDFN
                                                                   SEQ ID NO: 59

PPSSLIEGASEYYDPNYLRTDSDKDRFLQTMVKLFNRIKNNVAGEALLDKIINAIPYLGN

SYSLLDKFDTNSNSVSFNLLEQDPSGATTKSAMLTNLIIFGPGPVLNKNEVRGIVLRVDN

KNYFPCRDGFGSIMQMAFCPEYVPTFDNVIENITSLTIGKSKYFQDPALLLMHELIHVLH

GLYGMQVSSHEIIPSKQEIYMQHTYPISAFELFTFGGQDANLISIDIKNDLYEKTLNDYK

AIANKLSQVTSCNDPNIDIDSYKQIYQQKYQFDKDSNGQYIVNEDKFQILYNSIMYGFTE

IELGKKFNIKTRLSYFSMNHDPVKIPNLLDDTIYNDTEGFNIESKDLKSEYKGQNMRVNT

NAFRNVDGSGLVSKLIGLCHKAIDGRSLYNKTLDCIKIKNEDLTFIAE

KNSFSEEPFQDEIVSYNTKNKPLNFNYSLDKIIVDYNLQSKITLPNDRTTPVTKGIPYAP

EYKSNAASTIEIHNIDDNTIYQYLYAQKSPTTLQRITMTNSVDDALINSTKIYSYFPSVI

SKVNQGAQGILFLQWVRDIIDDFTNESSQKTTIDKISDVSTIVPYIGPALNIVKQGYEGN

FIGALETTGVVLLLEYIPEITLPVIAALSIAESSTQKEKIIKTIDNFLEKRYEKWIEVYK

LVKAKWLGTVNTQFQKRSYQMYRSLEYQVDAIKKIIDYEYKIYSGPDKEQIADEINNLKN

KLEEKANKAMININIFMRESSRSFLVNQMINEAKKQLLEFDTQSKNILMQYIKANSKFIG

ITELKKLESKINKVFSTPIPFSYSKNLDCWVDNEEDIDV (LH<sub>N</sub>/X with a C1 Activation Loop)

MKLEINKFNYNDPIDGINVITMRPPRHSDKINKGKGPPFKAFQVIKNIWIVPERYNFTNNT
                                                                   SEQ ID NO: 60

NDLNIPSEPIMEADAIYNPNYLNTPSEKDEFLQGVIKVLERIKSKPEGEKLLELISSSIP

LPLVSNGALTLSDNETIAYQENNNIVSNLQANLVIYGPGPDIANNATYGLYSTPISNGEG

TLSEVSFSPFYLKPFDESYGNYRSLVNIVNKFVKREFAPDPASTLMHELVHVTHNLYGIS

NRNFYYNFDTGKIETSRQQNSLIFEELLTFGGIDSKAISSLIIKKIIETAKNNYTTLISE

RLNTVTVENDLLKYIKNKIPVQGRLGNFKLDTAEFEKKLNTILFVLNESNLAQRFSILVR

KHYLKERPIDPIYVNILDDNSYSTLEGFNISSQGSNDFQGQLLESSYFEKIESNALRAFI

KICHKAIDGRSLYNKTLDCIEVENKDLFLISN

KDSLNDINLSEEKIKPETTVFFKDKLPPQDITLSNYDFTEANSIPSISQQNILERNEELY

EPIRNSLFEIKTIYVDKLTTFHFLEAQNIDESIDSSKIRVELTDSVDEALSNPNKVYSPF

KNMSNTINSIETGITSTYIFYQWLRSIVKDFSDETGKIDVIDKSSDTLAIVPYIGPLLNI

GNDIRHGDFVGAIELAGITALLEYVPEFTIPILVGLEVIGGELAREQVEAIVNNALDKRD

-continued

QKWAEVYNITKAQWWGTIHLQINTRLAHTYKALSRQANAIKMNMEFQLANYKGNIDDKAK

IKNAISETEILLNKSVEQAMKNTEKFMIKLSNSYLTKEMIPKVQDNLKNFDLETKKTLDK

FIKEKEDILGTNLSSSLRRKVSIRLNKNIAFDINDIPFSEFDDLINQYKNEIEDYEVLNL

GAEDGKIKDLSGTTSDINIGSDIE

EXAMPLES

Materials & Methods

Materials 5 ml HiTrap Butyl HP (GE #: 28411005)

5 ml HiTrap Q HP (GE #: 17-1154-01)

5 ml HiTrap Phenyl HP column (GE #17-5195-01)

CHT Type II column (Biorad #7324756)

TrypZean (Sigma #T3568)

Lys-C(Sigma #000000011047825001)

Enterokinase, light chain (NEB #P8070)

Factor Xa (NEB #P8010)

ACQUITY UPLC Protein BEH C4 Column (Waters #186004495)

Protein Purification

*E. coli* BL21 (DE3) or NiCo (DE3) (NEB) were utilized for protein expression. In general, bacteria were cultured at 37° C. until induction, temperature was dropped to 16° C. and protein expression was induced with 1 mM IPTG overnight.

BoNT/AC with a C1 Loop (SEQ ID NO: 13)

Bacterial pellets were disrupted in lysis buffer (50 mM Tris-HCl pH=8) by sonication and clarified by centrifugation. Ammonium sulphate concentration was adjusted to 1.3M and target protein was captured using Butyl HP resin (GE). Fractions containing target protein were desalted and loaded onto Q HP resin (GE). Purified protein was activated overnight at 4° C. with 6 μg/1 mg of BoNT Factor Xa (NEB), followed by polishing using Phenyl HP resin (GE).

BoNT/E with a C1 Loop (SEQ ID NO: 11)

Bacterial pellets were disrupted in lysis buffer (100 mM sodium phosphate pH=7.8; 100 mM NaCl) by sonication and clarified by centrifugation. Ammonium sulphate concentration was adjusted to 1.25 M and target protein was captured using Butyl HP resin (GE). Fractions containing target protein were desalted and loaded onto Q HP resin (GE). Purified protein was activated overnight at 4° C. with either 5 μg/1 mg of BoNT Factor Xa (NEB) or 80 U/ml of Enterokinase (NEB), followed by polishing using CHT Type II resin (Biorad).

BoNT/X (SEQ ID NO: 5)

Bacterial pellets were disrupted in lysis buffer (50 mM Tris-HCl pH=8, 500 mM NaCl) by sonication and clarified by centrifugation. Target protein was captured using HisTrap HP column (GE). Fractions containing target protein were desalted and loaded onto Q HP resin (GE). Purified protein was activated overnight at 4° C. with either 5 μg/1 mg of BoNT Factor Xa (NEB) or 80 U/1 mg of BoNT of Enterokinase (NEB), followed by polishing using 1 ml HisTrap column (GE).

LC/MS

Samples were buffer exchanged into 50 mM ammonium bicarbonate prior to analysis. Samples were either intact protein or reduced by incubation with 10 mM DTT for 30 minutes at 37° C. Samples were tested using Waters Acquity H-Class UPLC system combined with Waters Xevo G2-XS QToF mass spectrometer.

Mobile phase A 0.1% formic acid in water

Mobile phase B 0.1% formic acid in acetonitrile

Column: ACQUITY UPLC Protein BEH C4 (Waters)

Example 1

The BoNT/C1 Activation Loop can be Cleaved by Multiple Proteases

Figure 2B:
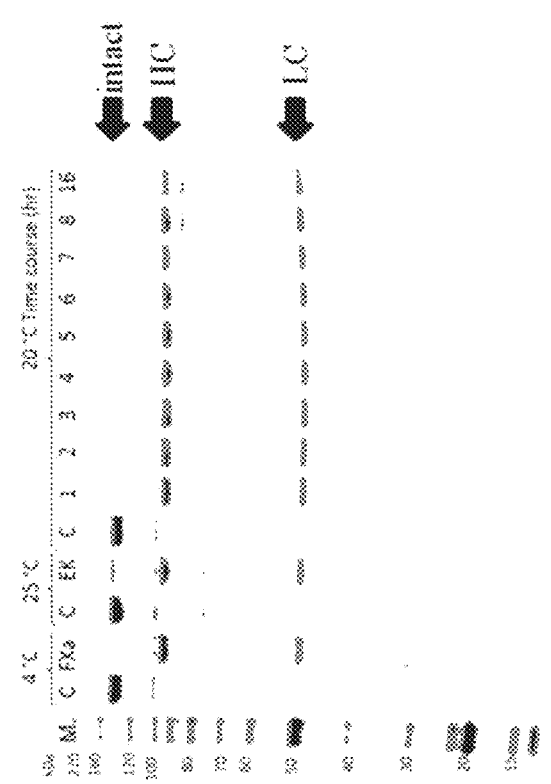
Figure 2A:
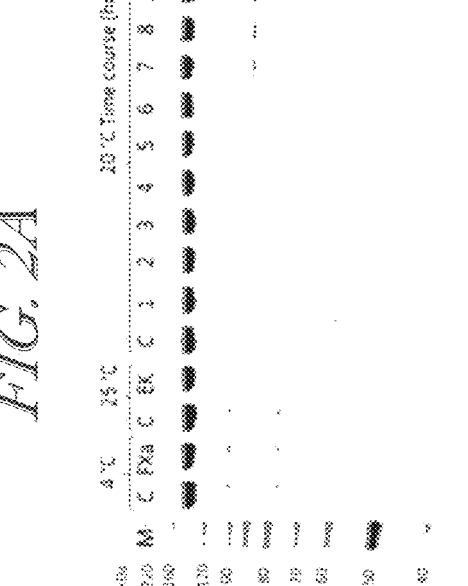

Inactive BoNT/C1 (0) (SEQ ID NO: 15) was incubated with a set of proteases: trypsin, Lys-C, enterokinase and Factor Xa. All proteases showed cleavage within the activation loop. BoNT/C1 (0) (SEQ ID NO: 15) was digested with enterokinase (EK) or factor Xa (FXa) overnight at 4° C. and 25° C. In addition, BoNT/C1 (0) was trypsin digested over a 16 hr timecourse at 20° C. (FIGS. 2 A, B). All three proteases can cleave the BoNT/C1 activation loop and create a di-chain molecule when compared to protease untreated control. However, additional cleavage products were visible after tryptic and Lys-C digest.

Example 2

Characterisation and Improvement of BoNT/X Proteolytic Activation

Partially purified wild-type BoNT/X-10HT (SEQ ID NO: 34) was incubated overnight at 4° C. with increasing amounts of trypsin (TrypZean) and Lys-C, as well as factor Xa (FXa) and enterokinase (EK).

Figure 3B:
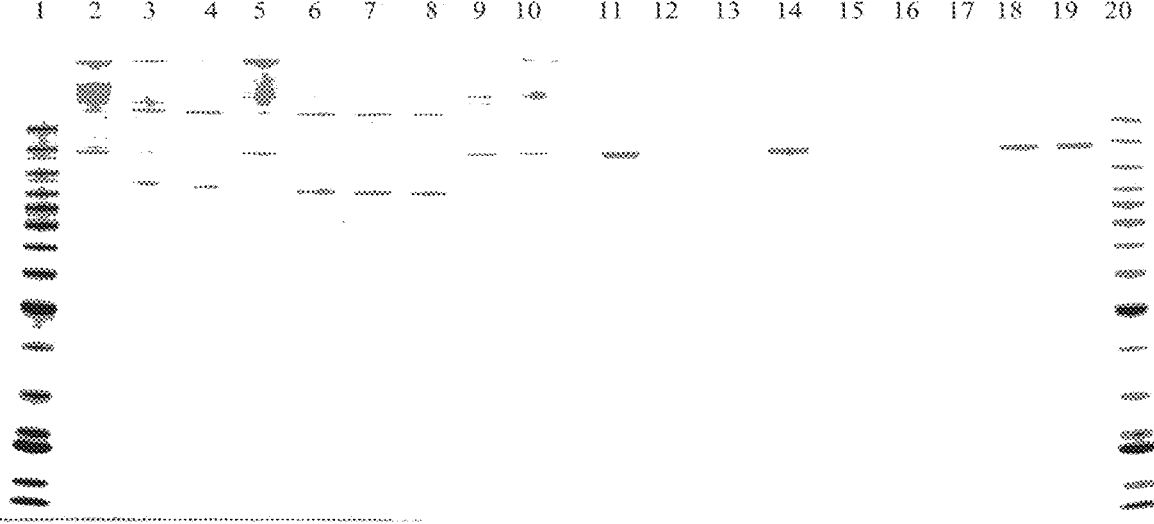
FIG. 3B shows BoNT/X cleavage by Trypsin (TrypZean), Factor Xa and Enterokinase. Samples were tested in non-reduced and reduced (+DTT) conditions. 1-Benchmark (5ul); 2-No protease control; 3-TrypZean 0.125 µg/ml; 4-TrypZean 0.25 µg/ml; 5-No protease control; 6-TrypZean 1 µg/ml; 7-TrypZean 2 µg/ml; 8-TrypZean 4 µg/ml; 9-Factor Xa 5 µg/ml; 10-Enterokinase 0.01 µg/ml; 11-No protease control +DTT; 12-TrypZean 0.125 µg/ml +DTT; 13-TrypZean 0.25 µg/ml +DTT; 14-No protease control +DTT; 15-TrypZean 1 µg/ml +DTT; 16-TrypZean 2 µg/ml +DTT; 17-TrypZean 4 µg/ml +DTT; 18-Factor Xa 5 µg/ml; 19-Enterokinase 0.01 µg/ml; and 20-Benchmark (5ul).

FIG. 3 shows that wild-type BoNT/X was completely degraded by both Lys-C (FIG. 3A) and trypsin (FIG. 3B, lanes 12-13 and 15-17). Notably, FXa and EK were unable to cleave the protein into a di-chain form (FIG. 3B, lanes 18 and 19, respectively).

Figure 4:
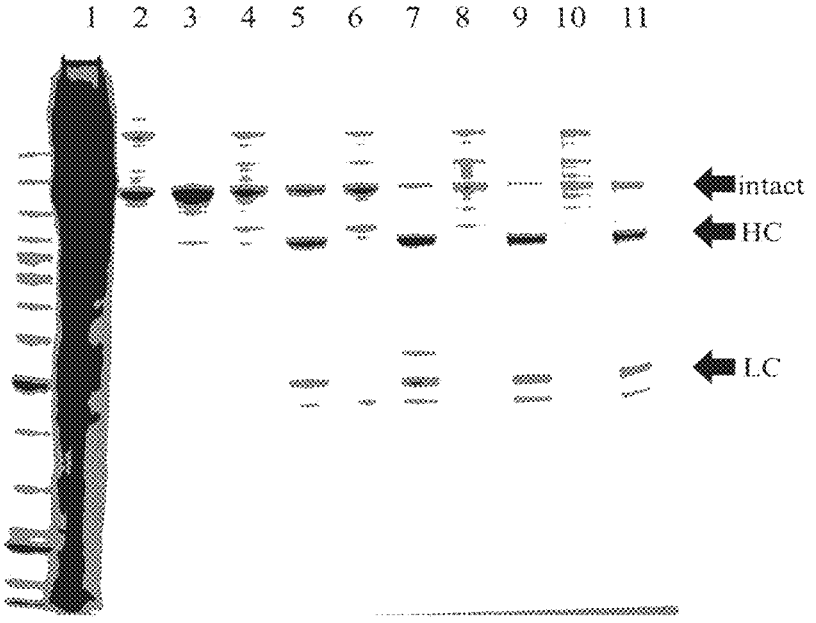
FIG. 4 shows engineered BoNT/X (SEQ ID NO: 5) treated with indicated proteases and successful BONT di-chain formation evident by comparison between non-reduced (-DTT) and reduced (+DTT) conditions. Lanes 4-7 show in-process samples. Lanes 8-11 show final samples after last polishing step. 1-capture HisHP load; 2-control-DTT-protease; 3-control +DTT-protease; 4-activated-DTT +EK; 5-activated +DTT +EK; 6-activated-DTT +FXa; 7-activated +DTT +FXa; 8-final-DTT EK active.; 9-final +DTT EK activ.; 10-final-DTT FXa activ.; 11-final +DTT FXa activ.

In an attempt to improve activation of BoNT/X, the BoNT/X activation loop was replaced by the BoNT/C1 activation loop (SEQ ID NO: 2) creating engineered BoNT protein SEQ ID NO: 5. The engineered BoNT was purified using several chromatographic steps and treated with enterokinase (EK) or factor Xa (FXa) to verify that the presence of BoNT/C loop allowed for production of a di-chain molecule. Surprisingly, FIG. 4 shows that EK and FXa specifically cleave engineered BoNT/X into the di-chain form.

Example 3

Characterisation and Improvement of BoNT/E Proteolytic Activation

Figure 5A:
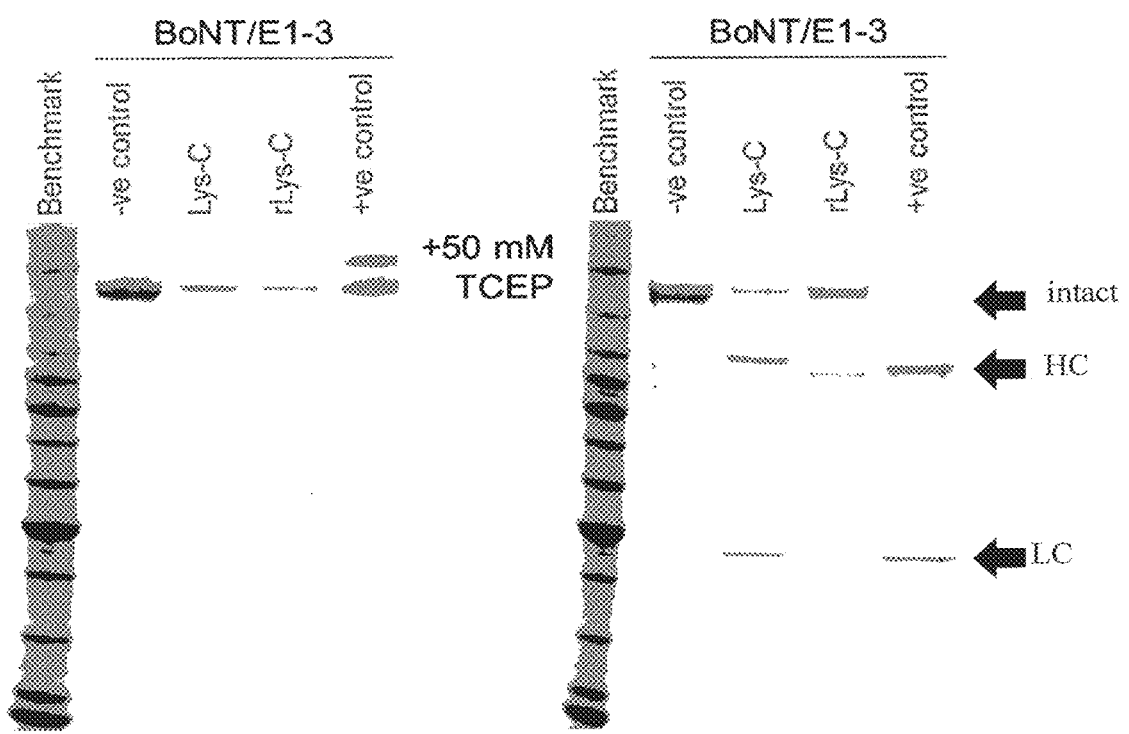
FIG. 5A shows BoNT/E tested with 10 µg/ml endoproteinase Lys-C from Lysobacter enzymogenes ("Lys-C") and *Pseudomonas aeruginosa* ("rLys-C") for 2 h @ 37° C. Samples were tested in non-reduced and reduced (+TCEP) conditions.
Figure 5B:
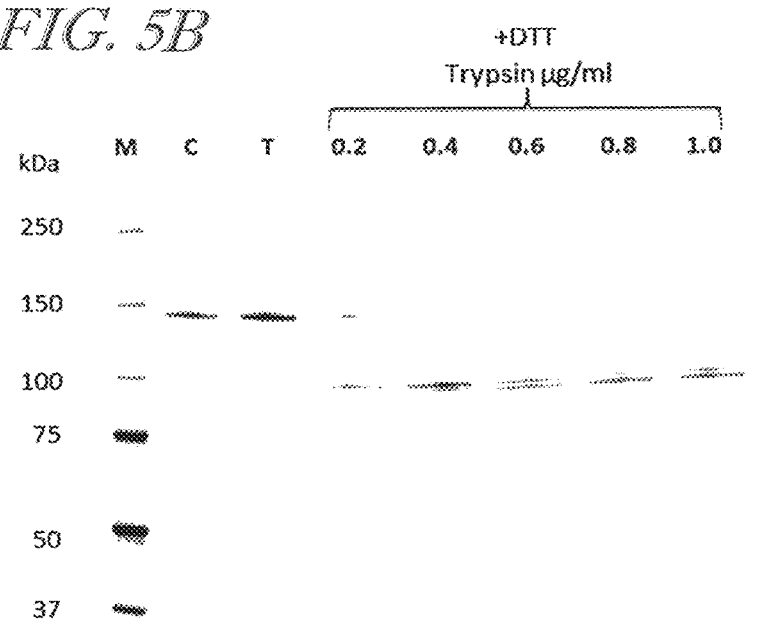
FIG. 5B shows BoNT/E treated with indicated amounts of Trypsin for 7 h at 20° C. (C)-sample stored at −20° C. (T)—no protease control at 20° C. Samples were tested in reduced (+DTT) conditions.

Wild-type BoNT/E was cleaved with Lys-C and trypsin (TryZean). FIG. 5A shows that Lys-C inaccurately cleaves/degrades BoNT/E. Treatment with trypsin resulted in truncation of BoNT/E meaning an additional purification step was required to separate the full-length protein from the truncation product (FIG. 5B).

In an attempt to improve activation of BoNT/E, the BoNT/E activation loop was replaced by the BoNT/C1 activation loop (SEQ ID NO: 2) creating engineered BoNT protein SEQ ID NO: 11. The engineered BoNT was purified using several chromatographic steps and treated with enterokinase (EK) or factor Xa (FXa) to verify that the presence of BoNT/C loop allowed for production of a di-chain molecule. Surprisingly, FIG. 6 shows that EK and FXa specifically cleave engineered BoNT/E into the di-chain form.

Example 4

Proteolytic Activation of a BoNT/A1C1 Chimera

The BoNT/C loop was introduced into a BoNT/A1C1 chimera (LH$_N$/A1 with a C1 H$_C$ domain) to facilitate proteolytic protein activation. The BoNT/A1 activation loop of BoNT/A1C1 was replaced with a BoNT/C1 loop creating engineered BoNT protein SEQ ID NO: 13. The engineered BoNT was purified using several chromatographic steps and treated with factor Xa (FXa) to verify that the presence of BoNT/C loop allowed for production of a di-chain molecule. FIG. 7A shows that FXa specifically cleaves engineered BoNT/A1C1 into the di-chain form. For comparison purposes, wild-type Met BoNT/A1 (commercially available from MetabiologicsA1080116) containing the A1 activation loop was incubated with FXa and EK. FIG. 7B shows that FXa does not cleave the A1 activation loop, while EK cleaves with only minimal activity, and both FXa and EK results in formation of additional improper cleavage products (degradation products).

Example 5

BoNTs Containing the C1 Loop Retain SNARE Cleavage Activity

Figures 8A, 8B:
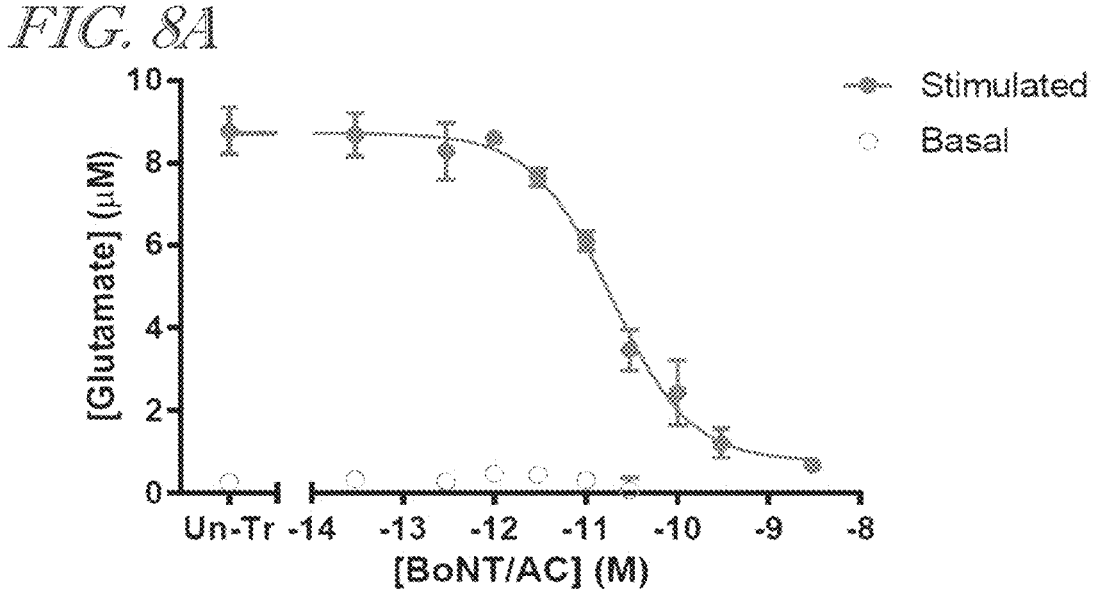
FIG. 8A shows BoNT/A1C1 and BeNT/C1 dose dependent inhibition of glutamate release from primary rat neurons.
FIG. 8B shows BoNT/C1 dose dependent inhibition of glutamate release from primary rat neurons.

Rat primary cortical neurons were treated for 24 h with BoNT/A1C1 (SEQ ID NO: 13) of Example 4 containing the BoNT/C1 activation loop and purified recombinant BoNT/C1 (SEQ ID NO: 17). SNARE-dependent glutamate release from the cells stimulated by potassium chloride was measured after incubation (FIG. 8). These data confirm activity of clostridial neurotoxins modified to include the BoNT/C1 activation loop.

Example 6

Factor Xa and Enterokinase Cleave BoNT/C Activation Loop at the Same Site IDGR↓SL Purified BoNT/E containing the BoNT/C1 loop (SEQ ID NO: 11) was activated by either enterokinase or factor Xa proteases and was incubated with 10 mM DTT to reduce disulphide bridges and separate light and heavy chain. Liquid chromatography-mass spectrometry analysis of intact protein mass was performed on reduced and non-reduced engineered BoNT/E (SEQ ID NO: 11) samples to map the cleavage sites of both proteases. Both proteases cleaved BoNT/E to produce light and heavy chain of the same size indicating that both enterokinase and factor Xa cleave at the same site (Table 1).

TABLE 1

Comparison of predicted and measured masses of engineered BoNT/E (SEQ ID NO: 11)after cleavage at IDGR↓SL site within the C-loop. Heavy chain mass indicates cleavage at the predicted site by both enterokinase and factor Xa.

Figure 9:
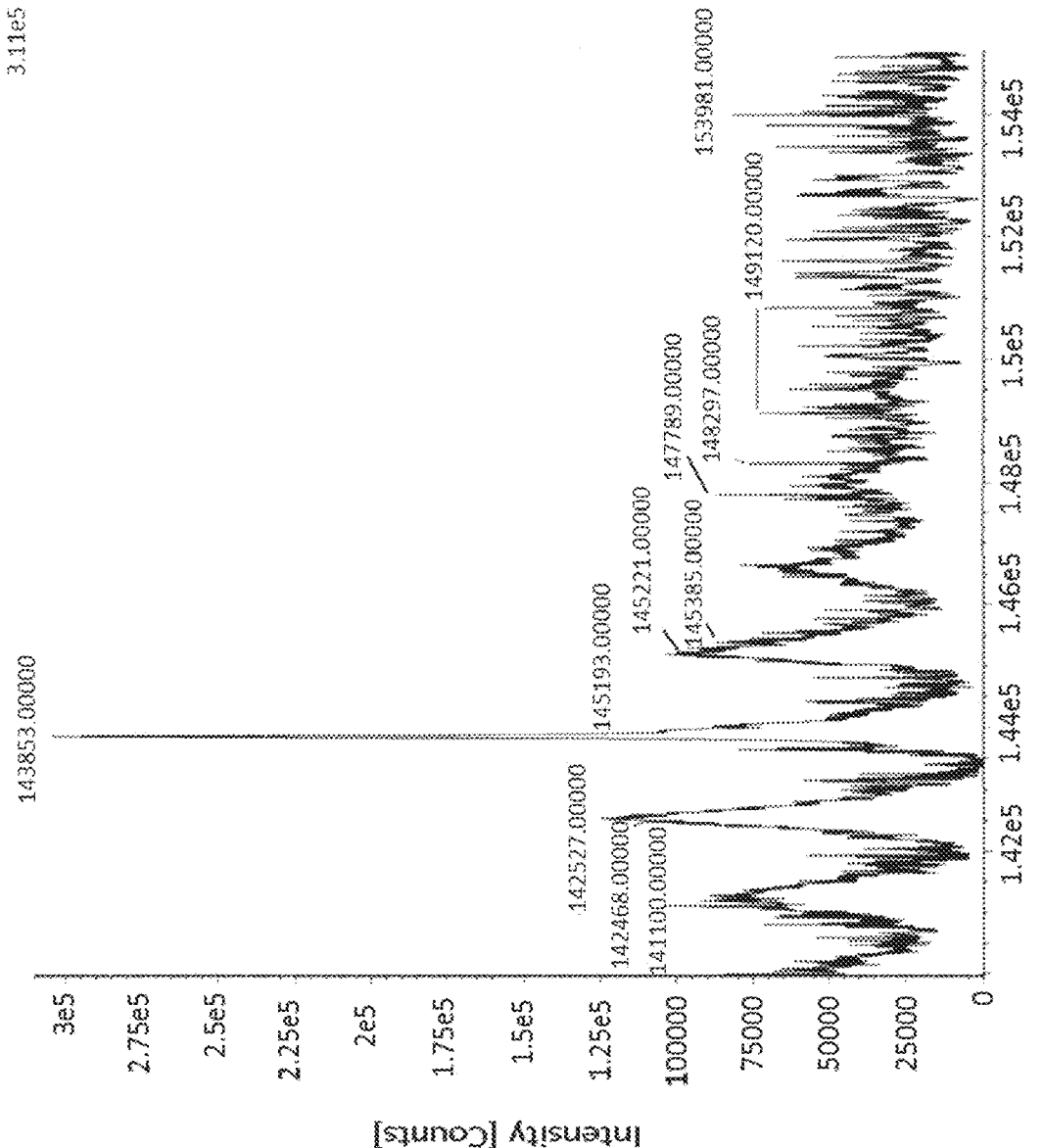
FIG. 9 shows intact mass analysis of non-reduced engineered BoNT/E (SEQ ID NO: 11) activated by enterokinase with an indicated mass of 143853 Da.
Figure 11:
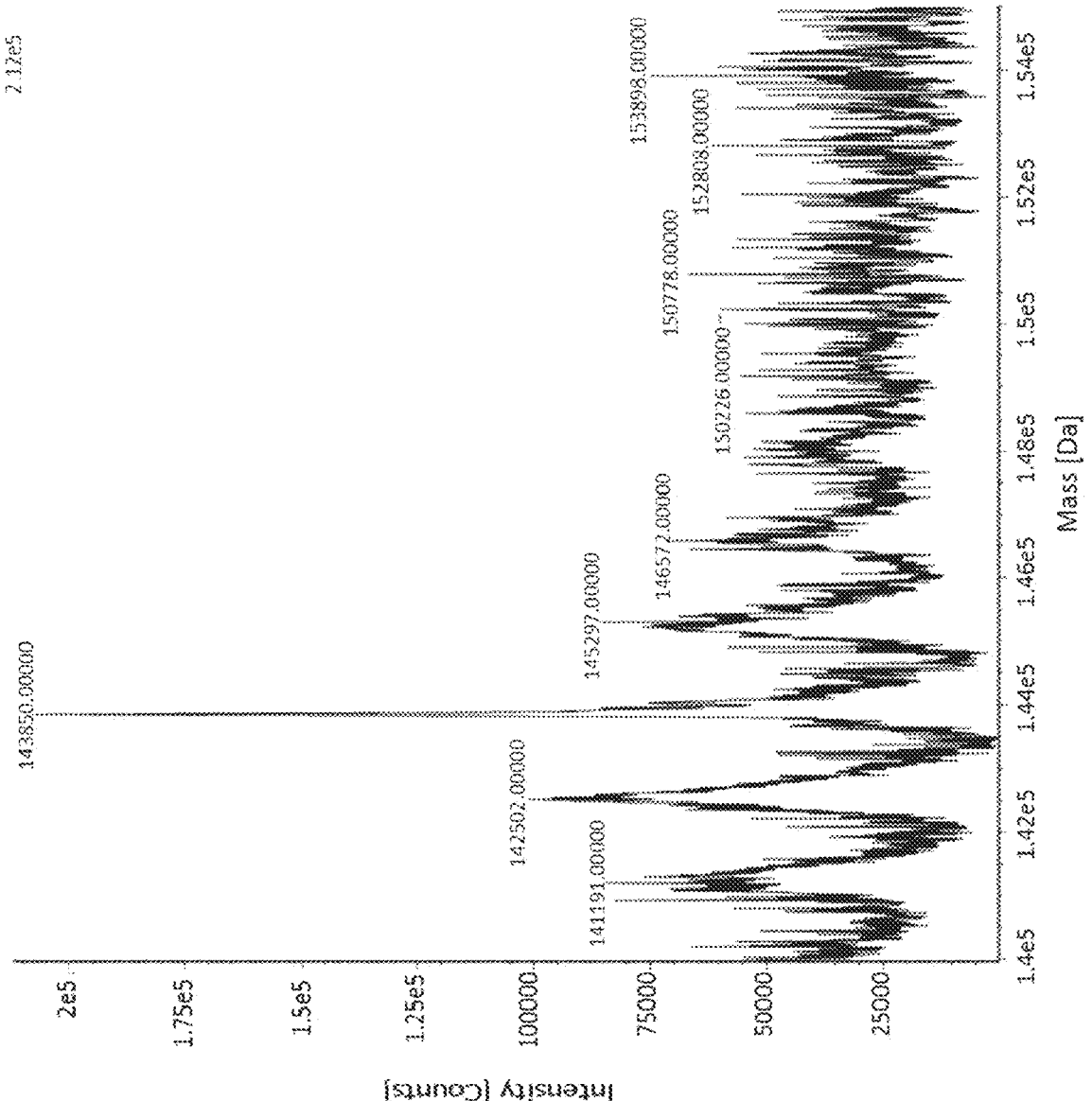
FIG. 11 shows intact mass analysis of non-reduced engineered BoNT/E (SEQ ID NO: 11) activated by factor Xa with an indicated mass of 143850 Da.

| | predicted theoretical mass [Da] | observed mass after EK cleavage [Da] | observed mass after FXa cleavage [Da] |
|---|---|---|---|
| intact molecule | 143952 | 143853 (FIG. 9) | 143850 (FIG. 11) |
| light chain | 47633 | 47518 (FIG. 10) | 47518 (FIG. 12) |
| heavy chain | 96337 | 96338 (FIG. 10) | 96335 (FIG. 12) |

Comparative Example 7

Insertion of a Protease Recognition Site into an Endogenous Loop

The BoNT/C1 activation loop is the only BoNT activation loop that contains a naturally occurring cleavage site for site specific proteases FXa (and surprisingly EK) (see FIG. 1). All other loops are cleaved by non-specific proteases such as trypsin or Lys-C. Cleavage by Lys-C and trypsin often leads to undesired protein truncation as the cleavage site is determined by protease accessibility rather than a specific recognition sequence.

Natural activation loops from different serotypes evolved to allow protease accessibility and process toxin into a di-chain form by *Clostridium*. Without wishing to be bound by theory, it is believed that mutating these loops to create a protease recognition site can lead to conformational changes, which could negatively affect cleavage efficiency.

Figure 13:
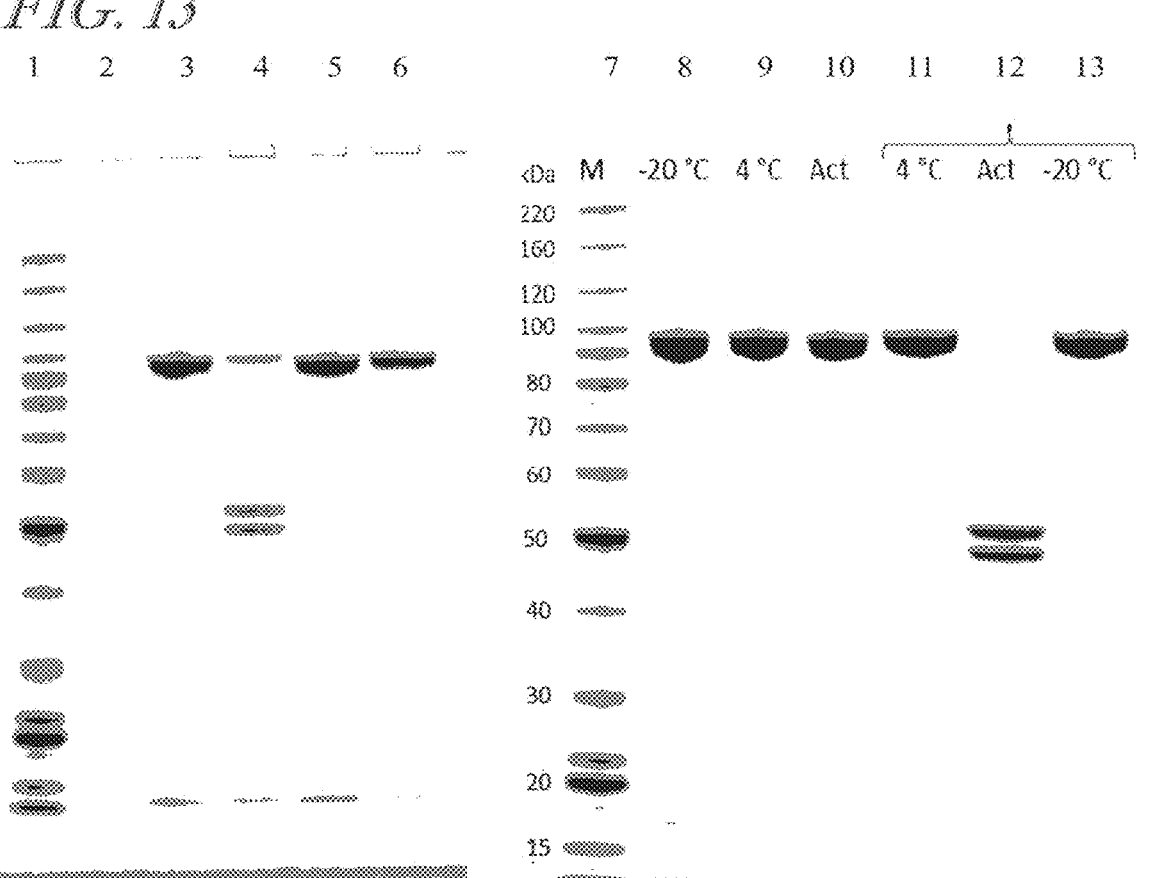
FIG. 13 shows LH$_N$/A1 containing an EK cleavage site inserted into the activation loop (SEQ ID NO: 44) and treated with EK compared to a native A1 loop (SEQ ID NO.

To test this hypothesis, a polypeptide having the BoNT/A1 light chain and translocation domain (LH$_N$/A1) was modified to include an EK protease recognition sequence DDDDK (SEQ ID NO: 44). The efficiency of proteolytic cleavage of modified LH$_N$/A1 with EK was assessed and compared with cleavage of the wild-type A1 activation loop with Lys-C (note owing to an absence of EK recognition sites in the wild-type loop a direct comparison using EK is not possible). FIG. 13 shows that cleavage of the modified loop is much less efficient than the wild-type loop.

Example 8

Proteolytic Activation of a BoNT/XA Chimera

A BoNT/XA chimera containing the light chain and translocation domain of BoNT/X, the binding domain of BoNT/A1, and the BoNT/C1 activation loop was manufactured (SEQ ID NO: 7). FIG. 14 shows that the di-chain form of the engineered BoNT/XA chimera was produced following activation with FXa.

Example 9

Proteolytic Activation of a BoNT/XB Chimera

A BoNT/XB chimera containing the light chain and translocation domain of BoNT/X, the binding domain of BoNT/B, and the BoNT/C1 activation loop was manufactured (SEQ ID NO: 9). FIG. 15 shows that the di-chain form of the engineered BoNT/XB chimera was produced following activation with FXa.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments.

Indeed, various modifications of the described modes for carrying out the invention which are obvious to those skilled in biochemistry and biotechnology or related fields are intended to be within the scope of the following claims.

The invention claimed is:

1. A method for proteolytically processing a single-chain clostridial neurotoxin into a corresponding di-chain clostridial neurotoxin, the method comprising contacting the single-chain clostridial neurotoxin with enterokinase, wherein the single-chain clostridial neurotoxin comprises an activation loop comprising the amino acid sequence of SEQ ID NO: 18 and wherein the amino acid sequence of the single-chain clostridial neurotoxin comprises an amino acid sequence selected from the group consisting of SEQ ID NO: 5, 7, 9, 11, and 13, and wherein the enterokinase hydrolyses a peptide bond of the activation loop thereby producing the di-chain clostridial neurotoxin.

2. The method of claim 1, wherein the single-chain clostridial neurotoxin comprises the amino acid sequence of SEQ ID NO: 5.

3. A method for proteolytically processing a single-chain clostridial neurotoxin into a corresponding di-chain clostridial neurotoxin, the method comprising contacting the single-chain clostridial neurotoxin with enterokinase, wherein the single-chain clostridial neurotoxin comprises an activation loop comprising the amino acid sequence of SEQ ID NO: 18 and wherein the amino acid sequence of the single-chain clostridial neurotoxin comprises: (a) the amino acid sequence of SEQ ID NO: 52 or a fragment thereof; and (b) an amino acid sequence selected from the group consisting of SEQ ID NO: 53, 54, 55, 56, 57, 58, 59, and 60, and wherein the enterokinase hydrolyses a peptide bond of the activation loop thereby producing the di-chain clostridial neurotoxin.

4. The method of claim 3, wherein the single-chain clostridial neurotoxin comprises the amino acid sequence of SEQ ID NO: 60.

5. The method of claim 3, wherein the single-chain clostridial neurotoxin lacks a functional Hc domain of a clostridial neurotoxin.

6. The method of claim 3, wherein the single-chain clostridial neurotoxin is a retargeted clostridial neurotoxin comprising a non-clostridial targeting moiety.

7. The method of claim 3, wherein the single-chain clostridial neurotoxin is a re-targeted clostridial neurotoxin comprising a targeting moiety that comprises an anthrax toxin protective antigen or a fragment thereof.

8. The method of claim 3, wherein the single-chain clostridial neurotoxin comprises a peptide bond outside of the activation loop that is hydrolyzed by trypsin or Lys-C.

* * * * *

```
                          SEQUENCE LISTING

<160> NUMBER OF SEQ ID NOS: 84

<210> SEQ ID NO 1
<211> LENGTH: 36
<212> TYPE: PRT
<213> ORGANISM: Artificial Sequence
<220> FEATURE:
<223> OTHER INFORMATION: C1 Activation Loop Consensus Sequence
<220> FEATURE:
<221> NAME/KEY: MOD_RES
<222> LOCATION: (2)..(11)
<223> OTHER INFORMATION: Any amino acid
<220> FEATURE:
<221> NAME/KEY: SITE
<222> LOCATION: (2)..(11)
<223> OTHER INFORMATION: This region may encompass 1-10 residues
<220> FEATURE:
<221> NAME/KEY: MOD_RES
<222> LOCATION: (13)..(13)
<223> OTHER INFORMATION: Asp or Glu
<220> FEATURE:
<221> NAME/KEY: MOD_RES
<222> LOCATION: (16)..(30)
<223> OTHER INFORMATION: Any amino acid
<220> FEATURE:
<221> NAME/KEY: SITE
<222> LOCATION: (16)..(35)
<223> OTHER INFORMATION: This region may encompass 4-20 residues

<400> SEQUENCE: 1

Cys Xaa Xaa Xaa Xaa Xaa Xaa Xaa Xaa Xaa Xaa Ile Xaa Gly Arg Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Cys
        35

<210> SEQ ID NO 2
<211> LENGTH: 17
<212> TYPE: PRT
<213> ORGANISM: Clostridium botulinum

<400> SEQUENCE: 2

Cys His Lys Ala Ile Asp Gly Arg Ser Leu Tyr Asn Lys Thr Leu Asp
1               5                   10                  15

Cys

<210> SEQ ID NO 3
<211> LENGTH: 17
<212> TYPE: PRT
<213> ORGANISM: Artificial Sequence
<220> FEATURE:
<223> OTHER INFORMATION: C1 Activation Loop Variant

<400> SEQUENCE: 3

Cys His Lys Ala Ile Glu Gly Arg Ser Leu Tyr Asn Lys Thr Leu Asp
1               5                   10                  15

Cys

<210> SEQ ID NO 4
<211> LENGTH: 3891
```

-continued

```
<212> TYPE: DNA
<213> ORGANISM: Artificial Sequence
<220> FEATURE:
<223> OTHER INFORMATION: BoNT/X with a C1 Activation Loop

<400> SEQUENCE: 4
atgaaactgg aaatcaacaa attcaactac aacgatccga tcgatggcat taatgttatt        60
accatgcgtc cgcctcgtca tagcgataaa atcaataaag gtaaaggtcc gttcaaagcc       120
tttcaggtga ttaaaaacat ttggattgtg ccggaacgct acaactttac caataatacc       180
aacgatctga acattccgag cgaaccgatt atggaagcag atgccattta taacccgaac       240
tatctgaata ccccgagcga aaaagatgaa tttctgcagg gtgttatcaa agtgctggaa       300
cgcattaaaa gcaaaccgga aggtgaaaaa ctgctggaac tgattagcag cagcattccg       360
ctgccgctgg ttagcaatgg tgcactgacc ctgagcgata tgaaaccat tgcatatcaa       420 gagaacaaca acattgtgag caatctgcag gcaaacctgg ttatttatgg tccgggtcct       480
gatattgcaa ataatgcaac ctatggtctg tatagcaccc cgattagtaa tggtgaaggt       540
acactgagcg aagttagctt tagcccgttt tatctgaaac cgtttgatga aagctatggc       600
aattatcgta gcctggtgaa tatcgtgaac aaattcgtga acgtgaatt tgcacctgat       660 ccggcaagca ccctgatgca tgaactggtt catgttaccc ataatctgta tggtattagc       720
aaccgcaact tctactataa cttttgacacc ggcaaaattg aaaccagccg tcagcagaat       780
agcctgattt ttgaagaact gctgaccttt ggtggcattg atagcaaagc aattagcagc       840
ctgatcatca agaaaattat cgaaaccgcc aagaacaact ataccacgct gattagcgaa       900
cgcctgaata ccgttaccgt tgaaaatgat ctgctgaaat atatcaaaaa caaaatcccg       960
gttcagggtc gtctgggtaa ctttaaactg gataccgcag aattcgagaa aaagctgaat      1020
accattctgt ttgtgctgaa cgaaagcaat ctggcacagc gttttagcat tctggttcgt      1080
aaacattacc tgaaagaacg tccgattgat ccgatttatg tgaacattct ggatgacaat      1140
agctacagca ccctggaagg ttttaacatt agcagtcagg gtagcaatga tttccaaggt      1200
cagctgctgg aaagcagcta ttttgaaaaa attgaaagca atgccctgcg tgcctttatc      1260
aaaatttgtc ataaagccat tgatggtcgc agcctgtata caaaacccct ggattgtatt      1320
gaggtggaaa acaaagacct gtttctgatt agcaacaaag atagcctgaa cgatattaac      1380
ctgagcgaag aaaaaatcaa accggaaacc accgtgttct tcaaagataa actgcctccg      1440
caggatatta cgctgagcaa ttatgatttt accgaagcca atagcattcc gagcattagc      1500
cagcagaaca ttctggaacg taatgaagaa ctgtatgaac cgattcgcaa tagcctgttt      1560
gaaatcaaaa ccatctatgt ggataagctg accacctttc attttctgga gcccagaat      1620 attgatgaga gcattgatag cagcaaaatt cgtgttgaac tgaccgatag cgttgatgaa      1680
gcactgagca atccgaataa agtttatagc ccgttcaaga acatgagcaa caccattaat      1740
agcattgaaa ccggtattac cagcacctac atctttttatc agtggctgcg tagcatcgtg      1800
aaagatttta gtgatgaaac cggcaaaatc gacgtgattg ataaaagcag cgataccctg      1860
gcaattgttc cgtatattgg tccgctgctg aatattggta tgatattcg tcatggcgat      1920 tttgtgggtg caattgaact ggcaggcatt accgcactgc tggaatatgt tccggaattt      1980
accattccga ttctggttgg tctggaagtt attggtggcg aactggcacg tgaacaggtt      2040
gaagcaattg ttaataatgc cctggataaa cgcgatcaga atgggcaga agtttacaat      2100 attaccaaag cacagtggtg gggcaccatt catttacaga ttaatacccg tctggcccat      2160
```

```
acctataaag ccctgagccg tcaggcaaat gccattaaaa tgaatatgga atttcagctg    2220
gccaactaca aaggcaacat tgatgataaa gccaagatca aaaacgccat cagcgaaacc    2280
gaaattctgc tgaacaaaag cgttgaacag gccatgaaaa acaccgagaa attcatgatt    2340
aaactgagca acagctacct gaccaaagaa atgattccga aagttcagga caacctgaaa    2400
aactttgatc tggaaaccaa aaagaccctg gacaagttca tcaaagagaa agaagatatc    2460
ctgggcacca atctgagcag cagcctgcgt cgtaaagtta gcattcgtct gaataaaaac    2520
attgccttcg acatcaacga tatcccgttt agcgaatttg atgatctgat caaccagtac    2580
aaaaacgaga tcgaagatta tgaagtgctg aatctgggtg cagaagatgg caaaatcaaa    2640
gatctgagcg gtacaaccag cgatatcaat attggttcag atatcgaact ggccgatggt    2700
cgtgaaaata aagcgattaa gattaaaggc agcgagaaca gcaccatcaa aattgcaatg    2760
aacaaatatc tgcgttttag cgcgaccgat aactttagca ttagcttttg gatcaaacat    2820
ccgaaaccga ccaatctgct taataacggt attgaatata ccctggtcga gaactttaat    2880
cagcgtggtt ggaaaattag catccaggat agcaaactga tttggtatct gcgcgatcac    2940
aataacagca tcaaaatcgt tacaccggat tatattgcgt ttaatggctg gaacctgatt    3000
accattacaa acaatcgtag caaaggcagc atcgtgtatg ttaacggtag caaaattgaa    3060
gagaaggaca ttagcagcat ttggaatacc gaagtggatg atccgattat cttccgcctg    3120
aaaaataacc gtgataccca ggcatttacc ctgctggatc agtttagcat ttatcgcaaa    3180
gaactgaacc agaacgaagt ggtgaaactg tataactact acttcaacag caactacatt    3240
cgcgatattt ggggtaatcc gctgcagtac aacaaaaaat actatctgca gacccaggac    3300
aaacctggta aggtctgat ccgcgaatat tggagcagct ttggttatga ttatgtgatt    3360
ctgagcgata gcaagaccat tacctttccg aataatatcc gttatggtgc cctgtataat    3420
ggtagcaaag tgctgatcaa gaacagcaaa aaactggatg gtctggtgcg caataaagat    3480
ttcattcagc tggaaatcga tggctataat atgggtatta gcgcagatcg ctttaacgag    3540
gataccaact atattggcac cacctatggt acaacccatg atctgaccac cgattttgaa    3600
attattcagc gccaagagaa ataccgcaat tattgtcagc tgaaaacccc gtataacatc    3660
tttcataaaa gcggtctgat gagcaccgaa accagcaaac cgaccttcca tgattatcgc    3720
gattgggttt atagcagcgc atggtatttt cagaactatg aaaatctgaa cctgcgcaaa    3780
cataccaaaa ccaactggta ttttatcccg aaagatgaag gttgggatga agatctggaa    3840
gtgctgtttc agggtccgca tcatcaccac catcaccatc atcatcactg a             3891
```

```
<210> SEQ ID NO 5
<211> LENGTH: 1296
<212> TYPE: PRT
<213> ORGANISM: Artificial Sequence
<220> FEATURE:
<223> OTHER INFORMATION: BoNT/X with a C1 Activation Loop

<400> SEQUENCE: 5

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60
```

-continued

```
Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
        290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
            325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
        370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
            405                 410                 415

Arg Ala Phe Ile Lys Ile Cys His Lys Ala Ile Asp Gly Arg Ser Leu
            420                 425                 430

Tyr Asn Lys Thr Leu Asp Cys Ile Glu Val Glu Asn Lys Asp Leu Phe
        435                 440                 445

Leu Ile Ser Asn Lys Asp Ser Leu Asn Asp Ile Asn Leu Ser Glu Glu
        450                 455                 460

Lys Ile Lys Pro Glu Thr Thr Val Phe Phe Lys Asp Lys Leu Pro Pro
465                 470                 475                 480
```

```
Gln Asp Ile Thr Leu Ser Asn Tyr Asp Phe Thr Glu Ala Asn Ser Ile
            485                 490                 495

Pro Ser Ile Ser Gln Gln Asn Ile Leu Glu Arg Asn Glu Glu Leu Tyr
            500                 505                 510

Glu Pro Ile Arg Asn Ser Leu Phe Glu Ile Lys Thr Ile Tyr Val Asp
            515                 520                 525

Lys Leu Thr Thr Phe His Phe Leu Glu Ala Gln Asn Ile Asp Glu Ser
        530                 535                 540

Ile Asp Ser Ser Lys Ile Arg Val Glu Leu Thr Asp Ser Val Asp Glu
545                 550                 555                 560

Ala Leu Ser Asn Pro Asn Lys Val Tyr Ser Pro Phe Lys Asn Met Ser
                565                 570                 575

Asn Thr Ile Asn Ser Ile Glu Thr Gly Ile Thr Ser Thr Tyr Ile Phe
            580                 585                 590

Tyr Gln Trp Leu Arg Ser Ile Val Lys Asp Phe Ser Asp Glu Thr Gly
            595                 600                 605

Lys Ile Asp Val Ile Asp Lys Ser Ser Asp Thr Leu Ala Ile Val Pro
        610                 615                 620

Tyr Ile Gly Pro Leu Leu Asn Ile Gly Asn Asp Ile Arg His Gly Asp
625                 630                 635                 640

Phe Val Gly Ala Ile Glu Leu Ala Gly Ile Thr Ala Leu Leu Glu Tyr
                645                 650                 655

Val Pro Glu Phe Thr Ile Pro Ile Leu Val Gly Leu Glu Val Ile Gly
            660                 665                 670

Gly Glu Leu Ala Arg Glu Gln Val Glu Ala Ile Val Asn Asn Ala Leu
            675                 680                 685

Asp Lys Arg Asp Gln Lys Trp Ala Glu Val Tyr Asn Ile Thr Lys Ala
        690                 695                 700

Gln Trp Trp Gly Thr Ile His Leu Gln Ile Asn Thr Arg Leu Ala His
705                 710                 715                 720

Thr Tyr Lys Ala Leu Ser Arg Gln Ala Asn Ala Ile Lys Met Asn Met
                725                 730                 735

Glu Phe Gln Leu Ala Asn Tyr Lys Gly Asn Ile Asp Asp Lys Ala Lys
            740                 745                 750

Ile Lys Asn Ala Ile Ser Glu Thr Glu Ile Leu Leu Asn Lys Ser Val
            755                 760                 765

Glu Gln Ala Met Lys Asn Thr Glu Lys Phe Met Ile Lys Leu Ser Asn
        770                 775                 780

Ser Tyr Leu Thr Lys Glu Met Ile Pro Lys Val Gln Asp Asn Leu Lys
785                 790                 795                 800

Asn Phe Asp Leu Glu Thr Lys Lys Thr Leu Asp Lys Phe Ile Lys Glu
                805                 810                 815

Lys Glu Asp Ile Leu Gly Thr Asn Leu Ser Ser Ser Leu Arg Arg Lys
            820                 825                 830

Val Ser Ile Arg Leu Asn Lys Asn Ile Ala Phe Asp Ile Asn Asp Ile
        835                 840                 845

Pro Phe Ser Glu Phe Asp Asp Leu Ile Asn Gln Tyr Lys Asn Glu Ile
        850                 855                 860

Glu Asp Tyr Glu Val Leu Asn Leu Gly Ala Glu Asp Gly Lys Ile Lys
865                 870                 875                 880

Asp Leu Ser Gly Thr Thr Ser Asp Ile Asn Ile Gly Ser Asp Ile Glu
                885                 890                 895

Leu Ala Asp Gly Arg Glu Asn Lys Ala Ile Lys Ile Lys Gly Ser Glu
```

-continued

```
             900               905               910
Asn Ser Thr Ile Lys Ile Ala Met Asn Lys Tyr Leu Arg Phe Ser Ala
         915               920               925

Thr Asp Asn Phe Ser Ile Ser Phe Trp Ile Lys His Pro Lys Pro Thr
     930               935               940

Asn Leu Leu Asn Asn Gly Ile Glu Tyr Thr Leu Val Glu Asn Phe Asn
945               950               955               960

Gln Arg Gly Trp Lys Ile Ser Ile Gln Asp Ser Lys Leu Ile Trp Tyr
             965               970               975

Leu Arg Asp His Asn Asn Ser Ile Lys Ile Val Thr Pro Asp Tyr Ile
             980               985               990

Ala Phe Asn Gly Trp Asn Leu Ile  Thr Ile Thr Asn Asn  Arg Ser Lys
         995               1000               1005

Gly Ser  Ile Val Tyr Val Asn  Gly Ser Lys Ile Glu  Glu Lys Asp
    1010               1015               1020

Ile Ser  Ser Ile Trp Asn Thr  Glu Val Asp Asp Pro  Ile Ile Phe
    1025               1030               1035

Arg Leu  Lys Asn Asn Arg Asp  Thr Gln Ala Phe Thr  Leu Leu Asp
    1040               1045               1050

Gln Phe  Ser Ile Tyr Arg Lys  Glu Leu Asn Gln Asn  Glu Val Val
    1055               1060               1065

Lys Leu  Tyr Asn Tyr Tyr Phe  Asn Ser Asn Tyr Ile  Arg Asp Ile
    1070               1075               1080

Trp Gly  Asn Pro Leu Gln Tyr  Asn Lys Lys Tyr Tyr  Leu Gln Thr
    1085               1090               1095

Gln Asp  Lys Pro Gly Lys Gly  Leu Ile Arg Glu Tyr  Trp Ser Ser
    1100               1105               1110

Phe Gly  Tyr Asp Tyr Val Ile  Leu Ser Asp Ser Lys  Thr Ile Thr
    1115               1120               1125

Phe Pro  Asn Asn Ile Arg Tyr  Gly Ala Leu Tyr Asn  Gly Ser Lys
    1130               1135               1140

Val Leu  Ile Lys Asn Ser Lys  Lys Leu Asp Gly Leu  Val Arg Asn
    1145               1150               1155

Lys Asp  Phe Ile Gln Leu Glu  Ile Asp Gly Tyr Asn  Met Gly Ile
    1160               1165               1170

Ser Ala  Asp Arg Phe Asn Glu  Asp Thr Asn Tyr Ile  Gly Thr Thr
    1175               1180               1185

Tyr Gly  Thr Thr His Asp Leu  Thr Thr Asp Phe Glu  Ile Ile Gln
    1190               1195               1200

Arg Gln  Glu Lys Tyr Arg Asn  Tyr Cys Gln Leu Lys  Thr Pro Tyr
    1205               1210               1215

Asn Ile  Phe His Lys Ser Gly  Leu Met Ser Thr Glu  Thr Ser Lys
    1220               1225               1230

Pro Thr  Phe His Asp Tyr Arg  Asp Trp Val Tyr Ser  Ser Ala Trp
    1235               1240               1245

Tyr Phe  Gln Asn Tyr Glu Asn  Leu Asn Leu Arg Lys  His Thr Lys
    1250               1255               1260

Thr Asn  Trp Tyr Phe Ile Pro  Lys Asp Glu Gly Trp  Asp Glu Asp
    1265               1270               1275

Leu Glu  Val Leu Phe Gln Gly  Pro His His His His  His His His
    1280               1285               1290

His His  His
    1295
```

```
<210> SEQ ID NO 6
<211> LENGTH: 3993
<212> TYPE: DNA
<213> ORGANISM: Artificial Sequence
<220> FEATURE:
<223> OTHER INFORMATION: BoNT/XA [LHNX-HCA] with a C1 Activation Loop

<400> SEQUENCE: 6
atgaaactgg aaatcaacaa attcaactac aacgatccga tcgatggcat taatgttatt        60
accatgcgtc cgcctcgtca tagcgataaa atcaataaag gtaaaggtcc gttcaaagcc       120
tttcaggtga ttaaaaacat ttggattgtg ccggaacgct acaactttac caataatacc       180
aacgatctga acattccgag cgaaccgatt atggaagcag atgccattta taacccgaac       240
tatctgaata ccccgagcga aaaagatgaa tttctgcagg gtgttatcaa agtgctggaa       300
cgcattaaaa gcaaaccgga aggtgaaaaa ctgctggaac tgattagcag cagcattccg       360
ctgccgctgg ttagcaatgg tgcactgacc ctgagcgata tgaaaccat  tgcatatcaa       420 gagaacaaca acattgtgag caatctgcag gcaaacctgg ttatttatgg tccgggtcct       480
gatattgcaa ataatgcaac ctatggtctg tatagcaccc cgattagtaa tggtgaaggt       540
acactgagcg aagttagctt tagcccgttt tatctgaaac cgtttgatga aagctatggc       600
aattatcgta gcctggtgaa tatcgtgaac aaattcgtga acgtgaatt  tgcacctgat       660 ccggcaagca ccctgatgca tgaactggtt catgttaccc ataatctgta tggtattagc       720
aaccgcaact tctactataa ctttgacacc ggcaaaattg aaaccagccg tcagcagaat       780
agcctgattt ttgaagaact gctgaccttt ggtggcattg atagcaaagc aattagcagc       840
ctgatcatca gaaaaattat cgaaaccgcc aagaacaact ataccacgct gattagcgaa       900
cgcctgaata ccgttaccgt tgaaaatgat ctgctgaaat atatcaaaaa caaaatcccg       960
gttcagggtc gtctgggtaa ctttaaactg gataccgcag aattcgagaa aaagctgaat      1020
accattctgt ttgtgctgaa cgaaagcaat ctggcacagc gttttagcat tctggttcgt      1080
aaacattacc tgaaagaacg tccgattgat ccgatttatg tgaacattct ggatgacaat      1140
agctacagca ccctggaagg ttttaacatt agcagtcagg gtagcaatga ttttcagggc      1200
cagctgctgg aaagcagcta ttttgaaaaa attgaatcca atgcgctgcg tgcctttatc      1260
aaaatttgtc ataaagccat tgatggtcgc agcctgtata caaaaccct  ggattgtatt      1320 gaagtggaaa acaaagacct gttcctgatt agcaataaag atagcctgaa cgatatcaac      1380
ctgagcgaag aaaaaatcaa accggaaacc accgtgttct tcaaagataa actgcctccg      1440
caggatatta ccctgagcaa ttatgatttt accgaagcca atagcattcc gagcattagc      1500
cagcagaaca ttctggaacg taatgaagaa ctgtatgaac cgattcgcaa tagcctgttt      1560
gaaatcaaaa ccatctatgt ggataagctg accaccttc  attttctgga agcccagaat      1620
attgatgaga gcattgatag cagcaaaatt cgtgttgaac tgaccgatag cgttgatgaa      1680
gcactgagca atccgaataa agtttatagc ccgttcaaga acatgagcaa caccattaat      1740
agcattgaaa ccggtattac cagcacctac atctttttatc agtggctgcg tagcatcgtg      1800 aaagattttat gtgatgaaac cggcaaaatc gacgtgatta taaaagcag  cgataccctg      1860 gccattgttc gtatattggt ccgctgctg  aatattggta atgatattcg tcatggcgat      1920
tttgtgggtg caattgaact ggcaggcatt accgcactgc tggaatatgt tccggaattt      1980
accattccga ttctggttgg tctggaagtt attggtggcg aactggcacg tgaacaggtt     2040
```

-continued

```
gaagcaattg ttaataatgc cctggataaa cgcgatcaga aatgggcaga agtttacaat        2100
attaccaaag cacagtggtg gggcaccatt catttacaga ttaatacccg tctggcccat        2160
acctataaag ccctgagccg tcaggcaaat gccattaaaa tgaatatgga atttcagctg        2220
gccaactaca aaggcaacat tgatgataaa gccaagatca aaaacgccat cagcgaaacc        2280
gaaattctgc tgaacaaaag cgttgaacag gccatgaaaa acaccgagaa attcatgatt        2340
aaactgagca acagctacct gaccaaagaa atgattccga aagttcagga caacctgaaa        2400
aactttgatc tggaaaccaa aaagaccctg gacaagttca tcaaagagaa agaagatatc        2460
ctgggcacca atctgagcag cagcctgcgt cgtaaagtta gcattcgtct gaataaaaac        2520
attgccttcg acatcaacga tatcccgttt agcgaatttg atgatctgat caaccagtac        2580
aaaaacgaga tcgaagatta tgaagtgctg aatctgggtg cagaagatgg caaaatcaaa        2640
gatctgagcg gtacaaccag cgatattaac attggtagcg atatcgaaat catcaacacc        2700
agcattctga tctgcgcta tgaaagcaat catctgattg atctgagccg ttatgcgtcc        2760
aaaatcaata ttggcagcaa agtgaatttc gacccgatcg ataaaaatca gatccagctg        2820
tttaatctgg aaagctccaa aattgaggtg attctgaaaa acgcgattgt gtacaatagc        2880
atgtatgaga atttctcaac cagcttctgg attcgcattc cgaaatactt taacagcatc        2940
agcctgaaca cgagtatac cattatcaac tgcatggaaa acaatagcgg ttggaaagtg        3000
agcctgaatt atggtgaaat tatctggacc ctgcaggata cccaagaaat caaacagcgt        3060
gttgtgttca aatacagcca gatgattaac atcagcgatt acattaaccg ctggatcttt        3120
gttaccatta ccaacaatcg cctgaataac agcaagatct atattaacgg tcgtctgatt        3180
gaccagaaac cgattagtaa tctgggtaat attcatgcca gcaacaacat catgttcaaa        3240
ctggatggtt gtcgtgatac ccatcgttat atttggatca agtatttaa cctgtttgat        3300 aaagaactga cgaaaaaga aattaaggat ctgtatgata accagtccaa tagcggcatc        3360
ctgaaggatt tttggggtga ttatctgcag tatgacaaac cgtattatat gctgaacctg        3420
tacgatccga acaaatatgt ggatgtgaat aatgtgggta tccgtggcta tatgtatctg        3480
aaaggtccgc gtggtagcgt tatgaccacc aacatttatc tgaatagcag cctgtatcgt        3540
ggcaccaaat tcatcatcaa aaaatacgcc agcggcaaca agataatat tgtgcgtaat        3600 aatgaccgcg tgtatatcaa tgtggtggtg aagaataaag aatatcgtct ggcaaccaat        3660
gcaagccagg caggcgttga aaaaattctg agcgcactgg aaatcccgga tgtgggtaat        3720
ctgagccagg ttgttgttat gaaaagcaaa aatgatcagg gcatcaccaa caagtgcaaa        3780
atgaatctgc aggacaataa cggcaacgac attggtttta ttggctttca ccagtttaac        3840
aacattgcca aactggttgc gagcaattgg tataatcgtc agattgaacg tagcagtcgt        3900
accctgggtt gtagctggga atttattccg gttgatgatg gttggggtga acgtccgctg        3960
catcatcacc accatcacca tcaccaccat taa                                    3993
```

<210> SEQ ID NO 7
<211> LENGTH: 1330
<212> TYPE: PRT
<213> ORGANISM: Artificial Sequence
<220> FEATURE:
<223> OTHER INFORMATION: BoNT/XA [LHNX-HCA] with a C1 Activation Loop
<400> SEQUENCE: 7

```
Met Lys Leu Glu Ile Asn Lys Phe Asn Tyr Asn Asp Pro Ile Asp Gly
1               5                   10                  15
```

-continued

```
Ile Asn Val Ile Thr Met Arg Pro Pro Arg His Ser Asp Lys Ile Asn
             20              25                  30

Lys Gly Lys Gly Pro Phe Lys Ala Phe Gln Val Ile Lys Asn Ile Trp
         35              40                  45

Ile Val Pro Glu Arg Tyr Asn Phe Thr Asn Asn Thr Asn Asp Leu Asn
     50              55              60

Ile Pro Ser Glu Pro Ile Met Glu Ala Asp Ala Ile Tyr Asn Pro Asn
65              70              75                  80

Tyr Leu Asn Thr Pro Ser Glu Lys Asp Glu Phe Leu Gln Gly Val Ile
             85              90                  95

Lys Val Leu Glu Arg Ile Lys Ser Lys Pro Glu Gly Glu Lys Leu Leu
         100             105                 110

Glu Leu Ile Ser Ser Ser Ile Pro Leu Pro Leu Val Ser Asn Gly Ala
         115             120                 125

Leu Thr Leu Ser Asp Asn Glu Thr Ile Ala Tyr Gln Glu Asn Asn Asn
     130             135             140

Ile Val Ser Asn Leu Gln Ala Asn Leu Val Ile Tyr Gly Pro Gly Pro
145             150             155                 160

Asp Ile Ala Asn Asn Ala Thr Tyr Gly Leu Tyr Ser Thr Pro Ile Ser
             165             170             175

Asn Gly Glu Gly Thr Leu Ser Glu Val Ser Phe Ser Pro Phe Tyr Leu
             180             185             190

Lys Pro Phe Asp Glu Ser Tyr Gly Asn Tyr Arg Ser Leu Val Asn Ile
         195             200             205

Val Asn Lys Phe Val Lys Arg Glu Phe Ala Pro Asp Pro Ala Ser Thr
     210             215             220

Leu Met His Glu Leu Val His Val Thr His Asn Leu Tyr Gly Ile Ser
225             230             235                 240

Asn Arg Asn Phe Tyr Tyr Asn Phe Asp Thr Gly Lys Ile Glu Thr Ser
             245             250             255

Arg Gln Gln Asn Ser Leu Ile Phe Glu Glu Leu Leu Thr Phe Gly Gly
         260             265             270

Ile Asp Ser Lys Ala Ile Ser Ser Leu Ile Ile Lys Lys Ile Ile Glu
         275             280             285

Thr Ala Lys Asn Asn Tyr Thr Thr Leu Ile Ser Glu Arg Leu Asn Thr
     290             295             300

Val Thr Val Glu Asn Asp Leu Leu Lys Tyr Ile Lys Asn Lys Ile Pro
305             310             315                 320

Val Gln Gly Arg Leu Gly Asn Phe Lys Leu Asp Thr Ala Glu Phe Glu
             325             330             335

Lys Lys Leu Asn Thr Ile Leu Phe Val Leu Asn Glu Ser Asn Leu Ala
         340             345             350

Gln Arg Phe Ser Ile Leu Val Arg Lys His Tyr Leu Lys Glu Arg Pro
         355             360             365

Ile Asp Pro Ile Tyr Val Asn Ile Leu Asp Asp Asn Ser Tyr Ser Thr
     370             375             380

Leu Glu Gly Phe Asn Ile Ser Ser Gln Gly Ser Asn Asp Phe Gln Gly
385             390             395                 400

Gln Leu Leu Glu Ser Ser Tyr Phe Glu Lys Ile Glu Ser Asn Ala Leu
             405             410             415

Arg Ala Phe Ile Lys Ile Cys His Lys Ala Ile Asp Gly Arg Ser Leu
             420             425             430

Tyr Asn Lys Thr Leu Asp Cys Ile Glu Val Glu Asn Lys Asp Leu Phe
```

```
              435                    440                    445

Leu Ile Ser Asn Lys Asp Ser Leu Asn Asp Ile Asn Leu Ser Glu Glu
    450                    455                    460

Lys Ile Lys Pro Glu Thr Thr Val Phe Phe Lys Asp Lys Leu Pro Pro
465                    470                    475                    480

Gln Asp Ile Thr Leu Ser Asn Tyr Asp Phe Thr Glu Ala Asn Ser Ile
                   485                    490                    495

Pro Ser Ile Ser Gln Gln Asn Ile Leu Glu Arg Asn Glu Glu Leu Tyr
                   500                    505                    510

Glu Pro Ile Arg Asn Ser Leu Phe Glu Ile Lys Thr Ile Tyr Val Asp
                   515                    520                    525

Lys Leu Thr Thr Phe His Phe Leu Glu Ala Gln Asn Ile Asp Glu Ser
    530                    535                    540

Ile Asp Ser Ser Lys Ile Arg Val Glu Leu Thr Asp Ser Val Asp Glu
545                    550                    555                    560

Ala Leu Ser Asn Pro Asn Lys Val Tyr Ser Pro Phe Lys Asn Met Ser
                   565                    570                    575

Asn Thr Ile Asn Ser Ile Glu Thr Gly Ile Thr Ser Thr Tyr Ile Phe
                   580                    585                    590

Tyr Gln Trp Leu Arg Ser Ile Val Lys Asp Phe Ser Asp Glu Thr Gly
                   595                    600                    605

Lys Ile Asp Val Ile Asp Lys Ser Ser Asp Thr Leu Ala Ile Val Pro
                   610                    615                    620

Tyr Ile Gly Pro Leu Leu Asn Ile Gly Asn Asp Ile Arg His Gly Asp
625                    630                    635                    640

Phe Val Gly Ala Ile Glu Leu Ala Gly Ile Thr Ala Leu Leu Glu Tyr
                   645                    650                    655

Val Pro Glu Phe Thr Ile Pro Ile Leu Val Gly Leu Glu Val Ile Gly
                   660                    665                    670

Gly Glu Leu Ala Arg Glu Gln Val Glu Ala Ile Val Asn Asn Ala Leu
                   675                    680                    685

Asp Lys Arg Asp Gln Lys Trp Ala Glu Val Tyr Asn Ile Thr Lys Ala
    690                    695                    700

Gln Trp Trp Gly Thr Ile His Leu Gln Ile Asn Thr Arg Leu Ala His
705                    710                    715                    720

Thr Tyr Lys Ala Leu Ser Arg Gln Ala Asn Ala Ile Lys Met Asn Met
                   725                    730                    735

Glu Phe Gln Leu Ala Asn Tyr Lys Gly Asn Ile Asp Asp Lys Ala Lys
                   740                    745                    750

Ile Lys Asn Ala Ile Ser Glu Thr Glu Ile Leu Leu Asn Lys Ser Val
                   755                    760                    765

Glu Gln Ala Met Lys Asn Thr Glu Lys Phe Met Ile Lys Leu Ser Asn
    770                    775                    780

Ser Tyr Leu Thr Lys Glu Met Ile Pro Lys Val Gln Asp Asn Leu Lys
785                    790                    795                    800

Asn Phe Asp Leu Glu Thr Lys Lys Thr Leu Asp Lys Phe Ile Lys Glu
                   805                    810                    815

Lys Glu Asp Ile Leu Gly Thr Asn Leu Ser Ser Ser Leu Arg Arg Lys
                   820                    825                    830

Val Ser Ile Arg Leu Asn Lys Asn Ile Ala Phe Asp Ile Asn Asp Ile
                   835                    840                    845

Pro Phe Ser Glu Phe Asp Asp Leu Ile Asn Gln Tyr Lys Asn Glu Ile
    850                    855                    860
```

```
Glu Asp Tyr Glu Val Leu Asn Leu Gly Ala Glu Asp Gly Lys Ile Lys
865             870             875             880

Asp Leu Ser Gly Thr Thr Ser Asp Ile Asn Ile Gly Ser Asp Ile Glu
                885             890             895

Ile Ile Asn Thr Ser Ile Leu Asn Leu Arg Tyr Glu Ser Asn His Leu
            900             905             910

Ile Asp Leu Ser Arg Tyr Ala Ser Lys Ile Asn Ile Gly Ser Lys Val
        915             920             925

Asn Phe Asp Pro Ile Asp Lys Asn Gln Ile Gln Leu Phe Asn Leu Glu
    930             935             940

Ser Ser Lys Ile Glu Val Ile Leu Lys Asn Ala Ile Val Tyr Asn Ser
945             950             955             960

Met Tyr Glu Asn Phe Ser Thr Ser Phe Trp Ile Arg Ile Pro Lys Tyr
                965             970             975

Phe Asn Ser Ile Ser Leu Asn Asn Glu Tyr Thr Ile Ile Asn Cys Met
            980             985             990

Glu Asn Asn Ser Gly Trp Lys Val  Ser Leu Asn Tyr Gly  Glu Ile Ile
        995             1000                1005

Trp Thr  Leu Gln Asp Thr Gln  Glu Ile Lys Gln Arg  Val Val Phe
    1010            1015            1020

Lys Tyr  Ser Gln Met Ile Asn  Ile Ser Asp Tyr Ile  Asn Arg Trp
    1025            1030            1035

Ile Phe  Val Thr Ile Thr Asn  Asn Arg Leu Asn Asn  Ser Lys Ile
    1040            1045            1050

Tyr Ile  Asn Gly Arg Leu Ile  Asp Gln Lys Pro Ile  Ser Asn Leu
    1055            1060            1065

Gly Asn  Ile His Ala Ser Asn  Asn Ile Met Phe Lys  Leu Asp Gly
    1070            1075            1080

Cys Arg  Asp Thr His Arg Tyr  Ile Trp Ile Lys Tyr  Phe Asn Leu
    1085            1090            1095

Phe Asp  Lys Glu Leu Asn Glu  Lys Glu Ile Lys Asp  Leu Tyr Asp
    1100            1105            1110

Asn Gln  Ser Asn Ser Gly Ile  Leu Lys Asp Phe Trp  Gly Asp Tyr
    1115            1120            1125

Leu Gln  Tyr Asp Lys Pro Tyr  Tyr Met Leu Asn Leu  Tyr Asp Pro
    1130            1135            1140

Asn Lys  Tyr Val Asp Val Asn  Asn Val Gly Ile Arg  Gly Tyr Met
    1145            1150            1155

Tyr Leu  Lys Gly Pro Arg Gly  Ser Val Met Thr Thr  Asn Ile Tyr
    1160            1165            1170

Leu Asn  Ser Ser Leu Tyr Arg  Gly Thr Lys Phe Ile  Ile Lys Lys
    1175            1180            1185

Tyr Ala  Ser Gly Asn Lys Asp  Asn Ile Val Arg Asn  Asn Asp Arg
    1190            1195            1200

Val Tyr  Ile Asn Val Val Val  Lys Asn Lys Glu Tyr  Arg Leu Ala
    1205            1210            1215

Thr Asn  Ala Ser Gln Ala Gly  Val Glu Lys Ile Leu  Ser Ala Leu
    1220            1225            1230

Glu Ile  Pro Asp Val Gly Asn  Leu Ser Gln Val Val  Val Met Lys
    1235            1240            1245

Ser Lys  Asn Asp Gln Gly Ile  Thr Asn Lys Cys Lys  Met Asn Leu
    1250            1255            1260
```

-continued

```
Gln Asp  Asn Asn Gly Asn Asp  Ile Gly Phe Ile Gly  Phe His Gln
    1265             1270              1275

Phe Asn  Asn Ile Ala Lys Leu  Val Ala Ser Asn Trp  Tyr Asn Arg
    1280             1285              1290

Gln Ile  Glu Arg Ser Ser Arg  Thr Leu Gly Cys Ser  Trp Glu Phe
    1295             1300              1305

Ile Pro  Val Asp Asp Gly Trp  Gly Glu Arg Pro Leu  His His His
    1310             1315              1320

His His  His His His His His
    1325             1330
```

```
<210> SEQ ID NO 8
<211> LENGTH: 4017
<212> TYPE: DNA
<213> ORGANISM: Artificial Sequence
<220> FEATURE:
<223> OTHER INFORMATION: BoNT/XB [LHNX-HCB] with a C1 Activation Loop

<400> SEQUENCE: 8
```

```
atgaaactgg aaatcaacaa attcaactac aacgatccga tcgatggcat taatgttatt      60
accatgcgtc cgcctcgtca tagcgataaa atcaataaag gtaaaggtcc gttcaaagcc     120
tttcaggtga ttaaaaacat ttggattgtg ccggaacgct acaactttac caataatacc     180
aacgatctga acattccgag cgaaccgatt atggaagcag atgccattta taccccgaac     240
tatctgaata ccccgagcga aaaagatgaa tttctgcagg gtgttatcaa agtgctggaa     300
cgcattaaaa gcaaaccgga aggtgaaaaa ctgctggaac tgattagcag cagcattccg     360
ctgccgctgg ttagcaatgg tgcactgacc ctgagcgata tgaaaccat tgcatatcaa     420 gagaacaaca cattgtgag caatctgcag gcaaacctgg ttatttatgg tccgggtcct     480
gatattgcaa ataatgcaac ctatggtctg tatagcaccc cgattagtaa tggtgaaggt     540
acactgagcg aagttagctt tagcccgttt tatctgaaac cgtttgatga aagctatggc     600
aattatcgta gcctggtgaa tatcgtgaac aaattcgtga acgtgaatt tgcacctgat     660 ccggcaagca ccctgatgca tgaactggtt catgttaccc ataatctgta tggtattagc     720
aaccgcaact ctactataaa ctttgacacc ggcaaaattg aaaccagccg tcagcagaat     780
agcctgattt ttgaagaact gctgacctt ggtggcattg atagcaaagc aattagcagc     840
ctgatcatca gaaaaattat cgaaccgcc aagaacaact ataccacgct gattagcgaa     900
cgcctgaata ccgttaccgt tgaaaatgat ctgctgaaat atatcaaaaa caaaatcccg     960
gttcagggtc gtctgggtaa ctttaaactg gataccgcag aattcgagaa aaagctgaat    1020
accattctgt ttgtgctgaa cgaaagcaat ctggcacagc gttttagcat tctggttcgt    1080
aaacattacc tgaaagaacg tccgattgat ccgatttatg tgaacattct ggatgacaat    1140
agctacagca ccctggaagg ttttaacatt agcagtcagg gtagcaatga ttttcagggc    1200
cagctgctgg aaagcagcta tttttgaaaaa attgaatcca atgcgctgcg tgcctttatc    1260
aaaatttgtc ataaagccat tgatggtcgc agcctgtata caaaaccct ggattgtatt    1320 gaagtggaaa acaaagacct gttcctgatt agcaataaag atagcctgaa cgatatcaac    1380
ctgagcgaag aaaaaatcaa accggaaacc accgtgttct tcaaagataa actgcctccg    1440
caggatatta ccctgagcaa ttatgatttt accgaagcca atagcattcc gagcattagc    1500
cagcagaaca ttctggaacg taatgaagaa ctgtatgaac cgattcgcaa tagcctgttt    1560
gaaatcaaaa ccatctatgt ggataagctg accacctttc attttctgga agcccagaat    1620
```

-continued

```
attgatgaga gcattgatag cagcaaaatt cgtgttgaac tgaccgatag cgttgatgaa   1680
gcactgagca atccgaataa agtttatagc ccgttcaaga acatgagcaa caccattaat   1740
agcattgaaa ccggtattac cagcacctac atcttttatc agtggctgcg tagcatcgtg   1800
aaagatttta gtgatgaaac cggcaaaatc gacgtgattg ataaaagcag cgataccctg   1860
gccattgttc cgtatattgg tccgctgctg aatattggta atgatattcg tcatggcgat   1920
tttgtgggtg caattgaact ggcaggcatt accgcactgc tggaatatgt tccggaattt   1980
accattccga ttctggttgg tctggaagtt attggtggcg aactggcacg tgaacaggtt   2040
gaagcaattg ttaataatgc cctggataaa cgcgatcaga aatgggcaga agtttacaat   2100
attaccaaag cacagtggtg gggcaccatt catttacaga ttaatacccg tctggcccat   2160
acctataaag ccctgagccg tcaggcaaat gccattaaaa tgaatatgga atttcagctg   2220
gccaactaca aaggcaacat tgatgataaa gccaagatca aaaacgccat cagcgaaacc   2280
gaaattctgc tgaacaaaag cgttgaacag gccatgaaaa acaccgagaa attcatgatt   2340
aaactgagca acagctacct gaccaaagaa atgattccga agttcaggga caacctgaaa   2400
aactttgatc tggaaaccaa aaagaccctg gacaagttca tcaaagagaa agaagatatc   2460
ctgggcacca atctgagcag cagcctgcgt cgtaaagtta gcattcgtct gaataaaaac   2520
attgccttcg acatcaacga tatcccgttt agcgaatttg atgatctgat caaccagtac   2580
aaaaacgaga tcgaagatta tgaagtgctg aatctgggtg cagaagatgg caaaatcaaa   2640
gatctgagcg gtacaaccag cgatattaac attggtagcg atatcgaaat cctgaacaac   2700
attattctga acctgcgcta taaagataac aacctgattg atctgagtgg ctatggtgca   2760
aaagttgaag tttatgatgg tgtggaactg aacgacaaaa accagttcaa actgaccagc   2820
agcgcaaatt caaaaattcg cgttacccag aaccagaaca tcattttaa cagcgtgttt   2880 ctggatttca gcgtgagctt ttggattcgt attccgaaat ataagaacga cggcatccag   2940
aactatatcc acaatgaata taccatcatc aactgcatga agaataacag cggttggaaa   3000
attagcatcc gtggcaatcg tattatttgg accctgatcg atattaatgg caaaaccaag   3060
agcgtgtttt tcgagtataa catccgtgaa gatatcagcg aatacatcaa ccgttggttt   3120
tttgtgacca ttaccaacaa tctgaacaac gccaaaatct acattaacgg caaactggaa   3180
agcaacaccg atatcaaaga tattcgtgaa gtgattgcca acggcgagat tatctttaaa   3240
ctggatggtg atattgatcg cacccagttt atttggatga aatacttcag catcttcaac   3300
accgaactga gccagagcaa tattgaagaa cgctataaaa tccagagcta cagcgagtat   3360
ctgaaagact tttggggtaa tccgctgatg tacaacaaag aatactacat gtttaatgcc   3420
ggtaacaaaa acagctatat caaactgaaa aaggatagtc cggtgggtga aattctgacc   3480
cgtagcaaat ataaccagaa tagcaagtat atcaactatc gcgatctgta catcggcgag   3540
aaatttatca ttcgtcgtaa aagcaactcc cagagcatta cgatgatat tgtgcgcaaa   3600 gaggattaca tctacctgga ttttttcaac ctgaatcaag agtggcgtgt gtacacctat   3660
aagtacttca aaaaagaaga aatgaaactg tttctggcac cgatctatga tagcgacgaa   3720
ttttacaata ccattcagat taaagaatat gatgaacagc cgacctatag ctgtcagctg   3780
ctgtttaaaa aggatgaaga aagcacggat gaaattggcc tgattggtat ccatcgtttt   3840
tatgaaagcg gcatcgtgtt cgaagagtac aaagattatt tctgcatcag caaatggtat   3900
cttaaagagg tgaaacgcaa accgtataat ctgaaactgg gttgcaattg gcagttcatc   3960
ccgaaagatg aaggttggac cgaacatcat caccaccatc accatcatca tcactga     4017
```

<210> SEQ ID NO 9
<211> LENGTH: 1338
<212> TYPE: PRT
<213> ORGANISM: Artificial Sequence
<220> FEATURE:
<223> OTHER INFORMATION: BoNT/XB [LHNX-HCB] with a C1 Activation Loop

<400> SEQUENCE: 9

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
                100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
        210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
        290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

-continued

```
Ile Asp Pro Ile Tyr Val Asn Ile Leu Asp Asp Asn Ser Tyr Ser Thr
    370             375             380

Leu Glu Gly Phe Asn Ile Ser Ser Gln Gly Ser Asn Asp Phe Gln Gly
385             390             395             400

Gln Leu Leu Glu Ser Ser Tyr Phe Glu Lys Ile Glu Ser Asn Ala Leu
            405             410             415

Arg Ala Phe Ile Lys Ile Cys His Lys Ala Ile Asp Gly Arg Ser Leu
            420             425             430

Tyr Asn Lys Thr Leu Asp Cys Ile Glu Val Glu Asn Lys Asp Leu Phe
            435             440             445

Leu Ile Ser Asn Lys Asp Ser Leu Asn Asp Ile Asn Leu Ser Glu Glu
    450             455             460

Lys Ile Lys Pro Glu Thr Thr Val Phe Phe Lys Asp Lys Leu Pro Pro
465             470             475             480

Gln Asp Ile Thr Leu Ser Asn Tyr Asp Phe Thr Glu Ala Asn Ser Ile
            485             490             495

Pro Ser Ile Ser Gln Gln Asn Ile Leu Glu Arg Asn Glu Glu Leu Tyr
            500             505             510

Glu Pro Ile Arg Asn Ser Leu Phe Glu Ile Lys Thr Ile Tyr Val Asp
            515             520             525

Lys Leu Thr Thr Phe His Phe Leu Glu Ala Gln Asn Ile Asp Glu Ser
    530             535             540

Ile Asp Ser Ser Lys Ile Arg Val Glu Leu Thr Asp Ser Val Asp Glu
545             550             555             560

Ala Leu Ser Asn Pro Asn Lys Val Tyr Ser Pro Phe Lys Asn Met Ser
            565             570             575

Asn Thr Ile Asn Ser Ile Glu Thr Gly Ile Thr Ser Thr Tyr Ile Phe
            580             585             590

Tyr Gln Trp Leu Arg Ser Ile Val Lys Asp Phe Ser Asp Glu Thr Gly
    595             600             605

Lys Ile Asp Val Ile Asp Lys Ser Ser Asp Thr Leu Ala Ile Val Pro
    610             615             620

Tyr Ile Gly Pro Leu Leu Asn Ile Gly Asn Asp Ile Arg His Gly Asp
625             630             635             640

Phe Val Gly Ala Ile Glu Leu Ala Gly Ile Thr Ala Leu Leu Glu Tyr
            645             650             655

Val Pro Glu Phe Thr Ile Pro Ile Leu Val Gly Leu Glu Val Ile Gly
            660             665             670

Gly Glu Leu Ala Arg Glu Gln Val Glu Ala Ile Val Asn Asn Ala Leu
    675             680             685

Asp Lys Arg Asp Gln Lys Trp Ala Glu Val Tyr Asn Ile Thr Lys Ala
    690             695             700

Gln Trp Trp Gly Thr Ile His Leu Gln Ile Asn Thr Arg Leu Ala His
705             710             715             720

Thr Tyr Lys Ala Leu Ser Arg Gln Ala Asn Ala Ile Lys Met Asn Met
            725             730             735

Glu Phe Gln Leu Ala Asn Tyr Lys Gly Asn Ile Asp Asp Lys Ala Lys
            740             745             750

Ile Lys Asn Ala Ile Ser Glu Thr Glu Ile Leu Leu Asn Lys Ser Val
    755             760             765

Glu Gln Ala Met Lys Asn Thr Glu Lys Phe Met Ile Lys Leu Ser Asn
    770             775             780
```

-continued

```
Ser Tyr Leu Thr Lys Glu Met Ile Pro Lys Val Gln Asp Asn Leu Lys
785             790             795             800

Asn Phe Asp Leu Glu Thr Lys Lys Thr Leu Asp Lys Phe Ile Lys Glu
                805             810             815

Lys Glu Asp Ile Leu Gly Thr Asn Leu Ser Ser Ser Leu Arg Arg Lys
            820             825             830

Val Ser Ile Arg Leu Asn Lys Asn Ile Ala Phe Asp Ile Asn Asp Ile
        835             840             845

Pro Phe Ser Glu Phe Asp Asp Leu Ile Asn Gln Tyr Lys Asn Glu Ile
    850             855             860

Glu Asp Tyr Glu Val Leu Asn Leu Gly Ala Glu Asp Gly Lys Ile Lys
865             870             875             880

Asp Leu Ser Gly Thr Thr Ser Asp Ile Asn Ile Gly Ser Asp Ile Glu
            885             890             895

Ile Leu Asn Asn Ile Ile Leu Asn Leu Arg Tyr Lys Asp Asn Asn Leu
            900             905             910

Ile Asp Leu Ser Gly Tyr Gly Ala Lys Val Glu Val Tyr Asp Gly Val
        915             920             925

Glu Leu Asn Asp Lys Asn Gln Phe Lys Leu Thr Ser Ser Ala Asn Ser
    930             935             940

Lys Ile Arg Val Thr Gln Asn Gln Asn Ile Ile Phe Asn Ser Val Phe
945             950             955             960

Leu Asp Phe Ser Val Ser Phe Trp Ile Arg Ile Pro Lys Tyr Lys Asn
            965             970             975

Asp Gly Ile Gln Asn Tyr Ile His Asn Glu Tyr Thr Ile Ile Asn Cys
        980             985             990

Met Lys Asn Asn Ser Gly Trp Lys  Ile Ser Ile Arg Gly  Asn Arg Ile
        995             1000             1005

Ile Trp  Thr Leu Ile Asp Ile  Asn Gly Lys Thr Lys  Ser Val Phe
    1010             1015             1020

Phe Glu  Tyr Asn Ile Arg Glu  Asp Ile Ser Glu Tyr  Ile Asn Arg
    1025             1030             1035

Trp Phe  Phe Val Thr Ile Thr  Asn Asn Leu Asn Asn  Ala Lys Ile
    1040             1045             1050

Tyr Ile  Asn Gly Lys Leu Glu  Ser Asn Thr Asp Ile  Lys Asp Ile
    1055             1060             1065

Arg Glu  Val Ile Ala Asn Gly  Glu Ile Ile Phe Lys  Leu Asp Gly
    1070             1075             1080

Asp Ile  Asp Arg Thr Gln Phe  Ile Trp Met Lys Tyr  Phe Ser Ile
    1085             1090             1095

Phe Asn  Thr Glu Leu Ser Gln  Ser Asn Ile Glu Glu  Arg Tyr Lys
    1100             1105             1110

Ile Gln  Ser Tyr Ser Glu Tyr  Leu Lys Asp Phe Trp  Gly Asn Pro
    1115             1120             1125

Leu Met  Tyr Asn Lys Glu Tyr  Tyr Met Phe Asn Ala  Gly Asn Lys
    1130             1135             1140

Asn Ser  Tyr Ile Lys Leu Lys  Lys Asp Ser Pro Val  Gly Glu Ile
    1145             1150             1155

Leu Thr  Arg Ser Lys Tyr Asn  Gln Asn Ser Lys Tyr  Ile Asn Tyr
    1160             1165             1170

Arg Asp  Leu Tyr Ile Gly Glu  Lys Phe Ile Ile Arg  Arg Lys Ser
    1175             1180             1185

Asn Ser  Gln Ser Ile Asn Asp  Asp Ile Val Arg Lys  Glu Asp Tyr
```

```
        1190              1195              1200

Ile Tyr  Leu Asp Phe Phe Asn  Leu Asn Gln Glu Trp  Arg Val Tyr
        1205              1210              1215

Thr Tyr  Lys Tyr Phe Lys Lys  Glu Glu Met Lys Leu  Phe Leu Ala
        1220              1225              1230

Pro Ile  Tyr Asp Ser Asp Glu  Phe Tyr Asn Thr Ile  Gln Ile Lys
        1235              1240              1245

Glu Tyr  Asp Glu Gln Pro Thr  Tyr Ser Cys Gln Leu  Leu Phe Lys
        1250              1255              1260

Lys Asp  Glu Glu Ser Thr Asp  Glu Ile Gly Leu Ile  Gly Ile His
        1265              1270              1275

Arg Phe  Tyr Glu Ser Gly Ile  Val Phe Glu Glu Tyr  Lys Asp Tyr
        1280              1285              1290

Phe Cys  Ile Ser Lys Trp Tyr  Leu Lys Glu Val Lys  Arg Lys Pro
        1295              1300              1305

Tyr Asn  Leu Lys Leu Gly Cys  Asn Trp Gln Phe Ile  Pro Lys Asp
        1310              1315              1320

Glu Gly  Trp Thr Glu His His  His His His His His  His His His
        1325              1330              1335
```

```
<210> SEQ ID NO 10
<211> LENGTH: 3762
<212> TYPE: DNA
<213> ORGANISM: Artificial Sequence
<220> FEATURE:
<223> OTHER INFORMATION: BoNT/E with a C1 Activation Loop

<400> SEQUENCE: 10
atgccgaaaa tcaactcttt caactacaac gacccggtta acgaccgtac catcctgtat      60
atcaaaccgg gtggttgcca ggagttctac aaatctttca acatcatgaa aaacatctgg     120
atcatcccgg aacgtaacgt tatcggtacc accccgcagg acttccaccc gccgacctct     180
ctgaaaaacg gtgactcttc ttactacgac ccgaactacc tccagtctga cgaagaaaaa     240
gaccgtttcc tgaaaatcgt taccaaaatc ttcaaccgta tcaacaacaa cctgtctggt     300
ggtatcctgc tggaagaact gtctaaagct aacccgtacc tgggtaacga caacaccccg     360
gacaaccagt tccacatcgg tgacgcttct gctgttgaaa tcaaattctc taacggttct     420
caggacatcc tgctgccgaa cgttatcatc atgggtgctg aaccggacct gttcgaaacc     480
aactcttcta acatctctct gcgtaacaac tacatgccgt ctaaccacgg tttcggttct     540
atcgctatcg ttaccttctc tccggaatac tctttccgtt tcaacgacaa cagcatgaac     600
gagttcatcc aggacccggc tctgaccctg atgcaccaac tgatctattc tctgcacggt     660
ctgtacggtg ctaaaggtat caccaccaaa tacaccatca cccagaaaca gaacccgctg     720
atcaccaaca tccgtggtac caacatcgaa gagttcctga ccttcggtgg taccgacctg     780
aacatcatca cctctgctca gtctaacgac atctacacca acctgctggc tgactacaaa     840
aaaatcgctt ctaaactgtc taaagttcag gtttctaacc cgctgctgaa cccgtacaaa     900
gacgttttcg aagctaaata cggtctggac aaagacgctt ctggtatcta ctctgttaac     960
atcaacaaat tcaacgacat cttcaaaaaa ctgtactctt tcaccgagtt cgacctggcg    1020
accaaattcc aggttaaatg ccgtcagacc tacatcggtc agtacaaata cttcaaactg    1080
tctaacctgc tgaacgactc tatctacaac atctctgaag ttacaacat caacaacctg    1140 aaagttaact tccgtggtca gaacgctaac ctgaacccgc gtatcatcac cccgatcacc    1200
```

-continued

```
ggtcgtggtc tggttaaaaa aatcatccgt ttctgccaca aagcgattga tggccgctct    1260
ctctataaca aaacgctgga ttgcatcgaa atcaacaacg gtgaactgtt cttcgttgct    1320
tctgaaaact cttacaacga cgacaacatc aacaccccga aagaaatcga cgacaccgtt    1380
acctctaaca acaactacga aaacgacctg gaccaggtta tcctgaactt caactctgaa    1440
tctgctccgg gtctgtctga cgaaaaactg aacctgacca tccagaacga cgcttacatc    1500
ccgaaatacg actctaacgg tacctctgac atcgaacagc acgacgttaa cgaactgaac    1560
gttttcttct acctggacgc tcagaaagtt ccggaaggtg aaaacaacgt taacctgacc    1620
tcttctatcg acaccgctct gctgaacag ccgaaaatct acaccttctt ctcttctgag    1680
ttcatcaaca acgttaacaa accggttcag gctgctctgt tcgtttcttg gattcagcag    1740
gttctggttg acttcaccac cgaagctaac cagaaatcta ccgttgacaa aatcgctgac    1800
atctctatcg ttgttccgta catcggtctg gctctgaaca tcggtaacga agctcagaaa    1860
ggtaacttca aagacgctct ggaactgctg ggtgctggta tcctgctgga gttcgaaccg    1920
gaactgctga tcccgaccat cctggttttc accatcaaat ctttcctggg ttcttctgac    1980
aacaaaaaca aagttatcaa agctatcaac aacgctctga agaacgtga cgaaaaatgg    2040 aaagaagttt actctttcat cgtttctaac tggatgacca aaatcaacac ccagttcaac    2100
aaacgtaaag aacagatgta ccaggctctc cagaaccagg ttaacgctat caaaaccatc    2160
atcgaatcta aatacaactc ttacaccctg gaagaaaaaa acgaactgac caacaaatac    2220
gacatcaaac agatcgaaaa cgaactgaac cagaaagttt ctatcgctat gaacaacatc    2280
gaccgtttcc tgaccgaatc ttctatctct tacctgatga aactcatcaa cgaagttaaa    2340
atcaacaaac tgcgtgaata cgacgaaaac gttaaaacct acctgctgaa ctacatcatc    2400
cagcacggtt ctatcctggg tgaatctcag caggaactga actctatggt taccgacacc    2460
ctgaacaact ctatcccgtt caaactgtct tcttacaccg acgacaaaat cctgatctct    2520
tacttcaaca aattctttaa acgcattaag agttcatcgg ttctgaatat gcggtacaaa    2580
aatgataaat atgtcgatac ttctggatat gatagcaata tcaacattaa cggcgacgtg    2640
tataaatatc cgacaaataa aaaccagttt gggatatata acgacaagct gtcggaggtc    2700
aatatttctc aaaacgacta tatcatttac gataataaat ataaaaactt tagcattagt    2760
ttttgggttc gtatacctaa ttatgacaat aaaattgtaa atgtgaataa cgagtatacc    2820
attataaact gtatgcgcga caataacagt ggttggaagg tatcgctgaa ccataatgag    2880
attatctgga ccctgcagga taatgcaggt ataaaccaga aactggcttt taactatgga    2940
aacgcaaatg ggatctcaga ttacattaat aaatggattt ttgttaccat tacgaacgat    3000
cgcttaggcg actcaaaact ttatattaat ggcaatctga tagatcagaa atcaatctta    3060
aatttgggca atattcatgt ctctgataac atcttgttca agatcgttaa ttgcagttac    3120
actcgttata ttggcattcg ttactttaat atcttcgata aagaactgga cgagacggaa    3180
atccagactc tgtattcaaa cgagcccaat actaatatat tgaaagattt ttggggtaac    3240 tatctttat atgataaaga atactatctc ctgaatgtat tgaagccaaa caatttcata    3300
gatagacgca aggatagcac attaagtatc aacaatatca gatctactat actgttagca    3360
aatcgcctct actccggtat taaagtgaag attcagcggg ttaataactc cagtaccaat    3420
gataatctgg tccgtaagaa cgatcaggta tacatcaatt tcgtcgcgag caaaactcat    3480
ctcttcccgc tttacgccga tacagctacg acaaacaagg aaaaaaccat aaaaatttcc    3540
agctccggaa acagattcaa tcaagtagtt gtaatgaact ctgtgggtaa taattgtacg    3600
```

-continued

```
atgaacttta agaataacaa tgggaacaat attggacttt tgggcttcaa agccgacaca      3660
gtggtggcgt ccacctggta ttacacgcac atgcgggacc atacgaattc gaacggttgc      3720
ttctggaact ttatctcgga agaacacggg tggcaagaaa aa                        3762
```

```
<210> SEQ ID NO 11
<211> LENGTH: 1254
<212> TYPE: PRT
<213> ORGANISM: Artificial Sequence
<220> FEATURE:
<223> OTHER INFORMATION: BoNT/E with a C1 Activation Loop

<400> SEQUENCE: 11

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
            115                 120                 125

Ala Ser Ala Val Glu Ile Lys Phe Ser Asn Gly Ser Gln Asp Ile Leu
        130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
            195                 200                 205

Thr Leu Met His Gln Leu Ile Tyr Ser Leu His Gly Leu Tyr Gly Ala
        210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
        290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335
```

-continued

```
Phe Asp Leu Ala Thr Lys Phe Gln Val Lys Cys Arg Gln Thr Tyr Ile
        340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
        370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys His Lys Ala Ile
                405                 410                 415

Asp Gly Arg Ser Leu Tyr Asn Lys Thr Leu Asp Cys Ile Glu Ile Asn
                420                 425                 430

Asn Gly Glu Leu Phe Phe Val Ala Ser Glu Asn Ser Tyr Asn Asp Asp
                435                 440                 445

Asn Ile Asn Thr Pro Lys Glu Ile Asp Asp Thr Val Thr Ser Asn Asn
        450                 455                 460

Asn Tyr Glu Asn Asp Leu Asp Gln Val Ile Leu Asn Phe Asn Ser Glu
465                 470                 475                 480

Ser Ala Pro Gly Leu Ser Asp Glu Lys Leu Asn Leu Thr Ile Gln Asn
                485                 490                 495

Asp Ala Tyr Ile Pro Lys Tyr Asp Ser Asn Gly Thr Ser Asp Ile Glu
                500                 505                 510

Gln His Asp Val Asn Glu Leu Asn Val Phe Phe Tyr Leu Asp Ala Gln
                515                 520                 525

Lys Val Pro Glu Gly Glu Asn Asn Val Asn Leu Thr Ser Ser Ile Asp
        530                 535                 540

Thr Ala Leu Leu Glu Gln Pro Lys Ile Tyr Thr Phe Phe Ser Ser Glu
545                 550                 555                 560

Phe Ile Asn Asn Val Asn Lys Pro Val Gln Ala Ala Leu Phe Val Ser
                565                 570                 575

Trp Ile Gln Gln Val Leu Val Asp Phe Thr Thr Glu Ala Asn Gln Lys
                580                 585                 590

Ser Thr Val Asp Lys Ile Ala Asp Ile Ser Ile Val Val Pro Tyr Ile
                595                 600                 605

Gly Leu Ala Leu Asn Ile Gly Asn Glu Ala Gln Lys Gly Asn Phe Lys
        610                 615                 620

Asp Ala Leu Glu Leu Leu Gly Ala Gly Ile Leu Leu Glu Phe Glu Pro
625                 630                 635                 640

Glu Leu Leu Ile Pro Thr Ile Leu Val Phe Thr Ile Lys Ser Phe Leu
                645                 650                 655

Gly Ser Ser Asp Asn Lys Asn Lys Val Ile Lys Ala Ile Asn Asn Ala
                660                 665                 670

Leu Lys Glu Arg Asp Glu Lys Trp Lys Glu Val Tyr Ser Phe Ile Val
                675                 680                 685

Ser Asn Trp Met Thr Lys Ile Asn Thr Gln Phe Asn Lys Arg Lys Glu
        690                 695                 700

Gln Met Tyr Gln Ala Leu Gln Asn Gln Val Asn Ala Ile Lys Thr Ile
705                 710                 715                 720

Ile Glu Ser Lys Tyr Asn Ser Tyr Thr Leu Glu Glu Lys Asn Glu Leu
                725                 730                 735

Thr Asn Lys Tyr Asp Ile Lys Gln Ile Glu Asn Glu Leu Asn Gln Lys
        740                 745                 750
```

-continued

```
Val Ser Ile Ala Met Asn Asn Ile Asp Arg Phe Leu Thr Glu Ser Ser
        755              760              765

Ile Ser Tyr Leu Met Lys Leu Ile Asn Glu Val Lys Ile Asn Lys Leu
        770              775              780

Arg Glu Tyr Asp Glu Asn Val Lys Thr Tyr Leu Leu Asn Tyr Ile Ile
785              790              795              800

Gln His Gly Ser Ile Leu Gly Glu Ser Gln Gln Glu Leu Asn Ser Met
                805              810              815

Val Thr Asp Thr Leu Asn Asn Ser Ile Pro Phe Lys Leu Ser Ser Tyr
            820              825              830

Thr Asp Asp Lys Ile Leu Ile Ser Tyr Phe Asn Lys Phe Phe Lys Arg
            835              840              845

Ile Lys Ser Ser Ser Val Leu Asn Met Arg Tyr Lys Asn Asp Lys Tyr
    850              855              860

Val Asp Thr Ser Gly Tyr Asp Ser Asn Ile Asn Ile Asn Gly Asp Val
865              870              875              880

Tyr Lys Tyr Pro Thr Asn Lys Asn Gln Phe Gly Ile Tyr Asn Asp Lys
                885              890              895

Leu Ser Glu Val Asn Ile Ser Gln Asn Asp Tyr Ile Ile Tyr Asp Asn
            900              905              910

Lys Tyr Lys Asn Phe Ser Ile Ser Phe Trp Val Arg Ile Pro Asn Tyr
            915              920              925

Asp Asn Lys Ile Val Asn Val Asn Asn Glu Tyr Thr Ile Ile Asn Cys
    930              935              940

Met Arg Asp Asn Asn Ser Gly Trp Lys Val Ser Leu Asn His Asn Glu
945              950              955              960

Ile Ile Trp Thr Leu Gln Asp Asn Ala Gly Ile Asn Gln Lys Leu Ala
            965              970              975

Phe Asn Tyr Gly Asn Ala Asn Gly Ile Ser Asp Tyr Ile Asn Lys Trp
            980              985              990

Ile Phe Val Thr Ile Thr Asn Asp  Arg Leu Gly Asp Ser  Lys Leu Tyr
        995              1000             1005

Ile Asn  Gly Asn Leu Ile Asp  Gln Lys Ser Ile Leu  Asn Leu Gly
    1010             1015             1020

Asn Ile  His Val Ser Asp Asn  Ile Leu Phe Lys Ile  Val Asn Cys
    1025             1030             1035

Ser Tyr  Thr Arg Tyr Ile Gly  Ile Arg Tyr Phe Asn  Ile Phe Asp
    1040             1045             1050

Lys Glu  Leu Asp Glu Thr Glu  Ile Gln Thr Leu Tyr  Ser Asn Glu
    1055             1060             1065

Pro Asn  Thr Asn Ile Leu Lys  Asp Phe Trp Gly Asn  Tyr Leu Leu
    1070             1075             1080

Tyr Asp  Lys Glu Tyr Tyr Leu  Leu Asn Val Leu Lys  Pro Asn Asn
    1085             1090             1095

Phe Ile  Asp Arg Arg Lys Asp  Ser Thr Leu Ser Ile  Asn Asn Ile
    1100             1105             1110

Arg Ser  Thr Ile Leu Leu Ala  Asn Arg Leu Tyr Ser  Gly Ile Lys
    1115             1120             1125

Val Lys  Ile Gln Arg Val Asn  Asn Ser Ser Thr Asn  Asp Asn Leu
    1130             1135             1140

Val Arg  Lys Asn Asp Gln Val  Tyr Ile Asn Phe Val  Ala Ser Lys
    1145             1150             1155

Thr His  Leu Phe Pro Leu Tyr  Ala Asp Thr Ala Thr  Thr Asn Lys
```

-continued

```
      1160                1165                1170

Glu Lys  Thr Ile Lys Ile Ser  Ser Ser Gly Asn Arg  Phe Asn Gln
    1175                1180                1185

Val Val  Val Met Asn Ser Val  Gly Asn Asn Cys Thr  Met Asn Phe
    1190                1195                1200

Lys Asn  Asn Asn Gly Asn Asn  Ile Gly Leu Leu Gly  Phe Lys Ala
    1205                1210                1215

Asp Thr  Val Val Ala Ser Thr  Trp Tyr Tyr Thr His  Met Arg Asp
    1220                1225                1230

His Thr  Asn Ser Asn Gly Cys  Phe Trp Asn Phe Ile  Ser Glu Glu
    1235                1240                1245

His Gly  Trp Gln Glu Lys
    1250
```

<210> SEQ ID NO 12
<211> LENGTH: 3867
<212> TYPE: DNA
<213> ORGANISM: Artificial Sequence
<220> FEATURE:
<223> OTHER INFORMATION: BoNT/A1C1 with a C1 Activation Loop

<400> SEQUENCE: 12

```
atgccattcg tcaacaagca attcaactac aaagacccag tcaacggcgt cgacatcgca    60
tacatcaaga ttccgaacgc cggtcaaatg cagccggtta aggcttttaa gatccacaac   120
aagatttggg ttatcccgga gcgtgacacc ttcacgaacc cggaagaagg cgatctgaac   180
ccgccaccgg aagcgaagca agtccctgtc agctactacg attcgacgta cctgagcacg   240
gataacgaaa aagataacta cctgaaaggt gtgaccaagc tgttcgaacg tatctacagc   300
acggatctgg gtcgcatgct gctgactagc attgttcgcg gtatcccgtt ctggggtggt   360
agcacgattg acaccgaact gaaggttatc gacactaact gcattaacgt tattcaaccg   420
gatggtagct atcgtagcga agagctgaat ctggtcatca ttggcccgag cgcagacatt   480
atccaattcg agtgcaagag ctttggtcac gaggttctga atctgacccg caatggctat   540
ggtagcaccc agtacattcg ttttttcgccg gattttacct tcggctttga agagagcctg   600
gaggttgata ccaatccgtt gctgggtgcg ggcaaattcg ctaccgatcc ggctgtcacg   660
ctggcccatg aactgatcca cgcaggccac cgcctgtacg gcattgccat caacccaaac   720
cgtgtgttca aggttaatac gaatgcatac tacgagatga gcggcctgga agtcagcttc   780
gaagaactgc gcaccttcgg tggccatgac gctaaattca ttgacagctt gcaagagaat   840
gagttccgtc tgtactacta taacaaattc aaagacattg caagcacgtt gaacaaggcc   900
aaaagcatcg ttggtactac cgcgtcgttg cagtatatga gaatgtgtt taaagagaag   960 tacctgctgt ccgaggatac ctccggcaag tttagcgttg ataagctgaa gtttgacaaa  1020
ctgtacaaga tgctgaccga gatttacacc gaggacaact ttgtgaaatt cttcaaagtg  1080
ttgaatcgta aaacctatct gaattttgac aaagcggttt tcaagattaa catcgtgccg  1140
aaggtgaact acaccatcta tgacggtttt aacctgcgta acaccaacct ggcggcgaac  1200
tttaacggtc agaatacgga aatcaacaac atgaatttca cgaagttgaa gaacttcacg  1260
ggtctgttcg agttctataa gctgctgtgc cacaaagcga ttgatggccg ctctctctat  1320
aacaaaacgc tggattgcat taaggtaaac aattgggatc tgttcttttc gccatccgaa  1380
gataatttta ccaacgacct gaacaagggt gaagaaatca ccagcgatac gaatattgaa  1440
gcagcggaag agaatatcag cctggatctg atccagcagt actatctgac ctttaacttc  1500
```

-continued

```
gacaatgaac cggagaacat tagcattgag aatctgagca gcgacattat cggtcagctg   1560
gaactgatgc cgaatatcga acgtttcccg aacggcaaaa agtacgagct ggacaagtac   1620
actatgttcc attacctgcg tgcacaggag tttgaacacg gtaaaagccg tatcgcgctg   1680
accaacagcg ttaacgaggc cctgctgaac ccgagccgtg tctatacctt cttcagcagc   1740
gactatgtta agaaagtgaa caaagccact gaggccgcga tgttcctggg ctgggtggaa   1800
cagctggtat atgacttcac ggacgagacg agcgaagtga gcactaccga caaaattgct   1860
gatattacca tcattatccc gtatattggt ccggcactga acattggcaa catgctgtac   1920
aaagacgatt ttgtgggtgc cctgatcttc tccggtgccg tgattctgct ggagttcatt   1980
ccggagattg cgatcccggt gttgggtacc ttcgcgctgg tgtcctacat cgcgaataag   2040
gttctgacgg ttcagaccat cgataacgcg ctgtcgaaac gtaatgaaaa atgggacgag   2100
gtttacaaat acattgttac gaattggctg gcgaaagtca atacccagat cgacctgatc   2160
cgtaagaaaa tgaaagaggc gctggagaat caggcggagg ccaccaaagc aattatcaac   2220
taccaataca accagtacac ggaagaagag aagaataaca ttaacttcaa tatcgatgat   2280
ttgagcagca agctgaatga atctatcaac aaagcgatga tcaatatcaa caagtttttg   2340
aatcagtgta gcgtttcgta cctgatgaat agcatgattc cgtatggcgt caaacgtctg   2400
gaggacttcg acgccagcct gaaagatgcg ttgctgaaat acatttacga caatcgtggt   2460
acgctgattg gccaagttga ccgcttgaaa gacaaagtta acaataccct gagcaccgac   2520
atcccatttc aactgagcaa gtatgttgat aatcaacgtc tgttgagcac tttcaccgag   2580
tatatcaaaa acattaatga cagcaaaatt ctgagcctgc agaatcgtaa gaatacgctg   2640
gtagatacca gtggatataa tgcggaagtc tcagaagagg gtgatgtaca gctgaacccg   2700
atctttccgt tcgactttaa actggggtct agtggtgaag atcgcggtaa agtgatcgtt   2760
acccaaaacg agaacattgt gtataacagc atgtacgaga gtttctcaat ttctttctgg   2820
attcgcatca ataaatgggt ttctaatttg cctggctata ccatcattga tagcgtcaaa   2880
aacaactcgg gctggtcgat tggcattatt agcaactttc tggtgtttac cctgaaacag   2940
aatgaggatt cggaacagag cattaacttc tcctacgaca tcagcaacaa tgcaccaggg   3000
tataacaaat ggttcttcgt aacggtgacg aacaatatga tgggcaatat gaaaatctac   3060
attaacggga aacttatcga caccattaaa gtgaaagagc ttactgggat caatttttagt   3120 aaaaccatta cctttgagat caacaaaatt ccggacacgg gtctgattac ctccgattcg   3180
gataatatca atatgtggat tcgcgacttt tatatcttcg ccaaagaact tgatggcaaa   3240
gatatcaaca ttttgtttaa ttccctgcag tataccaatg tcgttaagga ctattggggc   3300
aatgatctcc gctacaataa agaatactac atggttaaca tcgactatct caatcgctac   3360
atgtatgcta actcgcgtca aattgtgttt aacacacgtc gtaacaacaa cgattttaac   3420
gaaggttata aaatcattat caaacggatc cgcggcaata cgaacgatac tcgtgttcgt   3480
ggcggtgaca ttctgtattt cgacatgacg attaataata aagcgtacaa tctgttcatg   3540
aagaacgaaa ccatgtacgc cgataaccat tccactgaag atatctacgc aatcggactt   3600
cgcgaacaga ccaaagacat taacgacaac atcatctttc agattcaacc gatgaataat   3660
acctactact atgcctccca gatcttcaaa agtaatttca acggcgaaaa catttcaggc   3720
atttgctcaa tcggcactta tcggttccgg ttaggtggtg attggtatcg tcacaactac   3780
cttgttccca cagtgaaaca aggcaactat gcatcgctct tagaaagcac atctacgcat   3840
```

-continued

```
tggggttttg tgccagtcag tgaataa                                           3867
```

<210> SEQ ID NO 13
<211> LENGTH: 1288
<212> TYPE: PRT
<213> ORGANISM: Artificial Sequence
<220> FEATURE:
<223> OTHER INFORMATION: BoNT/A1C1 with a C1 Activation Loop

<400> SEQUENCE: 13

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
```

```
                355                    360                    365
Phe Asp Lys Ala Val Phe Lys Ile Asn Ile Val Pro Lys Val Asn Tyr
    370                    375                    380

Thr Ile Tyr Asp Gly Phe Asn Leu Arg Asn Thr Asn Leu Ala Ala Asn
385                    390                    395                    400

Phe Asn Gly Gln Asn Thr Glu Ile Asn Asn Met Asn Phe Thr Lys Leu
                405                    410                    415

Lys Asn Phe Thr Gly Leu Phe Glu Phe Tyr Lys Leu Leu Cys His Lys
                420                    425                    430

Ala Ile Asp Gly Arg Ser Leu Tyr Asn Lys Thr Leu Asp Cys Ile Lys
                435                    440                    445

Val Asn Asn Trp Asp Leu Phe Phe Ser Pro Ser Glu Asp Asn Phe Thr
    450                    455                    460

Asn Asp Leu Asn Lys Gly Glu Glu Ile Thr Ser Asp Thr Asn Ile Glu
465                    470                    475                    480

Ala Ala Glu Glu Asn Ile Ser Leu Asp Leu Ile Gln Gln Tyr Tyr Leu
                485                    490                    495

Thr Phe Asn Phe Asp Asn Glu Pro Glu Asn Ile Ser Ile Glu Asn Leu
                500                    505                    510

Ser Ser Asp Ile Ile Gly Gln Leu Glu Leu Met Pro Asn Ile Glu Arg
                515                    520                    525

Phe Pro Asn Gly Lys Lys Tyr Glu Leu Asp Lys Tyr Thr Met Phe His
    530                    535                    540

Tyr Leu Arg Ala Gln Glu Phe Glu His Gly Lys Ser Arg Ile Ala Leu
545                    550                    555                    560

Thr Asn Ser Val Asn Glu Ala Leu Leu Asn Pro Ser Arg Val Tyr Thr
                565                    570                    575

Phe Phe Ser Ser Asp Tyr Val Lys Lys Val Asn Lys Ala Thr Glu Ala
                580                    585                    590

Ala Met Phe Leu Gly Trp Val Glu Gln Leu Val Tyr Asp Phe Thr Asp
                595                    600                    605

Glu Thr Ser Glu Val Ser Thr Thr Asp Lys Ile Ala Asp Ile Thr Ile
    610                    615                    620

Ile Ile Pro Tyr Ile Gly Pro Ala Leu Asn Ile Gly Asn Met Leu Tyr
625                    630                    635                    640

Lys Asp Asp Phe Val Gly Ala Leu Ile Phe Ser Gly Ala Val Ile Leu
                645                    650                    655

Leu Glu Phe Ile Pro Glu Ile Ala Ile Pro Val Leu Gly Thr Phe Ala
                660                    665                    670

Leu Val Ser Tyr Ile Ala Asn Lys Val Leu Thr Val Gln Thr Ile Asp
                675                    680                    685

Asn Ala Leu Ser Lys Arg Asn Glu Lys Trp Asp Glu Val Tyr Lys Tyr
    690                    695                    700

Ile Val Thr Asn Trp Leu Ala Lys Val Asn Thr Gln Ile Asp Leu Ile
705                    710                    715                    720

Arg Lys Lys Met Lys Glu Ala Leu Glu Asn Gln Ala Glu Ala Thr Lys
                725                    730                    735

Ala Ile Ile Asn Tyr Gln Tyr Asn Gln Tyr Thr Glu Glu Glu Lys Asn
                740                    745                    750

Asn Ile Asn Phe Asn Ile Asp Asp Leu Ser Ser Lys Leu Asn Glu Ser
                755                    760                    765

Ile Asn Lys Ala Met Ile Asn Ile Asn Lys Phe Leu Asn Gln Cys Ser
    770                    775                    780
```

```
Val Ser Tyr Leu Met Asn Ser Met Ile Pro Tyr Gly Val Lys Arg Leu
785                 790             795                 800

Glu Asp Phe Asp Ala Ser Leu Lys Asp Ala Leu Leu Lys Tyr Ile Tyr
                805                 810                 815

Asp Asn Arg Gly Thr Leu Ile Gly Gln Val Asp Arg Leu Lys Asp Lys
            820                 825                 830

Val Asn Asn Thr Leu Ser Thr Asp Ile Pro Phe Gln Leu Ser Lys Tyr
            835                 840                 845

Val Asp Asn Gln Arg Leu Leu Ser Thr Phe Thr Glu Tyr Ile Lys Asn
850                 855                 860

Ile Asn Asp Ser Lys Ile Leu Ser Leu Gln Asn Arg Lys Asn Thr Leu
865                 870                 875                 880

Val Asp Thr Ser Gly Tyr Asn Ala Glu Val Ser Glu Glu Gly Asp Val
                885                 890                 895

Gln Leu Asn Pro Ile Phe Pro Phe Asp Phe Lys Leu Gly Ser Ser Gly
            900                 905                 910

Glu Asp Arg Gly Lys Val Ile Val Thr Gln Asn Glu Asn Ile Val Tyr
            915                 920                 925

Asn Ser Met Tyr Glu Ser Phe Ser Ile Ser Phe Trp Ile Arg Ile Asn
930                 935                 940

Lys Trp Val Ser Asn Leu Pro Gly Tyr Thr Ile Ile Asp Ser Val Lys
945                 950                 955                 960

Asn Asn Ser Gly Trp Ser Ile Gly Ile Ile Ser Asn Phe Leu Val Phe
                965                 970                 975

Thr Leu Lys Gln Asn Glu Asp Ser Glu Gln Ser Ile Asn Phe Ser Tyr
            980                 985                 990

Asp Ile Ser Asn Asn Ala Pro Gly  Tyr Asn Lys Trp Phe  Phe Val Thr
        995                 1000                1005

Val Thr  Asn Asn Met Met Gly  Asn Met Lys Ile Tyr  Ile Asn Gly
    1010                1015                1020

Lys Leu  Ile Asp Thr Ile Lys  Val Lys Glu Leu Thr  Gly Ile Asn
    1025                1030                1035

Phe Ser  Lys Thr Ile Thr Phe  Glu Ile Asn Lys Ile  Pro Asp Thr
    1040                1045                1050

Gly Leu  Ile Thr Ser Asp Ser  Asp Asn Ile Asn Met  Trp Ile Arg
    1055                1060                1065

Asp Phe  Tyr Ile Phe Ala Lys  Glu Leu Asp Gly Lys  Asp Ile Asn
    1070                1075                1080

Ile Leu  Phe Asn Ser Leu Gln  Tyr Thr Asn Val Val  Lys Asp Tyr
    1085                1090                1095

Trp Gly  Asn Asp Leu Arg Tyr  Asn Lys Glu Tyr Tyr  Met Val Asn
    1100                1105                1110

Ile Asp  Tyr Leu Asn Arg Tyr  Met Tyr Ala Asn Ser  Arg Gln Ile
    1115                1120                1125

Val Phe  Asn Thr Arg Arg Asn  Asn Asn Asp Phe Asn  Glu Gly Tyr
    1130                1135                1140

Lys Ile  Ile Ile Lys Arg Ile  Arg Gly Asn Thr Asn  Asp Thr Arg
    1145                1150                1155

Val Arg  Gly Gly Asp Ile Leu  Tyr Phe Asp Met Thr  Ile Asn Asn
    1160                1165                1170

Lys Ala  Tyr Asn Leu Phe Met  Lys Asn Glu Thr Met  Tyr Ala Asp
    1175                1180                1185
```

-continued

```
Asn His  Ser Thr Glu Asp Ile  Tyr Ala Ile Gly Leu  Arg Glu Gln
    1190             1195             1200
```

```
Thr Lys  Asp Ile Asn Asp Asn  Ile Ile Phe Gln Ile  Gln Pro Met
    1205             1210             1215
```

```
Asn Asn  Thr Tyr Tyr Tyr Ala  Ser Gln Ile Phe Lys  Ser Asn Phe
    1220             1225             1230
```

```
Asn Gly  Glu Asn Ile Ser Gly  Ile Cys Ser Ile Gly  Thr Tyr Arg
    1235             1240             1245
```

```
Phe Arg  Leu Gly Gly Asp Trp  Tyr Arg His Asn Tyr  Leu Val Pro
    1250             1255             1260
```

```
Thr Val  Lys Gln Gly Asn Tyr  Ala Ser Leu Leu Glu  Ser Thr Ser
    1265             1270             1275
```

```
Thr His  Trp Gly Phe Val Pro  Val Ser Glu
    1280             1285
```

<210> SEQ ID NO 14
<211> LENGTH: 3878
<212> TYPE: DNA
<213> ORGANISM: Artificial Sequence
<220> FEATURE:
<223> OTHER INFORMATION: BoNT/C1(0) (Endonegative)

<400> SEQUENCE: 14

```
atgccgatca cgattaataa tttcaactat agcgatccgg tggacaataa gaatattctg      60
tatctggata ctcatctgaa tacgctggct aacgaaccgg agaaagcgtt ccgcatcaca     120
ggcaacatct gggttattcc cgatcgcttt tcacgcaaca gcaaccctaa tctgaacaaa     180
cctcctcgtg tcaccagtcc taaatccggt tattacgacc caaactatct gagtacggat     240
agcgataaag atccctttct gaaagagatc attaagctgt tcaaacgcat taactctcgc     300
gaaattgggg aagagctgat ctatcggctt tcgacagata tcccgttccc aggtaacaat     360
aataccccga ttaatacttt cgactttgat gttgatttca attctgtgga tgtgaaaacg     420
cgtcaaggca ataattgggt gaaaactggt agcattaacc cgagtgtaat tatcacaggt     480
ccccgtgaga acatcatcga cccggaaacc tctaccttca agctgacgaa caacacgttt     540
gctgcacagg aagggtttgg tgccctgtca atcatttcca tctcaccgcg tttcatgtta     600
acctactcca atgccacaaa tgatgttggc gaaggacgtt ttagcaaatc agaattttgc     660
atggacccaa ttctcattct gatgggcacg ctgaacaatg cgatgcacaa cttgtatggc     720
attgctattc caaacgatca aaccattagc tccgttacca gtaatatctt ctatagccag     780
tataatgtca aattggagta tgccgaaatt tacgcctttg gaggcccgac cattgacctg     840
attccgaaat ctgcacgcaa atacttcgaa gaaaaggcgt tagattacta tcgcagcatc     900
gcgaaacgcc tgaactcgat taccacggcc aatccgtcgt cgttcaacaa atacattggt     960
gaatataaac agaaactgat tcgcaaatat cggtttgtcg tagaaagctc tggtgaagtg    1020
actgtaaacc gcaacaaatt tgtcgaactc tacaacgagt tgacccaaat ctttaccgag    1080
tttaactacg caaagatcta taacgtacag aaccgcaaga tttatcttag caatgtatac    1140
acaccggtta ctgcgaacat cttagacgac aatgtgtatg atattcagaa tggctttaac    1200
atcccgaaat caaatctgaa cgttctgttt atgggccaga acctgagtcg taatccagca    1260
ctgcgtaaag tgaacccgga aaatatgctc tacttgtttta ccaaattttg ccacaaagcg    1320
attgatggcc gctctctcta taacaaaacg ctggattgtc gtgagttact tgtgaagaac    1380
actgatttac cgttcattgg ggatatctcc gacgtgaaaa ccgatatctt cctgcgcaaa    1440
```

```
gacattaatg aagaaacgga agtcatctat taccccgaca atgtgagcgt tgatcaggtc      1500
attttatcga agaacacctc cgaacatggt cagttggatt tgctgtaccc tagcattgac      1560
tcggagagtg aaatccttcc gggcgaaaat caagtgtttt acgacaaccg tacccaaaat      1620
gttgattatt tgaattctta ttactacctg gaatctcaga aattgagcga caatgtggaa      1680
gatttcacgt tcacacgctc cattgaggaa gcgctggata atagcgcgaa agtgtatacg      1740
tatttcccta ccttggcgaa taaagtaaat gctggtgtcc agggaggctt atttctgatg      1800
tgggcgaatg atgtggtaga agattttacg accaatattt tgcgtaagga caccttagat      1860
aaaattagcg atgttagcgc catcatcccc tatattggcc cagcactgaa tatctcgaac      1920
tctgtgcgtc gcggaaactt caccgaagca tttgcggtga ccggggttac tattctgttg      1980
gaagcctttc cggagtttac tattccggcg ctgggtgcgt ttgtgattta ttcgaaagta      2040
caagaacgca atgaaattat caaaaccatc gataattgcc tggaacaacg cattaaacgc      2100
tggaaggatt cttatgaatg gatgatgggc acctggttat cccgtattat cacacagttt      2160
aacaacatct cgtatcagat gtacgattca ctgaactacc aagcaggggc gatcaaagcc      2220
aagatcgact tagaatacaa gaaatattca ggtagcgata aagagaatat taaaagccag      2280
gttgaaaacc tgaagaactc tctggatgtc aaaatttcag aggctatgaa caacattaac      2340
aaatttatcc gcgaatgtag cgtcacgtat ctgtttaaaa acatgctccc gaaagtgatt      2400
gatgagctca acgagtttga tcgcaacaca aaggccaaac tgattaacct gattgatagt      2460
cacaatatta ttttagtcgg tgaagttgac aagctgaagg ctaaggtcaa taacagcttt      2520
cagaacacta ttccgtttaa tattttctcc tatacgaaca atagtctgct gaaagacatt      2580
atcaacgaat acttcaacaa tattaatgac agcaaaattc tgagcctgca gaatcgtaag      2640
aatacgctgg tagataccag tggatataat gcggaagtct cagaagaggg tgatgtacag      2700
ctgaacccga tctttccgtt cgactttaaa ctggggtcta gtggtgaaga tcgcggtaaa      2760
gtgatcgtta cccaaaacga gaacattgtg tataacagca tgtacgagag tttctcaatt      2820
tctttctgga ttcgcatcaa taaatgggtt tctaatttgc ctggctatac catcattgat      2880
agcgtcaaaa acaactcggg ctggtcgatt ggcattatta gcaactttct ggtgtttacc      2940
ctgaaacaga atgaggattc ggaacagagc attaacttct cctacgacat cagcaacaat      3000
gcaccagggt ataacaaatg gttcttcgta acggtgacga acaatatgat gggcaatatg      3060
aaaatctaca ttaacgggaa acttatcgac accattaaag tgaaagagct tactgggatc      3120
aattttagta aaaccattac ctttgagatc aacaaaattc cggacacggg tctgattacc      3180
tccgattcgg ataatatcaa tatgtggatt cgcgacttttt atatcttcgc caaagaactt      3240
gatggcaaag atatcaacat tttgtttaat tccctgcagt ataccaatgt cgttaaggac      3300
tattggggca atgatctccg ctacaataaa gaatactaca tggttaacat cgactatctc      3360
aatcgctaca tgtatgctaa ctcgcgtcaa attgtgttta acacacgtcg taacaacaac      3420
gattttaacg aaggttataa aatcattatc aaacggatcc gcggcaatac gaacgatact      3480
cgtgttcgtg gcggtgacat tctgtatttc gacatgacga ttaataataa agcgtacaat      3540
ctgttcatga gaacgaaac catgtacgcc gataaccatt ccactgaaga tatctacgca      3600
atcggacttc gcgaacagac caaagacatt aacgacaaca tcatctttca gattcaaccg      3660
atgaataata cctactacta tgcctcccag atcttcaaaa gtaatttcaa cggcgaaaac      3720
atttcaggca tttgctcaat cggcacttat cggttccggt taggtggtga ttggtatcgt      3780
cacaactacc ttgttcccac agtgaaacaa ggcaactatg catcgctctt agaaagcaca      3840
```

-continued

```
tctacgcatt ggggttttgt gccagtcagt gaataatg                                    3878

<210> SEQ ID NO 15
<211> LENGTH: 1291
<212> TYPE: PRT
<213> ORGANISM: Artificial Sequence
<220> FEATURE:
<223> OTHER INFORMATION: BoNT/C1(0) (Endonegative)

<400> SEQUENCE: 15

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
        50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met Gly Thr Leu Asn Asn Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350
```

-continued

```
Glu Leu Thr Gln Ile Phe Thr Glu Phe Asn Tyr Ala Lys Ile Tyr Asn
    355             360             365

Val Gln Asn Arg Lys Ile Tyr Leu Ser Asn Val Tyr Thr Pro Val Thr
    370             375             380

Ala Asn Ile Leu Asp Asp Asn Val Tyr Asp Ile Gln Asn Gly Phe Asn
385             390             395             400

Ile Pro Lys Ser Asn Leu Asn Val Leu Phe Met Gly Gln Asn Leu Ser
                405             410             415

Arg Asn Pro Ala Leu Arg Lys Val Asn Pro Glu Asn Met Leu Tyr Leu
            420             425             430

Phe Thr Lys Phe Cys His Lys Ala Ile Asp Gly Arg Ser Leu Tyr Asn
            435             440             445

Lys Thr Leu Asp Cys Arg Glu Leu Leu Val Lys Asn Thr Asp Leu Pro
    450             455             460

Phe Ile Gly Asp Ile Ser Asp Val Lys Thr Asp Ile Phe Leu Arg Lys
465             470             475             480

Asp Ile Asn Glu Glu Thr Glu Val Ile Tyr Tyr Pro Asp Asn Val Ser
            485             490             495

Val Asp Gln Val Ile Leu Ser Lys Asn Thr Ser Glu His Gly Gln Leu
            500             505             510

Asp Leu Leu Tyr Pro Ser Ile Asp Ser Glu Ser Glu Ile Leu Pro Gly
            515             520             525

Glu Asn Gln Val Phe Tyr Asp Asn Arg Thr Gln Asn Val Asp Tyr Leu
    530             535             540

Asn Ser Tyr Tyr Tyr Leu Glu Ser Gln Lys Leu Ser Asp Asn Val Glu
545             550             555             560

Asp Phe Thr Phe Thr Arg Ser Ile Glu Glu Ala Leu Asp Asn Ser Ala
            565             570             575

Lys Val Tyr Thr Tyr Phe Pro Thr Leu Ala Asn Lys Val Asn Ala Gly
            580             585             590

Val Gln Gly Gly Leu Phe Leu Met Trp Ala Asn Asp Val Val Glu Asp
            595             600             605

Phe Thr Thr Asn Ile Leu Arg Lys Asp Thr Leu Asp Lys Ile Ser Asp
    610             615             620

Val Ser Ala Ile Ile Pro Tyr Ile Gly Pro Ala Leu Asn Ile Ser Asn
625             630             635             640

Ser Val Arg Arg Gly Asn Phe Thr Glu Ala Phe Ala Val Thr Gly Val
            645             650             655

Thr Ile Leu Leu Glu Ala Phe Pro Glu Phe Thr Ile Pro Ala Leu Gly
            660             665             670

Ala Phe Val Ile Tyr Ser Lys Val Gln Glu Arg Asn Glu Ile Ile Lys
            675             680             685

Thr Ile Asp Asn Cys Leu Glu Gln Arg Ile Lys Arg Trp Lys Asp Ser
    690             695             700

Tyr Glu Trp Met Met Gly Thr Trp Leu Ser Arg Ile Ile Thr Gln Phe
705             710             715             720

Asn Asn Ile Ser Tyr Gln Met Tyr Asp Ser Leu Asn Tyr Gln Ala Gly
            725             730             735

Ala Ile Lys Ala Lys Ile Asp Leu Glu Tyr Lys Lys Tyr Ser Gly Ser
            740             745             750

Asp Lys Glu Asn Ile Lys Ser Gln Val Glu Asn Leu Lys Asn Ser Leu
    755             760             765

Asp Val Lys Ile Ser Glu Ala Met Asn Asn Ile Asn Lys Phe Ile Arg
```

```
              770              775              780

Glu Cys Ser Val Thr Tyr Leu Phe Lys Asn Met Leu Pro Lys Val Ile
785              790              795              800

Asp Glu Leu Asn Glu Phe Asp Arg Asn Thr Lys Ala Lys Leu Ile Asn
              805              810              815

Leu Ile Asp Ser His Asn Ile Ile Leu Val Gly Glu Val Asp Lys Leu
              820              825              830

Lys Ala Lys Val Asn Asn Ser Phe Gln Asn Thr Ile Pro Phe Asn Ile
              835              840              845

Phe Ser Tyr Thr Asn Asn Ser Leu Leu Lys Asp Ile Ile Asn Glu Tyr
850              855              860

Phe Asn Asn Ile Asn Asp Ser Lys Ile Leu Ser Leu Gln Asn Arg Lys
865              870              875              880

Asn Thr Leu Val Asp Thr Ser Gly Tyr Asn Ala Glu Val Ser Glu Glu
              885              890              895

Gly Asp Val Gln Leu Asn Pro Ile Phe Pro Phe Asp Phe Lys Leu Gly
              900              905              910

Ser Ser Gly Glu Asp Arg Gly Lys Val Ile Val Thr Gln Asn Glu Asn
              915              920              925

Ile Val Tyr Asn Ser Met Tyr Glu Ser Phe Ser Ile Ser Phe Trp Ile
              930              935              940

Arg Ile Asn Lys Trp Val Ser Asn Leu Pro Gly Tyr Thr Ile Ile Asp
945              950              955              960

Ser Val Lys Asn Asn Ser Gly Trp Ser Ile Gly Ile Ile Ser Asn Phe
              965              970              975

Leu Val Phe Thr Leu Lys Gln Asn Glu Asp Ser Glu Gln Ser Ile Asn
              980              985              990

Phe Ser Tyr Asp Ile Ser Asn Asn  Ala Pro Gly Tyr Asn  Lys Trp Phe
              995              1000              1005

Phe Val  Thr Val Thr Asn Asn  Met Met Gly Asn Met  Lys Ile Tyr
     1010              1015              1020

Ile Asn  Gly Lys Leu Ile Asp  Thr Ile Lys Val Lys  Glu Leu Thr
     1025              1030              1035

Gly Ile  Asn Phe Ser Lys Thr  Ile Thr Phe Glu Ile  Asn Lys Ile
     1040              1045              1050

Pro Asp  Thr Gly Leu Ile Thr  Ser Asp Ser Asp Asn  Ile Asn Met
     1055              1060              1065

Trp Ile  Arg Asp Phe Tyr Ile  Phe Ala Lys Glu Leu  Asp Gly Lys
     1070              1075              1080

Asp Ile  Asn Ile Leu Phe Asn  Ser Leu Gln Tyr Thr  Asn Val Val
     1085              1090              1095

Lys Asp  Tyr Trp Gly Asn Asp  Leu Arg Tyr Asn Lys  Glu Tyr Tyr
     1100              1105              1110

Met Val  Asn Ile Asp Tyr Leu  Asn Arg Tyr Met Tyr  Ala Asn Ser
     1115              1120              1125

Arg Gln  Ile Val Phe Asn Thr  Arg Arg Asn Asn Asn  Asp Phe Asn
     1130              1135              1140

Glu Gly  Tyr Lys Ile Ile Ile  Lys Arg Ile Arg Gly  Asn Thr Asn
     1145              1150              1155

Asp Thr  Arg Val Arg Gly Gly  Asp Ile Leu Tyr Phe  Asp Met Thr
     1160              1165              1170

Ile Asn  Asn Lys Ala Tyr Asn  Leu Phe Met Lys Asn  Glu Thr Met
     1175              1180              1185
```

```
Tyr Ala  Asp Asn His Ser Thr  Glu Asp Ile Tyr Ala  Ile Gly Leu
    1190              1195             1200

Arg Glu  Gln Thr Lys Asp Ile  Asn Asp Asn Ile Ile  Phe Gln Ile
    1205              1210             1215

Gln Pro  Met Asn Asn Thr Tyr  Tyr Tyr Ala Ser Gln  Ile Phe Lys
    1220              1225             1230

Ser Asn  Phe Asn Gly Glu Asn  Ile Ser Gly Ile Cys  Ser Ile Gly
    1235              1240             1245

Thr Tyr  Arg Phe Arg Leu Gly  Gly Asp Trp Tyr Arg  His Asn Tyr
    1250              1255             1260

Leu Val  Pro Thr Val Lys Gln  Gly Asn Tyr Ala Ser  Leu Leu Glu
    1265              1270             1275

Ser Thr  Ser Thr His Trp Gly  Phe Val Pro Val Ser  Glu
    1280              1285             1290
```

<210> SEQ ID NO 16
<211> LENGTH: 3876
<212> TYPE: DNA
<213> ORGANISM: Clostridium botulinum

<400> SEQUENCE: 16

```
atgccgatca cgattaataa tttcaactat agcgatccgg tggacaataa gaatattctg      60
tatctggata ctcatctgaa tacgctggct aacgaaccgg agaaagcgtt ccgcatcaca     120
ggcaacatct gggttattcc cgatcgcttt tcacgcaaca gcaaccctaa tctgaacaaa     180
cctcctcgtg tcaccagtcc taaatccggt tattacgacc caaactatct gagtacggat     240
agcgataaag atccctttct gaaagagatc attaagctgt tcaaacgcat taactctcgc     300
gaaattgggg aagagctgat ctatcggctt tcgacagata tcccgttccc aggtaacaat     360 aatacccga ttaatacttt cgactttgat gttgatttca attctgtgga tgtgaaaacg     420
cgtcaaggca ataattgggt gaaaactggt agcattaacc cgagtgtaat tatcacaggt     480
ccccgtgaga acatcatcga cccggaaacc tctaccttca agctgacgaa caacacgttt     540
gctgcacagt aagggtttgg tgccctgtca atcatttcca tctcaccgcg tttcatgtta     600
acctactcca atgccacaaa tgatgttggc gaaggacgtt ttagcaaatc agaattttgc     660
atggacccaa ttctcattct gatgcacgag ctgaaccatg cgatgcacaa cttgtatggc     720
attgctattc caaacgatca aaccattagc tccgttacca gtaatatctt ctatagccag     780
tataatgtca aattggagta tgccgaaatt tacgcctttg gaggcccgac cattgacctg     840
attccgaaat ctgcacgcaa atacttcgaa gaaaaggcgt tagattacta tcgcagcatc     900
gcgaaacgcc tgaactcgat taccacggcc aatccgtcgt cgttcaacaa atacattggt     960
gaatataaac agaaactgat tcgcaaatat cggtttgtcg tagaaagctc tggtgaagtg    1020
actgtaaacc gcaacaaatt tgtcgaactc tacaacgagt tgacccaaat ctttaccgag    1080
tttaactacg caaagatcta taacgtacag aaccgcaaga tttatcttag caatgtatac    1140
acaccggtta ctgcgaacat cttagacgac aatgtgtatg atattcagaa tggctttaac    1200
atcccgaaat caaatctgaa cgttctgttt atgggccaga acctgagtcg taatccagca    1260
ctgcgtaaag tgaacccgga aaatatgctc tacttgttta ccaaattttg ccacaaagcg    1320
attgatggcc gctctctcta taacaaaacg ctggattgtc gtgagttact tgtgaagaac    1380
actgatttac cgttcattgg ggatatctcc gacgtgaaaa ccgatatctt cctgcgcaaa    1440
gacattaatg aagaaacgga agtcatctat taccccgaca atgtgagcgt tgatcaggtc    1500
```

-continued

```
attttatcga agaacacctc cgaacatggt cagttggatt tgctgtaccc tagcattgac   1560
tcggagagtg aaatccttcc gggcgaaaat caagtgtttt acgacaaccg tacccaaaat   1620
gttgattatt tgaattctta ttactacctg gaatctcaga aattgagcga caatgtggaa   1680
gatttcacgt tcacacgctc cattgaggaa gcgctggata atagcgcgaa agtgtatacg   1740
tatttcccta ccttggcgaa taaagtaaat gctggtgtcc agggaggctt atttctgatg   1800
tgggcgaatg atgtggtaga agattttacg accaatattt tgcgtaagga caccttagat   1860
aaaattagcg atgttagcgc catcatcccc tatattggcc cagcactgaa tatctcgaac   1920
tctgtgcgtc gcggaaactt caccgaagca tttgcggtga ccggggttac tattctgttg   1980
gaagcctttc cggagtttac tattccggcg ctgggtgcgt ttgtgattta ttcgaaagta   2040
caagaacgca atgaaattat caaaaccatc gataattgcc tggaacaacg cattaaacgc   2100
tggaaggatt cttatgaatg gatgatgggc acctggttat cccgtattat cacacagttt   2160
aacaacatct cgtatcagat gtacgattca ctgaactacc aagcaggggc gatcaaagcc   2220
aagatcgact tagaatacaa gaaatattca ggtagcgata aagagaatat taaaagccag   2280
gttgaaaacc tgaagaactc tctggatgtc aaaatttcag aggctatgaa caacattaac   2340
aaatttatcc gcgaatgtag cgtcacgtat ctgtttaaaa acatgctccc gaaagtgatt   2400
gatgagctca acgagtttga tcgcaacaca aaggccaaac tgattaacct gattgatagt   2460
cacaatatta ttttagtcgg tgaagttgac aagctgaagg ctaaggtcaa taacagcttt   2520
cagaacacta ttccgtttaa tattttctcc tatacgaaca atagtctgct gaaagacatt   2580
atcaacgaat acttcaacaa tattaatgac agcaaaattc tgagcctgca gaatcgtaag   2640
aatacgctgg tagataccag tggatataat gcggaagtct cagaagaggg tgatgtacag   2700
ctgaacccga tctttccgtt cgactttaaa ctggggtcta gtggtgaaga tcgcggtaaa   2760
gtgatcgtta cccaaaacga gaacattgtg tataacagca tgtacgagag tttctcaatt   2820
tctttctgga ttcgcatcaa taaatgggtt tctaatttgc ctggctatac catcattgat   2880
agcgtcaaaa acaactcggg ctggtcgatt ggcattatta gcaactttct ggtgtttacc   2940
ctgaaacaga atgaggattc ggaacagagc attaacttct cctacgacat cagcaacaat   3000
gcaccagggt ataacaaatg gttcttcgta acggtgacga acaatatgat gggcaatatg   3060
aaaatctaca ttaacgggaa acttatcgac accattaaag tgaaagagct tactgggatc   3120
aattttagta aaaccattac ctttgagatc aacaaaattc cggacacggg tctgattacc   3180
tccgattcgg ataatatcaa tatgtggatt cgcgactttt atatcttcgc caaagaactt   3240
gatggcaaag atatcaacat tttgtttaat tccctgcagt ataccaatgt cgttaaggac   3300
tattggggca atgatctccg ctacaataaa gaatactaca tggttaacat cgactatctc   3360
aatcgctaca tgtatgctaa ctcgcgtcaa attgtgttta acacacgtcg taacaacaac   3420
gattttaacg aaggttataa aatcattatc aaacggatcc gcggcaatac gaacgatact   3480
cgtgttcgtg gcggtgacat tctgtatttc gacatgacga ttaataataa agcgtacaat   3540
ctgttcatga agaacgaaac catgtacgcc gataaccatt ccactgaaga tatctacgca   3600
atcggacttc gcgaacagac caaagacatt aacgacaaca tcatctttca gattcaaccg   3660
atgaataata cctactacta tgcctcccag atcttcaaaa gtaatttcaa cggcgaaaac   3720
atttcaggca tttgctcaat cggcacttat cggttccggt taggtggtga ttggtatcgt   3780
cacaactacc ttgttcccac agtgaaacaa ggcaactatg catcgctctt agaaagcaca   3840
```
tctacgcatt ggggttttgt gccagtcagt gaataa                                              3876

<210> SEQ ID NO 17
<211> LENGTH: 1291
<212> TYPE: PRT
<213> ORGANISM: Clostridium botulinum

<400> SEQUENCE: 17

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
370             375             380

Ala Asn Ile Leu Asp Asp Asn Val Tyr Asp Ile Gln Asn Gly Phe Asn
385             390             395             400

Ile Pro Lys Ser Asn Leu Asn Val Leu Phe Met Gly Gln Asn Leu Ser
405             410             415

Arg Asn Pro Ala Leu Arg Lys Val Asn Pro Glu Asn Met Leu Tyr Leu
420             425             430

Phe Thr Lys Phe Cys His Lys Ala Ile Asp Gly Arg Ser Leu Tyr Asn
435             440             445

Lys Thr Leu Asp Cys Arg Glu Leu Leu Val Lys Asn Thr Asp Leu Pro
450             455             460

Phe Ile Gly Asp Ile Ser Asp Val Lys Thr Asp Ile Phe Leu Arg Lys
465             470             475             480

Asp Ile Asn Glu Glu Thr Glu Val Ile Tyr Tyr Pro Asp Asn Val Ser
485             490             495

Val Asp Gln Val Ile Leu Ser Lys Asn Thr Ser Glu His Gly Gln Leu
500             505             510

Asp Leu Leu Tyr Pro Ser Ile Asp Ser Glu Ser Glu Ile Leu Pro Gly
515             520             525

Glu Asn Gln Val Phe Tyr Asp Asn Arg Thr Gln Asn Val Asp Tyr Leu
530             535             540

Asn Ser Tyr Tyr Tyr Leu Glu Ser Gln Lys Leu Ser Asp Asn Val Glu
545             550             555             560

Asp Phe Thr Phe Thr Arg Ser Ile Glu Glu Ala Leu Asp Asn Ser Ala
565             570             575

Lys Val Tyr Thr Tyr Phe Pro Thr Leu Ala Asn Lys Val Asn Ala Gly
580             585             590

Val Gln Gly Gly Leu Phe Leu Met Trp Ala Asn Asp Val Val Glu Asp
595             600             605

Phe Thr Thr Asn Ile Leu Arg Lys Asp Thr Leu Asp Lys Ile Ser Asp
610             615             620

Val Ser Ala Ile Ile Pro Tyr Ile Gly Pro Ala Leu Asn Ile Ser Asn
625             630             635             640

Ser Val Arg Arg Gly Asn Phe Thr Glu Ala Phe Ala Val Thr Gly Val
645             650             655

Thr Ile Leu Leu Glu Ala Phe Pro Glu Phe Thr Ile Pro Ala Leu Gly
660             665             670

Ala Phe Val Ile Tyr Ser Lys Val Gln Glu Arg Asn Glu Ile Ile Lys
675             680             685

Thr Ile Asp Asn Cys Leu Glu Gln Arg Ile Lys Arg Trp Lys Asp Ser
690             695             700

Tyr Glu Trp Met Met Gly Thr Trp Leu Ser Arg Ile Ile Thr Gln Phe
705             710             715             720

Asn Asn Ile Ser Tyr Gln Met Tyr Asp Ser Leu Asn Tyr Gln Ala Gly
725             730             735

Ala Ile Lys Ala Lys Ile Asp Leu Glu Tyr Lys Lys Tyr Ser Gly Ser
740             745             750

Asp Lys Glu Asn Ile Lys Ser Gln Val Glu Asn Leu Lys Asn Ser Leu
755             760             765

Asp Val Lys Ile Ser Glu Ala Met Asn Asn Ile Asn Lys Phe Ile Arg
770             775             780

Glu Cys Ser Val Thr Tyr Leu Phe Lys Asn Met Leu Pro Lys Val Ile

-continued

```
785             790             795             800

Asp Glu Leu Asn Glu Phe Asp Arg Asn Thr Lys Ala Lys Leu Ile Asn
                805             810             815

Leu Ile Asp Ser His Asn Ile Ile Leu Val Gly Glu Val Asp Lys Leu
                820             825             830

Lys Ala Lys Val Asn Asn Ser Phe Gln Asn Thr Ile Pro Phe Asn Ile
                835             840             845

Phe Ser Tyr Thr Asn Asn Ser Leu Leu Lys Asp Ile Ile Asn Glu Tyr
    850             855             860

Phe Asn Asn Ile Asn Asp Ser Lys Ile Leu Ser Leu Gln Asn Arg Lys
865             870             875             880

Asn Thr Leu Val Asp Thr Ser Gly Tyr Asn Ala Glu Val Ser Glu Glu
                885             890             895

Gly Asp Val Gln Leu Asn Pro Ile Phe Pro Phe Asp Phe Lys Leu Gly
                900             905             910

Ser Ser Gly Glu Asp Arg Gly Lys Val Ile Val Thr Gln Asn Glu Asn
                915             920             925

Ile Val Tyr Asn Ser Met Tyr Glu Ser Phe Ser Ile Ser Phe Trp Ile
    930             935             940

Arg Ile Asn Lys Trp Val Ser Asn Leu Pro Gly Tyr Thr Ile Ile Asp
945             950             955             960

Ser Val Lys Asn Asn Ser Gly Trp Ser Ile Gly Ile Ile Ser Asn Phe
                965             970             975

Leu Val Phe Thr Leu Lys Gln Asn Glu Asp Ser Glu Gln Ser Ile Asn
                980             985             990

Phe Ser Tyr Asp Ile Ser Asn Asn  Ala Pro Gly Tyr Asn  Lys Trp Phe
        995             1000            1005

Phe Val  Thr Val Thr Asn Asn  Met Met Gly Asn Met  Lys Ile Tyr
    1010            1015            1020

Ile Asn  Gly Lys Leu Ile Asp  Thr Ile Lys Val Lys  Glu Leu Thr
    1025            1030            1035

Gly Ile  Asn Phe Ser Lys Thr  Ile Thr Phe Glu Ile  Asn Lys Ile
    1040            1045            1050

Pro Asp  Thr Gly Leu Ile Thr  Ser Asp Ser Asp Asn  Ile Asn Met
    1055            1060            1065

Trp Ile  Arg Asp Phe Tyr Ile  Phe Ala Lys Glu Leu  Asp Gly Lys
    1070            1075            1080

Asp Ile  Asn Ile Leu Phe Asn  Ser Leu Gln Tyr Thr  Asn Val Val
    1085            1090            1095

Lys Asp  Tyr Trp Gly Asn Asp  Leu Arg Tyr Asn Lys  Glu Tyr Tyr
    1100            1105            1110

Met Val  Asn Ile Asp Tyr Leu  Asn Arg Tyr Met Tyr  Ala Asn Ser
    1115            1120            1125

Arg Gln  Ile Val Phe Asn Thr  Arg Arg Asn Asn Asn  Asp Phe Asn
    1130            1135            1140

Glu Gly  Tyr Lys Ile Ile Ile  Lys Arg Ile Arg Gly  Asn Thr Asn
    1145            1150            1155

Asp Thr  Arg Val Arg Gly Gly  Asp Ile Leu Tyr Phe  Asp Met Thr
    1160            1165            1170

Ile Asn  Asn Lys Ala Tyr Asn  Leu Phe Met Lys Asn  Glu Thr Met
    1175            1180            1185

Tyr Ala  Asp Asn His Ser Thr  Glu Asp Ile Tyr Ala  Ile Gly Leu
    1190            1195            1200
```

-continued

```
Arg Glu  Gln Thr Lys Asp Ile  Asn Asp Asn Ile Ile  Phe Gln Ile
    1205             1210              1215

Gln Pro  Met Asn Asn Thr Tyr  Tyr Tyr Ala Ser Gln  Ile Phe Lys
    1220             1225              1230

Ser Asn  Phe Asn Gly Glu Asn  Ile Ser Gly Ile Cys  Ser Ile Gly
    1235             1240              1245

Thr Tyr  Arg Phe Arg Leu Gly  Gly Asp Trp Tyr Arg  His Asn Tyr
    1250             1255              1260

Leu Val  Pro Thr Val Lys Gln  Gly Asn Tyr Ala Ser  Leu Leu Glu
    1265             1270              1275

Ser Thr  Ser Thr His Trp Gly  Phe Val Pro Val Ser  Glu
    1280             1285              1290
```

```
<210> SEQ ID NO 18
<211> LENGTH: 4
<212> TYPE: PRT
<213> ORGANISM: Artificial Sequence
<220> FEATURE:
<223> OTHER INFORMATION: Enterokinase and Factor Xa Cleavage Site

<400> SEQUENCE: 18

Ile Asp Gly Arg
1
```

```
<210> SEQ ID NO 19
<211> LENGTH: 4
<212> TYPE: PRT
<213> ORGANISM: Artificial Sequence
<220> FEATURE:
<223> OTHER INFORMATION: Enterokinase and Factor Xa Cleavage Site
      Variant

<400> SEQUENCE: 19

Ile Glu Gly Arg
1
```

```
<210> SEQ ID NO 20
<211> LENGTH: 45
<212> TYPE: PRT
<213> ORGANISM: Clostridium botulinum

<400> SEQUENCE: 20

Cys Pro Arg Asn Gly Leu Leu Tyr Asn Ala Ile Tyr Arg Asn Ser Lys
1               5                   10                  15

Asn Tyr Leu Asn Asn Ile Asp Leu Glu Asp Lys Lys Thr Thr Ser Lys
            20                  25                  30

Thr Asn Val Ser Tyr Pro Cys Ser Leu Leu Asn Gly Cys
        35                  40                  45
```

```
<210> SEQ ID NO 21
<211> LENGTH: 25
<212> TYPE: PRT
<213> ORGANISM: Clostridium botulinum

<400> SEQUENCE: 21

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25
```

```
<210> SEQ ID NO 22
```

```
<211> LENGTH: 10
<212> TYPE: PRT
<213> ORGANISM: Clostridium botulinum

<400> SEQUENCE: 22

Cys Lys Ser Val Arg Ala Pro Gly Ile Cys
1               5                   10

<210> SEQ ID NO 23
<211> LENGTH: 14
<212> TYPE: PRT
<213> ORGANISM: Clostridium botulinum

<400> SEQUENCE: 23

Cys Leu Arg Leu Thr Lys Asn Ser Arg Asp Asp Ser Thr Cys
1               5                   10

<210> SEQ ID NO 24
<211> LENGTH: 15
<212> TYPE: PRT
<213> ORGANISM: Clostridium botulinum

<400> SEQUENCE: 24

Cys Lys Asn Ile Val Ser Val Lys Gly Ile Arg Lys Ser Ile Cys
1               5                   10                  15

<210> SEQ ID NO 25
<211> LENGTH: 17
<212> TYPE: PRT
<213> ORGANISM: Clostridium botulinum

<400> SEQUENCE: 25

Cys Lys Ser Val Ile Pro Arg Lys Gly Thr Lys Ala Pro Pro Arg Leu
1               5                   10                  15

Cys

<210> SEQ ID NO 26
<211> LENGTH: 17
<212> TYPE: PRT
<213> ORGANISM: Clostridium botulinum

<400> SEQUENCE: 26

Cys Lys Ser Ile Ile Pro Arg Lys Gly Thr Lys Gln Ser Pro Ser Leu
1               5                   10                  15

Cys

<210> SEQ ID NO 27
<211> LENGTH: 17
<212> TYPE: PRT
<213> ORGANISM: Clostridium botulinum

<400> SEQUENCE: 27

Cys Lys Ser Ile Ile Pro Arg Lys Gly Thr Lys Ala Pro Pro Arg Leu
1               5                   10                  15

Cys

<210> SEQ ID NO 28
<211> LENGTH: 15
<212> TYPE: PRT
<213> ORGANISM: Clostridium botulinum

<400> SEQUENCE: 28

Cys Leu Asn Ser Ser Phe Lys Lys Asn Thr Lys Lys Pro Leu Cys
```

```
1               5               10              15
```

```
<210> SEQ ID NO 29
<211> LENGTH: 15
<212> TYPE: PRT
<213> ORGANISM: Clostridium botulinum

<400> SEQUENCE: 29

Cys Lys Ser Ile Val Ser Lys Lys Gly Thr Lys Asn Ser Leu Cys
1               5               10              15

<210> SEQ ID NO 30
<211> LENGTH: 29
<212> TYPE: PRT
<213> ORGANISM: Clostridium tetani

<400> SEQUENCE: 30

Cys Lys Lys Ile Ile Pro Pro Thr Asn Ile Arg Glu Asn Leu Tyr Asn
1               5               10              15

Arg Thr Ala Ser Leu Thr Asp Leu Gly Gly Glu Leu Cys
            20              25

<210> SEQ ID NO 31
<211> LENGTH: 15
<212> TYPE: PRT
<213> ORGANISM: Clostridium botulinum

<400> SEQUENCE: 31

Cys Lys Pro Val Met Tyr Lys Asn Thr Gly Lys Ser Glu Gln Cys
1               5               10              15

<210> SEQ ID NO 32
<211> LENGTH: 3972
<212> TYPE: DNA
<213> ORGANISM: Artificial Sequence
<220> FEATURE:
<223> OTHER INFORMATION: Wild-Type BoNT/X-10HT

<400> SEQUENCE: 32
atgaaactgg aaatcaacaa attcaactac aacgatccga tcgatggcat taatgttatt      60
accatgcgtc cgcctcgtca tagcgataaa atcaataaag gtaaaggtcc gttcaaagcc     120
tttcaggtga ttaaaaacat ttggattgtg ccggaacgct acaactttac caataatacc     180
aacgatctga acattccgag cgaaccgatt atggaagcag atgccattta taacccgaac     240
tatctgaata ccccgagcga aaaagatgaa tttctgcagg gtgttatcaa agtgctggaa     300
cgcattaaaa gcaaaccgga aggtgaaaaa ctgctggaac tgattagcag cagcattccg     360
ctgccgctgg ttagcaatgg tgcactgacc ctgagcgata tgaaaccat tgcatatcaa     420 gagaacaaca acattgtgag caatctgcag gcaaacctgg ttatttatgg tccgggtcct     480
gatattgcaa ataatgcaac ctatggtctg tatagcaccc cgattagtaa tggtgaaggt     540
acactgagcg aagttagctt tagcccgttt tatctgaaac cgtttgatga aagctatggc     600
aattatcgta gcctggtgaa tatcgtgaac aaattcgtga acgtgaatt tgcacctgat     660 ccggcaagca ccctgatgca tgaactggtt catgttaccc ataatctgta tggtattagc     720
aaccgcaact tctactataa ctttgacacc ggcaaaattg aaaccagccg tcagcagaat     780
agcctgattt ttgaagaact gctgaccttt ggtggcattg atagcaaagc aattagcagc     840
ctgatcatca gaaaaattat cgaaaccgcc aagaacaact ataccacgct gattagcgaa     900
cgcctgaata ccgttaccgt tgaaaatgat ctgctgaaat atatcaaaaa caaaatcccg     960
```

-continued

```
gttcagggtc gtctgggtaa cttttaaactg gataccgcag aattcgagaa aaagctgaat    1020
accattctgt ttgtgctgaa cgaaagcaat ctggcacagc gttttagcat tctggttcgt    1080
aaacattacc tgaaagaacg tccgattgat ccgatttatg tgaacattct ggatgacaat    1140
agctacagca ccctggaagg tttttaacatt agcagtcagg gtagcaatga tttccaaggt    1200
cagctgctgg aaagcagcta ttttgaaaaa attgaaagca atgccctgcg tgccttcatt    1260
aaaatctgtc cgcgtaatgg tctgctgtat aatgccattt atcgcaacag caaaaactac    1320
ctgaacaaca ttgatctgga agataaaaag accacgagca aaaccaatgt tagctatccg    1380
tgtagcctgc tgaatggttg tattgaagtt gaaaacaaag acctgttcct gattagcaac    1440
aaagatagcc tgaacgatat taacctgagc gaagaaaaaa tcaaaccgga aaccaccgtg    1500
ttcttcaaag ataaactgcc tccgcaggat attacgctga gcaattatga tttttaccgaa    1560 gccaatagca ttccgagcat tagccagcag aacattctgg aacgtaatga agaactgtat    1620
gaaccgattc gcaatagcct gtttgaaatc aaaaccatct atgtggataa gctgaccacc    1680 tttcatttt tggaagccca gaatattgat gagagcattg atagcagcaa aattcgtgtt    1740
gaactgaccg atagcgttga tgaagcactg agcaatccga ataaagttta tagcccgttc    1800
aagaacatga gcaacaccat taatagcatt gaaaccggta ttaccagcac ctacatcttt    1860
tatcagtggc tgcgtagcat cgtgaaagat tttagtgatg aaaccggcaa aatcgacgtg    1920
attgataaaa gcagcgatac cctggcaatt gttccgtata ttggtccgct gctgaatatt    1980
ggtaatgata ttcgtcatgg cgatttttgtg ggtgcaattg aactggcagg cattaccgca    2040
ctgctggaat atgttccgga atttaccatt ccgattctgg ttggtctgga agttattggt    2100
ggcgaactgg cacgtgaaca ggttgaagca attgttaata atgccctgga taaacgcgat    2160
cagaaatggg cagaagttta caatattacc aaagcacagt ggtggggcac cattcattta    2220
cagattaata cccgtctggc ccataccctat aaagccctga gccgtcaggc aaatgccatt    2280
aaaatgaata tggaatttca gctggccaac tacaaaggca acatcgatga taaagccaaa    2340
atcaaaaacg ccatcagcga aaccgaaatc ctgctgaaca aaagcgttga acaggcaatg    2400
aaaaacaccg agaaattcat gatcaaactg agcaacagct atctgaccaa agaaatgatt    2460
ccgaaagtgc aggataacct gaaaaatttc gatctggaaa ccaagaaaac cctggacaaa    2520
tttatcaaag agaaagagga cattctgggc accaatctga gcagcagcct gcgtcgtaaa    2580
gttagcattc gtctgaataa aaacattgcc ttcgacatca acgatatccc gtttagcgaa    2640
tttgatgatc tgatcaacca gtacaaaaac gagatcgaag attatgaagt gctgaatctg    2700
ggtgcagaag atgggaaaat caaagatctg agcggtacaa ccagcgatat caatattggt    2760
tcagatatcg aactggccga tggtcgtgaa aataaagcca ttaagattaa aggcagcgag    2820
aacagcacca tcaaaattgc aatgaacaaa tatctgcgtt ttagcgcgac cgataacttt    2880
agcattagct tttggatcaa acatccgaaa ccgaccaatc tgcttaataa cggtattgaa    2940
tataccctgg tcgagaactt taatcagcgt ggttggaaaa ttagcatcca ggatagcaaa    3000
ctgatttggt atctgcgcga tcacaataac agcatcaaaa tcgttacacc ggattatatt    3060
gcgtttaatg gctggaacct gattaccatt acaaacaatc gtagcaaagg cagcattgtg    3120
tatgtgaacg gtagcaaaat tgaagagaag gatattagca gcatctggaa taccgaagtg    3180
gatgatccga ttatctttcg cctgaaaaac aatcgcgata cccaggcgtt taccctgctg    3240
gatcagttta gcatttatcg gaaagaactg aaccagaacg aagtggtgaa actgtataac    3300
```

-continued

```
tactacttca acagcaacta cattcgcgat atttggggta atccgctgca gtacaacaaa      3360
aaatactatc tgcagaccca ggacaaacct ggtaaaggtc tgatccgcga atattggagc      3420
agctttggtt atgattatgt gattctgagc gatagcaaga cgattacctt tccgaataat      3480
atccgttatg gtgccctgta taacggcagc aaagttctga tcaaaaatag caaaaaactg      3540
gatggtctgg tgcgcaataa agatttcatt cagctggaaa tcgatggcta atatatgggt      3600
attagcgcag atcgctttaa cgaggatacc aactatattg gcaccaccta tggtacaacc      3660
catgatctga ccaccgattt tgaaattatt cagcgccaag agaaataccg caattattgt      3720
cagctgaaaa ccccgtataa catctttcat aaaagcggtc tgatgagcac cgaaaccagc      3780
aaaccgacct ttcatgatta tcgtgactgg gtttatagca gcgcatggta tttttcagaac     3840 tatgaaaatc tgaacctgcg caaacatacc aaaaccaact ggtatttttat cccgaaagat     3900 gaaggttggg atgaagatct tgaagttctg tttcagggtc cgcatcatca ccaccatcac      3960
catcatcatc ac                                                          3972
```

```
<210> SEQ ID NO 33
<211> LENGTH: 1306
<212> TYPE: PRT
<213> ORGANISM: Clostridium botulinum

<400> SEQUENCE: 33

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255
```

-continued

```
Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
        290                 295                 300

Val Thr Val Glu Asn Asp Leu Leu Lys Tyr Ile Lys Asn Lys Ile Pro
    305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
        370                 375                 380

Leu Glu Gly Phe Asn Ile Ser Ser Gln Gly Ser Asn Asp Phe Gln Gly
    385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
                420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
        450                 455                 460

Asn Gly Cys Ile Glu Val Glu Asn Lys Asp Leu Phe Leu Ile Ser Asn
    465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
        530                 535                 540

Asn Ser Leu Phe Glu Ile Lys Thr Ile Tyr Val Asp Lys Leu Thr Thr
    545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
    610                 615                 620

Arg Ser Ile Val Lys Asp Phe Ser Asp Glu Thr Gly Lys Ile Asp Val
    625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670
```

-continued

```
Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
        690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
                755                 760                 765

Ala Asn Tyr Lys Gly Asn Ile Asp Asp Lys Ala Lys Ile Lys Asn Ala
        770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
                820                 825                 830

Glu Thr Lys Lys Thr Leu Asp Lys Phe Ile Lys Glu Lys Glu Asp Ile
                835                 840                 845

Leu Gly Thr Asn Leu Ser Ser Ser Leu Arg Arg Lys Val Ser Ile Arg
        850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
                900                 905                 910

Thr Thr Ser Asp Ile Asn Ile Gly Ser Asp Ile Glu Leu Ala Asp Gly
                915                 920                 925

Arg Glu Asn Lys Ala Ile Lys Ile Lys Gly Ser Glu Asn Ser Thr Ile
        930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
                980                 985                 990

Lys Ile Ser Ile Gln Asp Ser Lys  Leu Ile Trp Tyr Leu  Arg Asp His
        995                 1000                    1005

Asn Asn  Ser Ile Lys Ile Val  Thr Pro Asp Tyr Ile  Ala Phe Asn
    1010                1015                1020

Gly Trp  Asn Leu Ile Thr Ile  Thr Asn Asn Arg Ser  Lys Gly Ser
    1025                1030                1035

Ile Val  Tyr Val Asn Gly Ser  Lys Ile Glu Glu Lys  Asp Ile Ser
    1040                1045                1050

Ser Ile  Trp Asn Thr Glu Val  Asp Asp Pro Ile Ile  Phe Arg Leu
    1055                1060                1065

Lys Asn  Asn Arg Asp Thr Gln  Ala Phe Thr Leu Leu  Asp Gln Phe
    1070                1075                1080

Ser Ile  Tyr Arg Lys Glu Leu  Asn Gln Asn Glu Val  Val Lys Leu
```

-continued

```
      1085              1090              1095

Tyr Asn  Tyr Tyr Phe Asn Ser  Asn Tyr Ile Arg Asp  Ile Trp Gly
    1100              1105              1110

Asn Pro  Leu Gln Tyr Asn Lys  Lys Tyr Tyr Leu Gln  Thr Gln Asp
    1115              1120              1125

Lys Pro  Gly Lys Gly Leu Ile  Arg Glu Tyr Trp Ser  Ser Phe Gly
    1130              1135              1140

Tyr Asp  Tyr Val Ile Leu Ser  Asp Ser Lys Thr Ile  Thr Phe Pro
    1145              1150              1155

Asn Asn  Ile Arg Tyr Gly Ala  Leu Tyr Asn Gly Ser  Lys Val Leu
    1160              1165              1170

Ile Lys  Asn Ser Lys Lys Leu  Asp Gly Leu Val Arg  Asn Lys Asp
    1175              1180              1185

Phe Ile  Gln Leu Glu Ile Asp  Gly Tyr Asn Met Gly  Ile Ser Ala
    1190              1195              1200

Asp Arg  Phe Asn Glu Asp Thr  Asn Tyr Ile Gly Thr  Thr Tyr Gly
    1205              1210              1215

Thr Thr  His Asp Leu Thr Thr  Asp Phe Glu Ile Ile  Gln Arg Gln
    1220              1225              1230

Glu Lys  Tyr Arg Asn Tyr Cys  Gln Leu Lys Thr Pro  Tyr Asn Ile
    1235              1240              1245

Phe His  Lys Ser Gly Leu Met  Ser Thr Glu Thr Ser  Lys Pro Thr
    1250              1255              1260

Phe His  Asp Tyr Arg Asp Trp  Val Tyr Ser Ser Ala  Trp Tyr Phe
    1265              1270              1275

Gln Asn  Tyr Glu Asn Leu Asn  Leu Arg Lys His Thr  Lys Thr Asn
    1280              1285              1290

Trp Tyr  Phe Ile Pro Lys Asp  Glu Gly Trp Asp Glu  Asp
    1295              1300              1305

<210> SEQ ID NO 34
<211> LENGTH: 1324
<212> TYPE: PRT
<213> ORGANISM: Artificial Sequence
<220> FEATURE:
<223> OTHER INFORMATION: Wild-Type BoNT/X-10HT

<400> SEQUENCE: 34

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
```

```
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
                180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
        210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
        290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
        370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
        450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
            485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
        530                 535                 540

Asn Ser Leu Phe Glu Ile Lys Thr Ile Tyr Val Asp Lys Leu Thr Thr
545                 550                 555                 560
```

-continued

```
Phe His Phe Leu Glu Ala Gln Asn Ile Asp Glu Ser Ile Asp Ser Ser
            565             570             575

Lys Ile Arg Val Glu Leu Thr Asp Ser Val Asp Glu Ala Leu Ser Asn
            580             585             590

Pro Asn Lys Val Tyr Ser Pro Phe Lys Asn Met Ser Asn Thr Ile Asn
            595             600             605

Ser Ile Glu Thr Gly Ile Thr Ser Thr Tyr Ile Phe Tyr Gln Trp Leu
            610             615             620

Arg Ser Ile Val Lys Asp Phe Ser Asp Glu Thr Gly Lys Ile Asp Val
625             630             635             640

Ile Asp Lys Ser Ser Asp Thr Leu Ala Ile Val Pro Tyr Ile Gly Pro
            645             650             655

Leu Leu Asn Ile Gly Asn Asp Ile Arg His Gly Asp Phe Val Gly Ala
            660             665             670

Ile Glu Leu Ala Gly Ile Thr Ala Leu Leu Glu Tyr Val Pro Glu Phe
            675             680             685

Thr Ile Pro Ile Leu Val Gly Leu Glu Val Ile Gly Gly Glu Leu Ala
            690             695             700

Arg Glu Gln Val Glu Ala Ile Val Asn Asn Ala Leu Asp Lys Arg Asp
705             710             715             720

Gln Lys Trp Ala Glu Val Tyr Asn Ile Thr Lys Ala Gln Trp Trp Gly
            725             730             735

Thr Ile His Leu Gln Ile Asn Thr Arg Leu Ala His Thr Tyr Lys Ala
            740             745             750

Leu Ser Arg Gln Ala Asn Ala Ile Lys Met Asn Met Glu Phe Gln Leu
            755             760             765

Ala Asn Tyr Lys Gly Asn Ile Asp Asp Lys Ala Lys Ile Lys Asn Ala
            770             775             780

Ile Ser Glu Thr Glu Ile Leu Leu Asn Lys Ser Val Glu Gln Ala Met
785             790             795             800

Lys Asn Thr Glu Lys Phe Met Ile Lys Leu Ser Asn Ser Tyr Leu Thr
            805             810             815

Lys Glu Met Ile Pro Lys Val Gln Asp Asn Leu Lys Asn Phe Asp Leu
            820             825             830

Glu Thr Lys Lys Thr Leu Asp Lys Phe Ile Lys Glu Lys Glu Asp Ile
            835             840             845

Leu Gly Thr Asn Leu Ser Ser Ser Leu Arg Arg Lys Val Ser Ile Arg
            850             855             860

Leu Asn Lys Asn Ile Ala Phe Asp Ile Asn Asp Ile Pro Phe Ser Glu
865             870             875             880

Phe Asp Asp Leu Ile Asn Gln Tyr Lys Asn Glu Ile Glu Asp Tyr Glu
            885             890             895

Val Leu Asn Leu Gly Ala Glu Asp Gly Lys Ile Lys Asp Leu Ser Gly
            900             905             910

Thr Thr Ser Asp Ile Asn Ile Gly Ser Asp Ile Glu Leu Ala Asp Gly
            915             920             925

Arg Glu Asn Lys Ala Ile Lys Ile Lys Gly Ser Glu Asn Ser Thr Ile
            930             935             940

Lys Ile Ala Met Asn Lys Tyr Leu Arg Phe Ser Ala Thr Asp Asn Phe
945             950             955             960

Ser Ile Ser Phe Trp Ile Lys His Pro Lys Pro Thr Asn Leu Leu Asn
            965             970             975
```

-continued

```
Asn Gly Ile Glu Tyr Thr Leu Val Glu Asn Phe Asn Gln Arg Gly Trp
        980                 985                 990

Lys Ile Ser Ile Gln Asp Ser Lys  Leu Ile Trp Tyr Leu  Arg Asp His
        995                 1000                1005

Asn Asn Ser Ile Lys Ile Val  Thr Pro Asp Tyr Ile  Ala Phe Asn
    1010                1015                1020

Gly Trp Asn Leu Ile Thr Ile  Thr Asn Asn Arg Ser  Lys Gly Ser
    1025                1030                1035

Ile Val Tyr Val Asn Gly Ser  Lys Ile Glu Glu Lys  Asp Ile Ser
    1040                1045                1050

Ser Ile Trp Asn Thr Glu Val  Asp Asp Pro Ile Ile  Phe Arg Leu
    1055                1060                1065

Lys Asn Asn Arg Asp Thr Gln  Ala Phe Thr Leu Leu  Asp Gln Phe
    1070                1075                1080

Ser Ile Tyr Arg Lys Glu Leu  Asn Gln Asn Glu Val  Val Lys Leu
    1085                1090                1095

Tyr Asn Tyr Tyr Phe Asn Ser  Asn Tyr Ile Arg Asp  Ile Trp Gly
    1100                1105                1110

Asn Pro Leu Gln Tyr Asn Lys  Lys Tyr Tyr Leu Gln  Thr Gln Asp
    1115                1120                1125

Lys Pro Gly Lys Gly Leu Ile  Arg Glu Tyr Trp Ser  Ser Phe Gly
    1130                1135                1140

Tyr Asp Tyr Val Ile Leu Ser  Asp Ser Lys Thr Ile  Thr Phe Pro
    1145                1150                1155

Asn Asn Ile Arg Tyr Gly Ala  Leu Tyr Asn Gly Ser  Lys Val Leu
    1160                1165                1170

Ile Lys Asn Ser Lys Lys Leu  Asp Gly Leu Val Arg  Asn Lys Asp
    1175                1180                1185

Phe Ile Gln Leu Glu Ile Asp  Gly Tyr Asn Met Gly  Ile Ser Ala
    1190                1195                1200

Asp Arg Phe Asn Glu Asp Thr  Asn Tyr Ile Gly Thr  Thr Tyr Gly
    1205                1210                1215

Thr Thr His Asp Leu Thr Thr  Asp Phe Glu Ile Ile  Gln Arg Gln
    1220                1225                1230

Glu Lys Tyr Arg Asn Tyr Cys  Gln Leu Lys Thr Pro  Tyr Asn Ile
    1235                1240                1245

Phe His Lys Ser Gly Leu Met  Ser Thr Glu Thr Ser  Lys Pro Thr
    1250                1255                1260

Phe His Asp Tyr Arg Asp Trp  Val Tyr Ser Ser Ala  Trp Tyr Phe
    1265                1270                1275

Gln Asn Tyr Glu Asn Leu Asn  Leu Arg Lys His Thr  Lys Thr Asn
    1280                1285                1290

Trp Tyr Phe Ile Pro Lys Asp  Glu Gly Trp Asp Glu  Asp Leu Glu
    1295                1300                1305

Val Leu Phe Gln Gly Pro His  His His His His His  His His His
    1310                1315                1320

His
```

```
<210> SEQ ID NO 35
<211> LENGTH: 1296
<212> TYPE: PRT
<213> ORGANISM: Clostridium botulinum

<400> SEQUENCE: 35
```

-continued

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20              25                  30

Val Lys Ala Phe Lys Ile His Asn Lys Ile Trp Val Ile Pro Glu Arg
        35              40                  45

Asp Thr Phe Thr Asn Pro Glu Glu Gly Asp Leu Asn Pro Pro Pro Glu
    50              55                  60

Ala Lys Gln Val Pro Val Ser Tyr Tyr Asp Ser Thr Tyr Leu Ser Thr
65              70                  75                  80

Asp Asn Glu Lys Asp Asn Tyr Leu Lys Gly Val Thr Lys Leu Phe Glu
            85                  90                  95

Arg Ile Tyr Ser Thr Asp Leu Gly Arg Met Leu Leu Thr Ser Ile Val
            100             105                 110

Arg Gly Ile Pro Phe Trp Gly Gly Ser Thr Ile Asp Thr Glu Leu Lys
        115             120                 125

Val Ile Asp Thr Asn Cys Ile Asn Val Ile Gln Pro Asp Gly Ser Tyr
    130             135                 140

Arg Ser Glu Glu Leu Asn Leu Val Ile Ile Gly Pro Ser Ala Asp Ile
145             150                 155                 160

Ile Gln Phe Glu Cys Lys Ser Phe Gly His Glu Val Leu Asn Leu Thr
            165             170                 175

Arg Asn Gly Tyr Gly Ser Thr Gln Tyr Ile Arg Phe Ser Pro Asp Phe
            180             185                 190

Thr Phe Gly Phe Glu Glu Ser Leu Glu Val Asp Thr Asn Pro Leu Leu
            195             200                 205

Gly Ala Gly Lys Phe Ala Thr Asp Pro Ala Val Thr Leu Ala His Glu
    210             215                 220

Leu Ile His Ala Gly His Arg Leu Tyr Gly Ile Ala Ile Asn Pro Asn
225             230                 235                 240

Arg Val Phe Lys Val Asn Thr Asn Ala Tyr Tyr Glu Met Ser Gly Leu
            245             250                 255

Glu Val Ser Phe Glu Glu Leu Arg Thr Phe Gly Gly His Asp Ala Lys
            260             265                 270

Phe Ile Asp Ser Leu Gln Glu Asn Glu Phe Arg Leu Tyr Tyr Tyr Asn
    275             280                 285

Lys Phe Lys Asp Ile Ala Ser Thr Leu Asn Lys Ala Lys Ser Ile Val
    290             295                 300

Gly Thr Thr Ala Ser Leu Gln Tyr Met Lys Asn Val Phe Lys Glu Lys
305             310                 315                 320

Tyr Leu Leu Ser Glu Asp Thr Ser Gly Lys Phe Ser Val Asp Lys Leu
            325             330                 335

Lys Phe Asp Lys Leu Tyr Lys Met Leu Thr Glu Ile Tyr Thr Glu Asp
            340             345                 350

Asn Phe Val Lys Phe Phe Lys Val Leu Asn Arg Lys Thr Tyr Leu Asn
            355             360                 365

Phe Asp Lys Ala Val Phe Lys Ile Asn Ile Val Pro Lys Val Asn Tyr
    370             375                 380

Thr Ile Tyr Asp Gly Phe Asn Leu Arg Asn Thr Asn Leu Ala Ala Asn
385             390                 395                 400

Phe Asn Gly Gln Asn Thr Glu Ile Asn Asn Met Asn Phe Thr Lys Leu
            405             410                 415

Lys Asn Phe Thr Gly Leu Phe Glu Phe Tyr Lys Leu Leu Cys Val Arg
```

```
             420              425              430
Gly Ile Ile Thr Ser Lys Thr Lys Ser Leu Asp Lys Gly Tyr Asn Lys
        435              440              445

Ala Leu Asn Asp Leu Cys Ile Lys Val Asn Asn Trp Asp Leu Phe Phe
    450              455              460

Ser Pro Ser Glu Asp Asn Phe Thr Asn Asp Leu Asn Lys Gly Glu Glu
465              470              475              480

Ile Thr Ser Asp Thr Asn Ile Glu Ala Ala Glu Glu Asn Ile Ser Leu
                485              490              495

Asp Leu Ile Gln Gln Tyr Tyr Leu Thr Phe Asn Phe Asp Asn Glu Pro
            500              505              510

Glu Asn Ile Ser Ile Glu Asn Leu Ser Ser Asp Ile Ile Gly Gln Leu
        515              520              525

Glu Leu Met Pro Asn Ile Glu Arg Phe Pro Asn Gly Lys Lys Tyr Glu
        530              535              540

Leu Asp Lys Tyr Thr Met Phe His Tyr Leu Arg Ala Gln Glu Phe Glu
545              550              555              560

His Gly Lys Ser Arg Ile Ala Leu Thr Asn Ser Val Asn Glu Ala Leu
                565              570              575

Leu Asn Pro Ser Arg Val Tyr Thr Phe Phe Ser Ser Asp Tyr Val Lys
            580              585              590

Lys Val Asn Lys Ala Thr Glu Ala Ala Met Phe Leu Gly Trp Val Glu
            595              600              605

Gln Leu Val Tyr Asp Phe Thr Asp Glu Thr Ser Glu Val Ser Thr Thr
    610              615              620

Asp Lys Ile Ala Asp Ile Thr Ile Ile Ile Pro Tyr Ile Gly Pro Ala
625              630              635              640

Leu Asn Ile Gly Asn Met Leu Tyr Lys Asp Asp Phe Val Gly Ala Leu
            645              650              655

Ile Phe Ser Gly Ala Val Ile Leu Leu Glu Phe Ile Pro Glu Ile Ala
            660              665              670

Ile Pro Val Leu Gly Thr Phe Ala Leu Val Ser Tyr Ile Ala Asn Lys
        675              680              685

Val Leu Thr Val Gln Thr Ile Asp Asn Ala Leu Ser Lys Arg Asn Glu
    690              695              700

Lys Trp Asp Glu Val Tyr Lys Tyr Ile Val Thr Asn Trp Leu Ala Lys
705              710              715              720

Val Asn Thr Gln Ile Asp Leu Ile Arg Lys Lys Met Lys Glu Ala Leu
            725              730              735

Glu Asn Gln Ala Glu Ala Thr Lys Ala Ile Ile Asn Tyr Gln Tyr Asn
            740              745              750

Gln Tyr Thr Glu Glu Glu Lys Asn Asn Ile Asn Phe Asn Ile Asp Asp
        755              760              765

Leu Ser Ser Lys Leu Asn Glu Ser Ile Asn Lys Ala Met Ile Asn Ile
    770              775              780

Asn Lys Phe Leu Asn Gln Cys Ser Val Ser Tyr Leu Met Asn Ser Met
785              790              795              800

Ile Pro Tyr Gly Val Lys Arg Leu Glu Asp Phe Asp Ala Ser Leu Lys
            805              810              815

Asp Ala Leu Leu Lys Tyr Ile Tyr Asp Asn Arg Gly Thr Leu Ile Gly
            820              825              830

Gln Val Asp Arg Leu Lys Asp Lys Val Asn Asn Thr Leu Ser Thr Asp
            835              840              845
```

-continued

Ile Pro Phe Gln Leu Ser Lys Tyr Val Asp Asn Gln Arg Leu Leu Ser
850                855                860

Thr Phe Thr Glu Tyr Ile Lys Asn Ile Ile Asn Thr Ser Ile Leu Asn
865                870                875                880

Leu Arg Tyr Glu Ser Asn His Leu Ile Asp Leu Ser Arg Tyr Ala Ser
                885                890                895

Lys Ile Asn Ile Gly Ser Lys Val Asn Phe Asp Pro Ile Asp Lys Asn
                900                905                910

Gln Ile Gln Leu Phe Asn Leu Glu Ser Ser Lys Ile Glu Val Ile Leu
                915                920                925

Lys Asn Ala Ile Val Tyr Asn Ser Met Tyr Glu Asn Phe Ser Thr Ser
930                935                940

Phe Trp Ile Arg Ile Pro Lys Tyr Phe Asn Ser Ile Ser Leu Asn Asn
945                950                955                960

Glu Tyr Thr Ile Ile Asn Cys Met Glu Asn Asn Ser Gly Trp Lys Val
                965                970                975

Ser Leu Asn Tyr Gly Glu Ile Ile Trp Thr Leu Gln Asp Thr Gln Glu
                980                985                990

Ile Lys Gln Arg Val Val Phe Lys  Tyr Ser Gln Met Ile  Asn Ile Ser
                995                1000                1005

Asp Tyr  Ile Asn Arg Trp Ile  Phe Val Thr Ile Thr  Asn Asn Arg
        1010                1015                1020

Leu Asn  Asn Ser Lys Ile Tyr  Ile Asn Gly Arg Leu  Ile Asp Gln
        1025                1030                1035

Lys Pro  Ile Ser Asn Leu Gly  Asn Ile His Ala Ser  Asn Asn Ile
        1040                1045                1050

Met Phe  Lys Leu Asp Gly Cys  Arg Asp Thr His Arg  Tyr Ile Trp
        1055                1060                1065

Ile Lys  Tyr Phe Asn Leu Phe  Asp Lys Glu Leu Asn  Glu Lys Glu
        1070                1075                1080

Ile Lys  Asp Leu Tyr Asp Asn  Gln Ser Asn Ser Gly  Ile Leu Lys
        1085                1090                1095

Asp Phe  Trp Gly Asp Tyr Leu  Gln Tyr Asp Lys Pro  Tyr Tyr Met
        1100                1105                1110

Leu Asn  Leu Tyr Asp Pro Asn  Lys Tyr Val Asp Val  Asn Asn Val
        1115                1120                1125

Gly Ile  Arg Gly Tyr Met Tyr  Leu Lys Gly Pro Arg  Gly Ser Val
        1130                1135                1140

Met Thr  Thr Asn Ile Tyr Leu  Asn Ser Ser Leu Tyr  Arg Gly Thr
        1145                1150                1155

Lys Phe  Ile Ile Lys Lys Tyr  Ala Ser Gly Asn Lys  Asp Asn Ile
        1160                1165                1170

Val Arg  Asn Asn Asp Arg Val  Tyr Ile Asn Val Val  Val Lys Asn
        1175                1180                1185

Lys Glu  Tyr Arg Leu Ala Thr  Asn Ala Ser Gln Ala  Gly Val Glu
        1190                1195                1200

Lys Ile  Leu Ser Ala Leu Glu  Ile Pro Asp Val Gly  Asn Leu Ser
        1205                1210                1215

Gln Val  Val Val Met Lys Ser  Lys Asn Asp Gln Gly  Ile Thr Asn
        1220                1225                1230

Lys Cys  Lys Met Asn Leu Gln  Asp Asn Asn Gly Asn  Asp Ile Gly
        1235                1240                1245

-continued

```
Phe Ile  Gly Phe His Gln Phe  Asn Asn Ile Ala Lys  Leu Val Ala
    1250              1255              1260

Ser Asn  Trp Tyr Asn Arg Gln  Ile Glu Arg Ser Ser  Arg Thr Leu
    1265              1270              1275

Gly Cys  Ser Trp Glu Phe Ile  Pro Val Asp Asp Gly  Trp Gly Glu
    1280              1285              1290

Arg Pro  Leu
    1295

<210> SEQ ID NO 36
<211> LENGTH: 1291
<212> TYPE: PRT
<213> ORGANISM: Clostridium botulinum

<400> SEQUENCE: 36

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320
```

-continued

```
Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
                420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
                500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735
```

-continued

```
Arg Tyr Asn Ile Tyr Ser Glu Lys Glu Lys Ser Asn Ile Asn Ile Asp
            740             745             750

Phe Asn Asp Ile Asn Ser Lys Leu Asn Glu Gly Ile Asn Gln Ala Ile
            755             760             765

Asp Asn Ile Asn Asn Phe Ile Asn Gly Cys Ser Val Ser Tyr Leu Met
    770             775             780

Lys Lys Met Ile Pro Leu Ala Val Glu Lys Leu Leu Asp Phe Asp Asn
785             790             795             800

Thr Leu Lys Lys Asn Leu Leu Asn Tyr Ile Asp Glu Asn Lys Leu Tyr
            805             810             815

Leu Ile Gly Ser Ala Glu Tyr Glu Lys Ser Lys Val Asn Lys Tyr Leu
            820             825             830

Lys Thr Ile Met Pro Phe Asp Leu Ser Ile Tyr Thr Asn Asp Thr Ile
            835             840             845

Leu Ile Glu Met Phe Asn Lys Tyr Asn Ser Glu Ile Leu Asn Asn Ile
    850             855             860

Ile Leu Asn Leu Arg Tyr Lys Asp Asn Asn Leu Ile Asp Leu Ser Gly
865             870             875             880

Tyr Gly Ala Lys Val Glu Val Tyr Asp Gly Val Glu Leu Asn Asp Lys
            885             890             895

Asn Gln Phe Lys Leu Thr Ser Ser Ala Asn Ser Lys Ile Arg Val Thr
            900             905             910

Gln Asn Gln Asn Ile Ile Phe Asn Ser Val Phe Leu Asp Phe Ser Val
            915             920             925

Ser Phe Trp Ile Arg Ile Pro Lys Tyr Lys Asn Asp Gly Ile Gln Asn
    930             935             940

Tyr Ile His Asn Glu Tyr Thr Ile Ile Asn Cys Met Lys Asn Asn Ser
945             950             955             960

Gly Trp Lys Ile Ser Ile Arg Gly Asn Arg Ile Ile Trp Thr Leu Ile
            965             970             975

Asp Ile Asn Gly Lys Thr Lys Ser Val Phe Phe Glu Tyr Asn Ile Arg
            980             985             990

Glu Asp Ile Ser Glu Tyr Ile Asn  Arg Trp Phe Phe Val  Thr Ile Thr
            995             1000            1005

Asn Asn  Leu Asn Asn Ala Lys  Ile Tyr Ile Asn Gly  Lys Leu Glu
    1010            1015            1020

Ser Asn  Thr Asp Ile Lys Asp  Ile Arg Glu Val Ile  Ala Asn Gly
    1025            1030            1035

Glu Ile  Ile Phe Lys Leu Asp  Gly Asp Ile Asp Arg  Thr Gln Phe
    1040            1045            1050

Ile Trp  Met Lys Tyr Phe Ser  Ile Phe Asn Thr Glu  Leu Ser Gln
    1055            1060            1065

Ser Asn  Ile Glu Glu Arg Tyr  Lys Ile Gln Ser Tyr  Ser Glu Tyr
    1070            1075            1080

Leu Lys  Asp Phe Trp Gly Asn  Pro Leu Met Tyr Asn  Lys Glu Tyr
    1085            1090            1095

Tyr Met  Phe Asn Ala Gly Asn  Lys Asn Ser Tyr Ile  Lys Leu Lys
    1100            1105            1110

Lys Asp  Ser Pro Val Gly Glu  Ile Leu Thr Arg Ser  Lys Tyr Asn
    1115            1120            1125

Gln Asn  Ser Lys Tyr Ile Asn  Tyr Arg Asp Leu Tyr  Ile Gly Glu
    1130            1135            1140

Lys Phe  Ile Ile Arg Arg Lys  Ser Asn Ser Gln Ser  Ile Asn Asp
```

-continued

```
                1145                1150                1155

Asp Ile  Val Arg Lys Glu Asp  Tyr Ile Tyr Leu Asp  Phe Phe Asn
     1160                1165                1170

Leu Asn  Gln Glu Trp Arg Val  Tyr Thr Tyr Lys Tyr  Phe Lys Lys
     1175                1180                1185

Glu Glu  Glu Lys Leu Phe Leu  Ala Pro Ile Ser Asp  Ser Asp Glu
     1190                1195                1200

Phe Tyr  Asn Thr Ile Gln Ile  Lys Glu Tyr Asp Glu  Gln Pro Thr
     1205                1210                1215

Tyr Ser  Cys Gln Leu Leu Phe  Lys Lys Asp Glu Glu  Ser Thr Asp
     1220                1225                1230

Glu Ile  Gly Leu Ile Gly Ile  His Arg Phe Tyr Glu  Ser Gly Ile
     1235                1240                1245

Val Phe  Glu Glu Tyr Lys Asp  Tyr Phe Cys Ile Ser  Lys Trp Tyr
     1250                1255                1260

Leu Lys  Glu Val Lys Arg Lys  Pro Tyr Asn Leu Lys  Leu Gly Cys
     1265                1270                1275

Asn Trp  Gln Phe Ile Pro Lys  Asp Glu Gly Trp Thr  Glu
     1280                1285                1290

<210> SEQ ID NO 37
<211> LENGTH: 1291
<212> TYPE: PRT
<213> ORGANISM: Clostridium botulinum

<400> SEQUENCE: 37

Met Pro Ile Thr Ile Asn Asn Phe Asn Tyr Ser Asp Pro Val Asp Asn
1                5                  10                  15

Lys Asn Ile Leu Tyr Leu Asp Thr His Leu Asn Thr Leu Ala Asn Glu
                20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
        50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220
```

```
Leu Ile Leu Met His Glu Leu Asn His Ala Met His Asn Leu Tyr Gly
225             230              235              240

Ile Ala Ile Pro Asn Asp Gln Thr Ile Ser Ser Val Thr Ser Asn Ile
            245              250              255

Phe Tyr Ser Gln Tyr Asn Val Lys Leu Glu Tyr Ala Glu Ile Tyr Ala
            260              265              270

Phe Gly Gly Pro Thr Ile Asp Leu Ile Pro Lys Ser Ala Arg Lys Tyr
        275              280              285

Phe Glu Glu Lys Ala Leu Asp Tyr Tyr Arg Ser Ile Ala Lys Arg Leu
    290              295              300

Asn Ser Ile Thr Thr Ala Asn Pro Ser Ser Phe Asn Lys Tyr Ile Gly
305             310              315              320

Glu Tyr Lys Gln Lys Leu Ile Arg Lys Tyr Arg Phe Val Val Glu Ser
            325              330              335

Ser Gly Glu Val Thr Val Asn Arg Asn Lys Phe Val Glu Leu Tyr Asn
            340              345              350

Glu Leu Thr Gln Ile Phe Thr Glu Phe Asn Tyr Ala Lys Ile Tyr Asn
        355              360              365

Val Gln Asn Arg Lys Ile Tyr Leu Ser Asn Val Tyr Thr Pro Val Thr
    370              375              380

Ala Asn Ile Leu Asp Asp Asn Val Tyr Asp Ile Gln Asn Gly Phe Asn
385             390              395              400

Ile Pro Lys Ser Asn Leu Asn Val Leu Phe Met Gly Gln Asn Leu Ser
            405              410              415

Arg Asn Pro Ala Leu Arg Lys Val Asn Pro Glu Asn Met Leu Tyr Leu
            420              425              430

Phe Thr Lys Phe Cys His Lys Ala Ile Asp Gly Arg Ser Leu Tyr Asn
        435              440              445

Lys Thr Leu Asp Cys Arg Glu Leu Leu Val Lys Asn Thr Asp Leu Pro
    450              455              460

Phe Ile Gly Asp Ile Ser Asp Val Lys Thr Asp Ile Phe Leu Arg Lys
465             470              475              480

Asp Ile Asn Glu Glu Thr Glu Val Ile Tyr Tyr Pro Asp Asn Val Ser
            485              490              495

Val Asp Gln Val Ile Leu Ser Lys Asn Thr Ser Glu His Gly Gln Leu
            500              505              510

Asp Leu Leu Tyr Pro Ser Ile Asp Ser Glu Ser Glu Ile Leu Pro Gly
        515              520              525

Glu Asn Gln Val Phe Tyr Asp Asn Arg Thr Gln Asn Val Asp Tyr Leu
    530              535              540

Asn Ser Tyr Tyr Tyr Leu Glu Ser Gln Lys Leu Ser Asp Asn Val Glu
545             550              555              560

Asp Phe Thr Phe Thr Arg Ser Ile Glu Glu Ala Leu Asp Asn Ser Ala
            565              570              575

Lys Val Tyr Thr Tyr Phe Pro Thr Leu Ala Asn Lys Val Asn Ala Gly
            580              585              590

Val Gln Gly Gly Leu Phe Leu Met Trp Ala Asn Asp Val Val Glu Asp
        595              600              605

Phe Thr Thr Asn Ile Leu Arg Lys Asp Thr Leu Asp Lys Ile Ser Asp
    610              615              620

Val Ser Ala Ile Ile Pro Tyr Ile Gly Pro Ala Leu Asn Ile Ser Asn
625             630              635              640

Ser Val Arg Arg Gly Asn Phe Thr Glu Ala Phe Ala Val Thr Gly Val
```

-continued

```
                645                 650                 655

Thr Ile Leu Leu Glu Ala Phe Pro Glu Phe Thr Ile Pro Ala Leu Gly
             660                 665                 670

Ala Phe Val Ile Tyr Ser Lys Val Gln Glu Arg Asn Glu Ile Ile Lys
             675                 680                 685

Thr Ile Asp Asn Cys Leu Glu Gln Arg Ile Lys Arg Trp Lys Asp Ser
         690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                 725                 730                 735

Ala Ile Lys Ala Lys Ile Asp Leu Glu Tyr Lys Lys Tyr Ser Gly Ser
             740                 745                 750

Asp Lys Glu Asn Ile Lys Ser Gln Val Glu Asn Leu Lys Asn Ser Leu
             755                 760                 765

Asp Val Lys Ile Ser Glu Ala Met Asn Asn Ile Asn Lys Phe Ile Arg
         770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                 805                 810                 815

Leu Ile Asp Ser His Asn Ile Ile Leu Val Gly Glu Val Asp Lys Leu
             820                 825                 830

Lys Ala Lys Val Asn Asn Ser Phe Gln Asn Thr Ile Pro Phe Asn Ile
             835                 840                 845

Phe Ser Tyr Thr Asn Asn Ser Leu Leu Lys Asp Ile Ile Asn Glu Tyr
     850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                 885                 890                 895

Gly Asp Val Gln Leu Asn Pro Ile Phe Pro Phe Asp Phe Lys Leu Gly
                 900                 905                 910

Ser Ser Gly Glu Asp Arg Gly Lys Val Ile Val Thr Gln Asn Glu Asn
             915                 920                 925

Ile Val Tyr Asn Ser Met Tyr Glu Ser Phe Ser Ile Ser Phe Trp Ile
     930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                 965                 970                 975

Leu Val Phe Thr Leu Lys Gln Asn Glu Asp Ser Glu Gln Ser Ile Asn
             980                 985                 990

Phe Ser Tyr Asp Ile Ser Asn Asn  Ala Pro Gly Tyr Asn  Lys Trp Phe
         995                 1000                 1005

Phe Val  Thr Val Thr Asn Asn  Met Met Gly Asn Met  Lys Ile Tyr
     1010                 1015                 1020

Ile Asn  Gly Lys Leu Ile Asp  Thr Ile Lys Val Lys  Glu Leu Thr
     1025                 1030                 1035

Gly Ile  Asn Phe Ser Lys Thr  Ile Thr Phe Glu Ile  Asn Lys Ile
     1040                 1045                 1050

Pro Asp  Thr Gly Leu Ile Thr  Ser Asp Ser Asp Asn  Ile Asn Met
     1055                 1060                 1065
```

Trp Ile Arg Asp Phe Tyr Ile  Phe Ala Lys Glu Leu  Asp Gly Lys
    1070            1075              1080

Asp Ile Asn Ile Leu Phe Asn  Ser Leu Gln Tyr Thr  Asn Val Val
    1085            1090              1095

Lys Asp Tyr Trp Gly Asn Asp  Leu Arg Tyr Asn Lys  Glu Tyr Tyr
    1100            1105              1110

Met Val Asn Ile Asp Tyr Leu  Asn Arg Tyr Met Tyr  Ala Asn Ser
    1115            1120              1125

Arg Gln Ile Val Phe Asn Thr  Arg Arg Asn Asn Asn  Asp Phe Asn
    1130            1135              1140

Glu Gly Tyr Lys Ile Ile Ile  Lys Arg Ile Arg Gly  Asn Thr Asn
    1145            1150              1155

Asp Thr Arg Val Arg Gly Gly  Asp Ile Leu Tyr Phe  Asp Met Thr
    1160            1165              1170

Ile Asn Asn Lys Ala Tyr Asn  Leu Phe Met Lys Asn  Glu Thr Met
    1175            1180              1185

Tyr Ala Asp Asn His Ser Thr  Glu Asp Ile Tyr Ala  Ile Gly Leu
    1190            1195              1200

Arg Glu Gln Thr Lys Asp Ile  Asn Asp Asn Ile Ile  Phe Gln Ile
    1205            1210              1215

Gln Pro Met Asn Asn Thr Tyr  Tyr Tyr Ala Ser Gln  Ile Phe Lys
    1220            1225              1230

Ser Asn Phe Asn Gly Glu Asn  Ile Ser Gly Ile Cys  Ser Ile Gly
    1235            1240              1245

Thr Tyr Arg Phe Arg Leu Gly  Gly Asp Trp Tyr Arg  His Asn Tyr
    1250            1255              1260

Leu Val Pro Thr Val Lys Gln  Gly Asn Tyr Ala Ser  Leu Leu Glu
    1265            1270              1275

Ser Thr Ser Thr His Trp Gly  Phe Val Pro Val Ser  Glu
    1280            1285              1290

<210> SEQ ID NO 38
<211> LENGTH: 1276
<212> TYPE: PRT
<213> ORGANISM: Clostridium botulinum

<400> SEQUENCE: 38

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly

```
        130              135              140

Ser Trp Lys Val Thr Asn Ile Ile Thr Pro Ser Val Leu Ile Phe Gly
145              150              155              160

Pro Leu Pro Asn Ile Leu Asp Tyr Thr Ala Ser Leu Thr Leu Gln Gly
                165              170              175

Gln Gln Ser Asn Pro Ser Phe Glu Gly Phe Gly Thr Leu Ser Ile Leu
                180              185              190

Lys Val Ala Pro Glu Phe Leu Leu Thr Phe Ser Asp Val Thr Ser Asn
        195              200              205

Gln Ser Ser Ala Val Leu Gly Lys Ser Ile Phe Cys Met Asp Pro Val
        210              215              220

Ile Ala Leu Met His Glu Leu Thr His Ser Leu His Gln Leu Tyr Gly
225              230              235              240

Ile Asn Ile Pro Ser Asp Lys Arg Ile Arg Pro Gln Val Ser Glu Gly
                245              250              255

Phe Phe Ser Gln Asp Gly Pro Asn Val Gln Phe Glu Glu Leu Tyr Thr
                260              265              270

Phe Gly Gly Leu Asp Val Glu Ile Ile Pro Gln Ile Glu Arg Ser Gln
                275              280              285

Leu Arg Glu Lys Ala Leu Gly His Tyr Lys Asp Ile Ala Lys Arg Leu
        290              295              300

Asn Asn Ile Asn Lys Thr Ile Pro Ser Ser Trp Ile Ser Asn Ile Asp
305              310              315              320

Lys Tyr Lys Lys Ile Phe Ser Glu Lys Tyr Asn Phe Asp Lys Asp Asn
                325              330              335

Thr Gly Asn Phe Val Val Asn Ile Asp Lys Phe Asn Ser Leu Tyr Ser
                340              345              350

Asp Leu Thr Asn Val Met Ser Glu Val Val Tyr Ser Ser Gln Tyr Asn
                355              360              365

Val Lys Asn Arg Thr His Tyr Phe Ser Arg His Tyr Leu Pro Val Phe
        370              375              380

Ala Asn Ile Leu Asp Asp Asn Ile Tyr Thr Ile Arg Asp Gly Phe Asn
385              390              395              400

Leu Thr Asn Lys Gly Phe Asn Ile Glu Asn Ser Gly Gln Asn Ile Glu
                405              410              415

Arg Asn Pro Ala Leu Gln Lys Leu Ser Ser Glu Ser Val Val Asp Leu
                420              425              430

Phe Thr Lys Val Cys Leu Arg Leu Thr Lys Asn Ser Arg Asp Asp Ser
        435              440              445

Thr Cys Ile Lys Val Lys Asn Asn Arg Leu Pro Tyr Val Ala Asp Lys
        450              455              460

Asp Ser Ile Ser Gln Glu Ile Phe Glu Asn Lys Ile Ile Thr Asp Glu
465              470              475              480

Thr Asn Val Gln Asn Tyr Ser Asp Lys Phe Ser Leu Asp Glu Ser Ile
                485              490              495

Leu Asp Gly Gln Val Pro Ile Asn Pro Glu Ile Val Asp Pro Leu Leu
                500              505              510

Pro Asn Val Asn Met Glu Pro Leu Asn Leu Pro Gly Glu Glu Ile Val
                515              520              525

Phe Tyr Asp Asp Ile Thr Lys Tyr Val Asp Tyr Leu Asn Ser Tyr Tyr
        530              535              540

Tyr Leu Glu Ser Gln Lys Leu Ser Asn Asn Val Glu Asn Ile Thr Leu
545              550              555              560
```

-continued

```
Thr Thr Ser Val Glu Glu Ala Leu Gly Tyr Ser Asn Lys Ile Tyr Thr
            565             570             575

Phe Leu Pro Ser Leu Ala Glu Lys Val Asn Lys Gly Val Gln Ala Gly
            580             585             590

Leu Phe Leu Asn Trp Ala Asn Glu Val Val Glu Asp Phe Thr Thr Asn
            595             600             605

Ile Met Lys Lys Asp Thr Leu Asp Lys Ile Ser Asp Val Ser Val Ile
            610             615             620

Ile Pro Tyr Ile Gly Pro Ala Leu Asn Ile Gly Asn Ser Ala Leu Arg
625             630             635             640

Gly Asn Phe Asn Gln Ala Phe Ala Thr Ala Gly Val Ala Phe Leu Leu
            645             650             655

Glu Gly Phe Pro Glu Phe Thr Ile Pro Ala Leu Gly Val Phe Thr Phe
            660             665             670

Tyr Ser Ser Ile Gln Glu Arg Glu Lys Ile Ile Lys Thr Ile Glu Asn
            675             680             685

Cys Leu Glu Gln Arg Val Lys Arg Trp Lys Asp Ser Tyr Gln Trp Met
            690             695             700

Val Ser Asn Trp Leu Ser Arg Ile Thr Thr Gln Phe Asn His Ile Asn
705             710             715             720

Tyr Gln Met Tyr Asp Ser Leu Ser Tyr Gln Ala Asp Ala Ile Lys Ala
            725             730             735

Lys Ile Asp Leu Glu Tyr Lys Lys Tyr Ser Gly Ser Asp Lys Glu Asn
            740             745             750

Ile Lys Ser Gln Val Glu Asn Leu Lys Asn Ser Leu Asp Val Lys Ile
            755             760             765

Ser Glu Ala Met Asn Asn Ile Asn Lys Phe Ile Arg Glu Cys Ser Val
            770             775             780

Thr Tyr Leu Phe Lys Asn Met Leu Pro Lys Val Ile Asp Glu Leu Asn
785             790             795             800

Lys Phe Asp Leu Arg Thr Lys Thr Glu Leu Ile Asn Leu Ile Asp Ser
            805             810             815

His Asn Ile Ile Leu Val Gly Glu Val Asp Arg Leu Lys Ala Lys Val
            820             825             830

Asn Glu Ser Phe Glu Asn Thr Met Pro Phe Asn Ile Phe Ser Tyr Thr
            835             840             845

Asn Asn Ser Leu Leu Lys Asp Ile Ile Asn Glu Tyr Phe Asn Ser Ile
            850             855             860

Asn Asp Ser Lys Ile Leu Ser Leu Gln Asn Lys Lys Asn Ala Leu Val
865             870             875             880

Asp Thr Ser Gly Tyr Asn Ala Glu Val Arg Val Gly Asp Asn Val Gln
            885             890             895

Leu Asn Thr Ile Tyr Thr Asn Asp Phe Lys Leu Ser Ser Ser Gly Asp
            900             905             910

Lys Ile Ile Val Asn Leu Asn Asn Asn Ile Leu Tyr Ser Ala Ile Tyr
            915             920             925

Glu Asn Ser Ser Val Ser Phe Trp Ile Lys Ile Ser Lys Asp Leu Thr
            930             935             940

Asn Ser His Asn Glu Tyr Thr Ile Ile Asn Ser Ile Glu Gln Asn Ser
945             950             955             960

Gly Trp Lys Leu Cys Ile Arg Asn Gly Asn Ile Glu Trp Ile Leu Gln
            965             970             975
```

-continued

```
Asp Val Asn Arg Lys Tyr Lys Ser Leu Ile Phe Asp Tyr Ser Glu Ser
            980                 985                 990

Leu Ser His Thr Gly Tyr Thr Asn  Lys Trp Phe Phe Val  Thr Ile Thr
        995                 1000                1005

Asn Asn  Ile Met Gly Tyr Met  Lys Leu Tyr Ile Asn  Gly Glu Leu
    1010                1015                1020

Lys Gln  Ser Gln Lys Ile Glu  Asp Leu Asp Glu Val  Lys Leu Asp
    1025                1030                1035

Lys Thr  Ile Val Phe Gly Ile  Asp Glu Asn Ile Asp  Glu Asn Gln
    1040                1045                1050

Met Leu  Trp Ile Arg Asp Phe  Asn Ile Phe Ser Lys  Glu Leu Ser
    1055                1060                1065

Asn Glu  Asp Ile Asn Ile Val  Tyr Glu Gly Gln Ile  Leu Arg Asn
    1070                1075                1080

Val Ile  Lys Asp Tyr Trp Gly  Asn Pro Leu Lys Phe  Asp Thr Glu
    1085                1090                1095

Tyr Tyr  Ile Ile Asn Asp Asn  Tyr Ile Asp Arg Tyr  Ile Ala Pro
    1100                1105                1110

Glu Ser  Asn Val Leu Val Leu  Val Gln Tyr Pro Asp  Arg Ser Lys
    1115                1120                1125

Leu Tyr  Thr Gly Asn Pro Ile  Thr Ile Lys Ser Val  Ser Asp Lys
    1130                1135                1140

Asn Pro  Tyr Ser Arg Ile Leu  Asn Gly Asp Asn Ile  Ile Leu His
    1145                1150                1155

Met Leu  Tyr Asn Ser Arg Lys  Tyr Met Ile Ile Arg  Asp Thr Asp
    1160                1165                1170

Thr Ile  Tyr Ala Thr Gln Gly  Gly Glu Cys Ser Gln  Asn Cys Val
    1175                1180                1185

Tyr Ala  Leu Lys Leu Gln Ser  Asn Leu Gly Asn Tyr  Gly Ile Gly
    1190                1195                1200

Ile Phe  Ser Ile Lys Asn Ile  Val Ser Lys Asn Lys  Tyr Cys Ser
    1205                1210                1215

Gln Ile  Phe Ser Ser Phe Arg  Glu Asn Thr Met Leu  Leu Ala Asp
    1220                1225                1230

Ile Tyr  Lys Pro Trp Arg Phe  Ser Phe Lys Asn Ala  Tyr Thr Pro
    1235                1240                1245

Val Ala  Val Thr Asn Tyr Glu  Thr Lys Leu Leu Ser  Thr Ser Ser
    1250                1255                1260

Phe Trp  Lys Phe Ile Ser Arg  Asp Pro Gly Trp Val  Glu
    1265                1270                1275
```

```
<210> SEQ ID NO 39
<211> LENGTH: 1251
<212> TYPE: PRT
<213> ORGANISM: Clostridium botulinum

<400> SEQUENCE: 39

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60
```

-continued

```
Asp Ser Ser Tyr Tyr Asp Pro Asn Tyr Leu Gln Ser Asp Glu Glu Lys
65              70              75              80

Asp Arg Phe Leu Lys Ile Val Thr Lys Ile Phe Asn Arg Ile Asn Asn
            85              90              95

Asn Leu Ser Gly Gly Ile Leu Leu Glu Glu Leu Ser Lys Ala Asn Pro
            100             105             110

Tyr Leu Gly Asn Asp Asn Thr Pro Asp Asn Gln Phe His Ile Gly Asp
            115             120             125

Ala Ser Ala Val Glu Ile Lys Phe Ser Asn Gly Ser Gln Asp Ile Leu
    130             135             140

Leu Pro Asn Val Ile Ile Met Gly Ala Glu Pro Asp Leu Phe Glu Thr
145             150             155             160

Asn Ser Ser Asn Ile Ser Leu Arg Asn Asn Tyr Met Pro Ser Asn His
            165             170             175

Arg Phe Gly Ser Ile Ala Ile Val Thr Phe Ser Pro Glu Tyr Ser Phe
            180             185             190

Arg Phe Asn Asp Asn Cys Met Asn Glu Phe Ile Gln Asp Pro Ala Leu
            195             200             205

Thr Leu Met His Glu Leu Ile His Ser Leu His Gly Leu Tyr Gly Ala
    210             215             220

Lys Gly Ile Thr Thr Lys Tyr Thr Ile Thr Gln Lys Gln Asn Pro Leu
225             230             235             240

Ile Thr Asn Ile Arg Gly Thr Asn Ile Glu Glu Phe Leu Thr Phe Gly
            245             250             255

Gly Thr Asp Leu Asn Ile Ile Thr Ser Ala Gln Ser Asn Asp Ile Tyr
            260             265             270

Thr Asn Leu Leu Ala Asp Tyr Lys Lys Ile Ala Ser Lys Leu Ser Lys
            275             280             285

Val Gln Val Ser Asn Pro Leu Leu Asn Pro Tyr Lys Asp Val Phe Glu
    290             295             300

Ala Lys Tyr Gly Leu Asp Lys Asp Ala Ser Gly Ile Tyr Ser Val Asn
305             310             315             320

Ile Asn Lys Phe Asn Asp Ile Phe Lys Lys Leu Tyr Ser Phe Thr Glu
            325             330             335

Phe Asp Leu Arg Thr Lys Phe Gln Val Lys Cys Arg Gln Thr Tyr Ile
            340             345             350

Gly Gln Tyr Lys Tyr Phe Lys Leu Ser Asn Leu Leu Asn Asp Ser Ile
            355             360             365

Tyr Asn Ile Ser Glu Gly Tyr Asn Ile Asn Asn Leu Lys Val Asn Phe
    370             375             380

Arg Gly Gln Asn Ala Asn Leu Asn Pro Arg Ile Ile Thr Pro Ile Thr
385             390             395             400

Gly Arg Gly Leu Val Lys Lys Ile Ile Arg Phe Cys Lys Asn Ile Val
            405             410             415

Ser Val Lys Gly Ile Arg Lys Ser Ile Cys Ile Glu Ile Asn Asn Gly
            420             425             430

Glu Leu Phe Phe Val Ala Ser Glu Asn Ser Tyr Asn Asp Asp Asn Ile
            435             440             445

Asn Thr Pro Lys Glu Ile Asp Asp Thr Val Thr Ser Asn Asn Asn Tyr
    450             455             460

Glu Asn Asp Leu Asp Gln Val Ile Leu Asn Phe Asn Ser Glu Ser Ala
465             470             475             480
```

-continued

```
Pro Gly Leu Ser Asp Glu Lys Leu Asn Leu Thr Ile Gln Asn Asp Ala
                485             490             495

Tyr Ile Pro Lys Tyr Asp Ser Asn Gly Thr Ser Asp Ile Glu Gln His
            500             505             510

Asp Val Asn Glu Leu Asn Val Phe Phe Tyr Leu Asp Ala Gln Lys Val
            515             520             525

Pro Glu Gly Glu Asn Asn Val Asn Leu Thr Ser Ser Ile Asp Thr Ala
        530             535             540

Leu Leu Glu Gln Pro Lys Ile Tyr Thr Phe Phe Ser Ser Glu Phe Ile
545             550             555             560

Asn Asn Val Asn Lys Pro Val Gln Ala Ala Leu Phe Val Ser Trp Ile
            565             570             575

Gln Gln Val Leu Val Asp Phe Thr Thr Glu Ala Asn Gln Lys Ser Thr
            580             585             590

Val Asp Lys Ile Ala Asp Ile Ser Ile Val Val Pro Tyr Ile Gly Leu
            595             600             605

Ala Leu Asn Ile Gly Asn Glu Ala Gln Lys Gly Asn Phe Lys Asp Ala
        610             615             620

Leu Glu Leu Leu Gly Ala Gly Ile Leu Leu Glu Phe Glu Pro Glu Leu
625             630             635             640

Leu Ile Pro Thr Ile Leu Val Phe Thr Ile Lys Ser Phe Leu Gly Ser
            645             650             655

Ser Asp Asn Lys Asn Lys Val Ile Lys Ala Ile Asn Asn Ala Leu Lys
            660             665             670

Glu Arg Asp Glu Lys Trp Lys Glu Val Tyr Ser Phe Ile Val Ser Asn
            675             680             685

Trp Met Thr Lys Ile Asn Thr Gln Phe Asn Lys Arg Lys Glu Gln Met
        690             695             700

Tyr Gln Ala Leu Gln Asn Gln Val Asn Ala Ile Lys Thr Ile Ile Glu
705             710             715             720

Ser Lys Tyr Asn Ser Tyr Thr Leu Glu Glu Lys Asn Glu Leu Thr Asn
            725             730             735

Lys Tyr Asp Ile Lys Gln Ile Glu Asn Glu Leu Asn Gln Lys Val Ser
            740             745             750

Ile Ala Met Asn Asn Ile Asp Arg Phe Leu Thr Glu Ser Ser Ile Ser
            755             760             765

Tyr Leu Met Lys Ile Ile Asn Glu Val Lys Ile Asn Lys Leu Arg Glu
        770             775             780

Tyr Asp Glu Asn Val Lys Thr Tyr Leu Leu Asn Tyr Ile Ile Gln His
785             790             795             800

Gly Ser Ile Leu Gly Glu Ser Gln Gln Glu Leu Asn Ser Met Val Thr
            805             810             815

Asp Thr Leu Asn Asn Ser Ile Pro Phe Lys Leu Ser Ser Tyr Thr Asp
            820             825             830

Asp Lys Ile Leu Ile Ser Tyr Phe Asn Lys Phe Phe Lys Arg Ile Lys
            835             840             845

Ser Ser Ser Val Leu Asn Met Arg Tyr Lys Asn Asp Lys Tyr Val Asp
        850             855             860

Thr Ser Gly Tyr Asp Ser Asn Ile Asn Ile Asn Gly Asp Val Tyr Lys
865             870             875             880

Tyr Pro Thr Asn Lys Asn Gln Phe Gly Ile Tyr Asn Asp Lys Leu Ser
            885             890             895

Glu Val Asn Ile Ser Gln Asn Asp Tyr Ile Ile Tyr Asp Asn Lys Tyr
```

-continued

```
                900                905                910
Lys Asn Phe Ser Ile Ser Phe Trp Val Arg Ile Pro Asn Tyr Asp Asn
      915                920                925

Lys Ile Val Asn Val Asn Asn Glu Tyr Thr Ile Ile Asn Cys Met Arg
      930                935                940

Asp Asn Asn Ser Gly Trp Lys Val Ser Leu Asn His Asn Glu Ile Ile
945                950                955                960

Trp Thr Phe Glu Asp Asn Arg Gly Ile Asn Gln Lys Leu Ala Phe Asn
            965                970                975

Tyr Gly Asn Ala Asn Gly Ile Ser Asp Tyr Ile Asn Lys Trp Ile Phe
            980                985                990

Val Thr Ile Thr Asn Asp Arg Leu  Gly Asp Ser Lys Leu  Tyr Ile Asn
      995                1000               1005

Gly Asn  Leu Ile Asp Gln Lys  Ser Ile Leu Asn Leu  Gly Asn Ile
      1010               1015               1020

His Val  Ser Asp Asn Ile Leu  Phe Lys Ile Val Asn  Cys Ser Tyr
      1025               1030               1035

Thr Arg  Tyr Ile Gly Ile Arg  Tyr Phe Asn Ile Phe  Asp Lys Glu
      1040               1045               1050

Leu Asp  Glu Thr Glu Ile Gln  Thr Leu Tyr Ser Asn  Glu Pro Asn
      1055               1060               1065

Thr Asn  Ile Leu Lys Asp Phe  Trp Gly Asn Tyr Leu  Leu Tyr Asp
      1070               1075               1080

Lys Glu  Tyr Tyr Leu Leu Asn  Val Leu Lys Pro Asn  Asn Phe Ile
      1085               1090               1095

Asp Arg  Arg Lys Asp Ser Thr  Leu Ser Ile Asn Asn  Ile Arg Ser
      1100               1105               1110

Thr Ile  Leu Leu Ala Asn Arg  Leu Tyr Ser Gly Ile  Lys Val Lys
      1115               1120               1125

Ile Gln  Arg Val Asn Asn Ser  Ser Thr Asn Asp Asn  Leu Val Arg
      1130               1135               1140

Lys Asn  Asp Gln Val Tyr Ile  Asn Phe Val Ala Ser  Lys Thr His
      1145               1150               1155

Leu Phe  Pro Leu Tyr Ala Asp  Thr Ala Thr Thr Asn  Lys Glu Lys
      1160               1165               1170

Thr Ile  Lys Ile Ser Ser Ser  Gly Asn Arg Phe Asn  Gln Val Val
      1175               1180               1185

Val Met  Asn Ser Val Gly Asn  Cys Thr Met Asn Phe  Lys Asn Asn
      1190               1195               1200

Asn Gly  Asn Asn Ile Gly Leu  Leu Gly Phe Lys Ala  Asp Thr Val
      1205               1210               1215

Val Ala  Ser Thr Trp Tyr Tyr  Thr His Met Arg Asp  His Thr Asn
      1220               1225               1230

Ser Asn  Gly Cys Phe Trp Asn  Phe Ile Ser Glu Glu  His Gly Trp
      1235               1240               1245

Gln Glu  Lys
      1250
```

<210> SEQ ID NO 40
<211> LENGTH: 1278
<212> TYPE: PRT
<213> ORGANISM: Clostridium botulinum
<400> SEQUENCE: 40

-continued

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
```

-continued

```
                420             425             430

Ile Pro Arg Lys Gly Thr Lys Ala Pro Pro Arg Leu Cys Ile Arg Val
        435             440             445

Asn Asn Arg Glu Leu Phe Phe Val Ala Ser Glu Ser Ser Tyr Asn Glu
    450             455             460

Asn Asp Ile Asn Thr Pro Lys Glu Ile Asp Asp Thr Thr Asn Leu Asn
465             470             475             480

Asn Asn Tyr Arg Asn Asn Leu Asp Glu Val Ile Leu Asp Tyr Asn Ser
            485             490             495

Glu Thr Ile Pro Gln Ile Ser Asn Gln Thr Leu Asn Thr Leu Val Gln
        500             505             510

Asp Asp Ser Tyr Val Pro Arg Tyr Asp Ser Asn Gly Thr Ser Glu Ile
        515             520             525

Glu Glu His Asn Val Val Asp Leu Asn Val Phe Phe Tyr Leu His Ala
    530             535             540

Gln Lys Val Pro Glu Gly Glu Thr Asn Ile Ser Leu Thr Ser Ser Ile
545             550             555             560

Asp Thr Ala Leu Ser Glu Glu Ser Gln Val Tyr Thr Phe Phe Ser Ser
            565             570             575

Glu Phe Ile Asn Thr Ile Asn Lys Pro Val His Ala Ala Leu Phe Ile
            580             585             590

Ser Trp Ile Asn Gln Val Ile Arg Asp Phe Thr Thr Glu Ala Thr Gln
        595             600             605

Lys Ser Thr Phe Asp Lys Ile Ala Asp Ile Ser Leu Val Val Pro Tyr
    610             615             620

Val Gly Leu Ala Leu Asn Ile Gly Asn Glu Val Gln Lys Glu Asn Phe
625             630             635             640

Lys Glu Ala Phe Glu Leu Leu Gly Ala Gly Ile Leu Leu Glu Phe Val
            645             650             655

Pro Glu Leu Leu Ile Pro Thr Ile Leu Val Phe Thr Ile Lys Ser Phe
            660             665             670

Ile Gly Ser Ser Glu Asn Lys Asn Lys Ile Ile Lys Ala Ile Asn Asn
        675             680             685

Ser Leu Met Glu Arg Glu Thr Lys Trp Lys Glu Ile Tyr Ser Trp Ile
    690             695             700

Val Ser Asn Trp Leu Thr Arg Ile Asn Thr Gln Phe Asn Lys Arg Lys
705             710             715             720

Glu Gln Met Tyr Gln Ala Leu Gln Asn Gln Val Asp Ala Ile Lys Thr
            725             730             735

Val Ile Glu Tyr Lys Tyr Asn Asn Tyr Thr Ser Asp Glu Arg Asn Arg
            740             745             750

Leu Glu Ser Glu Tyr Asn Ile Asn Asn Ile Arg Glu Glu Leu Asn Lys
        755             760             765

Lys Val Ser Leu Ala Met Glu Asn Ile Glu Arg Phe Ile Thr Glu Ser
    770             775             780

Ser Ile Phe Tyr Leu Met Lys Leu Ile Asn Glu Ala Lys Val Ser Lys
785             790             795             800

Leu Arg Glu Tyr Asp Glu Gly Val Lys Glu Tyr Leu Leu Asp Tyr Ile
            805             810             815

Ser Glu His Arg Ser Ile Leu Gly Asn Ser Val Gln Glu Leu Asn Asp
        820             825             830

Leu Val Thr Ser Thr Leu Asn Asn Ser Ile Pro Phe Glu Leu Ser Ser
        835             840             845
```

-continued

```
Tyr Thr Asn Asp Lys Ile Leu Ile Leu Tyr Phe Asn Lys Leu Tyr Lys
850             855             860

Lys Ile Lys Asp Asn Ser Ile Leu Asp Met Arg Tyr Glu Asn Asn Lys
865             870             875             880

Phe Ile Asp Ile Ser Gly Tyr Gly Ser Asn Ile Ser Ile Asn Gly Asp
                885             890             895

Val Tyr Ile Tyr Ser Thr Asn Arg Asn Gln Phe Gly Ile Tyr Ser Ser
            900             905             910

Lys Pro Ser Glu Val Asn Ile Ala Gln Asn Asn Asp Ile Ile Tyr Asn
            915             920             925

Gly Arg Tyr Gln Asn Phe Ser Ile Ser Phe Trp Val Arg Ile Pro Lys
        930             935             940

Tyr Phe Asn Lys Val Asn Leu Asn Asn Glu Tyr Thr Ile Ile Asp Cys
945             950             955             960

Ile Arg Asn Asn Asn Ser Gly Trp Lys Ile Ser Leu Asn Tyr Asn Lys
            965             970             975

Ile Ile Trp Thr Leu Gln Asp Thr Ala Gly Asn Asn Gln Lys Leu Val
            980             985             990

Phe Asn Tyr Thr Gln Met Ile Ser  Ile Ser Asp Tyr Ile  Asn Lys Trp
        995             1000            1005

Ile Phe  Val Thr Ile Thr Asn  Asn Arg Leu Gly Asn  Ser Arg Ile
    1010            1015            1020

Tyr Ile  Asn Gly Asn Leu Ile  Asp Glu Lys Ser Ile  Ser Asn Leu
    1025            1030            1035

Gly Asp  Ile His Val Ser Asp  Asn Ile Leu Phe Lys  Ile Val Gly
    1040            1045            1050

Cys Asn  Asp Thr Arg Tyr Val  Gly Ile Arg Tyr Phe  Lys Val Phe
    1055            1060            1065

Asp Thr  Glu Leu Gly Lys Thr  Glu Ile Glu Thr Leu  Tyr Ser Asp
    1070            1075            1080

Glu Pro  Asp Pro Ser Ile Leu  Lys Asp Phe Trp Gly  Asn Tyr Leu
    1085            1090            1095

Leu Tyr  Asn Lys Arg Tyr Tyr  Leu Leu Asn Leu Leu  Arg Thr Asp
    1100            1105            1110

Lys Ser  Ile Thr Gln Asn Ser  Asn Phe Leu Asn Ile  Asn Gln Gln
    1115            1120            1125

Arg Gly  Val Tyr Gln Lys Pro  Asn Ile Phe Ser Asn  Thr Arg Leu
    1130            1135            1140

Tyr Thr  Gly Val Glu Val Ile  Ile Arg Lys Asn Gly  Ser Thr Asp
    1145            1150            1155

Ile Ser  Asn Thr Asp Asn Phe  Val Arg Lys Asn Asp  Leu Ala Tyr
    1160            1165            1170

Ile Asn  Val Val Asp Arg Asp  Val Glu Tyr Arg Leu  Tyr Ala Asp
    1175            1180            1185

Ile Ser  Ile Ala Lys Pro Glu  Lys Ile Ile Lys Leu  Ile Arg Thr
    1190            1195            1200

Ser Asn  Ser Asn Asn Ser Leu  Gly Gln Ile Ile Val  Met Asp Ser
    1205            1210            1215

Ile Gly  Asn Asn Cys Thr Met  Asn Phe Gln Asn Asn  Asn Gly Gly
    1220            1225            1230

Asn Ile  Gly Leu Leu Gly Phe  His Ser Asn Asn Leu  Val Ala Ser
    1235            1240            1245
```

-continued

```
Ser Trp  Tyr Tyr Asn Asn Ile  Arg Lys Asn Thr Ser  Ser Asn Gly
    1250             1255             1260

Cys Phe  Trp Ser Phe Ile Ser  Lys Glu His Gly Trp  Gln Glu Asn
    1265             1270             1275

<210> SEQ ID NO 41
<211> LENGTH: 1297
<212> TYPE: PRT
<213> ORGANISM: Clostridium botulinum
<220> FEATURE:
<221> NAME/KEY: SITE
<222> LOCATION: (7)..(7)
<223> OTHER INFORMATION: Xaa can be any naturally occurring amino acid

<400> SEQUENCE: 41

Met Pro Val Asn Ile Lys Xaa Phe Asn Tyr Asn Asp Pro Ile Asn Asn
1               5               10              15

Asp Asp Ile Ile Met Met Glu Pro Phe Asn Asp Pro Gly Pro Gly Thr
            20              25              30

Tyr Tyr Lys Ala Phe Arg Ile Ile Asp Arg Ile Trp Ile Val Pro Glu
        35              40              45

Arg Phe Thr Tyr Gly Phe Gln Pro Asp Gln Phe Asn Ala Ser Thr Gly
    50              55              60

Val Phe Ser Lys Asp Val Tyr Glu Tyr Tyr Asp Pro Thr Tyr Leu Lys
65              70              75              80

Thr Asp Ala Glu Lys Asp Lys Phe Leu Lys Thr Met Ile Lys Leu Phe
            85              90              95

Asn Arg Ile Asn Ser Lys Pro Ser Gly Gln Arg Leu Leu Asp Met Ile
            100             105             110

Val Asp Ala Ile Pro Tyr Leu Gly Asn Ala Ser Thr Pro Pro Asp Lys
        115             120             125

Phe Ala Ala Asn Val Ala Asn Val Ser Ile Asn Lys Lys Ile Ile Gln
    130             135             140

Pro Gly Ala Glu Asp Gln Ile Lys Gly Leu Met Thr Asn Leu Ile Ile
145             150             155             160

Phe Gly Pro Gly Pro Val Leu Ser Asp Asn Phe Thr Asp Ser Met Ile
            165             170             175

Met Asn Gly His Ser Pro Ile Ser Glu Gly Phe Gly Ala Arg Met Met
            180             185             190

Ile Arg Phe Cys Pro Ser Cys Leu Asn Val Phe Asn Asn Val Gln Glu
        195             200             205

Asn Lys Asp Thr Ser Ile Phe Ser Arg Arg Ala Tyr Phe Ala Asp Pro
    210             215             220

Ala Leu Thr Leu Met His Glu Leu Ile His Val Leu His Gly Leu Tyr
225             230             235             240

Gly Ile Lys Ile Ser Asn Leu Pro Ile Thr Pro Asn Thr Lys Glu Phe
            245             250             255

Phe Met Gln His Ser Asp Pro Val Gln Ala Glu Glu Leu Tyr Thr Phe
            260             265             270

Gly Gly His Asp Pro Ser Val Ile Ser Pro Ser Thr Asp Met Asn Ile
            275             280             285

Tyr Asn Lys Ala Leu Gln Asn Phe Gln Asp Ile Ala Asn Arg Leu Asn
    290             295             300

Ile Val Ser Ser Ala Gln Gly Ser Gly Ile Asp Ile Ser Leu Tyr Lys
305             310             315             320

Gln Ile Tyr Lys Asn Lys Tyr Asp Phe Val Glu Asp Pro Asn Gly Lys
```

-continued

```
                 325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
            355                 360                 365

Arg Tyr Ser Tyr Phe Ser Glu Tyr Leu Pro Pro Ile Lys Thr Glu Lys
        370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
            435                 440                 445

Gln Cys Ile Ile Val Asn Asn Glu Asp Leu Phe Phe Ile Ala Asn Lys
        450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
                500                 505                 510

Glu Pro Phe Thr Asn Phe Asp Asp Ile Asp Ile Pro Val Tyr Ile Lys
            515                 520                 525

Gln Ser Ala Leu Lys Lys Ile Phe Val Asp Gly Asp Ser Leu Phe Glu
        530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
        610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
            675                 680                 685

Asn Ala Leu Lys Lys Arg Asp Gln Lys Trp Thr Asp Met Tyr Gly Leu
        690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
            725                 730                 735

Lys Ile Ile Glu Asp Gln Tyr Asn Arg Tyr Ser Glu Glu Asp Lys Met
            740                 745                 750
```

-continued

```
Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
                820                 825                 830

Val Asn Arg His Leu Lys Asp Ser Ile Pro Phe Asp Leu Ser Leu Tyr
                835                 840                 845

Thr Lys Asp Thr Ile Leu Ile Gln Val Phe Asn Asn Tyr Ile Ser Asn
        850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
                900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
        930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
                980                 985                 990

Phe Phe Glu Tyr Ser Ile Lys Asp  Asn Ile Ser Asp Tyr  Ile Asn Lys
        995                 1000                1005

Trp Phe  Ser Ile Thr Ile Thr  Asn Asp Arg Leu Gly  Asn Ala Asn
    1010                1015                1020

Ile Tyr  Ile Asn Gly Ser Leu  Lys Lys Ser Glu Lys  Ile Leu Asn
    1025                1030                1035

Leu Asp  Arg Ile Asn Ser Ser  Asn Asp Ile Asp Phe  Lys Leu Ile
    1040                1045                1050

Asn Cys  Thr Asp Thr Thr Lys  Phe Val Trp Ile Lys  Asp Phe Asn
    1055                1060                1065

Ile Phe  Gly Arg Glu Leu Asn  Ala Thr Glu Val Ser  Ser Leu Tyr
    1070                1075                1080

Trp Ile  Gln Ser Ser Thr Asn  Thr Leu Lys Asp Phe  Trp Gly Asn
    1085                1090                1095

Pro Leu  Arg Tyr Asp Thr Gln  Tyr Tyr Leu Phe Asn  Gln Gly Met
    1100                1105                1110

Gln Asn  Ile Tyr Ile Lys Tyr  Phe Ser Lys Ala Ser  Met Gly Glu
    1115                1120                1125

Thr Ala  Pro Arg Thr Asn Phe  Asn Asn Ala Ala Ile  Asn Tyr Gln
    1130                1135                1140

Asn Leu  Tyr Leu Gly Leu Arg  Phe Ile Ile Lys Lys  Ala Ser Asn
    1145                1150                1155
```

-continued

Ser Arg  Asn Ile Asn Asn Asp  Asn Ile Val Arg Glu  Gly Asp Tyr
    1160                    1165                    1170

Ile Tyr  Leu Asn Ile Asp Asn  Ile Ser Asp Glu Ser  Tyr Arg Val
    1175                    1180                    1185

Tyr Val  Leu Val Asn Ser Lys  Glu Ile Gln Thr Gln  Leu Phe Leu
    1190                    1195                    1200

Ala Pro  Ile Asn Asp Asp Pro  Thr Phe Tyr Asp Val  Leu Gln Ile
    1205                    1210                    1215

Lys Lys  Tyr Tyr Glu Lys Thr  Thr Tyr Asn Cys Gln  Ile Leu Cys
    1220                    1225                    1230

Glu Lys  Asp Thr Lys Thr Phe  Gly Leu Phe Gly Ile  Gly Lys Phe
    1235                    1240                    1245

Val Lys  Asp Tyr Gly Tyr Val  Trp Asp Thr Tyr Asp  Asn Tyr Phe
    1250                    1255                    1260

Cys Ile  Ser Gln Trp Tyr Leu  Arg Arg Ile Ser Glu  Asn Ile Asn
    1265                    1270                    1275

Lys Leu  Arg Leu Gly Cys Asn  Trp Gln Phe Ile Pro  Val Asp Glu
    1280                    1285                    1290

Gly Trp  Thr Glu
    1295

<210> SEQ ID NO 42
<211> LENGTH: 1315
<212> TYPE: PRT
<213> ORGANISM: Clostridium tetani

<400> SEQUENCE: 42

Met Pro Ile Thr Ile Asn Asn Phe Arg Tyr Ser Asp Pro Val Asn Asn
1                5                10               15

Asp Thr Ile Ile Met Met Glu Pro Pro Tyr Cys Lys Gly Leu Asp Ile
            20               25               30

Tyr Tyr Lys Ala Phe Lys Ile Thr Asp Arg Ile Trp Ile Val Pro Glu
        35               40               45

Arg Tyr Glu Phe Gly Thr Lys Pro Glu Asp Phe Asn Pro Pro Ser Ser
    50               55               60

Leu Ile Glu Gly Ala Ser Glu Tyr Tyr Asp Pro Asn Tyr Leu Arg Thr
65               70               75               80

Asp Ser Asp Lys Asp Arg Phe Leu Gln Thr Met Val Lys Leu Phe Asn
            85               90               95

Arg Ile Lys Asn Asn Val Ala Gly Glu Ala Leu Leu Asp Lys Ile Ile
            100              105              110

Asn Ala Ile Pro Tyr Leu Gly Asn Ser Tyr Ser Leu Leu Asp Lys Phe
        115              120              125

Asp Thr Asn Ser Asn Ser Val Ser Phe Asn Leu Leu Glu Gln Asp Pro
    130              135              140

Ser Gly Ala Thr Thr Lys Ser Ala Met Leu Thr Asn Leu Ile Ile Phe
145              150              155              160

Gly Pro Gly Pro Val Leu Asn Lys Asn Glu Val Arg Gly Ile Val Leu
            165              170              175

Arg Val Asp Asn Lys Asn Tyr Phe Pro Cys Arg Asp Gly Phe Gly Ser
            180              185              190

Ile Met Gln Met Ala Phe Cys Pro Glu Tyr Val Pro Thr Phe Asp Asn
        195              200              205

Val Ile Glu Asn Ile Thr Ser Leu Thr Ile Gly Lys Ser Lys Tyr Phe
    210              215              220

```
Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
                260                 265                 270

Phe Thr Phe Gly Gly Gln Asp Ala Asn Leu Ile Ser Ile Asp Ile Lys
            275                 280                 285

Asn Asp Leu Tyr Glu Lys Thr Leu Asn Asp Tyr Lys Ala Ile Ala Asn
        290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
            595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640
```

-continued

```
Thr Ile Val Pro Tyr Ile Gly Pro Ala Leu Asn Ile Val Lys Gln Gly
              645             650             655

Tyr Glu Gly Asn Phe Ile Gly Ala Leu Glu Thr Thr Gly Val Val Leu
          660             665             670

Leu Leu Glu Tyr Ile Pro Glu Ile Thr Leu Pro Val Ile Ala Ala Leu
          675             680             685

Ser Ile Ala Glu Ser Ser Thr Gln Lys Glu Lys Ile Ile Lys Thr Ile
      690             695             700

Asp Asn Phe Leu Glu Lys Arg Tyr Glu Lys Trp Ile Glu Val Tyr Lys
705             710             715             720

Leu Val Lys Ala Lys Trp Leu Gly Thr Val Asn Thr Gln Phe Gln Lys
              725             730             735

Arg Ser Tyr Gln Met Tyr Arg Ser Leu Glu Tyr Gln Val Asp Ala Ile
          740             745             750

Lys Lys Ile Ile Asp Tyr Glu Tyr Lys Ile Tyr Ser Gly Pro Asp Lys
          755             760             765

Glu Gln Ile Ala Asp Glu Ile Asn Asn Leu Lys Asn Lys Leu Glu Glu
      770             775             780

Lys Ala Asn Lys Ala Met Ile Asn Ile Asn Ile Phe Met Arg Glu Ser
785             790             795             800

Ser Arg Ser Phe Leu Val Asn Gln Met Ile Asn Glu Ala Lys Lys Gln
              805             810             815

Leu Leu Glu Phe Asp Thr Gln Ser Lys Asn Ile Leu Met Gln Tyr Ile
          820             825             830

Lys Ala Asn Ser Lys Phe Ile Gly Ile Thr Glu Leu Lys Lys Leu Glu
          835             840             845

Ser Lys Ile Asn Lys Val Phe Ser Thr Pro Ile Pro Phe Ser Tyr Ser
      850             855             860

Lys Asn Leu Asp Cys Trp Val Asp Asn Glu Glu Asp Ile Asp Val Ile
865             870             875             880

Leu Lys Lys Ser Thr Ile Leu Asn Leu Asp Ile Asn Asn Asp Ile Ile
              885             890             895

Ser Asp Ile Ser Gly Phe Asn Ser Ser Val Ile Thr Tyr Pro Asp Ala
          900             905             910

Gln Leu Val Pro Gly Ile Asn Gly Lys Ala Ile His Leu Val Asn Asn
          915             920             925

Glu Ser Ser Glu Val Ile Val His Lys Ala Met Asp Ile Glu Tyr Asn
      930             935             940

Asp Met Phe Asn Asn Phe Thr Val Ser Phe Trp Leu Arg Val Pro Lys
945             950             955             960

Val Ser Ala Ser His Leu Glu Gln Tyr Gly Thr Asn Glu Tyr Ser Ile
              965             970             975

Ile Ser Ser Met Lys Lys His Ser Leu Ser Ile Gly Ser Gly Trp Ser
          980             985             990

Val Ser Leu Lys Gly Asn Asn Leu  Ile Trp Thr Leu Lys  Asp Ser Ala
          995             1000            1005

Gly Glu  Val Arg Gln Ile Thr  Phe Arg Asp Leu Pro  Asp Lys Phe
      1010            1015            1020

Asn Ala  Tyr Leu Ala Asn Lys  Trp Val Phe Ile Thr  Ile Thr Asn
      1025            1030            1035

Asp Arg  Leu Ser Ser Ala Asn  Leu Tyr Ile Asn Gly  Val Leu Met
      1040            1045            1050

Gly Ser  Ala Glu Ile Thr Gly  Leu Gly Ala Ile Arg  Glu Asp Asn
```

-continued

```
        1055               1060               1065

Asn Ile  Thr Leu Lys Leu Asp  Arg Cys Asn Asn  Asn Gln Tyr
    1070              1075              1080

Val Ser  Ile Asp Lys Phe Arg  Ile Phe Cys Lys Ala  Leu Asn Pro
    1085              1090              1095

Lys Glu  Ile Glu Lys Leu Tyr  Thr Ser Tyr Leu Ser  Ile Thr Phe
    1100              1105              1110

Leu Arg  Asp Phe Trp Gly Asn  Pro Leu Arg Tyr Asp  Thr Glu Tyr
    1115              1120              1125

Tyr Leu  Ile Pro Val Ala Ser  Ser Ser Lys Asp Val  Gln Leu Lys
    1130              1135              1140

Asn Ile  Thr Asp Tyr Met Tyr  Leu Thr Asn Ala Pro  Ser Tyr Thr
    1145              1150              1155

Asn Gly  Lys Leu Asn Ile Tyr  Tyr Arg Arg Leu Tyr  Asn Gly Leu
    1160              1165              1170

Lys Phe  Ile Ile Lys Arg Tyr  Thr Pro Asn Asn Glu  Ile Asp Ser
    1175              1180              1185

Phe Val  Lys Ser Gly Asp Phe  Ile Lys Leu Tyr Val  Ser Tyr Asn
    1190              1195              1200

Asn Asn  Glu His Ile Val Gly  Tyr Pro Lys Asp Gly  Asn Ala Phe
    1205              1210              1215

Asn Asn  Leu Asp Arg Ile Leu  Arg Val Gly Tyr Asn  Ala Pro Gly
    1220              1225              1230

Ile Pro  Leu Tyr Lys Lys Met  Glu Ala Val Lys Leu  Arg Asp Leu
    1235              1240              1245

Lys Thr  Tyr Ser Val Gln Leu  Lys Leu Tyr Asp Asp  Lys Asn Ala
    1250              1255              1260

Ser Leu  Gly Leu Val Gly Thr  His Asn Gly Gln Ile  Gly Asn Asp
    1265              1270              1275

Pro Asn  Arg Asp Ile Leu Ile  Ala Ser Asn Trp Tyr  Phe Asn His
    1280              1285              1290

Leu Lys  Asp Lys Ile Leu Gly  Cys Asp Trp Tyr Phe  Val Pro Thr
    1295              1300              1305

Asp Glu  Gly Trp Thr Asn Asp
    1310              1315
```

```
<210> SEQ ID NO 43
<211> LENGTH: 2634
<212> TYPE: DNA
<213> ORGANISM: Artificial Sequence
<220> FEATURE:
<223> OTHER INFORMATION: LHN/A1 with an EK Cleavage Site

<400> SEQUENCE: 43
atggagttcg ttaacaaaca gttcaactat aaagacccag ttaacggtgt tgacattgct      60
tacatcaaaa tcccgaacgc tggccagatg cagccggtaa aggcattcaa atccacaac      120 aaaatctggg ttatcccgga acgtgatacc tttactaacc cggaagaagg tgacctgaac     180
ccgccaccgg aagcgaaaca ggtgccggta tcttactatg actccaccta cctgtctacc     240
gataacgaaa aggacaacta cctgaaaggt gttactaaac tgttcgagcg tatttactcc     300
accgacctgg ccgtatgct gctgactagc atcgttcgcg gtatcccgtt ctggggcggt     360
tctaccatcg ataccgaact gaaagtaatc gacactaact gcatcaacgt tattcagccg     420
gacggttcct atcgttccga agaactgaac ctggtgatca tcggcccgtc tgctgatatc     480
```

-continued

```
atccagttcg agtgtaagag ctttggtcac gaagttctga acctcacccg taacggctac      540
ggttccactc agtacatccg tttctctccg gacttcacct tcggttttga agaatccctg      600
gaagtagaca cgaacccact gctgggcgct ggtaaattcg caactgatcc tgcggttacc      660
ctggctcacg aactgattca tgcaggccac cgcctgtacg gtatcgccat caatccgaac      720
cgtgtcttca aagttaacac caacgcgtat tacgagatgt ccggtctgga agttagcttc      780
gaagaactgc gtacttttgg cggtcacgac gctaaattca tcgactctct gcaagaaaac      840
gagttccgtc tgtactacta taacaagttc aaagatatcg catccaccct gaacaaagcg      900
aaatccatcg tgggtaccac tgcttctctc cagtacatga agaacgtttt taaagaaaaa      960
tacctgctca gcgaagacac ctccggcaaa ttctctgtag acaagttgaa attcgataaa     1020
ctttacaaaa tgctgactga aatttacacc gaagacaact tcgttaagtt ctttaaagtt     1080
ctgaaccgca aaacctatct gaacttcgac aaggcagtat tcaaaatcaa catcgtgccg     1140
aaagttaact acactatcta cgatggtttc aacctgcgta acaccaacct ggctgctaat     1200
tttaacggcc agaacacgga aatcaacaac atgaacttca caaaactgaa aaacttcact     1260
ggtctgttcg agttttacaa gctgctgtgc gtcgacggca tcattacctc caaaactaaa     1320
tctgacgatg acgataaaaa caaagcgctg aacctgcagt gtatcaaggt taacaactgg     1380
gatttattct tcagcccgag tgaagacaac ttcaccaacg acctgaacaa aggtgaagaa     1440
atcacctcag atactaacat cgaagcagcc gaagaaaaca tctcgctgga cctgatccag     1500
cagtactacc tgacctttaa tttcgacaac gagccggaaa acatttctat cgaaaacctg     1560
agctctgata tcatcggcca gctggaactg atgccgaaca tcgaacgttt cccaaacggt     1620
aaaaagtacg agctggacaa atataccatg ttccactacc tgcgcgcgca ggaatttgaa     1680
cacggcaaat cccgtatcgc actgactaac tccgttaacg aagctctgct caacccgtcc     1740
cgtgtataca ccttcttctc tagcgactac gtgaaaaagg tcaacaaagc gactgaagct     1800
gcaatgttct tgggttgggt tgaacagctt gtttatgatt ttaccgacga gacgtccgaa     1860
gtatctacta ccgacaaaat tgcggatatc actatcatca tcccgtacat cggtccggct     1920
ctgaacattg gcaacatgct gtacaaagac gacttcgttg gcgcactgat cttctccggt     1980
gcggtgatcc tgctggagtt catcccggaa atcgccatcc cggtactggg cacctttgct     2040
ctggtttctt acattgcaaa caaggttctg actgtacaaa ccatcgacaa cgcgctgagc     2100
aaacgtaacg aaaaatggga tgaagtttac aaatatatcg tgaccaactg gctggctaag     2160
gttaatactc agatcgacct catccgcaaa aaaatgaaag aagcactgga aaaccaggcg     2220
gaagctacca aggcaatcat taactaccag tacaaccagt acaccgagga agaaaaaaac     2280
aacatcaact tcaacatcga cgatctgtcc tctaaactga cgaatccat caacaaagct      2340 atgatcaaca tcaacaagtt cctgaaccag tgctctgtaa gctatctgat gaactccatg     2400
atcccgtacg gtgttaaacg tctggaggac ttcgatgcgt ctctgaaaga cgccctgctg     2460
aaatacattt acgacaaccg tggcactctg atcggtcagg ttgatcgtct gaaggacaaa     2520
gtgaacaata ccttatcgac cgacatccct tttcagctca gtaaatatgt cgataaccaa     2580
cgccttttgt ccactctaga agcacaccat catcaccacc atcaccatca ccat           2634
```

<210> SEQ ID NO 44
<211> LENGTH: 878
<212> TYPE: PRT
<213> ORGANISM: Artificial Sequence
<220> FEATURE:
<223> OTHER INFORMATION: LHN/A1 with an EK Cleavage Site

<400> SEQUENCE: 44

Met Glu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu

-continued

```
                405              410              415

Lys Asn Phe Thr Gly Leu Phe Glu Phe Tyr Lys Leu Leu Cys Val Asp
            420              425              430

Gly Ile Ile Thr Ser Lys Thr Lys Ser Asp Asp Asp Lys Asn Lys
            435              440              445

Ala Leu Asn Leu Gln Cys Ile Lys Val Asn Asn Trp Asp Leu Phe Phe
        450              455              460

Ser Pro Ser Glu Asp Asn Phe Thr Asn Asp Leu Asn Lys Gly Glu Glu
    465              470              475              480

Ile Thr Ser Asp Thr Asn Ile Glu Ala Ala Glu Glu Asn Ile Ser Leu
                485              490              495

Asp Leu Ile Gln Gln Tyr Tyr Leu Thr Phe Asn Phe Asp Asn Glu Pro
            500              505              510

Glu Asn Ile Ser Ile Glu Asn Leu Ser Ser Asp Ile Ile Gly Gln Leu
            515              520              525

Glu Leu Met Pro Asn Ile Glu Arg Phe Pro Asn Gly Lys Lys Tyr Glu
        530              535              540

Leu Asp Lys Tyr Thr Met Phe His Tyr Leu Arg Ala Gln Glu Phe Glu
    545              550              555              560

His Gly Lys Ser Arg Ile Ala Leu Thr Asn Ser Val Asn Glu Ala Leu
                565              570              575

Leu Asn Pro Ser Arg Val Tyr Thr Phe Phe Ser Ser Asp Tyr Val Lys
            580              585              590

Lys Val Asn Lys Ala Thr Glu Ala Ala Met Phe Leu Gly Trp Val Glu
            595              600              605

Gln Leu Val Tyr Asp Phe Thr Asp Glu Thr Ser Glu Val Ser Thr Thr
        610              615              620

Asp Lys Ile Ala Asp Ile Thr Ile Ile Ile Pro Tyr Ile Gly Pro Ala
    625              630              635              640

Leu Asn Ile Gly Asn Met Leu Tyr Lys Asp Asp Phe Val Gly Ala Leu
                645              650              655

Ile Phe Ser Gly Ala Val Ile Leu Leu Glu Phe Ile Pro Glu Ile Ala
                660              665              670

Ile Pro Val Leu Gly Thr Phe Ala Leu Val Ser Tyr Ile Ala Asn Lys
            675              680              685

Val Leu Thr Val Gln Thr Ile Asp Asn Ala Leu Ser Lys Arg Asn Glu
        690              695              700

Lys Trp Asp Glu Val Tyr Lys Tyr Ile Val Thr Asn Trp Leu Ala Lys
    705              710              715              720

Val Asn Thr Gln Ile Asp Leu Ile Arg Lys Lys Met Lys Glu Ala Leu
            725              730              735

Glu Asn Gln Ala Glu Ala Thr Lys Ala Ile Ile Asn Tyr Gln Tyr Asn
            740              745              750

Gln Tyr Thr Glu Glu Glu Lys Asn Asn Ile Asn Phe Asn Ile Asp Asp
        755              760              765

Leu Ser Ser Lys Leu Asn Glu Ser Ile Asn Lys Ala Met Ile Asn Ile
    770              775              780

Asn Lys Phe Leu Asn Gln Cys Ser Val Ser Tyr Leu Met Asn Ser Met
    785              790              795              800

Ile Pro Tyr Gly Val Lys Arg Leu Glu Asp Phe Asp Ala Ser Leu Lys
                805              810              815

Asp Ala Leu Leu Lys Tyr Ile Tyr Asp Asn Arg Gly Thr Leu Ile Gly
            820              825              830
```

-continued

```
Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Leu Glu Ala His His His His His His His His His
865                 870                 875
```

```
<210> SEQ ID NO 45
<211> LENGTH: 3996
<212> TYPE: DNA
<213> ORGANISM: Clostridium botulinum

<400> SEQUENCE: 45
atgaaactgg aaatcaacaa attcaactac aacgatccga tcgatggcat taatgttatt      60
accatgcgtc cgcctcgtca tagcgataaa atcaataaag gtaaaggtcc gttcaaagcc     120
tttcaggtga ttaaaaacat ttggattgtg ccggaacgct acaactttac caataatacc     180
aacgatctga acattccgag cgaaccgatt atggaagcag atgccattta taacccgaac     240
tatctgaata ccccgagcga aaaagatgaa tttctgcagg gtgttatcaa agtgctggaa     300
cgcattaaaa gcaaaccgga aggtgaaaaa ctgctggaac tgattagcag cagcattccg     360
ctgccgctgg ttagcaatgg tgcactgacc ctgagcgata tgaaaccat tgcatatcaa     420 gagaacaaca cattgtgag caatctgcag gcaaacctgg ttatttatgg tccgggtcct     480
gatattgcaa ataatgcaac ctatggtctg tatagcaccc cgattagtaa tggtgaaggt     540
acactgagcg aagttagctt tagcccgttt tatctgaaac cgtttgatga aagctatggc     600
aattatcgta gcctggtgaa tatcgtgaac aaaattcgtga aacgtgaatt tgcacctgat     660
ccggcaagca ccctgatgca tgaactggtt catgttaccc ataatctgta tggtattagc     720
aaccgcaact tctactataa ctttgacacc ggcaaaattg aaaccagccg tcagcagaat     780
agcctgattt ttgaagaact gctgacctttt ggtggcattg atagcaaagc aattagcagc     840
ctgatcatca gaaaattat cgaaaccgcc aagaacaact ataccacgct gattagcgaa     900
cgcctgaata ccgttaccgt tgaaaatgat ctgctgaaat atatcaaaaa caaaatcccg     960
gttcagggtc gtctgggtaa ctttaaactg gataccgcag aattcgagaa aaagctgaat    1020
accattctgt ttgtgctgaa cgaaagcaat ctggcacagc gtttttagcat tctggttcgt    1080 aaacattacc tgaaagaacg tccgattgat ccgatttatg tgaacattct ggatgacaat    1140
agctacagca ccctggaagg ttttaacatt agcagtcagg gtagcaatga tttccaaggt    1200
cagctgctgg aaagcagcta ttttgaaaaa attgaaagca atgccctgcg tgccttcatt    1260 aaaatcgtc cgcgtaatgg tctgctgtat aatgccattt atcgcaacag caaaaatctg    1320
gaagttctgt ttcagggtcc gcatcatcac caccatcacc atcatcatca cctggaagtg    1380
ttatttcagg accgtatct gaataacatt gatctggaag ataaaaagac cacgagcaaa    1440
accaatgtta gctatccgtg tagcctgctg aatggttgta ttgaagttga aaacaaagac    1500
ctgttcctga ttagcaacaa agatagcctg aacgatatta acctgagcga agaaaaaatc    1560
aaaccggaaa ccaccgtgtt cttcaaagat aaactgcctc cgcaggatat tacgctgagc    1620
aattatgatt ttaccgaagc caatagcatt ccgagcatta gccagcagaa cattctggaa    1680
cgtaatgaag aactgtatga accgattcgc aatagcctgt ttgaaatcaa aaccatctat    1740
gtggataagc tgaccaccctt tcattttctg gaagcccaga atattgatga gagcattgat    1800
agcagcaaaa ttcgtgttga actgaccgat agcgttgatg aagcactgag caatccgaat    1860
```

-continued

```
aaagtttata gcccgttcaa gaacatgagc aacaccatta atagcattga aaccggtatt      1920
accagcacct acatctttta tcagtggctg cgtagcatcg tgaaagattt tagtgatgaa      1980
accggcaaaa tcgacgtgat tgataaaagc agcgataccc tggcaattgt tccgtatatt      2040
ggtccgctgc tgaatattgg taatgatatt cgtcatggcg attttgtggg tgcaattgaa      2100
ctggcaggca ttaccgcact gctggaatat gttccggaat ttaccattcc gattctggtt      2160
ggtctggaag tgattggtgg cgaactggca cgtgaacagg ttgaagcaat tgttaataat      2220
gccctggata aacgcgatca gaaatgggca gaagtttaca atattaccaa agcacagtgg      2280
tggggcacca ttcatttaca gattaatacc cgtctggccc atacctataa agccctgagc      2340
cgtcaggcaa atgccattaa aatgaatatg gaatttcagc tggccaacta caaaggcaac      2400
attgatgata aagccaagat caaaaacgcc atcagcgaaa ccgaaattct gctgaacaaa      2460
agcgttgaac aggccatgaa aaacaccgag aaattcatga ttaaactgag caacagctac      2520
ctgaccaaag aaatgattcc gaaagttcag gacaacctga aaaactttga cctggaaacc      2580
aaaaaaaccc tggacaagtt catcaaagag aaagaagata tcctgggcac caatctgagc      2640
agcagcctgc gtcgtaaagt tagcattcgt ctgaataaaa acattgcctt cgacatcaac      2700
gatatcccgt ttagcgaatt tgatgatctg atcaaccagt acaaaaacga gatcgaagat      2760
tatgaagtgc tgaatctggg tgcagaagat ggcaaaatca aagatctgag cggtacaacc      2820
agcgatatca atattggttc agatatcgaa ctggccgatg gtcgtgaaaa taaagccatt      2880
aagattaaag gcagcgagaa cagcaccatc aaaattgcaa tgaacaaata tctgcgtttt      2940
agcgccaccg ataactttag cattagcttt tggatcaaac atccgaaacc gaccaatctg      3000
cttaataacg gtattgaata taccctggtc gagaacttta atcagcgtgg ttggaaaatt      3060
agcatccagg atagcaaact gatttggtat ctgcgcgatc acaataacag catcaaaatc      3120
gttacaccgg attatattgc gtttaatggc tggaacctga tcaccattac gaataatcgt      3180
agcaaaggca gcatcgtgta tgtgaatggt agcaaaattg aagagaagga cattagcagc      3240
atttggaata ccgaagtgga tgatccgatt atcttccgcc tgaaaaataa ccgtgatacc      3300
caggcattta ccctgctgga tcagtttagc atttatcgga aagaactgaa ccagaacgaa      3360
gtggtgaaac tgtataacta ctacttcaac agcaactaca ttcgcgatat ttggggtaat      3420
ccgctgcagt acaacaaaaa atactatctg cagacccagg acaaacctgg taaaggtctg      3480
atccgcgaat attggagcag ctttggttat gattatgtga ttctgagcga tagcaagacg      3540
attacctttc cgaacaatat ccgttatggt gccctgtata acggtagcaa agttctgatc      3600
aagaacagca agaaattaga tggtctggtg cgcaataaag atttcattca gctggaaatc      3660
gatggctata atatgggtat tagcgcagat cgctttaacg aggataccaa ctatattggc      3720
accacctatg gtacaaccca tgatctgacc accgattttg aaattattca gcgccaagag      3780
aaataccgca attattgtca gctgaaaacc ccgtataaca tctttcataa aagcggtctg      3840
atgagcaccg aaaccagcaa accgaccttc catgattatc gcgattgggt ttatagcagc      3900
gcatggtatt ttcagaacta tgaaaatctg aacctgcgca aacataccaa aaccaactgg      3960
tattttatcc cgaaagatga aggttgggac gaagat                               3996
```

```
<210> SEQ ID NO 46
<211> LENGTH: 1332
<212> TYPE: PRT
<213> ORGANISM: Clostridium botulinum
```

```
<400> SEQUENCE: 46

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
        210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
        290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
        370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415
```

-continued

```
Arg Ala Phe Ile Lys Ile Cys Pro Arg Asn Gly Leu Leu Tyr Asn Ala
            420                 425                 430

Ile Tyr Arg Asn Ser Lys Asn Leu Glu Val Leu Phe Gln Gly Pro His
        435                 440                 445

His His His His His His His His His Leu Glu Val Leu Phe Gln Gly
    450                 455                 460

Pro Tyr Leu Asn Asn Ile Asp Leu Glu Asp Lys Lys Thr Thr Ser Lys
465                 470                 475                 480

Thr Asn Val Ser Tyr Pro Cys Ser Leu Leu Asn Gly Cys Ile Glu Val
                485                 490                 495

Glu Asn Lys Asp Leu Phe Leu Ile Ser Asn Lys Asp Ser Leu Asn Asp
            500                 505                 510

Ile Asn Leu Ser Glu Glu Lys Ile Lys Pro Glu Thr Thr Val Phe Phe
        515                 520                 525

Lys Asp Lys Leu Pro Pro Gln Asp Ile Thr Leu Ser Asn Tyr Asp Phe
    530                 535                 540

Thr Glu Ala Asn Ser Ile Pro Ser Ile Ser Gln Gln Asn Ile Leu Glu
545                 550                 555                 560

Arg Asn Glu Glu Leu Tyr Glu Pro Ile Arg Asn Ser Leu Phe Glu Ile
            565                 570                 575

Lys Thr Ile Tyr Val Asp Lys Leu Thr Thr Phe His Phe Leu Glu Ala
            580                 585                 590

Gln Asn Ile Asp Glu Ser Ile Asp Ser Ser Lys Ile Arg Val Glu Leu
        595                 600                 605

Thr Asp Ser Val Asp Glu Ala Leu Ser Asn Pro Asn Lys Val Tyr Ser
    610                 615                 620

Pro Phe Lys Asn Met Ser Asn Thr Ile Asn Ser Ile Glu Thr Gly Ile
625                 630                 635                 640

Thr Ser Thr Tyr Ile Phe Tyr Gln Trp Leu Arg Ser Ile Val Lys Asp
                645                 650                 655

Phe Ser Asp Glu Thr Gly Lys Ile Asp Val Ile Asp Lys Ser Ser Asp
            660                 665                 670

Thr Leu Ala Ile Val Pro Tyr Ile Gly Pro Leu Leu Asn Ile Gly Asn
        675                 680                 685

Asp Ile Arg His Gly Asp Phe Val Gly Ala Ile Glu Leu Ala Gly Ile
    690                 695                 700

Thr Ala Leu Leu Glu Tyr Val Pro Glu Phe Thr Ile Pro Ile Leu Val
705                 710                 715                 720

Gly Leu Glu Val Ile Gly Gly Glu Leu Ala Arg Glu Gln Val Glu Ala
                725                 730                 735

Ile Val Asn Asn Ala Leu Asp Lys Arg Asp Gln Lys Trp Ala Glu Val
            740                 745                 750

Tyr Asn Ile Thr Lys Ala Gln Trp Trp Gly Thr Ile His Leu Gln Ile
        755                 760                 765

Asn Thr Arg Leu Ala His Thr Tyr Lys Ala Leu Ser Arg Gln Ala Asn
    770                 775                 780

Ala Ile Lys Met Asn Met Glu Phe Gln Leu Ala Asn Tyr Lys Gly Asn
785                 790                 795                 800

Ile Asp Asp Lys Ala Lys Ile Lys Asn Ala Ile Ser Glu Thr Glu Ile
                805                 810                 815

Leu Leu Asn Lys Ser Val Glu Gln Ala Met Lys Asn Thr Glu Lys Phe
            820                 825                 830
```

-continued

```
Met Ile Lys Leu Ser Asn Ser Tyr Leu Thr Lys Glu Met Ile Pro Lys
        835                 840                 845

Val Gln Asp Asn Leu Lys Asn Phe Asp Leu Glu Thr Lys Lys Thr Leu
    850                 855                 860

Asp Lys Phe Ile Lys Glu Lys Glu Asp Ile Leu Gly Thr Asn Leu Ser
865                 870                 875                 880

Ser Ser Leu Arg Arg Lys Val Ser Ile Arg Leu Asn Lys Asn Ile Ala
                885                 890                 895

Phe Asp Ile Asn Asp Ile Pro Phe Ser Glu Phe Asp Asp Leu Ile Asn
                900                 905                 910

Gln Tyr Lys Asn Glu Ile Glu Asp Tyr Glu Val Leu Asn Leu Gly Ala
        915                 920                 925

Glu Asp Gly Lys Ile Lys Asp Leu Ser Gly Thr Thr Ser Asp Ile Asn
    930                 935                 940

Ile Gly Ser Asp Ile Glu Leu Ala Asp Gly Arg Glu Asn Lys Ala Ile
945                 950                 955                 960

Lys Ile Lys Gly Ser Glu Asn Ser Thr Ile Lys Ile Ala Met Asn Lys
                965                 970                 975

Tyr Leu Arg Phe Ser Ala Thr Asp Asn Phe Ser Ile Ser Phe Trp Ile
                980                 985                 990

Lys His Pro Lys Pro Thr Asn Leu  Leu Asn Asn Gly Ile  Glu Tyr Thr
            995                 1000                 1005

Leu Val  Glu Asn Phe Asn Gln  Arg Gly Trp Lys Ile  Ser Ile Gln
    1010                 1015                 1020

Asp Ser  Lys Leu Ile Trp Tyr  Leu Arg Asp His Asn  Asn Ser Ile
    1025                 1030                 1035

Lys Ile  Val Thr Pro Asp Tyr  Ile Ala Phe Asn Gly  Trp Asn Leu
    1040                 1045                 1050

Ile Thr  Ile Thr Asn Asn Arg  Ser Lys Gly Ser Ile  Val Tyr Val
    1055                 1060                 1065

Asn Gly  Ser Lys Ile Glu Glu  Lys Asp Ile Ser Ser  Ile Trp Asn
    1070                 1075                 1080

Thr Glu  Val Asp Asp Pro Ile  Ile Phe Arg Leu Lys  Asn Asn Arg
    1085                 1090                 1095

Asp Thr  Gln Ala Phe Thr Leu  Leu Asp Gln Phe Ser  Ile Tyr Arg
    1100                 1105                 1110

Lys Glu  Leu Asn Gln Asn Glu  Val Val Lys Leu Tyr  Asn Tyr Tyr
    1115                 1120                 1125

Phe Asn  Ser Asn Tyr Ile Arg  Asp Ile Trp Gly Asn  Pro Leu Gln
    1130                 1135                 1140

Tyr Asn  Lys Lys Tyr Tyr Leu  Gln Thr Gln Asp Lys  Pro Gly Lys
    1145                 1150                 1155

Gly Leu  Ile Arg Glu Tyr Trp  Ser Ser Phe Gly Tyr  Asp Tyr Val
    1160                 1165                 1170

Ile Leu  Ser Asp Ser Lys Thr  Ile Thr Phe Pro Asn  Asn Ile Arg
    1175                 1180                 1185

Tyr Gly  Ala Leu Tyr Asn Gly  Ser Lys Val Leu Ile  Lys Asn Ser
    1190                 1195                 1200

Lys Lys  Leu Asp Gly Leu Val  Arg Asn Lys Asp Phe  Ile Gln Leu
    1205                 1210                 1215

Glu Ile  Asp Gly Tyr Asn Met  Gly Ile Ser Ala Asp  Arg Phe Asn
    1220                 1225                 1230

Glu Asp  Thr Asn Tyr Ile Gly  Thr Thr Tyr Gly Thr  Thr His Asp
```

```
        1235              1240              1245

Leu Thr  Thr Asp Phe Glu Ile  Ile Gln Arg Gln Glu  Lys Tyr Arg
    1250              1255              1260

Asn Tyr  Cys Gln Leu Lys Thr  Pro Tyr Asn Ile Phe  His Lys Ser
    1265              1270              1275

Gly Leu  Met Ser Thr Glu Thr  Ser Lys Pro Thr Phe  His Asp Tyr
    1280              1285              1290

Arg Asp  Trp Val Tyr Ser Ser  Ala Trp Tyr Phe Gln  Asn Tyr Glu
    1295              1300              1305

Asn Leu  Asn Leu Arg Lys His  Thr Lys Thr Asn Trp  Tyr Phe Ile
    1310              1315              1320

Pro Lys  Asp Glu Gly Trp Asp  Glu Asp
    1325              1330

<210> SEQ ID NO 47
<211> LENGTH: 247
<212> TYPE: PRT
<213> ORGANISM: Artificial Sequence
<220> FEATURE:
<223> OTHER INFORMATION: Trypsin

<400> SEQUENCE: 47

Met His Pro Leu Leu Ile Leu Ala Phe Val Gly Ala Ala Val Ala Phe
1               5                   10                  15

Pro Ser Asp Asp Asp Asp Lys Ile Val Gly Gly Tyr Thr Cys Ala Glu
            20                  25                  30

Asn Ser Val Pro Tyr Gln Val Ser Leu Asn Ala Gly Tyr His Phe Cys
            35                  40                  45

Gly Gly Ser Leu Ile Asn Asp Gln Trp Val Val Ser Ala Ala His Cys
        50                  55                  60

Tyr Gln Tyr His Ile Gln Val Arg Leu Gly Glu Tyr Asn Ile Asp Val
65                  70                  75                  80

Leu Glu Gly Gly Glu Gln Phe Ile Asp Ala Ser Lys Ile Ile Arg His
                85                  90                  95

Pro Lys Tyr Ser Ser Trp Thr Leu Asp Asn Asp Ile Leu Leu Ile Lys
            100                 105                 110

Leu Ser Thr Pro Ala Val Ile Asn Ala Arg Val Ser Thr Leu Ala Leu
            115                 120                 125

Pro Ser Ala Cys Ala Ser Gly Ser Thr Glu Cys Leu Ile Ser Gly Trp
        130                 135                 140

Gly Asn Thr Leu Ser Ser Gly Val Asn Tyr Pro Asp Leu Leu Gln Cys
145                 150                 155                 160

Leu Glu Ala Pro Leu Leu Ser His Ala Asp Cys Glu Ala Ser Tyr Pro
                165                 170                 175

Gly Glu Ile Thr Asn Asn Met Ile Cys Ala Gly Phe Leu Glu Gly Gly
            180                 185                 190

Lys Asp Ser Cys Gln Gly Asp Ser Gly Gly Pro Val Ala Cys Asn Gly
            195                 200                 205

Gln Leu Gln Gly Ile Val Ser Trp Gly Tyr Gly Cys Ala Gln Lys Gly
        210                 215                 220

Lys Pro Gly Val Tyr Thr Lys Val Cys Asn Tyr Val Asp Trp Ile Gln
225                 230                 235                 240

Glu Thr Ile Ala Ala Asn Ser
                245
```

```
<210> SEQ ID NO 48
<211> LENGTH: 269
<212> TYPE: PRT
<213> ORGANISM: Artificial Sequence
<220> FEATURE:
<223> OTHER INFORMATION: Lys-C

<400> SEQUENCE: 48

Gly Val Ser Gly Ser Cys Asn Ile Asp Val Val Cys Pro Glu Gly Asn
1               5                   10                  15

Gly His Arg Asp Val Ile Arg Ser Val Ala Ala Tyr Ser Lys Gln Gly
                20                  25                  30

Thr Met Trp Cys Thr Gly Ser Leu Val Asn Asn Ser Ala Asn Asp Lys
            35                  40                  45

Lys Met Tyr Phe Leu Thr Ala Asn His Cys Gly Met Thr Thr Ala Ala
        50                  55                  60

Ile Ala Ser Ser Met Val Val Tyr Trp Asn Tyr Gln Asn Ser Thr Cys
65                  70                  75                  80

Arg Ala Pro Gly Ser Ser Ser Gly Ala Asn Gly Asp Gly Ser Leu
                85                  90                  95

Ala Gln Ser Gln Thr Gly Ala Val Val Arg Ala Thr Asn Ala Ala Ser
                100                 105                 110

Asp Phe Thr Leu Leu Glu Leu Asn Thr Ala Ala Asn Pro Ala Tyr Asn
            115                 120                 125

Leu Phe Trp Ala Gly Trp Asp Arg Arg Asp Gln Asn Phe Ala Gly Ala
        130                 135                 140

Thr Ala Ile His His Pro Asn Val Ala Glu Lys Arg Ile Ser His Ser
145                 150                 155                 160

Thr Val Ala Thr Glu Ile Ser Gly Tyr Asn Gly Ala Thr Gly Thr Ser
                165                 170                 175

His Leu His Val Phe Trp Gln Ala Ser Gly Gly Val Thr Glu Pro Gly
            180                 185                 190

Ser Ser Gly Ser Pro Ile Tyr Ser Pro Glu Lys Arg Val Leu Gly Gln
            195                 200                 205

Leu His Gly Gly Pro Ser Ser Cys Ser Ala Thr Gly Ala Asp Arg Ser
        210                 215                 220

Asp Tyr Tyr Gly Arg Val Phe Thr Ser Trp Thr Gly Gly Gly Thr Ser
225                 230                 235                 240

Ala Thr Arg Leu Ser Asp Trp Leu Asp Ala Ala Gly Thr Gly Ala Gln
                245                 250                 255

Phe Ile Asp Gly Leu Asp Ser Thr Gly Thr Pro Pro Val
            260                 265

<210> SEQ ID NO 49
<211> LENGTH: 235
<212> TYPE: PRT
<213> ORGANISM: Artificial Sequence
<220> FEATURE:
<223> OTHER INFORMATION: Enterokinase Light Chain

<400> SEQUENCE: 49

Ile Val Gly Gly Ser Asp Ser Arg Glu Gly Ala Trp Pro Trp Val Val
1               5                   10                  15

Ala Leu Tyr Phe Asp Asp Gln Gln Val Cys Gly Ala Ser Leu Val Ser
                20                  25                  30

Arg Asp Trp Leu Val Ser Ala Ala His Cys Val Tyr Gly Arg Asn Met
        35                  40                  45
```

-continued

```
Glu Pro Ser Lys Trp Lys Ala Val Leu Gly Leu His Met Ala Ser Asn
50          55              60

Leu Thr Ser Pro Gln Ile Glu Thr Arg Leu Ile Asp Gln Ile Val Ile
65              70              75              80

Asn Arg His Tyr Asn Lys Arg Arg Lys Asn Asn Asp Ile Ala Met Met
                85              90              95

His Leu Glu Met Lys Val Asn Tyr Thr Asp Tyr Ile Gln Pro Ile Cys
            100             105             110

Leu Pro Glu Glu Asn Gln Val Phe Pro Pro Gly Arg Ile Cys Ser Ile
            115             120             125

Ala Gly Trp Gly Ala Leu Ile Tyr Gln Gly Ser Thr Ala Asp Val Leu
            130             135             140

Gln Glu Ala Asp Val Pro Leu Leu Ser Asn Glu Lys Cys Gln Gln Gln
145             150             155             160

Met Pro Glu Tyr Asn Ile Thr Glu Asn Met Val Cys Ala Gly Tyr Asp
                165             170             175

Ala Gly Gly Val Asp Ser Cys Gln Gly Asp Ser Gly Gly Pro Leu Met
            180             185             190

Cys Gln Glu Asn Asn Arg Trp Leu Leu Ala Gly Val Thr Ser Phe Gly
            195             200             205

Tyr Gln Cys Ala Leu Pro Asn Arg Pro Gly Val Tyr Ala Arg Val Pro
    210             215             220

Arg Phe Thr Glu Trp Ile Gln Ser Phe Leu His
225             230             235
```

```
<210> SEQ ID NO 50
<211> LENGTH: 259
<212> TYPE: PRT
<213> ORGANISM: Artificial Sequence
<220> FEATURE:
<223> OTHER INFORMATION: Factor Xa Heavy Chain

<400> SEQUENCE: 50
```

```
Ile Val Gly Gly Arg Asp Cys Ala Glu Gly Glu Cys Pro Trp Gln Ala
1               5               10              15

Leu Leu Val Asn Glu Glu Asn Glu Gly Phe Cys Gly Gly Thr Ile Leu
                20              25              30

Asn Glu Phe Tyr Val Leu Thr Ala Ala His Cys Leu His Gln Ala Lys
            35              40              45

Arg Phe Thr Val Arg Val Gly Asp Arg Asn Thr Glu Gln Glu Glu Gly
    50              55              60

Asn Glu Met Ala His Glu Val Glu Met Thr Val Lys His Ser Arg Phe
65              70              75              80

Val Lys Glu Thr Tyr Asp Phe Asp Ile Ala Val Leu Arg Leu Lys Thr
                85              90              95

Pro Ile Arg Phe Arg Arg Asn Val Ala Pro Ala Cys Leu Pro Glu Lys
            100             105             110

Asp Trp Ala Glu Ala Thr Leu Met Thr Gln Lys Thr Gly Ile Val Ser
            115             120             125

Gly Phe Gly Arg Thr His Glu Lys Gly Arg Leu Ser Ser Thr Leu Lys
            130             135             140

Met Leu Glu Val Pro Tyr Val Asp Arg Ser Thr Cys Lys Leu Ser Ser
145             150             155             160

Ser Phe Thr Ile Thr Pro Asn Met Phe Cys Ala Gly Tyr Asp Thr Gln
                165             170             175
```

-continued

```
Pro Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
            195                 200                 205

Cys Ala Arg Lys Gly Lys Phe Gly Val Tyr Thr Lys Val Ser Asn Phe
            210                 215                 220

Leu Lys Trp Ile Asp Lys Ile Met Lys Ala Arg Ala Gly Ala Ala Gly
225                 230                 235                 240

Ser Arg Gly His Ser Glu Ala Pro Ala Thr Trp Thr Val Pro Pro Pro
            245                 250                 255

Leu Pro Leu

<210> SEQ ID NO 51
<211> LENGTH: 140
<212> TYPE: PRT
<213> ORGANISM: Artificial Sequence
<220> FEATURE:
<223> OTHER INFORMATION: Factor Xa Light Chain

<400> SEQUENCE: 51

Ala Asn Ser Phe Leu Glu Glu Val Lys Gln Gly Asn Leu Glu Arg Glu
1               5                   10                  15

Cys Leu Glu Glu Ala Cys Ser Leu Glu Glu Ala Arg Glu Val Phe Glu
            20                  25                  30

Asp Ala Glu Gln Thr Asp Glu Phe Trp Ser Lys Tyr Lys Asp Gly Asp
            35                  40                  45

Gln Cys Glu Gly His Pro Cys Leu Asn Gln Gly His Cys Lys Asp Gly
    50                  55                  60

Ile Gly Asp Tyr Thr Cys Thr Cys Ala Glu Gly Phe Glu Gly Lys Asn
65                  70                  75                  80

Cys Glu Phe Ser Thr Arg Glu Ile Cys Ser Leu Asp Asn Gly Gly Cys
                85                  90                  95

Asp Gln Phe Cys Arg Glu Glu Arg Ser Glu Val Arg Cys Ser Cys Ala
            100                 105                 110

His Gly Tyr Val Leu Gly Asp Asp Ser Lys Ser Cys Val Ser Thr Glu
            115                 120                 125

Arg Phe Pro Cys Gly Lys Phe Thr Gln Gly Arg Ser
            130                 135                 140

<210> SEQ ID NO 52
<211> LENGTH: 764
<212> TYPE: PRT
<213> ORGANISM: Bacillus anthracis

<400> SEQUENCE: 52

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
            35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95
```

-continued

```
Phe Ile Lys Val Lys Lys Ser Asp Glu Tyr Thr Phe Ala Thr Ser Ala
        100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
        130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
        180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
        210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
                260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
        290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
                340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
        370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
                420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
        450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
        500                 505                 510
```

```
Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
        530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
                580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
        610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
                660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
        690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
                740                 745                 750

Ile Leu Ile Phe Ser Lys Lys Gly Tyr Glu Ile Gly
                755                 760
```

<210> SEQ ID NO 53
<211> LENGTH: 863
<212> TYPE: PRT
<213> ORGANISM: Artificial Sequence
<220> FEATURE:
<223> OTHER INFORMATION: LHN/A with a C1 Activation Loop

<400> SEQUENCE: 53

```
Met Pro Phe Val Asn Lys Gln Phe Asn Tyr Lys Asp Pro Val Asn Gly
1                   5                   10                  15

Val Asp Ile Ala Tyr Ile Lys Ile Pro Asn Val Gly Gln Met Gln Pro
                20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110
```

-continued

```
Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
                195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys His Lys
                420                 425                 430

Ala Ile Asp Gly Arg Ser Leu Tyr Asn Lys Thr Leu Asp Cys Ile Lys
        435                 440                 445

Val Asn Asn Trp Asp Leu Phe Phe Ser Pro Ser Glu Asp Asn Phe Thr
        450                 455                 460

Asn Asp Leu Asn Lys Gly Glu Glu Ile Thr Ser Asp Thr Asn Ile Glu
465                 470                 475                 480

Ala Ala Glu Glu Asn Ile Ser Leu Asp Leu Ile Gln Gln Tyr Tyr Leu
                485                 490                 495

Thr Phe Asn Phe Asp Asn Glu Pro Glu Asn Ile Ser Ile Glu Asn Leu
                500                 505                 510

Ser Ser Asp Ile Ile Gly Gln Leu Glu Leu Met Pro Asn Ile Glu Arg
        515                 520                 525

Phe Pro Asn Gly Lys Lys Tyr Glu Leu Asp Lys Tyr Thr Met Phe His
```

-continued

```
                530             535             540

Tyr Leu Arg Ala Gln Glu Phe Glu His Gly Lys Ser Arg Ile Ala Leu
545             550             555             560

Thr Asn Ser Val Asn Glu Ala Leu Leu Asn Pro Ser Arg Val Tyr Thr
                565             570             575

Phe Phe Ser Ser Asp Tyr Val Lys Lys Val Asn Lys Ala Thr Glu Ala
                580             585             590

Ala Met Phe Leu Gly Trp Val Glu Gln Leu Val Tyr Asp Phe Thr Asp
                595             600             605

Glu Thr Ser Glu Val Ser Thr Thr Asp Lys Ile Ala Asp Ile Thr Ile
        610             615             620

Ile Ile Pro Tyr Ile Gly Pro Ala Leu Asn Ile Gly Asn Met Leu Tyr
625             630             635             640

Lys Asp Asp Phe Val Gly Ala Leu Ile Phe Ser Gly Ala Val Ile Leu
                645             650             655

Leu Glu Phe Ile Pro Glu Ile Ala Ile Pro Val Leu Gly Thr Phe Ala
                660             665             670

Leu Val Ser Tyr Ile Ala Asn Lys Val Leu Thr Val Gln Thr Ile Asp
                675             680             685

Asn Ala Leu Ser Lys Arg Asn Glu Lys Trp Asp Glu Val Tyr Lys Tyr
        690             695             700

Ile Val Thr Asn Trp Leu Ala Lys Val Asn Thr Gln Ile Asp Leu Ile
705             710             715             720

Arg Lys Lys Met Lys Glu Ala Leu Glu Asn Gln Ala Glu Ala Thr Lys
                725             730             735

Ala Ile Ile Asn Tyr Gln Tyr Asn Gln Tyr Thr Glu Glu Glu Lys Asn
                740             745             750

Asn Ile Asn Phe Asn Ile Asp Asp Leu Ser Ser Lys Leu Asn Glu Ser
                755             760             765

Ile Asn Lys Ala Met Ile Asn Ile Asn Lys Phe Leu Asn Gln Cys Ser
        770             775             780

Val Ser Tyr Leu Met Asn Ser Met Ile Pro Tyr Gly Val Lys Arg Leu
785             790             795             800

Glu Asp Phe Asp Ala Ser Leu Lys Asp Ala Leu Leu Lys Tyr Ile Tyr
                805             810             815

Asp Asn Arg Gly Thr Leu Ile Gly Gln Val Asp Arg Leu Lys Asp Lys
                820             825             830

Val Asn Asn Thr Leu Ser Thr Asp Ile Pro Phe Gln Leu Ser Lys Tyr
                835             840             845

Val Asp Asn Gln Arg Leu Leu Ser Thr Phe Thr Glu Tyr Ile Lys
        850             855             860
```

<210> SEQ ID NO 54
<211> LENGTH: 865
<212> TYPE: PRT
<213> ORGANISM: Artificial Sequence
<220> FEATURE:
<223> OTHER INFORMATION: LHN/B with a C1 Activation Loop

<400> SEQUENCE: 54

```
Met Pro Val Thr Ile Asn Asn Phe Asn Tyr Asn Asp Pro Ile Asp Asn
1               5               10              15

Asn Asn Ile Ile Met Met Glu Pro Pro Phe Ala Arg Gly Thr Gly Arg
                20              25              30

Tyr Tyr Lys Ala Phe Lys Ile Thr Asp Arg Ile Trp Ile Ile Pro Glu
```

-continued

```
                35              40                45

Arg Tyr Thr Phe Gly Tyr Lys Pro Glu Asp Phe Asn Lys Ser Ser Gly
    50              55              60

Ile Phe Asn Arg Asp Val Cys Glu Tyr Tyr Asp Pro Asp Tyr Leu Asn
65              70              75              80

Thr Asn Asp Lys Lys Asn Ile Phe Leu Gln Thr Met Ile Lys Leu Phe
                85              90              95

Asn Arg Ile Lys Ser Lys Pro Leu Gly Glu Lys Leu Leu Glu Met Ile
            100             105             110

Ile Asn Gly Ile Pro Tyr Leu Gly Asp Arg Arg Val Pro Leu Glu Glu
            115             120             125

Phe Asn Thr Asn Ile Ala Ser Val Thr Val Asn Lys Leu Ile Ser Asn
    130             135             140

Pro Gly Glu Val Glu Arg Lys Lys Gly Ile Phe Ala Asn Leu Ile Ile
145             150             155             160

Phe Gly Pro Gly Pro Val Leu Asn Glu Asn Glu Thr Ile Asp Ile Gly
            165             170             175

Ile Gln Asn His Phe Ala Ser Arg Glu Gly Phe Gly Gly Ile Met Gln
            180             185             190

Met Lys Phe Cys Pro Glu Tyr Val Ser Val Phe Asn Asn Val Gln Glu
            195             200             205

Asn Lys Gly Ala Ser Ile Phe Asn Arg Arg Gly Tyr Phe Ser Asp Pro
    210             215             220

Ala Leu Ile Leu Met His Glu Leu Ile His Val Leu His Gly Leu Tyr
225             230             235             240

Gly Ile Lys Val Asp Asp Leu Pro Ile Val Pro Asn Glu Lys Lys Phe
            245             250             255

Phe Met Gln Ser Thr Asp Ala Ile Gln Ala Glu Glu Leu Tyr Thr Phe
            260             265             270

Gly Gly Gln Asp Pro Ser Ile Ile Thr Pro Ser Thr Asp Lys Ser Ile
            275             280             285

Tyr Asp Lys Val Leu Gln Asn Phe Arg Gly Ile Val Asp Arg Leu Asn
    290             295             300

Lys Val Leu Val Cys Ile Ser Asp Pro Asn Ile Asn Ile Asn Ile Tyr
305             310             315             320

Lys Asn Lys Phe Lys Asp Lys Tyr Lys Phe Val Glu Asp Ser Glu Gly
            325             330             335

Lys Tyr Ser Ile Asp Val Glu Ser Phe Asp Lys Leu Tyr Lys Ser Leu
            340             345             350

Met Phe Gly Phe Thr Glu Thr Asn Ile Ala Glu Asn Tyr Lys Ile Lys
            355             360             365

Thr Arg Ala Ser Tyr Phe Ser Asp Ser Leu Pro Pro Val Lys Ile Lys
    370             375             380

Asn Leu Leu Asp Asn Glu Ile Tyr Thr Ile Glu Glu Gly Phe Asn Ile
385             390             395             400

Ser Asp Lys Asp Met Glu Lys Glu Tyr Arg Gly Gln Asn Lys Ala Ile
            405             410             415

Asn Lys Gln Ala Tyr Glu Glu Ile Ser Lys Glu His Leu Ala Val Tyr
            420             425             430

Lys Ile Gln Met Cys His Lys Ala Ile Asp Gly Arg Ser Leu Tyr Asn
            435             440             445

Lys Thr Leu Asp Cys Ile Asp Val Asp Asn Glu Asp Leu Phe Phe Ile
    450             455             460
```

-continued

```
Ala Asp Lys Asn Ser Phe Ser Asp Asp Leu Ser Lys Asn Glu Arg Ile
465                 470                 475                 480

Glu Tyr Asn Thr Gln Ser Asn Tyr Ile Glu Asn Asp Phe Pro Ile Asn
                    485                 490                 495

Glu Leu Ile Leu Asp Thr Asp Leu Ile Ser Lys Ile Glu Leu Pro Ser
                500                 505                 510

Glu Asn Thr Glu Ser Leu Thr Asp Phe Asn Val Asp Val Pro Val Tyr
                515                 520                 525

Glu Lys Gln Pro Ala Ile Lys Lys Ile Phe Thr Asp Glu Asn Thr Ile
                530                 535                 540

Phe Gln Tyr Leu Tyr Ser Gln Thr Phe Pro Leu Asp Ile Arg Asp Ile
545                 550                 555                 560

Ser Leu Thr Ser Ser Phe Asp Asp Ala Leu Leu Phe Ser Asn Lys Val
                565                 570                 575

Tyr Ser Phe Phe Ser Met Asp Tyr Ile Lys Thr Ala Asn Lys Val Val
                580                 585                 590

Glu Ala Gly Leu Phe Ala Gly Trp Val Lys Gln Ile Val Asn Asp Phe
                595                 600                 605

Val Ile Glu Ala Asn Lys Ser Asn Thr Met Asp Lys Ile Ala Asp Ile
                610                 615                 620

Ser Leu Ile Val Pro Tyr Ile Gly Leu Ala Leu Asn Val Gly Asn Glu
625                 630                 635                 640

Thr Ala Lys Gly Asn Phe Glu Asn Ala Phe Glu Ile Ala Gly Ala Ser
                645                 650                 655

Ile Leu Leu Glu Phe Ile Pro Glu Leu Leu Ile Pro Val Val Gly Ala
                660                 665                 670

Phe Leu Leu Glu Ser Tyr Ile Asp Asn Lys Asn Lys Ile Ile Lys Thr
                675                 680                 685

Ile Asp Asn Ala Leu Thr Lys Arg Asn Glu Lys Trp Ser Asp Met Tyr
    690                 695                 700

Gly Leu Ile Val Ala Gln Trp Leu Ser Thr Val Asn Thr Gln Phe Tyr
705                 710                 715                 720

Thr Ile Lys Glu Gly Met Tyr Lys Ala Leu Asn Tyr Gln Ala Gln Ala
                725                 730                 735

Leu Glu Glu Ile Ile Lys Tyr Arg Tyr Asn Ile Tyr Ser Glu Lys Glu
                740                 745                 750

Lys Ser Asn Ile Asn Ile Asp Phe Asn Asp Ile Asn Ser Lys Leu Asn
                755                 760                 765

Glu Gly Ile Asn Gln Ala Ile Asp Asn Ile Asn Asn Phe Ile Asn Gly
                770                 775                 780

Cys Ser Val Ser Tyr Leu Met Lys Lys Met Ile Pro Leu Ala Val Glu
785                 790                 795                 800

Lys Leu Leu Asp Phe Asp Asn Thr Leu Lys Lys Asn Leu Leu Asn Tyr
                805                 810                 815

Ile Asp Glu Asn Lys Leu Tyr Leu Ile Gly Ser Ala Glu Tyr Glu Lys
                820                 825                 830

Ser Lys Val Asn Lys Tyr Leu Lys Thr Ile Met Pro Phe Asp Leu Ser
                835                 840                 845

Ile Tyr Thr Asn Asp Thr Ile Leu Ile Glu Met Phe Asn Lys Tyr Asn
    850                 855                 860

Ser
865
```

-continued

```
<210> SEQ ID NO 55
<211> LENGTH: 865
<212> TYPE: PRT
<213> ORGANISM: Artificial Sequence
<220> FEATURE:
<223> OTHER INFORMATION: LHN/D with a C1 Activation Loop

<400> SEQUENCE: 55

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
        50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365
```

-continued

```
Val Lys Asn Arg Thr His Tyr Phe Ser Arg His Tyr Leu Pro Val Phe
    370             375             380

Ala Asn Ile Leu Asp Asp Asn Ile Tyr Thr Ile Arg Asp Gly Phe Asn
385             390             395             400

Leu Thr Asn Lys Gly Phe Asn Ile Glu Asn Ser Gly Gln Asn Ile Glu
            405             410             415

Arg Asn Pro Ala Leu Gln Lys Leu Ser Ser Glu Ser Val Val Asp Leu
            420             425             430

Phe Thr Lys Val Cys His Lys Ala Ile Asp Gly Arg Ser Leu Tyr Asn
        435             440             445

Lys Thr Leu Asp Cys Ile Lys Val Lys Asn Asn Arg Leu Pro Tyr Val
    450             455             460

Ala Asp Lys Asp Ser Ile Ser Gln Glu Ile Phe Glu Asn Lys Ile Ile
465             470             475             480

Thr Asp Glu Thr Asn Val Gln Asn Tyr Ser Asp Lys Phe Ser Leu Asp
            485             490             495

Glu Ser Ile Leu Asp Gly Gln Val Pro Ile Asn Pro Glu Ile Val Asp
            500             505             510

Pro Leu Leu Pro Asn Val Asn Met Glu Pro Leu Asn Leu Pro Gly Glu
        515             520             525

Glu Ile Val Phe Tyr Asp Asp Ile Thr Lys Tyr Val Asp Tyr Leu Asn
    530             535             540

Ser Tyr Tyr Tyr Leu Glu Ser Gln Lys Leu Ser Asn Asn Val Glu Asn
545             550             555             560

Ile Thr Leu Thr Thr Ser Val Glu Glu Ala Leu Gly Tyr Ser Asn Lys
            565             570             575

Ile Tyr Thr Phe Leu Pro Ser Leu Ala Glu Lys Val Asn Lys Gly Val
            580             585             590

Gln Ala Gly Leu Phe Leu Asn Trp Ala Asn Glu Val Val Glu Asp Phe
        595             600             605

Thr Thr Asn Ile Met Lys Lys Asp Thr Leu Asp Lys Ile Ser Asp Val
    610             615             620

Ser Val Ile Ile Pro Tyr Ile Gly Pro Ala Leu Asn Ile Gly Asn Ser
625             630             635             640

Ala Leu Arg Gly Asn Phe Asn Gln Ala Phe Ala Thr Ala Gly Val Ala
            645             650             655

Phe Leu Leu Glu Gly Phe Pro Glu Phe Thr Ile Pro Ala Leu Gly Val
            660             665             670

Phe Thr Phe Tyr Ser Ser Ile Gln Glu Arg Glu Lys Ile Ile Lys Thr
        675             680             685

Ile Glu Asn Cys Leu Glu Gln Arg Val Lys Arg Trp Lys Asp Ser Tyr
    690             695             700

Gln Trp Met Val Ser Asn Trp Leu Ser Arg Ile Thr Thr Gln Phe Asn
705             710             715             720

His Ile Asn Tyr Gln Met Tyr Asp Ser Leu Ser Tyr Gln Ala Asp Ala
            725             730             735

Ile Lys Ala Lys Ile Asp Leu Glu Tyr Lys Lys Tyr Ser Gly Ser Asp
            740             745             750

Lys Glu Asn Ile Lys Ser Gln Val Glu Asn Leu Lys Asn Ser Leu Asp
        755             760             765

Val Lys Ile Ser Glu Ala Met Asn Asn Ile Asn Lys Phe Ile Arg Glu
    770             775             780

Cys Ser Val Thr Tyr Leu Phe Lys Asn Met Leu Pro Lys Val Ile Asp
```

-continued

```
785               790               795               800
Glu Leu Asn Lys Phe Asp Leu Arg Thr Lys Thr Glu Leu Ile Asn Leu
              805               810               815

Ile Asp Ser His Asn Ile Ile Leu Val Gly Glu Val Asp Arg Leu Lys
              820               825               830

Ala Lys Val Asn Glu Ser Phe Glu Asn Thr Met Pro Phe Asn Ile Phe
              835               840               845

Ser Tyr Thr Asn Ser Leu Leu Lys Asp Ile Ile Asn Glu Tyr Phe
    850               855               860

Asn
865
```

```
<210> SEQ ID NO 56
<211> LENGTH: 847
<212> TYPE: PRT
<213> ORGANISM: Artificial Sequence
<220> FEATURE:
<223> OTHER INFORMATION: LHN/E with a C1 Activation Loop

<400> SEQUENCE: 56
```

```
Met Pro Lys Ile Asn Ser Phe Asn Tyr Asn Asp Pro Val Asn Asp Arg
1               5               10               15

Thr Ile Leu Tyr Ile Lys Pro Gly Gly Cys Gln Glu Phe Tyr Lys Ser
              20               25               30

Phe Asn Ile Met Lys Asn Ile Trp Ile Ile Pro Glu Arg Asn Val Ile
              35               40               45

Gly Thr Thr Pro Gln Asp Phe His Pro Pro Thr Ser Leu Lys Asn Gly
    50               55               60

Asp Ser Ser Tyr Tyr Asp Pro Asn Tyr Leu Gln Ser Asp Glu Glu Lys
65               70               75               80

Asp Arg Phe Leu Lys Ile Val Thr Lys Ile Phe Asn Arg Ile Asn Asn
              85               90               95

Asn Leu Ser Gly Gly Ile Leu Leu Glu Glu Leu Ser Lys Ala Asn Pro
              100               105               110

Tyr Leu Gly Asn Asp Asn Thr Pro Asp Asn Gln Phe His Ile Gly Asp
              115               120               125

Ala Ser Ala Val Glu Ile Lys Phe Ser Asn Gly Ser Gln Asp Ile Leu
    130               135               140

Leu Pro Asn Val Ile Ile Met Gly Ala Glu Pro Asp Leu Phe Glu Thr
145               150               155               160

Asn Ser Ser Asn Ile Ser Leu Arg Asn Asn Tyr Met Pro Ser Asn His
              165               170               175

Arg Phe Gly Ser Ile Ala Ile Val Thr Phe Ser Pro Glu Tyr Ser Phe
              180               185               190

Arg Phe Asn Asp Asn Cys Met Asn Glu Phe Ile Gln Asp Pro Ala Leu
              195               200               205

Thr Leu Met His Glu Leu Ile His Ser Leu His Gly Leu Tyr Gly Ala
    210               215               220

Lys Gly Ile Thr Thr Lys Tyr Thr Ile Thr Gln Lys Gln Asn Pro Leu
225               230               235               240

Ile Thr Asn Ile Arg Gly Thr Asn Ile Glu Glu Phe Leu Thr Phe Gly
              245               250               255

Gly Thr Asp Leu Asn Ile Ile Thr Ser Ala Gln Ser Asn Asp Ile Tyr
              260               265               270

Thr Asn Leu Leu Ala Asp Tyr Lys Lys Ile Ala Ser Lys Leu Ser Lys
```

```
              275                    280                    285

Val Gln Val Ser Asn Pro Leu Leu Asn Pro Tyr Lys Asp Val Phe Glu
    290                    295                    300

Ala Lys Tyr Gly Leu Asp Lys Asp Ala Ser Gly Ile Tyr Ser Val Asn
305                    310                    315                    320

Ile Asn Lys Phe Asn Asp Ile Phe Lys Lys Leu Tyr Ser Phe Thr Glu
                   325                    330                    335

Phe Asp Leu Arg Thr Lys Phe Gln Val Lys Cys Arg Gln Thr Tyr Ile
                   340                    345                    350

Gly Gln Tyr Lys Tyr Phe Lys Leu Ser Asn Leu Leu Asn Asp Ser Ile
                   355                    360                    365

Tyr Asn Ile Ser Glu Gly Tyr Asn Ile Asn Asn Leu Lys Val Asn Phe
    370                    375                    380

Arg Gly Gln Asn Ala Asn Leu Asn Pro Arg Ile Ile Thr Pro Ile Thr
385                    390                    395                    400

Gly Arg Gly Leu Val Lys Lys Ile Ile Arg Phe Cys His Lys Ala Ile
                   405                    410                    415

Asp Gly Arg Ser Leu Tyr Asn Lys Thr Leu Asp Cys Ile Glu Ile Asn
                   420                    425                    430

Asn Gly Glu Leu Phe Phe Val Ala Ser Glu Asn Ser Tyr Asn Asp Asp
              435                    440                    445

Asn Ile Asn Thr Pro Lys Glu Ile Asp Asp Thr Val Thr Ser Asn Asn
    450                    455                    460

Asn Tyr Glu Asn Asp Leu Asp Gln Val Ile Leu Asn Phe Asn Ser Glu
465                    470                    475                    480

Ser Ala Pro Gly Leu Ser Asp Glu Lys Leu Asn Leu Thr Ile Gln Asn
                   485                    490                    495

Asp Ala Tyr Ile Pro Lys Tyr Asp Ser Asn Gly Thr Ser Asp Ile Glu
                   500                    505                    510

Gln His Asp Val Asn Glu Leu Asn Val Phe Phe Tyr Leu Asp Ala Gln
              515                    520                    525

Lys Val Pro Glu Gly Glu Asn Asn Val Asn Leu Thr Ser Ser Ile Asp
    530                    535                    540

Thr Ala Leu Leu Glu Gln Pro Lys Ile Tyr Thr Phe Phe Ser Ser Glu
545                    550                    555                    560

Phe Ile Asn Asn Val Asn Lys Pro Val Gln Ala Ala Leu Phe Val Ser
                   565                    570                    575

Trp Ile Gln Gln Val Leu Val Asp Phe Thr Thr Glu Ala Asn Gln Lys
                   580                    585                    590

Ser Thr Val Asp Lys Ile Ala Asp Ile Ser Ile Val Val Pro Tyr Ile
                   595                    600                    605

Gly Leu Ala Leu Asn Ile Gly Asn Glu Ala Gln Lys Gly Asn Phe Lys
    610                    615                    620

Asp Ala Leu Glu Leu Leu Gly Ala Gly Ile Leu Leu Glu Phe Glu Pro
625                    630                    635                    640

Glu Leu Leu Ile Pro Thr Ile Leu Val Phe Thr Ile Lys Ser Phe Leu
                   645                    650                    655

Gly Ser Ser Asp Asn Lys Asn Lys Val Ile Lys Ala Ile Asn Asn Ala
              660                    665                    670

Leu Lys Glu Arg Asp Glu Lys Trp Lys Glu Val Tyr Ser Phe Ile Val
              675                    680                    685

Ser Asn Trp Met Thr Lys Ile Asn Thr Gln Phe Asn Lys Arg Lys Glu
    690                    695                    700
```

-continued

```
Gln Met Tyr Gln Ala Leu Gln Asn Gln Val Asn Ala Ile Lys Thr Ile
705                 710                 715                 720

Ile Glu Ser Lys Tyr Asn Ser Tyr Thr Leu Glu Glu Lys Asn Glu Leu
                725                 730                 735

Thr Asn Lys Tyr Asp Ile Lys Gln Ile Glu Asn Glu Leu Asn Gln Lys
            740                 745                 750

Val Ser Ile Ala Met Asn Asn Ile Asp Arg Phe Leu Thr Glu Ser Ser
            755                 760                 765

Ile Ser Tyr Leu Met Lys Ile Ile Asn Glu Val Lys Ile Asn Lys Leu
        770                 775                 780

Arg Glu Tyr Asp Glu Asn Val Lys Thr Tyr Leu Leu Asn Tyr Ile Ile
785                 790                 795                 800

Gln His Gly Ser Ile Leu Gly Glu Ser Gln Gln Glu Leu Asn Ser Met
                805                 810                 815

Val Thr Asp Thr Leu Asn Asn Ser Ile Pro Phe Lys Leu Ser Ser Tyr
            820                 825                 830

Thr Asp Asp Lys Ile Leu Ile Ser Tyr Phe Asn Lys Phe Phe Lys
            835                 840                 845
```

<210> SEQ ID NO 57
<211> LENGTH: 864
<212> TYPE: PRT
<213> ORGANISM: Artificial Sequence
<220> FEATURE:
<223> OTHER INFORMATION: LHN/F with a C1 Activation Loop

<400> SEQUENCE: 57

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220
```

-continued

```
Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
                275                 280                 285

Asn Leu Leu Ala Asn Tyr Glu Lys Ile Ala Thr Arg Leu Ser Arg Val
                290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
                340                 345                 350

Glu Ile Asp Leu Ala Asn Lys Phe Lys Val Lys Cys Arg Asn Thr Tyr
                355                 360                 365

Phe Ile Lys Tyr Gly Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys His Lys Ala
                420                 425                 430

Ile Asp Gly Arg Ser Leu Tyr Asn Lys Thr Leu Asp Cys Ile Arg Val
                435                 440                 445

Asn Asn Arg Glu Leu Phe Phe Val Ala Ser Glu Ser Ser Tyr Asn Glu
                450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
                500                 505                 510

Asp Asp Ser Tyr Val Pro Arg Tyr Asp Ser Asn Gly Thr Ser Glu Ile
                515                 520                 525

Glu Glu His Asn Val Val Asp Leu Asn Val Phe Phe Tyr Leu His Ala
                530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
                580                 585                 590

Ser Trp Ile Asn Gln Val Ile Arg Asp Phe Thr Thr Glu Ala Thr Gln
                595                 600                 605

Lys Ser Thr Phe Asp Lys Ile Ala Asp Ile Ser Leu Val Val Pro Tyr
                610                 615                 620

Val Gly Leu Ala Leu Asn Ile Gly Asn Glu Val Gln Lys Glu Asn Phe
625                 630                 635                 640
```

```
Lys Glu Ala Phe Glu Leu Leu Gly Ala Gly Ile Leu Leu Glu Phe Val
                645                 650                 655

Pro Glu Leu Leu Ile Pro Thr Ile Leu Val Phe Thr Ile Lys Ser Phe
                660                 665                 670

Ile Gly Ser Ser Glu Asn Lys Asn Lys Ile Ile Lys Ala Ile Asn Asn
                675                 680                 685

Ser Leu Met Glu Arg Glu Thr Lys Trp Lys Glu Ile Tyr Ser Trp Ile
        690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Asn Tyr Thr Ser Asp Glu Arg Asn Arg
                740                 745                 750

Leu Glu Ser Glu Tyr Asn Ile Asn Asn Ile Arg Glu Glu Leu Asn Lys
                755                 760                 765

Lys Val Ser Leu Ala Met Glu Asn Ile Glu Arg Phe Ile Thr Glu Ser
        770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
                805                 810                 815

Ser Glu His Arg Ser Ile Leu Gly Asn Ser Val Gln Glu Leu Asn Asp
                820                 825                 830

Leu Val Thr Ser Thr Leu Asn Asn Ser Ile Pro Phe Glu Leu Ser Ser
                835                 840                 845

Tyr Thr Asn Asp Lys Ile Leu Ile Leu Tyr Phe Asn Lys Leu Tyr Lys
        850                 855                 860
```

```
<210> SEQ ID NO 58
<211> LENGTH: 865
<212> TYPE: PRT
<213> ORGANISM: Artificial Sequence
<220> FEATURE:
<223> OTHER INFORMATION: LHN/G with a C1 Activation Loop
<220> FEATURE:
<221> NAME/KEY: SITE
<222> LOCATION: (7)..(7)
<223> OTHER INFORMATION: Xaa can be any naturally occurring amino acid

<400> SEQUENCE: 58
```

```
Met Pro Val Asn Ile Lys Xaa Phe Asn Tyr Asn Asp Pro Ile Asn Asn
1                   5                   10                  15

Asp Asp Ile Ile Met Met Glu Pro Phe Asn Asp Pro Gly Pro Gly Thr
                20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
        50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
                100                 105                 110

Val Asp Ala Ile Pro Tyr Leu Gly Asn Ala Ser Thr Pro Pro Asp Lys
                115                 120                 125
```

```
Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
                180                 185                 190

Ile Arg Phe Cys Pro Ser Cys Leu Asn Val Phe Asn Asn Val Gln Glu
                195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
                260                 265                 270

Gly Gly His Asp Pro Ser Val Ile Ser Pro Ser Thr Asp Met Asn Ile
                275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
                340                 345                 350

Phe Gly Phe Thr Glu Thr Asn Leu Ala Gly Glu Tyr Gly Ile Lys Thr
                355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
                420                 425                 430

Ile Ala Met Cys His Lys Ala Ile Asp Gly Arg Ser Leu Tyr Asn Lys
                435                 440                 445

Thr Leu Asp Cys Ile Ile Val Asn Asn Glu Asp Leu Phe Phe Ile Ala
    450                 455                 460

Asn Lys Asp Ser Phe Ser Lys Asp Leu Ala Lys Ala Glu Thr Ile Ala
465                 470                 475                 480

Tyr Asn Thr Gln Asn Asn Thr Ile Glu Asn Asn Phe Ser Ile Asp Gln
                485                 490                 495

Leu Ile Leu Asp Asn Asp Leu Ser Ser Gly Ile Asp Leu Pro Asn Glu
                500                 505                 510

Asn Thr Glu Pro Phe Thr Asn Phe Asp Asp Ile Asp Ile Pro Val Tyr
                515                 520                 525

Ile Lys Gln Ser Ala Leu Lys Lys Ile Phe Val Asp Gly Asp Ser Leu
    530                 535                 540
```

```
Phe Glu Tyr Leu His Ala Gln Thr Phe Pro Ser Asn Ile Glu Asn Leu
545                 550                 555                 560

Gln Leu Thr Asn Ser Leu Asn Asp Ala Leu Arg Asn Asn Asn Lys Val
                565                 570                 575

Tyr Thr Phe Phe Ser Thr Asn Leu Val Glu Lys Ala Asn Thr Val Val
                580                 585                 590

Gly Ala Ser Leu Phe Val Asn Trp Val Lys Gly Val Ile Asp Asp Phe
                595                 600                 605

Thr Ser Glu Ser Thr Gln Lys Ser Thr Ile Asp Lys Val Ser Asp Val
        610                 615                 620

Ser Ile Ile Ile Pro Tyr Ile Gly Pro Ala Leu Asn Val Gly Asn Glu
625                 630                 635                 640

Thr Ala Lys Glu Asn Phe Lys Asn Ala Phe Glu Ile Gly Gly Ala Ala
                645                 650                 655

Ile Leu Met Glu Phe Ile Pro Glu Leu Ile Val Pro Ile Val Gly Phe
                660                 665                 670

Phe Thr Leu Glu Ser Tyr Val Gly Asn Lys Gly His Ile Ile Met Thr
                675                 680                 685

Ile Ser Asn Ala Leu Lys Lys Arg Asp Gln Lys Trp Thr Asp Met Tyr
        690                 695                 700

Gly Leu Ile Val Ser Gln Trp Leu Ser Thr Val Asn Thr Gln Phe Tyr
705                 710                 715                 720

Thr Ile Lys Glu Arg Met Tyr Asn Ala Leu Asn Asn Gln Ser Gln Ala
                725                 730                 735

Ile Glu Lys Ile Ile Glu Asp Gln Tyr Asn Arg Tyr Ser Glu Glu Asp
                740                 745                 750

Lys Met Asn Ile Asn Ile Asp Phe Asn Asp Ile Asp Phe Lys Leu Asn
                755                 760                 765

Gln Ser Ile Asn Leu Ala Ile Asn Asn Ile Asp Asp Phe Ile Asn Gln
        770                 775                 780

Cys Ser Ile Ser Tyr Leu Met Asn Arg Met Ile Pro Leu Ala Val Lys
785                 790                 795                 800

Lys Leu Lys Asp Phe Asp Asp Asn Leu Lys Arg Asp Leu Leu Glu Tyr
                805                 810                 815

Ile Asp Thr Asn Glu Leu Tyr Leu Leu Asp Glu Val Asn Ile Leu Lys
                820                 825                 830

Ser Lys Val Asn Arg His Leu Lys Asp Ser Ile Pro Phe Asp Leu Ser
        835                 840                 845

Leu Tyr Thr Lys Asp Thr Ile Leu Ile Gln Val Phe Asn Asn Tyr Ile
    850                 855                 860

Ser
865
```

```
<210> SEQ ID NO 59
<211> LENGTH: 867
<212> TYPE: PRT
<213> ORGANISM: Artificial Sequence
<220> FEATURE:
<223> OTHER INFORMATION: LHN/TeNT with a C1 Activation Loop

<400> SEQUENCE: 59

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30
```

-continued

```
Tyr Tyr Lys Ala Phe Lys Ile Thr Asp Arg Ile Trp Ile Val Pro Glu
        35              40              45

Arg Tyr Glu Phe Gly Thr Lys Pro Glu Asp Phe Asn Pro Pro Ser Ser
        50              55              60

Leu Ile Glu Gly Ala Ser Glu Tyr Tyr Asp Pro Asn Tyr Leu Arg Thr
65              70              75              80

Asp Ser Asp Lys Asp Arg Phe Leu Gln Thr Met Val Lys Leu Phe Asn
                85              90              95

Arg Ile Lys Asn Asn Val Ala Gly Glu Ala Leu Leu Asp Lys Ile Ile
                100             105             110

Asn Ala Ile Pro Tyr Leu Gly Asn Ser Tyr Ser Leu Leu Asp Lys Phe
        115             120             125

Asp Thr Asn Ser Asn Ser Val Ser Phe Asn Leu Leu Glu Gln Asp Pro
        130             135             140

Ser Gly Ala Thr Thr Lys Ser Ala Met Leu Thr Asn Leu Ile Ile Phe
145             150             155             160

Gly Pro Gly Pro Val Leu Asn Lys Asn Glu Val Arg Gly Ile Val Leu
                165             170             175

Arg Val Asp Asn Lys Asn Tyr Phe Pro Cys Arg Asp Gly Phe Gly Ser
                180             185             190

Ile Met Gln Met Ala Phe Cys Pro Glu Tyr Val Pro Thr Phe Asp Asn
        195             200             205

Val Ile Glu Asn Ile Thr Ser Leu Thr Ile Gly Lys Ser Lys Tyr Phe
        210             215             220

Gln Asp Pro Ala Leu Leu Leu Met His Glu Leu Ile His Val Leu His
225             230             235             240

Gly Leu Tyr Gly Met Gln Val Ser Ser His Glu Ile Ile Pro Ser Lys
                245             250             255

Gln Glu Ile Tyr Met Gln His Thr Tyr Pro Ile Ser Ala Glu Glu Leu
                260             265             270

Phe Thr Phe Gly Gly Gln Asp Ala Asn Leu Ile Ser Ile Asp Ile Lys
        275             280             285

Asn Asp Leu Tyr Glu Lys Thr Leu Asn Asp Tyr Lys Ala Ile Ala Asn
        290             295             300

Lys Leu Ser Gln Val Thr Ser Cys Asn Asp Pro Asn Ile Asp Ile Asp
305             310             315             320

Ser Tyr Lys Gln Ile Tyr Gln Gln Lys Tyr Gln Phe Asp Lys Asp Ser
                325             330             335

Asn Gly Gln Tyr Ile Val Asn Glu Asp Lys Phe Gln Ile Leu Tyr Asn
                340             345             350

Ser Ile Met Tyr Gly Phe Thr Glu Ile Glu Leu Gly Lys Lys Phe Asn
        355             360             365

Ile Lys Thr Arg Leu Ser Tyr Phe Ser Met Asn His Asp Pro Val Lys
        370             375             380

Ile Pro Asn Leu Leu Asp Asp Thr Ile Tyr Asn Asp Thr Glu Gly Phe
385             390             395             400

Asn Ile Glu Ser Lys Asp Leu Lys Ser Glu Tyr Lys Gly Gln Asn Met
                405             410             415

Arg Val Asn Thr Asn Ala Phe Arg Asn Val Asp Gly Ser Gly Leu Val
                420             425             430

Ser Lys Leu Ile Gly Leu Cys His Lys Ala Ile Asp Gly Arg Ser Leu
        435             440             445

Tyr Asn Lys Thr Leu Asp Cys Ile Lys Ile Lys Asn Glu Asp Leu Thr
```

-continued

```
        450             455             460

Phe Ile Ala Glu Lys Asn Ser Phe Ser Glu Glu Pro Phe Gln Asp Glu
465             470             475             480

Ile Val Ser Tyr Asn Thr Lys Asn Lys Pro Leu Asn Phe Asn Tyr Ser
                485             490             495

Leu Asp Lys Ile Ile Val Asp Tyr Asn Leu Gln Ser Lys Ile Thr Leu
            500             505             510

Pro Asn Asp Arg Thr Thr Pro Val Thr Lys Gly Ile Pro Tyr Ala Pro
            515             520             525

Glu Tyr Lys Ser Asn Ala Ala Ser Thr Ile Glu Ile His Asn Ile Asp
        530             535             540

Asp Asn Thr Ile Tyr Gln Tyr Leu Tyr Ala Gln Lys Ser Pro Thr Thr
545             550             555             560

Leu Gln Arg Ile Thr Met Thr Asn Ser Val Asp Asp Ala Leu Ile Asn
                565             570             575

Ser Thr Lys Ile Tyr Ser Tyr Phe Pro Ser Val Ile Ser Lys Val Asn
            580             585             590

Gln Gly Ala Gln Gly Ile Leu Phe Leu Gln Trp Val Arg Asp Ile Ile
        595             600             605

Asp Asp Phe Thr Asn Glu Ser Ser Gln Lys Thr Thr Ile Asp Lys Ile
        610             615             620

Ser Asp Val Ser Thr Ile Val Pro Tyr Ile Gly Pro Ala Leu Asn Ile
625             630             635             640

Val Lys Gln Gly Tyr Glu Gly Asn Phe Ile Gly Ala Leu Glu Thr Thr
                645             650             655

Gly Val Val Leu Leu Leu Glu Tyr Ile Pro Glu Ile Thr Leu Pro Val
                660             665             670

Ile Ala Ala Leu Ser Ile Ala Glu Ser Ser Thr Gln Lys Glu Lys Ile
            675             680             685

Ile Lys Thr Ile Asp Asn Phe Leu Glu Lys Arg Tyr Glu Lys Trp Ile
        690             695             700

Glu Val Tyr Lys Leu Val Lys Ala Lys Trp Leu Gly Thr Val Asn Thr
705             710             715             720

Gln Phe Gln Lys Arg Ser Tyr Gln Met Tyr Arg Ser Leu Glu Tyr Gln
                725             730             735

Val Asp Ala Ile Lys Lys Ile Ile Asp Tyr Glu Tyr Lys Ile Tyr Ser
            740             745             750

Gly Pro Asp Lys Glu Gln Ile Ala Asp Glu Ile Asn Asn Leu Lys Asn
            755             760             765

Lys Leu Glu Glu Lys Ala Asn Lys Ala Met Ile Asn Ile Asn Ile Phe
        770             775             780

Met Arg Glu Ser Ser Arg Ser Phe Leu Val Asn Gln Met Ile Asn Glu
785             790             795             800

Ala Lys Lys Gln Leu Leu Glu Phe Asp Thr Gln Ser Lys Asn Ile Leu
                805             810             815

Met Gln Tyr Ile Lys Ala Asn Ser Lys Phe Ile Gly Ile Thr Glu Leu
                820             825             830

Lys Lys Leu Glu Ser Lys Ile Asn Lys Val Phe Ser Thr Pro Ile Pro
            835             840             845

Phe Ser Tyr Ser Lys Asn Leu Asp Cys Trp Val Asp Asn Glu Glu Asp
        850             855             860

Ile Asp Val
865
```

```
<210> SEQ ID NO 60
<211> LENGTH: 896
<212> TYPE: PRT
<213> ORGANISM: Artificial Sequence
<220> FEATURE:
<223> OTHER INFORMATION: LHN/X with a C1 Activation Loop

<400> SEQUENCE: 60

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365
```

-continued

```
Ile Asp Pro Ile Tyr Val Asn Ile Leu Asp Asp Asn Ser Tyr Ser Thr
    370             375             380

Leu Glu Gly Phe Asn Ile Ser Ser Gln Gly Ser Asn Asp Phe Gln Gly
385             390             395             400

Gln Leu Leu Glu Ser Ser Tyr Phe Glu Lys Ile Glu Ser Asn Ala Leu
            405             410             415

Arg Ala Phe Ile Lys Ile Cys His Lys Ala Ile Asp Gly Arg Ser Leu
            420             425             430

Tyr Asn Lys Thr Leu Asp Cys Ile Glu Val Glu Asn Lys Asp Leu Phe
        435             440             445

Leu Ile Ser Asn Lys Asp Ser Leu Asn Asp Ile Asn Leu Ser Glu Glu
    450             455             460

Lys Ile Lys Pro Glu Thr Thr Val Phe Phe Lys Asp Lys Leu Pro Pro
465             470             475             480

Gln Asp Ile Thr Leu Ser Asn Tyr Asp Phe Thr Glu Ala Asn Ser Ile
            485             490             495

Pro Ser Ile Ser Gln Gln Asn Ile Leu Glu Arg Asn Glu Glu Leu Tyr
            500             505             510

Glu Pro Ile Arg Asn Ser Leu Phe Glu Ile Lys Thr Ile Tyr Val Asp
        515             520             525

Lys Leu Thr Thr Phe His Phe Leu Glu Ala Gln Asn Ile Asp Glu Ser
    530             535             540

Ile Asp Ser Ser Lys Ile Arg Val Glu Leu Thr Asp Ser Val Asp Glu
545             550             555             560

Ala Leu Ser Asn Pro Asn Lys Val Tyr Ser Pro Phe Lys Asn Met Ser
            565             570             575

Asn Thr Ile Asn Ser Ile Glu Thr Gly Ile Thr Ser Thr Tyr Ile Phe
            580             585             590

Tyr Gln Trp Leu Arg Ser Ile Val Lys Asp Phe Ser Asp Glu Thr Gly
        595             600             605

Lys Ile Asp Val Ile Asp Lys Ser Ser Asp Thr Leu Ala Ile Val Pro
    610             615             620

Tyr Ile Gly Pro Leu Leu Asn Ile Gly Asn Asp Ile Arg His Gly Asp
625             630             635             640

Phe Val Gly Ala Ile Glu Leu Ala Gly Ile Thr Ala Leu Leu Glu Tyr
            645             650             655

Val Pro Glu Phe Thr Ile Pro Ile Leu Val Gly Leu Glu Val Ile Gly
            660             665             670

Gly Glu Leu Ala Arg Glu Gln Val Glu Ala Ile Val Asn Asn Ala Leu
        675             680             685

Asp Lys Arg Asp Gln Lys Trp Ala Glu Val Tyr Asn Ile Thr Lys Ala
    690             695             700

Gln Trp Trp Gly Thr Ile His Leu Gln Ile Asn Thr Arg Leu Ala His
705             710             715             720

Thr Tyr Lys Ala Leu Ser Arg Gln Ala Asn Ala Ile Lys Met Asn Met
            725             730             735

Glu Phe Gln Leu Ala Asn Tyr Lys Gly Asn Ile Asp Asp Lys Ala Lys
            740             745             750

Ile Lys Asn Ala Ile Ser Glu Thr Glu Ile Leu Leu Asn Lys Ser Val
        755             760             765

Glu Gln Ala Met Lys Asn Thr Glu Lys Phe Met Ile Lys Leu Ser Asn
    770             775             780
```

```
Ser Tyr Leu Thr Lys Glu Met Ile Pro Lys Val Gln Asp Asn Leu Lys
785             790             795             800

Asn Phe Asp Leu Glu Thr Lys Lys Thr Leu Asp Lys Phe Ile Lys Glu
                805             810             815

Lys Glu Asp Ile Leu Gly Thr Asn Leu Ser Ser Ser Leu Arg Arg Lys
            820             825             830

Val Ser Ile Arg Leu Asn Lys Asn Ile Ala Phe Asp Ile Asn Asp Ile
        835             840             845

Pro Phe Ser Glu Phe Asp Asp Leu Ile Asn Gln Tyr Lys Asn Glu Ile
        850             855             860

Glu Asp Tyr Glu Val Leu Asn Leu Gly Ala Glu Asp Gly Lys Ile Lys
865             870             875             880

Asp Leu Ser Gly Thr Thr Ser Asp Ile Asn Ile Gly Ser Asp Ile Glu
            885             890             895
```

```
<210> SEQ ID NO 61
<211> LENGTH: 14
<212> TYPE: PRT
<213> ORGANISM: Artificial Sequence
<220> FEATURE:
<223> OTHER INFORMATION: BoNT/DC Activation Loop

<400> SEQUENCE: 61

Cys Leu Arg Leu Thr Arg Asn Ser Arg Asp Asp Ser Thr Cys
1               5               10
```

```
<210> SEQ ID NO 62
<211> LENGTH: 25
<212> TYPE: PRT
<213> ORGANISM: Clostridium botulinum

<400> SEQUENCE: 62

Cys Val Arg Gly Ile Ile Thr Ser Lys Thr Lys Ser Leu Asp Glu Gly
1               5               10              15

Tyr Asn Lys Ala Leu Asn Glu Leu Cys
            20              25
```

```
<210> SEQ ID NO 63
<211> LENGTH: 25
<212> TYPE: PRT
<213> ORGANISM: Clostridium botulinum

<400> SEQUENCE: 63

Cys Val Arg Gly Ile Ile Thr Ser Lys Thr Lys Ser Leu Asp Glu Gly
1               5               10              15

Tyr Asn Lys Ala Leu Asn Asp Leu Cys
            20              25
```

```
<210> SEQ ID NO 64
<211> LENGTH: 25
<212> TYPE: PRT
<213> ORGANISM: Clostridium botulinum

<400> SEQUENCE: 64

Cys Val Arg Gly Ile Ile Pro Phe Lys Thr Lys Ser Leu Asp Glu Gly
1               5               10              15

Tyr Asn Lys Ala Leu Asn Tyr Leu Cys
            20              25
```

```
<210> SEQ ID NO 65
<211> LENGTH: 25
```

<212> TYPE: PRT
<213> ORGANISM: Clostridium botulinum

<400> SEQUENCE: 65

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 66
<211> LENGTH: 11
<212> TYPE: PRT
<213> ORGANISM: Clostridium botulinum

<400> SEQUENCE: 66

Cys Ser Asn Ser Asn Thr Lys Asn Ser Leu Cys
1               5                   10

<210> SEQ ID NO 67
<211> LENGTH: 15
<212> TYPE: PRT
<213> ORGANISM: Clostridium botulinum

<400> SEQUENCE: 67

Cys Thr Asn Ile Phe Ser Pro Lys Gly Ile Arg Lys Ser Ile Cys
1               5                   10                  15

<210> SEQ ID NO 68
<211> LENGTH: 15
<212> TYPE: PRT
<213> ORGANISM: Clostridium botulinum

<400> SEQUENCE: 68

Cys Lys Asn Ile Val Phe Ser Lys Gly Ile Thr Lys Ser Ile Cys
1               5                   10                  15

<210> SEQ ID NO 69
<211> LENGTH: 15
<212> TYPE: PRT
<213> ORGANISM: Clostridium botulinum

<400> SEQUENCE: 69

Cys Lys Asn Ile Val Phe Ser Lys Gly Ile Arg Lys Ser Ile Cys
1               5                   10                  15

<210> SEQ ID NO 70
<211> LENGTH: 10
<212> TYPE: PRT
<213> ORGANISM: Clostridium botulinum

<400> SEQUENCE: 70

Cys Lys Ser Val Lys Val Pro Gly Ile Cys
1               5                   10

<210> SEQ ID NO 71
<211> LENGTH: 10
<212> TYPE: PRT
<213> ORGANISM: Clostridium botulinum

<400> SEQUENCE: 71

Cys Lys Ser Val Lys Ala Pro Gly Ile Cys
1               5                   10

<210> SEQ ID NO 72

```
<211> LENGTH: 5
<212> TYPE: PRT
<213> ORGANISM: Artificial Sequence
<220> FEATURE:
<223> OTHER INFORMATION: Enterokinase Cleavage Site

<400> SEQUENCE: 72

Asp Asp Asp Asp Lys
1               5

<210> SEQ ID NO 73
<211> LENGTH: 23
<212> TYPE: PRT
<213> ORGANISM: Artificial Sequence
<220> FEATURE:
<223> OTHER INFORMATION: Influenza Virus Haemagglutinin Translocation
      Domain

<400> SEQUENCE: 73

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 74
<211> LENGTH: 7
<212> TYPE: PRT
<213> ORGANISM: Artificial Sequence
<220> FEATURE:
<223> OTHER INFORMATION: Leucine-Based Motif
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (3)..(5)
<223> OTHER INFORMATION: Xaa can be any naturally occurring amino acid

<400> SEQUENCE: 74

Xaa Asp Xaa Xaa Xaa Leu Leu
1               5

<210> SEQ ID NO 75
<211> LENGTH: 7
<212> TYPE: PRT
<213> ORGANISM: Artificial Sequence
<220> FEATURE:
<223> OTHER INFORMATION: Leucine-Based Motif
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (3)..(5)
<223> OTHER INFORMATION: Xaa can be any naturally occurring amino acid

<400> SEQUENCE: 75

Xaa Glu Xaa Xaa Xaa Leu Leu
1               5

<210> SEQ ID NO 76
<211> LENGTH: 7
<212> TYPE: PRT
<213> ORGANISM: Artificial Sequence
<220> FEATURE:
<223> OTHER INFORMATION: Leucine-Based Motif
<220> FEATURE:
<221> NAME/KEY: SITE
```

```
<222> LOCATION: (1)..(1)
<223> OTHER INFORMATION: Xaa can be any naturally occurring amino acid
<220> FEATURE:
<221> NAME/KEY: SITE
<222> LOCATION: (3)..(5)
<223> OTHER INFORMATION: Xaa can be any naturally occurring amino acid

<400> SEQUENCE: 76

Xaa Glu Xaa Xaa Xaa Ile Leu
1               5

<210> SEQ ID NO 77
<211> LENGTH: 7
<212> TYPE: PRT
<213> ORGANISM: Artificial Sequence
<220> FEATURE:
<223> OTHER INFORMATION: Leucine-Based Motif
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (3)..(5)
<223> OTHER INFORMATION: Xaa can be any naturally occurring amino acid

<400> SEQUENCE: 77

Xaa Glu Xaa Xaa Xaa Leu Met
1               5

<210> SEQ ID NO 78
<211> LENGTH: 4
<212> TYPE: PRT
<213> ORGANISM: Artificial Sequence
<220> FEATURE:
<223> OTHER INFORMATION: Tyrosine-Based Motif
<220> FEATURE:
<221> NAME/KEY: SITE
<222> LOCATION: (2)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa is a hydrophobic amino acid

<400> SEQUENCE: 78

Tyr Xaa Xaa Xaa
1

<210> SEQ ID NO 79
<211> LENGTH: 7
<212> TYPE: PRT
<213> ORGANISM: Artificial Sequence
<220> FEATURE:
<223> OTHER INFORMATION: TEV Cleavage Site

<400> SEQUENCE: 79

Glu Asn Leu Tyr Phe Gln Gly
1               5

<210> SEQ ID NO 80
<211> LENGTH: 6
<212> TYPE: PRT
<213> ORGANISM: Artificial Sequence
<220> FEATURE:
<223> OTHER INFORMATION: Thrombin Cleavage Site

<400> SEQUENCE: 80

Leu Val Pro Arg Gly Ser
1               5
```

-continued

```
<210> SEQ ID NO 81
<211> LENGTH: 8
<212> TYPE: PRT
<213> ORGANISM: Artificial Sequence
<220> FEATURE:
<223> OTHER INFORMATION: PreScission Cleavage Site

<400> SEQUENCE: 81

Leu Glu Val Leu Phe Gln Gly Pro
1               5

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp or Glu

<400> SEQUENCE: 82

Ile Xaa Gly Arg
1

<210> SEQ ID NO 83
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: SITE
<222> LOCATION: (2)..(11)
<223> OTHER INFORMATION: This region may encompass 1-10 residues
<220> FEATURE:
<221> NAME/KEY: MOD_RES
<222> LOCATION: (16)..(35)
<223> OTHER INFORMATION: Any amino acid
<220> FEATURE:
<221> NAME/KEY: SITE
<222> LOCATION: (16)..(35)
<223> OTHER INFORMATION: This region may encompass 4-20 residues

<400> SEQUENCE: 83

Cys Xaa Xaa Xaa Xaa Xaa Xaa Xaa Xaa Xaa Xaa Ile Asp Gly Arg Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Cys
        35

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 84

Ser Leu Tyr Asn Lys Thr Leu Asp Cys
1               5
```